(12) United States Patent  (10) Patent No.: US 7,304,071 B2
Cochran et al.  (45) Date of Patent: Dec. 4, 2007

(54) PROTEIN KINASE INHIBITORS AND USES THEREOF

(75) Inventors: John Cochran, Marshfield, MA (US); Jeremy Green, Burlington, MA (US); Michael R. Hale, Bedford, MA (US); Brian Ledford, Attleboro, MA (US); Francois Maltais, Tewksbury, MA (US); Suganthini Nanthakumar, Newton, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 345 days.

(21) Appl. No.: 10/639,784

(22) Filed: Aug. 12, 2003

(65) Prior Publication Data

US 2004/0106615 A1  Jun. 3, 2004

Related U.S. Application Data

(60) Provisional application No. 60/416,802, filed on Oct. 8, 2002, provisional application No. 60/403,256, filed on Aug. 14, 2002.

(51) Int. Cl.
C07D 239/42 (2006.01)
A61K 31/505 (2006.01)

(52) U.S. Cl. .................. 514/275; 544/332
(58) Field of Classification Search ............ 544/332; 514/275
See application file for complete search history.

(56) References Cited

U.S. PATENT DOCUMENTS

| 6,949,544 B2 | 9/2005 | Bethiel et al. ........... 514/235.8 |
| 2004/0147507 A1 | 7/2004 | Ledeboer et al. ...... 514/217.04 |
| 2004/0176271 A1 | 9/2004 | Bethiel et al. ............ 514/2 |

FOREIGN PATENT DOCUMENTS

| WO | WO 95/09847 | 4/1995 |
| WO | WO 95/09851 | 4/1995 |
| WO | WO 95/09853 | 4/1995 |
| WO | WO 97/19065 | 5/1997 |
| WO | WO 97/19065 A1 | 5/1997 |
| WO | WO 99/65897 | 12/1999 |
| WO | WO 01/29009 | 4/2001 |
| WO | WO 01/29009 A1 | 4/2001 |
| WO | WO 02/20495 | * 3/2002 |
| WO | WO 02/22601 | 3/2002 |
| WO | WO 02/46170 | 6/2002 |
| WO | WO 02/46171 | 6/2002 |
| WO | WO 02/46171 A2 | 6/2002 |
| WO | WO 02/079193 A1 | 10/2002 |
| WO | WO 02/079197 | 10/2002 |
| WO | WO 03/030909 A1 | 4/2003 |

OTHER PUBLICATIONS

Damasio, Alzheimer's Disease and Related Dementias, Cecil Textbook of Medicine, 20th Edition, vol. 2, pp. 1992-1996, 1996.*
Layzer, Degenerative diseases of the Nervous System, Cecil Textbook of Medicine, 20th Edition, vol. 2, pp. 2050-2057, 1996.*
Casanova et al., PubMed Abstract (Rev Neurol 28(9):909-15) May 1999.*
Douglas, Jr. Introduction to Viral Diseases, Cecil Textbook of Medicine, 20th Edition, vol. 2, pp. 1739-1747, 1996.*
Simone, Oncology: Introduction, Cecil Textbook of Medicine, 20th Edition, vol. 1 pp. 1004-1010, 1996.*
Hardt et al., Glycogen Synthase Kinase-3beta A Novel Regulator of Cardiac Hypertrophy and Development, Circulation Research, 90:1055-1063, 2002.*
Taxler, Protein Tyrosine Kinase inhibitors in cancer treatment, Exp. Opin. Ther. Patents, 7(6):571-588, 1997.*
Chang et al., "Role of cAMP-dependent pathway in eosinophil apoptosis and survival," Cell. Immunology, 203(1):29-38 (2000).
Frey et al., "TGF-beta regulation of mitogen-activated protein kinases in human breast cancer cells," Cancer Letters, 177(1):41-50 (1997).
Fukunaga et al., "Role of MAP kinase in neurons," Molecular Neurobiology, 16(1):79-95 (1998).

(Continued)

Primary Examiner—Deepak Rao
(74) Attorney, Agent, or Firm—Daniel A. Pearson

(57) ABSTRACT

Described herein are compounds that are useful as protein kinase inhibitors having the formulae I and V:

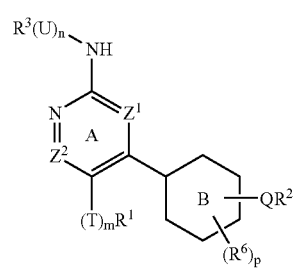

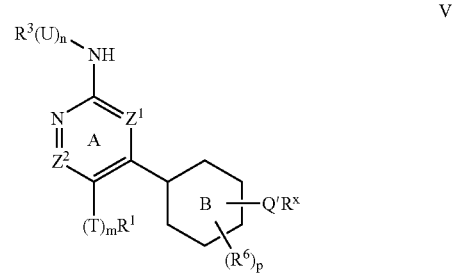

or a pharmaceutically acceptable salt thereof, wherein Ring B, $Z^1$, $Z^2$, U, T, m, n, p, Q, Q', $R^1$, $R^2$, $R^x$, $R^3$, and $R^6$ are as defined herein. These compounds, and pharmaceutically acceptable compositions thereof, are useful for treating or lessening the severity of a variety of disorders, including stroke, inflammatory disorders, autoimmune diseases such as SLE lupus and psoriasis, proliferative disorders such as cancer, and conditions associated with organ transplantation.

20 Claims, No Drawings

OTHER PUBLICATIONS

Hoshino et al., "Constitutive activation of the 41-/43-kDa mitogen-activated protein kinase signaling pathway in human tumors," Oncogene, 18:813-22 (1999).

Hu et al., "Protein kinase and protein phosphatase expression in amyotrophic lateral sclerosis spinal cord," J. Neurochemistry, 85(2):432-42 (2003).

Illenberger et al. "The endogenous and cell cycle-dependent phosphorylation of tau protein in living cells: implications for Alzheimer's disease," Molecular Biology of The Cell, 9(6):1495-512 (1998).

Kodama et al., "Significance of ERK cascade compared with JAK/STAT and PI3-K pathway in gp130-mediated cardiac hypertrophy," Am. J. Physiol. Heart Circ. Physiol., 279(4):H1635-44 (2000).

Kortylewski et al., "Mitogen-activated protein kinases control p27/Kip1 expression and growth of human melanoma cells," Biochemical Journal, 357(Pt 1):297-303 (2001).

Kyosseva et al., "Mitogen-activated protein kinases in schizophrenia," Society of Biological Psychiatry, 46(5):689-96 (1999).

Lee et al., "ICAM-1-induced expression of proinflammatory cytokines in astrocytes: involvement of extracellular signal-regulated kinase and p38 mitogen-activated protein kinase pathways," The Journal of Immunology. 168(8):4658-66 (2000).

Namura et al., "Intravenous administration of MEK inhibitor U0126 affords brain protection against forebrain ischemia and focal cerebral ischemia," Proc. Natl. Acad. Sci. U.S.A. 98(20):11569-74 (2001).

Putz et al., "Epidermal growth factor (EGF) receptor blockade inhibits the action of EGF, insulin-like growth factor I, and a protein kinase A activator on the mitogen-activated protein kinase pathway in prostate cancer cell lines," Cancer Research, 59(1):227-33 (1999).

Raghunandan et al., "Hyperphosphorylation of the cytoskeletal protein Tau by the MAP-kinase PK40erk2: regulation by prior phosphorylation with cAMP-dependent protein kinase A," Biochemical and Biophysical Research Communications, 215(3):1056-66 (1995).

Slevin et al., "Activation of MAP kinase (ERK-1/ERK-2), tyrosine kinase and VEGF in the human brain following acute ischaemic stroke," NeuroReport 11(12):2759-64 (2000).

Tack et al., "Autocrine activation of the IGF-1 signaling pathway in mesangial cells isolated from diabetic NOD mice," Diabetes 51(1):182-8 (2002).

Takeishi et al., "Activation of mitogen-activated protein kinases and p60 ribosomal S6 kinase in failing human hearts with dilated cardiomyopathy," Cardiovascular Research 53:131-137 (2002).

Pintucci et al., "Lack of ERK activation and cell migration in FGF-2-deficient endothelial cells," The FASEB Journal 16(2):598-600 (2002).

Moses, et al., "Injury-induced osteopontin gene expression in rat arterial smooth muscle cells in dependent on mitogen-activated protein kinases ERK1/ERK2," Archives of Biochemistry and Biophysics 396(1):133-137 (2001).

Wersinger and Sidhu, "Inflammation and Parkinson's Disease," Current Drug Targets, 1(3): 221-242 (2002).

* cited by examiner

PROTEIN KINASE INHIBITORS AND USES THEREOF

CROSS REFERENCE TO RELATED APPLICATIONS

This application claims priority to U.S. Provisional Patent Applications 60/403,256 filed Aug. 14, 2002 and 60/416,802 filed Oct. 8, 2002, the contents of which are incorporated herein by reference.

FIELD OF THE INVENTION

The present invention is in the field of medicinal chemistry and relates to pyrimidine compounds that are protein kinase inhibitors, compositions containing such compounds and methods of use. The compounds are useful for treating cancer, neurological disorders, autoimmune disorders, and other diseases that are alleviated by protein kinase inhibitors.

BACKGROUND OF THE INVENTION

The search for new therapeutic agents has been greatly aided in recent years by a better understanding of the structure of enzymes and other biomolecules associated with target diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. (1995) The Protein Kinase Facts Book, I and II, Academic Press, San Diego, Calif.). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., FASEB J., 9:576-596 (1995); Knighton et al., Science, 253:407-414 (1991); Hiles et al., Cell, 70:419-429 (1992); Kunz et al., Cell,73:585-596 (1993); Garcia-Bustos et al., EMBO J., 13:2352-2361 (1994)).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O2$), cytokines (e.g., interleukin-1 (IL-1) and tumor necrosis factor a (TNF-a)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies and asthma, Alzheimer's disease and hormone-related diseases. Accordingly, there has been a substantial effort in medicinal chemistry to find protein kinase inhibitors that are effective as therapeutic agents. However, considering the lack of currently available treatment options for the majority of the conditions associated with protein kinases, there is still a great need for new therapeutic agents that inhibit these protein targets.

Mammalian cells respond to extracellular stimuli by activating signaling cascades that are mediated by members of the mitogen-activated protein (MAP) kinase family, which include the extracellular signal regulated kinases (ERKs), the p38 MAP kinases and the c-Jun N-terminal kinases (JNKs). MAP kinases (MAPKs) are activated by a variety of signals including growth factors, cytokines, UV radiation, and stress-inducing agents. MAPKs are serine/threonine kinases and their activation occur by dual phosphorylation of threonine and tyrosine at the Thr-X-Tyr segment in the activation loop. MAPKs phosphorylate various substrates including transcription factors, which in turn regulate the expression of specific sets of genes and thus mediate a specific response to the stimulus.

ERK2 is a widely distributed protein kinase that achieves maximum activity when both Thr183 and Tyr185 are phosphorylated by the upstream MAP kinase kinase, MEK1 (Anderson et al., 1990, Nature 343, 651; Crews et al., 1992, Science 258, 478). Upon activation, ERK2 phosphorylates many regulatory proteins, including the protein kinases Rsk90 (Bjorbaek et al., 1995, J. Biol. Chem. 270, 18848) and MAPKAP2 (Rouse et al., 1994, Cell 78, 1027), and transcription factors such as ATF2 (Raingeaud et al., 1996, Mol. Cell Biol. 16, 1247), Elk-1 (Raingeaud et al. 1996), c-Fos (Chen et al., 1993 Proc. Natl. Acad. Sci. USA 90, 10952), and c-Myc (Oliver et al., 1995, Proc. Soc. Exp. Biol. Med. 210, 162). ERK2 is also a downstream target of the Ras/Raf dependent pathways (Moodie et al., 1993, Science 260, 1658) and relays the signals from these potentially oncogenic proteins. ERK2 has been shown to play a role in the negative growth control of breast cancer cells (Frey and Mulder, 1997, Cancer Res. 57, 628) and hyperexpression of ERK2 in human breast cancer has been reported (Sivaraman et al., 1997, J. Clin. Invest. 99, 1478). Activated ERK2 has also been implicated in the proliferation of endothelin-stimulated airway smooth muscle cells, suggesting a role for this kinase in asthma (Whelchel et al., 1997, Am. J. Respir. Cell Mol. Biol. 16, 589).

Overexpression of receptor tyrosine kinases such as EGFR and ErbB2 (Arteaga C L, 2002, Semin Oncol. 29, 3-9; Eccles S A, 2001, J Mammary Gland Biol Neoplasia 6:393-406; Mendelsohn J & Baselga J, 2000, Oncogene 19, 6550-65), as well as activating mutations in the Ras GTPase proteins (Nottage M & Siu L L, 2002, Curr Pharm Des 8, 2231-42; Adjei A A, 2001, J Natl Cancer Inst 93, 1062-74) or B-Raf mutants (Davies H. et al., 2002, Nature 417, 949-54; Brose et al., 2002, Cancer Res 62, 6997-7000) are major contributors to human cancer. These genetic alterations are correlated with poor clinical prognosis and result in activation of the Raf-1/2/3-MEK1/2-ERK1/2 signal transduction cascade in a broad panel of human tumors. Activated ERK (i.e. ERK1 and/or ERK2) is a central signaling molecule that has been associated with the control of proliferation, differentiation, anchorage-independent cell survival, and angiogenesis, contributing to a number of processes that are important for the formation and progression of malignant tumors. These data suggest that an ERK1/2 inhibitor will exert pleiotropic activity, including proapoptotic, anti-proliferative, anti-metastatic and anti-angiogenic effects, and offer a therapeutic opportunity against a very broad panel of human tumors.

There is a growing body of evidence that implicates constitutive activation of the ERK MAPK pathway in the oncogenic behavior of select cancers. Activating mutations of Ras are found in ~30% of all cancers, with some, such as pancreatic (90%) and colon (50%) cancer, harboring particularly high mutation rates (ref). Ras mutations have also been identified in 9-15% of melanomas, but B-Raf somatic missense mutations conferring constitutive activation are more frequent and found in 60-66% malignant melanomas. Activating mutations of Ras, Raf and MEK are able to oncogenically transform fibroblasts in vitro, and Ras or Raf mutations in conjunction with the loss of a tumor suppressor gene (e.g. p16INK4A) can cause spontaneous tumor development in vivo. Increased ERK activity has been demonstrated in these models and has also been widely reported in appropriate human tumors. In melanoma, high basal ERK activity resulting from either B-Raf or N-Ras mutations or autocrine growth factor activation is well documented and has been associated with rapid tumor growth, increased cell survival and resistance to apoptosis. Additionally, ERK activation is considered a major driving force behind the highly metastatic behavior of melanoma associated with increased expression of both extracellular matrix degrading proteases and invasion-promoting integrins as well as the downregulation of E-cadherin adhesion molecules that normally mediate keratinocyte interactions to control melanocyte growth. These data taken together, indicate ERK as promising therapeutic target for the treatment of melanoma, a currently untreatable disease.

One particularly interesting kinase family is the c-Jun $NH_2$-terminal protein kinases, also known as JNKs. Three distinct genes, JNK1, JNK2, JNK3 have been identified and at least ten different splicing isoforms of JNKs exist in mammalian cells [Gupta et al., *EMBO J.*, 15:2760-70 (1996)]. Members of the JNK family are activated by proinflammatory cytokines, such as tumor necrosis factor-α (TNFα) and interleukin-1 β (IL-1β), as well as by environmental stress, including anisomycin, UV irradiation, hypoxia, and osmotic shock [Minden et al., *Biochemica et Biophysica Acta*, 1333:F85-F104 (1997)].

The down-stream substrates of JNKs include transcription factors c-Jun, ATF-2, Elk1, p53 and a cell death domain protein (DENN) [Zhang et al. *Proc. Natl. Acad. Sci. USA*, 95:2586-91 (1998)]. Each JNK isoform binds to these substrates with different affinities, suggesting a regulation of signaling pathways by substrate specificity of different JNKs in vivo (Gupta et al., supra).

JNKs, along with other MAPKs, have been implicated in having a role in mediating cellular response to cancer, thrombin-induced platelet aggregation, immunodeficiency disorders, autoimmune diseases, cell death, allergies, osteoporosis and heart disease. The therapeutic targets related to activation of the JNK pathway include chronic myelogenous leukemia (CML), rheumatoid arthritis, asthma, osteoarthritis, ischemia, cancer and neurodegenerative diseases.

Several reports have detailed the importance of JNK activation associated with liver disease or episodes of hepatic ischemia [*Nat. Genet.* 21:326-9 (1999); *FEBS Lett.* 420:201-4 (1997); *J. Clin. Invest.* 102:1942-50 (1998); *Hepatology* 28:1022-30 (1998)]. Therefore, inhibitors of JNK may be useful to treat various hepatic disorders.

A role for JNK in cardiovascular disease such as myocardial infarction or congestive heart failure has also been reported as it has been shown JNK mediates hypertrophic responses to various forms of cardiac stress [*Circ. Res.* 83:167-78 (1998); *Circulation* 97:1731-7 (1998); *J. Biol. Chem.* 272:28050-6 (1997); *Circ. Res.* 79:162-73 (1996); *Circ. Res.* 78:947-53 (1996); *J. Clin. Invest.* 97:508-14 (1996)].

It has been demonstrated that the JNK cascade also plays a role in T-cell activation, including activation of the IL-2 promoter. Thus, inhibitors of JNK may have therapeutic value in altering pathologic immune responses [*J. Immunol.* 162:3176-87 (1999); *Eur. J. Immunol.* 28:3867-77 (1998); *J. Exp. Med.* 186:941-53 (1997); *Eur. J. Immunol.* 26:989-94 (1996)].

A role for JNK activation in various cancers has also been established, suggesting the potential use of JNK inhibitors in cancer. For example, constitutively activated JNK is associated with HTLV-1 mediated tumorigenesis [*Oncogene* 13:135-42 (1996)]. JNK may play a role in Kaposi's sarcoma (KS) because it is thought that the proliferative effects of bFGF and OSM on KS cells are mediated by their activation of the JNK signaling pathway [*J. Clin. Invest.* 99:1798-804 (1997)]. Other proliferative effects of other cytokines implicated in KS proliferation, such as vascular endothelial growth factor (VEGF), IL-6 and TNFα, may also be mediated by JNK. In addition, regulation of the c-jun gene in p210 BCR-ABL transformed cells corresponds with activity of JNK, suggesting a role for JNK inhibitors in the treatment for chronic myelogenous leukemia (CML) [*Blood* 92:2450-60 (1998)].

JNK1 and JNK2 are widely expressed in a variety of tissues. In contrast, JNK3, is selectively expressed in the brain and to a lesser extent in the heart and testis [Gupta et al., supra; Mohit et al., *Neuron* 14:67-78 (1995); Martin et al., *Brain Res. Mol. Brain Res.* 35:47-57 (1996)]. JNK3 has been linked to neuronal apoptosis induced by kainic acid, indicating a role of JNK in the pathogenesis of glutamate neurotoxicity. In the adult human brain, JNK3 expression is localized to a subpopulation of pyramidal neurons in the CA1, CA4 and subiculum regions of the hippocampus and layers 3 and 5 of the neocortex [Mohit et al., supra]. The CA1 neurons of patients with acute hypoxia showed strong nuclear JNK3-immunoreactivity compared to minimal, diffuse cytoplasmic staining of the hippocampal neurons from brain tissues of normal patients [Zhang et al., supra]. Thus, JNK3 appears to be involved involved in hypoxic and ischemic damage of CA1 neurons in the hippocampus.

In addition, JNK3 co-localizes immunochemically with neurons vulnerable in Alzheimer's disease [Mohit et al., supra]. Disruption of the JNK3 gene caused resistance of mice to the excitotoxic glutamate receptor agonist kainic acid, including the effects on seizure activity, AP-1 transcriptional activity and apoptosis of hippocampal neurons, indicating that the JNK3 signaling pathway is a critical component in the pathogenesis of glutamate neurotoxicity (Yang et al., *Nature*, 389:865-870 (1997)].

Based on these findings, JNK signaling, especially that of JNK3, has been implicated in the areas of apoptosis-driven neurodegenerative diseases such as Alzheimer's Disease, Parkinson's Disease, ALS (Amyotrophic Lateral Sclerosis), epilepsy and seizures, Huntington's Disease, traumatic brain injuries, as well as ischemic and hemorrhaging stroke.

AKT (also known as PKB or Rac-PK beta), a serine/threonine protein kinase, has been shown to be overexpressed in several types of cancer and is a mediator of normal cell functions [(Khwaja, A., *Nature* 1999, 401, 33-34); (Yuan, Z. Q., et al., *Oncogene* 2000, 19, 2324-2330); (Namikawa, K., et al., *J. Neurosci.* 2000, 20, 2875-2886)]. AKT comprises an N-terminal pleckstrin homology (PH) domain, a kinase domain and a C-terminal "tail" region. Three isoforms of human AKT kinase (AKT-1, -2 and -3) have been reported so far [(Cheng, J. Q., *Proc. Natl. Acad. Sci. USA* 1992, 89, 9267-9271); (Brodbeck, D. et al., *J. Biol. Chem.* 1999, 274, 9133-9136)]. The PH domain binds 3-phosphoinositides, which are synthesized by phosphatidyl inositol 3-kinase (PI3K) upon stimulation by growth factors such as platelet derived growth factor (PDGF), nerve growth factor (NGF) and insulin-like growth factor (IGF-1) [(Kulik et al., *Mol. Cell. Biol.*, 1997, 17, 1595-1606); (Hemmings, B. A., *Science*, 1997, 275, 628-630)]. Lipid binding to the PH domain promotes translocation of AKT to the plasma membrane and facilitates phosphorylation by another PH-domain-containing protein kinases, PDK1 at Thr308, Thr309, and Thr305 for the AKT isoforms 1, 2 and 3, respectively. A second, as of yet unknown, kinase is required for the phosphorylation of Ser473, Ser474 or Ser472 in the C-terminal tails of AKT-1, -2 and -3 respectively, in order to yield a fully activated AKT enzyme.

Once localized to the membrane, AKT mediates several functions within the cell including the metabolic effects of insulin (Calera, M. R. et al., *J. Biol. Chem.* 1998, 273, 7201-7204) induction of differentiation and/or proliferation, protein synthesis and stress responses (Alessi, D. R. et al., *Curr. Opin. Genet. Dev.* 1998, 8, 55-62).

Manifestations of altered AKT regulation appear in both injury and disease, the most important role being in cancer. The first account of AKT was in association with human ovarian carcinomas where expression of AKT was found to be amplified in 15% of cases (Cheng, J. Q. et al., *Proc. Natl. Acad. Sci. U.S.A.* 1992, 89, 9267-9271). It has also been found to be overexpressed in 12% of pancreatic cancers (Cheng, J. Q. et al., *Proc. Natl. Acad. Sci. U.S.A.* 1996, 93, 3636-3641). It was demonstrated that AKT-2 was overexpressed in 12% of ovarian carcinomas and that amplification of AKT was especially frequent in 50% of undifferentiated tumours, suggesting that AKT is also associated with tumour aggressiveness (Bellacosa, et al., *Int. J. Cancer* 1995, 64, 280-285).

Glycogen synthase kinase-3 (GSK-3) is a serine/threonine protein kinase comprised of α and β isoforms that are each encoded by distinct genes [Coghlan et al., *Chemistry & Biology*, 7, 793-803 (2000); Kim and Kimmel, *Curr. Opinion Genetics Dev.*, 10, 508-514 (2000)]. GSK-3 has been implicated in various diseases including diabetes, Alzheimer's disease, CNS disorders such as manic depressive disorder and neurodegenerative diseases, and cardiomyocyte hypertrophy [see, e.g., WO 99/65897; WO 00/38675; Kaytor and Orr, *Curr. Opin. Neurobiol.*, 12, 275-8 (2000); Haq et al., *J. Cell Biol.*, 151, 117-30 (2000); Eldar-Finkelman, *Trends Mol. Med.*, 8, 126-32 (2002)]. These diseases are associated with the abnormal operation of certain cell signaling pathways in which GSK-3 plays a role.

GSK-3 has been found to phosphorylate and modulate the activity of a number of regulatory proteins. These include glycogen synthase, which is the rate-limiting enzyme required for glycogen synthesis, the microtubule-associated protein Tau, the gene transcription factor β-catenin, the translation initiation factor eIF-2B, as well as ATP citrate lyase, axin, heat shock factor-1, c-Jun, c-myc, c-myb, CREB, and CEPBα. These diverse targets implicate GSK-3 in many aspects of cellular metabolism, proliferation, differentiation and development.

In a GSK-3 mediated pathway that is relevant for the treatment of type II diabetes, insulin-induced signaling leads to cellular glucose uptake and glycogen synthesis. GSK-3 is a negative regulator of the insulin-induced signal in this pathway. Normally, the presence of insulin causes inhibition of GSK-3-mediated phosphorylation and deactivation of glycogen synthase. The inhibition of GSK-3 leads to increased glycogen synthesis and glucose uptake [Klein et al., *PNAS*, 93, 8455-9 (1996); Cross et al., *Biochem. J.*, 303, 21-26 (1994); Cohen, *Biochem. Soc. Trans.*, 21, 555-567 (1993); and Massillon et al., *Biochem J.* 299, 123-128 (1994); Cohen and Frame, *Nat. Rev. Mol. Cell. Biol.*, 2, 769-76 (2001)]. However, where the insulin response is impaired in a diabetic patient, glycogen synthesis and glucose uptake fail to increase despite the presence of relatively high blood levels of insulin. This leads to abnormally high blood levels of glucose with acute and chronic effects that may ultimately result in cardiovascular disease, renal failure and blindness. In such patients, the normal insulin-induced inhibition of GSK-3 fails to occur. It has also been reported that GSK-3 is overexpressed in patients with type II diabetes [WO 00/38675]. Therapeutic inhibitors of GSK-3 are therefore useful for treating diabetic patients suffering from an impaired response to insulin.

Apoptosis has been implicated in the pathophysiology of ischemic brain damage (Li et al., 1997; Choi, et al., 1996; Charriaut-Marlangue et al., 1998; Grahm and Chen, 2001; Murphy et al., 1999; Nicotera et al., 1999). Recent publications indicate that activation of GSK-3β may be involved in apoptotic mechanisms (Kaytor and Orr, 2002; Culbert et al., 2001). Studies in rat models of ischemic stroke induced by middle cerebral artery occlusion (MCAO) showed increased GSK-3β expression is following ischemia (Wang et al., Brain Res, 859, 381-5, 2000; Sasaki et al., Neurol Res, 23, 588-92,2001). Fibroblast growth factor (FGF) reduced ischemic brain injury after permanent middle cerebral artery occlusion (MCO) in rats (Fisher et al. 1995; Song et al. 2002). Indeed, the neuroprotective effects of FGF demonstrated in ischemia models in rats may be mediated by a PI-3 kinase/AKT-dependent inactivation of GSK-30 (Hashimoto et al., 2002). Thus, inhibition of GSK-3β after a cerebral ischemic event may ameliorate ischemic brain damage.

GSK-3 is also implicated in mycardial infarction. See Jonassen et al., Circ Res, 89:1191, 2001 (The reduction in myocardial infarction by insulin administration at reperfusion is mediated via Akt dependent signaling pathway); Matsui et al., Circulation, 104:330, 2001 (Akt activation preserves cardiac function and prevents cardiomyocyte injury after transient cardiac ischemia in vivo); Miao et al., J Mol Cell Cardiol, 32:2397, 2000 (Intracoronary, adenovirus-mediated Akt gene delivery in heart reduced gross infarct size following ischemia-reperfusion injury in vivo); and Fujio et al., Circulation et al., 101:660, 2000 (Akt signaling inhibits cardiac myocyte apoptosis in vitro and protects against ischemia-reperfusion injury in mouse heart).

GSK-3 activity plays a role in head trauma. See Noshita et al., Neurobiol Dis, 9:294, 2002 (Upregulation of Akt/PI3-kinase pathway may be crucial for cell survival after traumatic brain injury) and Dietrich et al., J Neurotrauma, 13:309, 1996 (Posttraumatic administration of bFGF significantly reduced damaged cortical neurons & total contusion volume in a rat model of traumatic brain injury).

GSK-3 is also known to play a role in psychiatric disorders. See Eldar-Finkelman, Trends Mol Med, 8:126, 2002; Li et al., Bipolar Disord, 4:137, 2002 (LiCl and Valproic acid, anti-psychotic, mood stabilizing drugs, decrease GSK3 activities and increase beta-catenin) and Lijam et al., Cell, 90:895, 1997 (Dishevelled KO mice showed abnormal social behavior and defective sensorimotor gating. Dishevelled, a cytoplamic protein involved in WNT pathway, inhibits GSK3beta activities).

It has been shown that GSK3 inhibition by lithium and valproic acid induces axonal remodeling and change synaptic connectivity. See Kaytor & Orr, Curr Opin Neurobiol, 12:275, 2002 (Downregulation of GSK3 causes changes in mirotubule-associated proteins: tau, MAP1 & 2) and Hall et al., Mol Cell Neurosci, 20:257, 2002 (Lithium and valproic acid induces the formation of growth cone-like structures along the axons).

GSK-3 activity is also associated with Alzheimer's disease. This disease is characterized by the presence of the well-known β-amyloid peptide and the formation of intracellular neurofibrillary tangles. The neurofibrillary tangles contain hyperphosphorylated Tau protein, in which Tau is phosphorylated on abnormal sites. GSK-3 has been shown to phosphorylate these abnormal sites in cell and animal models. Furthermore, inhibition of GSK-3 has been shown to prevent hyperphosphorylation of Tau in cells [Lovestone et al., *Curr. Biol.*, 4, 1077-86 (1994); and Brownlees et al., *Neuroreport* 8, 3251-55 (1997); Kaytor and Orr, *Curr. Opin. Neurobiol.*, 12, 275-8 (2000)]. In transgenic mice overexpressing GSK3, significant increased Tau hyperphosphorylation and abnormal morphology of neurons were observed [Lucas et al., EMBO J, 20:27-39 (2001)]. Active GSK3 accumulates in cytoplasm of pretangled neurons, which can lead to neurofibrillary tangles in brains of patients with AD [Pei et al., *J Neuropathol Exp Neurol*, 58, 1010-19 (1999)]. Therefore, inhibition of GSK-3 slows or halts the generation of neurofibrillary tangles and thus treats or reduces the severity of Alzheimer's disease.

Evidence for the role GSK-3 plays in Alzheimer's disease has been shown in vitro. See Aplin et al (1996), J Neurochem 67:699; Sun et al (2002), Neurosci Lett 321:61 (GSK3b phosphorylates cytoplasmic domain of Amyloid Precursor Protein (APP) and GSK3b inhibition reduces Ab40 & Ab42 secretion in APP-transfected cells); Takashima et al (1998), PNAS 95:9637; Kirschenbaum et al (2001), J Biol Chem 276:7366 (GSK3b complexes with and phosphorylates presenilin-1, which is associated with gamma-secretase activity in the synthesis of Ab from APP); Takashima et al (1998), Neurosci Res 31:317 (Activation of GSK3b by Ab(25-35) enhances phosphorylation of tau in hippocampal neurons. This observation provides a link between Ab and neurofibrillary tangles composed of hyperphosphorylated tau, another pathological hallmark of AD); Takashima et al (1993), PNAS 90:7789 (Blockade of GSK3b expression or activity prevents Ab-induced neurodegeneration of cortical and hippocampal primary cultures); Suhara et al (2003), Neurobiol Aging. 24:437 (Intracellular Ab42 is toxic to endothelial cells by interfering with activation of Akt/GSK-3b signaling-dependent mechanism); De Ferrari et al (2003) Mol Psychiatry 8:195 (Lithium protects N2A cells & primary hippocampal neurons from Ab fibrils-induced cytotoxicity, & reduced nuclear translocation/destabilization of b-catenin); and Pigino et al., J Neurosci, 23:4499, 2003 (The mutations in Alzheimer's presenilin 1 may deregulate and increase GSK-3 activity, which in turn, impairs axonal transport in neurons. The consequent reductions in axonal transport in affected neurons can ultimately lead to neurodegeneration).

Evidence for the role GSK-3 plays in Alzheimer's disease has been shown in vivo. See Yamaguchi et al (1996), Acta Neuropathol 92:232; Pei et al (1999), J Neuropath Exp Neurol 58:1010 (GSK3b immunoreactivity is elevated in susceptible regions of AD brains); Hernandez et al (2002), J Neurochem 83:1529 (Transgenic mice with conditional GSK3b overexpression exhibit cognitive deficits similar to those in transgenic APP mouse models of AD); De Ferrari et al (2003) Mol Psychiatry 8:195 (Chronic lithium treatment rescued neurodegeneration and behavioral impairments (Morris water maze) caused by intrahippocampal injection of Ab fibrils.); McLaurin et al., Nature Med, 8:1263, 2002 (Immunization with Ab in a transgenic model of AD reduces both AD-like neuropathology and the spatial memory impairments); and Phiel et al (2003) Nature 423:435 (GSK3 regulates amyloid-beta peptide production via direct inhibition of gamma secretase in AD tg mice).

Presenilin-1 and kinesin-1 are also substrates for GSK-3 and relate to another mechanism for the role GSK-3 plays in Alzheimer's disease, as was recently described by Pigino, G., et al., *Journal of Neuroscience* (23:4499, 2003). It was found that GSK3beta phosphorylates kinsesin-1 light chain, which results in a release of kinesin-1 from membrane-bound organelles, leading to a reduction in fast anterograde axonal transport (Morfini et al., 2002). The authors suggest that the mutations in PS1 may deregulate and increase GSK-3 activity, which in turn, impairs axonal transport in neurons. The consequent reductions in axonal transport in affected neurons ultimately lead to neurodegeneration.

GSK-3 is also associated with amyotrophic lateral sclerosis (ALS). See Williamson and Cleveland, 1999 (Axonal transport is retarded in a very early phase of ALS in mSOD1 mice); Morfini et al., 2002 (GSK3 phosphorylates kinesin light chains and inhibit anterograde axonal transport); Warita et al., Apoptosis, 6:345, 2001 (The majority of spinal motor neurons lost the immunoreactivities for both PI3-K and Akt in the early and presymptomatic stage that preceded significant loss of the neurons in this SOD1 tg animal model of ALS); and Sanchez et al., 2001 (The inhibition of PI-3K induces neurite retraction mediated by GSK3 activation).

GSK-3 activity is also linked to spinal cord and peripheral nerve injuries. It has been shown that GSK3 inhibition by lithium and valproic acid can induce axonal remodeling and change synaptic connectivity. See Kaytor & Orr, Curr Opin Neurobiol, 12:275, 2002 (Downregulation of GSK3 causes changes in mirotubule-associated proteins: tau, MAP1 & 2) and Hall et al., Mol Cell Neurosci, 20:257, 2002 (Lithium and valproic acid induces the formation of growth cone-like structures along the axons). See also Grothe et al., Brain Res, 885:172, 2000 (FGF2 stimulate Schwann cell proliferation and inhibit myelination during axonal growth); Grothe and Nikkhah, 2001 (FGF-2 is up regulated in the proximal and distal nerve stumps within 5 hours after nerve crush); and Sanchez et al., 2001 (The inhibition of PI-3K induces neurite retraction mediated by GSK3 activation).

Another substrate of GSK-3 is β-catenin, which is degraded after phosphorylation by GSK-3. Reduced levels of β-catenin have been reported in schizophrenic patients and have also been associated with other diseases related to increase in neuronal cell death [Zhong et al., *Nature*, 395, 698-702 (1998); Takashima et al., *PNAS*, 90, 7789-93 (1993); Pei et al., *J. Neuropathol. Exp*, 56, 70-78 (1997); and Smith et al., *Bio-org. Med. Chem.* 11, 635-639 (2001)]. Furthermore, β-catenin and Tcf-4 play a dual role in vascular remodeling by inhibiting vascular smooth muscle cell apoptosis and promoting proliferation (Wang et al., Circ Res, 90:340, 2002). Accordingly, GSK-3 is associated with angiogenic disorders. See also Liu et al., FASEB J, 16:950, 2002 (Activation of GSK3 reduces hepatocyte growth factor, leading to altered endothelial cell barrier function and diminished vascular integrity) and Kim et al., k J Biol Chem, 277:41888, 2002 (GSK3beta activation inhibits angiogenesis in vivo using Matrigel plug assay: the inhibition of GSK3beta signaling enhances capillary formation).

Association between GSK-3 and Huntington's disease has been shown. See Carmichael et al., J Biol. Chem., 277:33791, 2002 (GSK3beta inhibition protect cells from poly-glutamine-induced neuronal and non-neuronal cell death via increases in b-catenin and its associated transcriptional pathway). Overexpression of GSK3 reduced the activation of heat shock transcription factor-1 and heat shock protein HSP70 (Bijur et al., J Biol Chem, 275:7583, 2000) that are shown to decrease both poly-(Q) aggregates and cell death in in vitro HD model (Wyttenbach et al., Hum Mol Genet, 11:1137, 2002).

GSK-3 effects the levels of FGF-2 and their receptors are increased during remyelination of brain aggregate cultures remyelinating rat brains. See Copelman et al., 2000, Messersmith, et al., 2000; and Hinks and Franklin, 2000. It was also found that FGF-2 induces process outgrowth by oligodendrocytes implicating involvement of FGF in remyelination (Oh and Yong, 1996; Gogate et al., 1994) and that FGF-2 gene therapy has shown to improve the recovery of experimental allergic encephalomyelitis (EAE) mice (Ruffini, et al., 2001).

GSK-3 has also been associated with hair growth because Wnt/beta-catenin signaling is shown to play a major role in hair follicle morphogenesis and differentiation (Kishimotot et al. Genes Dev, 14:1181, 2000; Millar, J Invest Dermatol, 118:216, 2002). It was found that mice with constitutive overexpression of the inhibitors of Wnt signaling in skin failed to develop hair follicles. Wnt signals are required for the initial development of hair follicles and GSK3 constitutively regulates Wnt pathways by inhibiting beta-catenin. (Andl et al., Dev Cell 2:643, 2002). A transient Wnt signal provides the crucial initial stimulus for the start of a new hair growth cycle, by activating beta-catenin and TCF-regulated gene transcription in epithelial hair follicle precursors (Van Mater et al., Genes Dev, 17:1219, 2003)

Because GSK-3 activity is associated with sperm motility, GSK-3 inhibition is useful as a male contraceptive. It was shown that a decline in sperm GSK3 activity is associated with sperm motility development in bovine and monkey epididymis (Vijayaraghavan et al., Biol Reprod, 54: 709, 1996; Smith et al., J Androl, 20:47, 1999). Furthermore, tyrosine & serine/threonine phosphorylation of GSK3 is high in motile compared to immotile sperm in bulls (Vijayaraghavan et al., Biol Reprod, 62:1647, 2000). This effect was also demonstrated with human sperm (Luconi et al., Human Reprod, 16:1931, 2001).

The Tec family of non-receptor tyrosine kinases plays a central role in signalling through antigen-receptors such as the TCR, BCR and Fce receptors (reviewed in Miller A, et al. Current Opinion in Immunology 14;331-340 (2002). Tec family kinases are essential for T cell activation. Three members of the Tec family, Itk, Rlk and Tec, are activated downstream of antigen receptor engagement in T cells and transmit signals to downstream effectors, including PLC-g. Combined deletion of Itk and Rlk in mice leads to a profound inhibition of TCR responses including proliferation, cytokine production and immune responses to an intracellular parasite (*Toxoplasma gondii*) (Schaeffer et al, Science 284; 638-641 (1999)). Intracellular signalling following TCR engagement is effected in Itk/Rlk deficient T cells; inositol triphosphate production, calcium mobilization and MAP kinase activation are all reduced.

Tec family kinases are also essential for B cell development and activation. Patients with mutations in Btk have a profound block in B cell development, resulting in the almost complete absence of B lymphocytes and plasma cells, severely reduced Ig levels and a profound inhibition of humoral response to recall antigens (reviewed in Vihinen et al Frontiers in Bioscience 5:d917-928). Mice deficient in Btk also have a reduced number of peripheral B cells and greatly decreased levels of IgM and IgG3. Btk deletion in mice has a profound effect on B cell proliferation induced by anti-IgM, and inhibits immune responses to thymus-independent type II antigens (Ellmeier et al, J Exp Med 192: 1611-1623 (2000)). Btk also plays a crucial role in mast cell activation through the high-affinity IgE receptor (FceRI). Btk deficient murine mast cells have reduced degranulation and decreased production of proinfllammatory cytokines following FceRI cross-linking (Kawakami et al. Journal of leukocyte biology 65:286-290).

The ribosomal protein kinases p70S6K-1 and -2 are members of the AGC sub-family of protein kinases that consists of, amongst others, PKB and MSK. The p70S6 kinases catalyze the phosphorylation and subsequent activation of the ribosomal protein S6, which has been implicated in the translational up-regulation of mRNAs coding for the components of the protein synthetic apparatus.

These mRNAs contain an oligopyrimidine tract at their 5' transcriptional start site, termed a 5'TOP, which has been shown to be essential for their regulation at the translational level (Volarevic, S. et al., *Prog. Nucleic Acid Res. Mol. Biol.* 2001, 65, 101-186). p70 S6K dependent S6 phosphorylation is stimulated in response to a variety of hormones and growth factors primarily via the PI3K pathway (Coffer, P. J. et al., *Biochem. Biophys. Res. Commun*, 1994 198, 780-786), which maybe under the regulation of mTOR, since rapamycin acts to inhibit p70S6K activity and blocks protein synthesis, specifically as a result of a down-regulation of translation of these mRNA's encoding ribosomal proteins (Kuo, C. J. et al., *Nature* 1992, 358, 70-73).

In vitro PDK1 catalyses the phosphorylation of Thr252 in the activation loop of the p70 catalytic domain, which is indispensable for p70 activity (Alessi, D. R., *Curr. Biol.*, 1998, 8, 69-81). The use of rapamycin and gene deletion studies of dp70S6K from Drosophila and p70S6K1 from mouse have established the central role p70 plays in both cell growth and proliferation signaling.

The 3-phosphoinositide-dependent protein kinase-1 (PDK1) plays a key role in regulating the activity of a number of kinases belonging to the AGC subfamily of protein kinases (Alessi, D. et al., *Biochem. Soc. Trans* 2001, 29, 1). These include isoforms of protein kinase B (PKB, also known as AKT), p70 ribosomal S6 kinase (S6K) (Avruch, J. et al., *Prog. Mol. Subcell. Biol.* 2001, 26, 115), and p90 ribosomal S6 kinase (Frödin, M. et al., *EMBO J.* 2000, 19, 2924-2934). PDK1 mediated signaling is activated in response to insulin and growth factors and as a consequence of attachment of the cell to the extracellular matrix (integrin signaling). Once activated these enzymes mediate many diverse cellular events by phosphorylating key regulatory proteins that play important roles controlling processes such as cell survival, growth, proliferation and glucose regulation [(Lawlor, M. A. et al., *J. Cell Sci.* 2001, 114, 2903-2910), (Lawlor, M. A. et al., *EMBO J.* 2002, 21, 3728-3738)]. PDK1 is a 556 amino acid protein, with an N-terminal catalytic domain and a C-terminal pleckstrin homology (PH) domain, which activates its substrates by phosphorylating these kinases at their activation loop (Belham, C. et al., *Curr. Biol.* 1999, 9, R93-R96). Many human cancers including prostate and NSCL have elevated PDK1 signaling pathway function resulting from a number of distinct genetic events such as PTEN mutations or overexpression of certain key regulatory proteins [(Graff, J. R., *Expert Opin. Ther. Targets* 2002, 6, 103-113), (Brognard, J., et al., *Cancer Res.* 2001, 61, 3986-3997)]. Inhibition of PDK1 as a potential mechanism to treat cancer was demonstrated by transfection of a PTEN negative human cancer cell line (U87MG) with antisense oligonucleotides directed against PDK1. The resulting decrease in PDK1 protein levels led to a reduction in cellular proliferation and survival (Flynn, P., et al., *Curr. Biol.* 2000, 10, 1439-1442). Consequently the design of ATP binding site inhibitors of PDK1 offers, amongst other treatments, an attractive target for cancer chemotherapy.

The diverse range of cancer cell genotypes has been attributed to the manifestation of the following six essential alterations in cell physiology: self-sufficiency in growth signaling, evasion of apoptosis, insensitivity to growth-inhibitory signaling, limitless replicative potential, sustained angiogenesis, and tissue invasion leading to metastasis (Hanahan, D. et al., *Cell* 2000, 100, 57-70). PDK1 is a critical mediator of the PI3K signalling pathway, which regulates a multitude of cellular function including growth, proliferation and survival. Consequently, inhibition of this pathway could affect four or more of the six defining requirements for cancer progression. As such it is anticipated that a PDK1 inhibitor will have an effect on the growth of a very wide range of human cancers.

Specifically, increased levels of PI3K pathway activity has been directly associated with the development of a number of human caners, progression to an aggressive refractory state (acquired resistance to chemotherapies) and poor prognosis. This increased activity has been attributed to a series of key events including decreased activity of negative pathway regulators such as the phosphatase PTEN, activating mutations of positive pathway regulators such as Ras, and overexpression of components of the pathway itself such as PKB, examples include: brain (gliomas), breast, colon, head and neck, kidney, lung, liver, melanoma, ovarian, pancreatic, prostate, sarcoma, thyroid [(Teng, D. H. et al., *Cancer Res.,* 1997 57, 5221-5225), (Brognard, J. et al., *Cancer Res.,* 2001, 61, 3986-3997), (Cheng, J. Q. et al., *Proc. Natl. Acad. Sci.* 1996, 93, 3636-3641), (*Int. J. Cancer* 1995, 64, 280), (Graff, J. R., *Expert Opin. Ther. Targets* 2002, 6, 103-113), (*Am. J. Pathol.* 2001, 159, 431)].

Additionally, decreased pathway function through gene knockout, gene knockdown, dominant negative studies, and small molecule inhibitors of the pathway have been demonstrated to reverse many of the cancer phenotypes in vitro (some studies have also demonstrated a similar effect in vivo) such as block proliferation, reduce viability and sensitize cancer cells to known chemotherapies in a series of cell lines, representing the following cancers: pancreatic [(Cheng, J. Q. et al., *Proc. Natl. Acad. Sci.* 1996, 93, 3636-3641), (*Neoplasia* 2001, 3, 278)], lung [(Brognard, J. et al., *Cancer Res.* 2001, 61, 3986-3997), (*Neoplasia* 2001, 3, 278)], ovarian [(Hayakawa, J. et al., *Cancer Res.* 2000, 60, 5988-5994), (*Neoplasia* 2001, 3, 278)], breast (*Mol. Cancer Ther.* 2002, 1, 707), colon [(*Neoplasia* 2001, 3, 278), (Arico, S. et al., *J. Biol. Chem.* 2002, 277, 2761327621)], cervical (*Neoplasia* 2001, 3, 278), prostate [(*Endocrinology* 2001, 142, 4795), (Thakkar, H. et al. *J. Biol. Chem.* 2001, 276, 38361-38369), (Chen, X. et al., *Oncogene* 2001, 20, 6073-6083)] and brain (glioblastomas) [(Flynn, P. et al., *Curr. Biol.* 2000, 10, 1439-1442)].

The Aurora family of serine/threonine kinases is essential for cell proliferation [Bischoff, J. R. & Plowman, G. D. (The Aurora/Ipl1p kinase family: regulators of chromosome segregation and cytokinesis) *Trends in Cell Biology* 9, 454-459 (1999); Giet, R. and Prigent, C. (Aurora/Ipl1p-related kinases, a new oncogenic family of mitotic serine-threonine kinases) *Journal of Cell Science* 112, 3591-3601 (1999); Nigg, E. A. (Mitotic kinases as regulators of cell division and its checkpoints) *Nat. Rev. Mol. Cell Biol.* 2, 21-32 (2001); Adams, R. R, Carmena, M., and Earnshaw, W. C. (Chromosomal passengers and the (aurora) ABCs of mitosis) *Trends in Cell Biology* 11, 49-54 (2001)]. Inhibitors of the Aurora kinase family therefore have the potential to block growth of all tumour types.

The three known mammalian family members, Aurora-A ("1"), B ("2") and C ("3"), are highly homologous proteins responsible for chromosome segregation, mitotic spindle function and cytokinesis. Aurora expression is low or undetectable in resting cells, with expression and activity peaking during the G2 and mitotic phases in cycling cells. In mammalian cells proposed substrates for Aurora include histone $H_3$, a protein involved in chromosome condensation, and CENP-A, myosin II regulatory light chain, protein phosphatase 1, TPX2, all of which are required forcell division.

Since its discovery in 1997 the mammalian Aurora kinase family has been closely linked to tumorigenesis. The most compelling evidence for this is that over-expression of Aurora-A transforms rodent fibroblasts (Bischoff, J. R., et al. A homologue of *Drosophila aurora* kinase is oncogenic and amplified in human colorectal cancers. *EMBO J.* 17, 3052-3065 (1998)). Cells with elevated levels of this kinase contain multiple centrosomes and multipolar spindles, and rapidly become aneuploid. The oncogenic activity of Aurora kinases is likely to be linked to the generation of such genetic instability. Indeed, a correlation between amplification of the aurora-A locus and chromosomal instability in mammary and gastric tumours has been observed. (Miyoshi, Y., Iwao, K., Egawa, C., and Noguchi, S. Association of centrosomal kinase STK15/BTAK mRNA expression with chromosomal instability in human breast cancers. *Int. J. Cancer* 92, 370-373 (2001). (Sakakura, C. et al. Tumor-amplified kinase BTAK is amplified and overexpressed in gastric cancers with possible involvement in aneuploid formation. *British Journal of Cancer* 84, 824-831 (2001)). The Aurora kinases have been reported to be over-expressed in a wide range of human tumours. Elevated expression of Aurora-A has been detected in over 50% of colorectal (Bischoff, J. R., et al. A homologue of *Drosophila aurora* kinase is oncogenic and amplified in human colorectal cancers. *EMBO J.* 17, 3052-3065 (1998)) (Takahashi, T., et al. Centrosomal kinases, HsAIRk1 and HsAIRK3, are over-expressed in primary colorectal cancers. *Jpn. J. Cancer Res.* 91, 1007-1014 (2000)). ovarian (Gritsko, T. M. et al. Activation and overexpression of centrosome kinase BTAK/Aurora-A in human ovarian cancer. *Clinical Cancer Research* 9, 1420-1426 (2003)), and gastric tumors (Sakakura, C. et al. Tumor-amplified kinase BTAK is amplified and overexpressed in gastric cancers with possible involvement in aneuploid formation. *British Journal of Cancer* 84, 824-831 (2001)), and in 94% of invasive duct adenocarcinomas of the breast (Tanaka, T., et al. Centrosomal kinase AIK1 is overexpressed in invasive ductal carcinoma of the breast. *Cancer Research.* 59, 2041-2044 (1999)). High levels of Aurora-A have also been reported in renal, cervical, neuroblastoma, melanoma, lymphoma, pancreatic and prostate tumour cell lines. (Bischoff, J. R., et al. A homologue of *Drosophila aurora* kinase is oncogenic and amplified in human colorectal cancers. *EMBO J.* 17, 3052-3065 (1998) (Kimura, M., Matsuda, Y., Yoshioka, T., and Okano, Y. Cell cycle-dependent expression and centrosomal localization of a third human AuroratIpl1-related protein kinase, AIK3. *Journal of Biological Chemistry* 274, 7334-7340 (1999))(Zhou et al. Tumour amplifiec kinase STK15/BTAK induces centrosome amplification, aneuploidy and transformation *Nature Genetics* 20: 189-193 (1998))(Li et al. Overexpression of oncogenic STK15/BTAK/Aurora-A kinase in human pancreatic cancer *Clin Cancer Res.* 9(3): 991-7 (2003)). Amplification/overexpression of Aurora-A is observed in human bladder cancers and amplification of Aurora-A is associated with aneuploidy and aggressive clinical behaviour (Sen S. et al Amplification/overexpression of a mitotic kinase gene in human bladder cancer *J Natl Cancer Inst.* 94(17): 1320-9 (2002)). Moreover, amplification of the aurora-A locus (20q13) correlates with poor prognosis for patients with node-negative breast cancer (Isola, J. J., et al. Genetic aberrations detected by comparative genomic hybridization predict outcome in node-negative breast cancer. *American Journal of Pathology* 147, 905-911 (1995)). Aurora-B is highly expressed in multiple human tumour cell lines, including leukemic cells (Katayama et al. Human AIM-1: cDNA cloning and reduced expression during endomitosis in megakaryocyte-lineage cells. *Gene* 244:1-7)). Levels of this enzyme increase as a function of Duke's stage in primary colorectal cancers (Katayama, H. et al. Mitotic kinase expression and colorectal cancer progression. *Journal of the National Cancer Institute* 91, 1160-1162 (1999)). Aurora-C, which is normally only found in germ cells, is also over-expressed in a high percentage of primary colorectal cancers and in a variety of tumour cell lines including cervical adenocarinoma and breast carcinoma cells (Kimura, M., Matsuda, Y., Yoshioka, T., and Okano, Y. Cell cycle-dependent expression and centrosomal localization of a third human Aurora/Ipl1-related protein kinase, AIK3. *Journal of Biological Chemistry* 274, 7334-7340 (1999). (Takahashi, T., et al. Centrosomal kinases, HsAIRk1 and HsAIRK3, are overexpressed in primary colorectal cancers. *Jpn. J. Cancer Res.* 91, 1007-1014 (2000)).

Based on the known function of the Aurora kinases, inhibition of their activity should disrupt mitosis leading to cell cycle arrest. In vivo, an Aurora inhibitor therefore slows tumor growth and induces regression.

Elevated levels of all Aurora family members are observed in a wide variety of tumour cell lines. Aurora kinases are over-expressed in many human tumors and this is reported to be associated with chromosomal instability in mammary tumors (Miyoshi et al 2001 92, 370-373).

Aurora-2 is highly expressed in multiple human tumor cell lines and levels increase as a function of Duke's stage in primary colorectal cancers [Katayama, H. et al. (Mitotic kinase expression and colorectal cancer progression) *Journal of the National Cancer Institute* 91, 1160-1162 (1999)]. Aurora-2 plays a role in controlling the accurate segregation of chromosomes during mitosis. Misregulation of the cell cycle can lead to cellular proliferation and other abnormalities. In human colon cancer tissue, the Aurora-2 protein is over expressed [Bischoff et al., *EMBO J.*, 17, 3052-3065 (1998); Schumacher et al., *J. Cell Biol.*, 143, 1635-1646 (1998); Kimura et al., *J. Biol. Chem.*, 272, 13766-13771 (1997)]. Aurora-2 is over-expressed in the majority of transformed cells. Bischoff et al found high levels of Aurora-2 in 96% of cell lines derived from lung, colon, renal, melanoma and breast tumors (Bischoff et al EMBO J. 1998 17, 3052-3065). Two extensive studies show elevated Aurora-2 in 54% and 68% (Bishoff et al EMBO J. 1998 17, 3052-3065) (Takahashi et al 2000 Jpn J Cancer Res. 91, 1007-1014) of colorectal tumours and in 94% of invasive duct adenocarcinomas of the breast (Tanaka et al 1999 59, 2041-2044).

Aurora-1 expression is elevated in cell lines derived from tumors of the colon, breast, lung, melanoma, kidney, ovary, pancreas, CNS, gastric tract and leukemias (Tatsuka et al 1998 58, 4811-4816).

High levels of Aurora-3 have been detected in several tumour cell lines, although it is restricted to testis in normal tissues (Kimura et al 1999 274, 7334-7340). Over-expression of Aurora-3 in a high percentage (c. 50%) of colorectal cancers has also been documented (Takahashi et al 2000 Jpn J Cancer Res. 91, 1007-1014). In contrast, the Aurora family is expressed at a low level in the majority of normal tissues, the exceptions being tissues with a high proportion of dividing cells such as the thymus and testis (Bischoff et al EMBO J. 1998 17, 3052-3065).

For further review of the role Aurora kinases play in proliferative disorders, see Bischoff, J. R. & Plowman, G. D. (The Aurora/Ipl1p kinase family:regulators of chromosome segregation and cytokinesis) *Trends in Cell Biology* 9, 454-459 (1999); Giet, R. and Prigent, C. (Aurora/Ipl1p-related kinases, a new oncogenic family of mitotic serine-threonine kinases) *Journal of Cell Science* 112, 3591-3601 (1999); Nigg, E. A. (Mitotic kinases as regulators of cell division and its checkpoints) *Nat. Rev. Mol. Cell Biol.* 2, 21-32 (2001); Adams, R. R, Carmena, M., and Earnshaw, W. C. (Chromosomal passengers and the (aurora) ABCs of mitosis) *Trends in Cell Biology* 11, 49-54 (2001); and Dutertre, S., Descamps, S., & Prigent, P. (On the role of aurora-A in centrosome function) *Oncogene* 21, 6175-6183 (2002).

The type III receptor tyrosine kinase, Flt3, plays an important role in the maintenance, growth and development of hematopoietic and non-hematopoietic cells. [Scheijen, B, Griffin J D, *Oncogene*, 2002, 21, 3314-3333 and Reilly, J T, *British Journal of Haematology*, 2002, 116, 744-757]. FLT-3 regulates maintenance of stem cell/early progenitor pools as well the development of mature lymphoid and myeloid cells [Lyman, S, Jacobsen, S, *Blood*, 1998, 91, 1101-1134]. FLT-3 contains an intrinsic kinase domain that is activated upon ligand-mediated dimerization of the receptors. Upon activation, the kinase domain induces autophosphorylation of the receptor as well as the phosphorylation of various cytoplasmic proteins that help propogate the activation signal leading to growth, differentiation and survival. Some of the downstream regulators of FLT-3 receptor signaling include, PLCγ, PI3-kinase, Grb-2, SHIP and Src related kinases [Scheijen, B, Griffin J D, *Oncogene*, 2002, 21, 3314-3333]. FLT-3 kinase plays a role in a variety of hematopoietic and non-hematopoietic malignancies. Mutations that induce ligand independent activation of FLT-3 have been implicated in acute-myelogenous leukemia (AML), acute lymphocytic leukemia (ALL), mastocytosis and gastrointestinal stromal tumor (GIST). These mutations include single amino acid changes in the kinase domain or internal tandem duplications, point mutations or in-frame deletions of the juxtamembrane region of the receptors. In addition to activating mutations, ligand dependent (autocrine or paracrine) stimulation of over-expressed wild-type FLT-3 contributes to the malignant phenotype [Scheijen, B, Griffin J D, *Oncogene*, 2002, 21, 3314-3333]. See also Sawyer, C. 1. (Finding the next Gleevec: FLT3 targeted kinase inhibitor therapy for acute myeloid leukaemia) *Cancer Cell.* 1, 413-415 (2002).

Cyclin-dependent kinases (CDKs) are serine/threonine protein kinases consisting of a b-sheet rich amino-terminal lobe and a larger carboxy-terminal lobe that is largely a-helical. The CDKs display the 11 subdomains shared by all protein kinases and range in molecular mass from 33 to 44 kD. This family of kinases, which includes CDK1, CKD2, CDK4, and CDK6, requires phosphorylation at the residue corresponding to CDK2 Thr160 in order to be fully active [Meijer, L., Drug Resistance Updates 2000, 3, 83-88].

Each CDK complex is formed from a regulatory cyclin subunit (e.g., cyclin A, B1, B2, D1, D2, D3, and E) and a catalytic kinase subunit (e.g., CDK1, CDK2, CDK4, CDK5, and CDK6). Each different kinase/cyclin pair functions to regulate the different and specific phases of the cell cycle known as the G1, S, G2, and M phases [Nigg, E., Nature Reviews 2001, 2, 21-32; Flatt, P., Pietenpol, J., Drug Metabolism Reviews 2000, 32, 283-305].

The CDKs have been implicated in cell proliferation disorders, particularly in cancer. Cell proliferation is a result of the direct or indirect deregulation of the cell division cycle and the CDKs play a critical role in the regulation of the various phases of this cycle. For example, the overexpression of cyclin D1 is commonly associated with numerous human cancers including breast, colon, hepatocellular carcinomas and gliomas [Flatt, P., Pietenpol, J., Drug Metabolism Reviews 2000, 32, 283-305]. The CDK2/cyclin E complex plays a key role in the progression from the early G1 to S phases of the cell cycle and the overexpression of cyclin E has been associated with various solid tumors. Therefore, inhibitors of cyclins D1, E, or their associated CDKs are useful targets for cancer therapy [Kaubisch, A., Schwartz, G., The Cancer Journal 2000, 6, 192-212].

CDKs, especially CDK2, also play a role in apoptosis and T-cell development. CDK2 has been identified as a key regulator of thymocyte apoptosis [Williams, O., et al, European Journal of Immunology 2000, 709-713]. Stimulation of CDK2 kinase activity is associated with the progression of apoptosis in thymocytes, in response to specific stimuli. Inhibition of CDK2 kinase activity blocks this apoptosis resulting in the protection of thymocytes.

In addition to regulating the cell cycle and apoptosis, the CDKs are directly involved in the process of transcription. Numerous viruses require CDKs for their replication process. Examples where CDK inhibitors restrain viral replication include human cytomegalovirus, herpes virus, and varicella-zoster virus [Meijer, L., Drug Resistance Updates 2000, 3, 83-88].

Inhibition of CDK is also useful for the treatment of neurodegenerative disorders such as Alzheimer's disease. The appearance of Paired Helical Filaments (PHF), associated with Alzheimer's disease, is caused by the hyperphosphorylation of Tau protein by CDK5/p25 [Meijer, L., Drug Resistance Updates, 2000 3, 83-88].

PIM-1 is the protooncogene activated by murine leukemia virus (Provirus integration site for Moloney murine leukemia virus) [Cuypers, H. T. et al., Cell 1984, 37, 141-150]. The expression of the protoconcogene produces a non-transmembrane serine/threonine kinase of 313 residues, including a kinase domain consisting of 253 amino acid residues. Two isoforms are known through alternative initiation (p44 and p33) [Saris, C. J. M. et al., EMBO J. 1991, 10, 655-664]. Two PIM-1 homologs have been described [Baytel, D. Biochim Biophys Acta 1998, 1442, 274-85; Feldman, J. et al., J Biol Chem 1998, 273, 16535-16543]. PIM-2 and PIM-3 are respectively 58% and 69% identical to Pim-1 at the amino acid level. PIM-1 is highly expressed in the liver and spleen during hematopoiesis, and expression is induced by cytokines such as GM-CSF, G-SCF, IL-3, IF-α, and IL-6 [Lilly, M. et al., Oncogene 1992, 7, 727-732; Sato, N. et al., EMBO J. 1993, 12, 4181-4189; Jaster, R. et al., Cell Signal 1999, 11, 331-335; Matikainen, S. et al., Blood 1999, 93, 1980-1991].

PIM-1 has been implicated in lymphoma development. Induced expression of PIM-1 and the protooncogene c-myc synergize to increase the incidence of lymphomagenesis [Breuer, M. et al., Nature 1989, 340, 61-63; van Lohuizen, M. et al., Cell 1991, 65, 737-52]. PIM-1 functions in cytokine signaling pathways and has been shown to play a role in T-cell development [Schmidt, T. et al., EMBO J. 17, 1998, 5349-5359; Jacobs, H. et al., JEM 1999, 190, 1059-1068]. Signaling through gp130, a subunit common to receptors of the IL-6 cytokine family, activates the transcription factor STAT3 and can lead to the proliferation of hematopoietic cells [Hirano, T. et al., Oncogene 2000, 19, 2548-2556]. A kinase-active PIM-1 appears to be essential for the gp130-mediated STAT3 proliferation signal. In cooperation with the c-myc, PIM-1 can promote STAT3-mediated cell cycle progression and antiapoptosis [Shirogane, T. et al., Immunity 1999, 11, 709-719]. PIM-1 also appears to be necessary for IL-3-stimulated growth in bone marrow-derived mast cells [Domen, J. et al., Blood 1993, 82, 1445-52] and survival of FDCP1 cells after IL-3 withdrawal [Lilly, M. et al., Oncogene 1999, 18, 4022-4031].

Additionally, control of cell proliferation and survival by PIM-1 may be effected by means of its phosphorylation of the well established cell cycle regulators cdc25 [Mochizuki, T. et al., J. Biol. Chem. 1999, 274, 18659-18666] and/or p21(Cip1/WAF1)[Wang, Z. et al., Biochim. Biophys. Acta 2002, 1593, 45-55] or phosphorylation of heterochromatin protein 1, a molecule involved in chromatin structure and transcriptional regulation [Koike, N. et al., FEBS Lett. 2000, 467, 17-21].

A family of type III receptor tyrosine kinases including Flt3, c-Kit, PDGF-receptor and c-Fms play an important role in the maintenance, growth and development of hematopoietic and non-hematopoietic cells. [Scheijen, B, Griffin J D, Oncogene, 2002, 21, 3314-3333 and Reilly, J T, British Journal of Haematology, 2002, 116, 744-757]. FLT-3 and c-Kit regulate maintenance of stem cell/early progenitor pools as well the development of mature lymphoid and myeloid cells [Lyman, S, Jacobsen, S, Blood, 1998, 91, 1101-1134]. Both receptors contain an intrinsic kinase domain that is activated upon ligand-mediated dimerization of the receptors. Upon activation, the kinase domain induces autophosphorylation of the receptor as well as the phosphorylation of various cytoplasmic proteins that help propogate the activation signal leading to growth, differentiation and survival. Some of the downstream regulators of FLT-3 and c-Kit receptor signaling include, PLCγ, PI3-kinase, Grb-2, SHIP and Src related kinases [Scheijen, B, Griffin J D, Oncogene, 2002, 21, 3314-3333]. Both receptor tyrosine kinases have been shown to play a role in a variety of hematopoietic and non-hematopoietic malignancies. Mutations that induce ligand independent activation of FLT-3 and c-Kit have been implicated acute-myelogenous leukemia (AML), acute lymphocytic leukemia (ALL), mastocytosis and gastrointestinal stromal tumor (GIST). These mutations include single amino acid changes in the kinase domain or internal tandem duplications, point mutations or in-frame deletions of the juxtamembrane region of the receptors. In addition to activating mutations, ligand dependent (autocrine or paracrine) stimulation of over-expressed wild-type FLT-3 or c-Kit can contribute to the malignant phenotype [Scheijen, B, Griffin J D, Oncogene, 2002, 21, 3314-3333].

c-fms encodes for macrophage colony stimulating factor receptor (M-CSF-1R) which is expressed predominately in the monocytes/macrophage lineage [Dai, X M et al., *Blood*, 2002, 99, 111-120]. MCSF-1R and its ligand regulate macrophage lineage growth and differentiation. Like the other family members, MCSF-1R contains an intrinsic kinase domain that is activated upon ligand-induced dimerization of the receptor. MCSF-1R is is also expressed in non-hematopoietic cells including mammary gland epithelial cells and neurons. Mutations in this receptor are potentially linked to myeloid leukemias and its expression is correlated with metastatic breast, ovarian and endometrial carcinomas [Reilly, J T, *British Journal of Haematology*, 2002, 116, 744-757 and Kacinski, B M, *Mol. Reprod and Devel.*, 1997, 46, 71-74]. Another possible indication for antagonists of MCSF-1R is osteoporosis [Teitelbaum, S, *Science* 2000, 289, 1504-1508.

PDGF-receptor (PDGFR) has two subunits-PDGFR-α and PDGRR-β, which can form homo or heterodimers upon ligand binding. There are several PDGF ligands: AB, BB, CC and DD. PDGFR is expressed on early stem cells, mast cells, myeloid cells, mesenchymal cells and smooth muscle cells [Scheijen, B, Griffin J D, *Oncogene*, 2002, 21, 3314-3333]. Only PDGFR-β has been implicated in myeloid leukemias—usually as a translocation partner with Tel, Huntingtin interacting protein (HIP1) or Rabaptin5. Recently it was shown that activation mutations in PDGFR-α kinase domain are in gastrointestinal stromal tumors (GIST) [Heinrich, M C et al., *Sciencexpress*, 2003]

Another kinase family of particular interest is the Src family of kinases. These kinases are implicated in cancer, immune system dysfunction and bone remodeling diseases. For general reviews, see Thomas and Brugge, *Annu. Rev. Cell Dev. Biol.* 1997, 13, 513; Lawrence and Niu, *Pharmacol. Ther.* 1998, 77, 81; Tatosyan and Mizenina, *Biochemistry* (Moscow) 2000, 65, 49-58; Boschelli et al., *Drugs of the Future* 2000, 25(7), 717.

Members of the Src family include the following eight kinases in mammals: Src, Fyn, Yes, Fgr, Lyn, Hck, Lck, and Blk. These are nonreceptor protein kinases that range in molecular mass from 52 to 62 kD. All are characterized by a common structural organization that is comprised of six distinct functional domains: Src homology domain 4 (SH4), a unique domain, SH3 domain, SH2 domain, a catalytic domain (SH1), and a C-terminal regulatory region. Tatosyan et al. *Biochemistry* (Moscow) 2000, 65, 49-58.

Based on published studies, Src kinases are considered as potential therapeutic targets for various human diseases. Mice that are deficient in Src develop osteopetrosis, or bone build-up, because of depressed bone resorption by osteoclasts. This shows that osteoporosis resulting from abnormally high bone resorption is treated by inhibiting Src. Soriano et al., *Cell* 1992, 69, 551 and Soriano et al., *Cell* 1991, 64, 693.

Suppression of arthritic bone destruction has been achieved by the overexpression of CSK in rheumatoid synoviocytes and osteoclasts. Takayanagi et al., *J. Clin. Invest.* 1999, 104, 137. CSK, or C-terminal Src kinase, phosphorylates and thereby inhibits Src catalytic activity. This implies that Src inhibition may prevent joint destruction that is characteristic in patients suffering from rheumatoid arthritis. Boschelli et al., *Drugs of the Future* 2000, 25(7), 717.

Src also plays a role in the replication of hepatitis B virus. The virally encoded transcription factor HBx activates Src in a step required for propagation of the virus. Klein et al., *EMBO J.* 1999, 18, 5019, and Klein et al., *Mol. Cell. Biol.* 1997, 17, 6427.

A number of studies have linked Src expression to cancers such as colon, breast, hepatic and pancreatic cancer, certain B-cell leukemias and lymphomas. Talamonti et al., *J. Clin. Invest.* 1993, 91, 53; Lutz et al., *Biochem. Biophys. Res.* 1998 243, 503; Rosen et al., *J. Biol. Chem.* 1986, 261, 13754; Bolen et al., *Proc. Natl. Acad. Sci. USA* 1987, 84, 2251; Masaki et al., *Hepatology* 1998, 27, 1257; Biscardi et al., *Adv. Cancer Res.* 1999, 76, 61; Lynch et al., *Leukemia* 1993, 7, 1416. Furthermore, antisense Src expressed in ovarian and colon tumor cells has been shown to inhibit tumor growth. Wiener et al., *Clin. Cancer Res.*, 1999, 5, 2164; Staley et al., *Cell Growth Diff.* 1997, 8, 269.

Other Src family kinases are also potential therapeutic targets. Lck plays a role in T-cell signaling. Mice that lack the Lck gene have a poor ability to develop thymocytes. The function of Lck as a positive activator of T-cell signaling suggests that Lck inhibitors may be useful for treating autoimmune disease such as rheumatoid arthritis. Molina et al., *Nature*, 1992, 357, 161. Hck, Fgr and Lyn have been identified as important mediators of integrin signaling in myeloid leukocytes. Lowell et al., *J. Leukoc. Biol.*, 1999, 65, 313. Inhibition of these kinase mediators may therefore be useful for treating inflammation. Boschelli et al., *Drugs of the Future* 2000, 25(7), 717.

Syk is a tyrosine kinase that plays a critical role in FcεR1 mediated mast cell degranulation and eosinophil activation. Accordingly, Syk kinase is implicated in various allergic disorders, in particular asthma. It has been shown that Syk binds to the phosphorylated gamma chain of the FcεRI receptor via N-terminal SH2 domains and is essential for downstream signaling [Taylor et al., *Mol. Cell. Biol.* 1995, 15, 4149].

Inhibition of eosinophil apoptosis has been proposed as a key mechanism for the development of blood and tissue eosinophilia in asthma. IL-5 and GM-CSF are upregulated in asthma and are proposed to cause blood and tissue eosinophilia by inhibition of eosinophil apoptosis. Inhibition of eosinophil apoptosis has been proposed as a key mechanism for the development of blood and tissue eosinophilia in asthma. It has been reported that Syk kinase is required for the prevention of eosinophil apoptosis by cytokines (using antisense)[Yousefi et al., *J. Exp. Med.* 1996, 183, 1407].

The role of Syk in FcγR dependent and independent response in bone marrow derived macrophages has been determined by using irradiated mouse chimeras reconstituted with fetal liver cells from Syk -/- embryos. Syk deficient macrophages were defective in phagocytosis induced by FcγR but showed normal phagocytosis in response to complement [Kiefer et al., *Mol. Cell. Biol.* 1998, 18, 4209]. It has also been reported that aerosolized Syk antisense suppresses Syk expression and mediator release from macrophages [Stenton et al., *J. Immunology* 2000, 164, 3790].

Another kinase family of interest is Rho-associated coiled-coil forming protein serine/threonine kinase (ROCK), which is believed to be an effector of Ras-related small GTPase Rho. The ROCK family includes p160ROCK (ROCK-1) (Ishizaki et al., *EMBO J.* 1996, 15, 1885-1893) and ROKα/Rho-kinase/ROCK-II (Leung et al., *J. Biol. Chem.* 1995, 270, 29051-29054; Matsui et al., *EMBO J.* 1996, 15, 2208-2216; Nakagawa et al., *FEBS Lett.* 1996, 392, 189-193), protein kinase PKN (Amano et al., *Science* 1996, 271, 648-650; Watanabe et al., *Science* 1996, 271, 645-648), and citron and citron kinase (Madaule et al., *Nature* 1998, 394, 491-494; Madaule et al., *FEBS Lett.* 1995, 377, 243-248). The ROCK family of kinases have been shown to be involved in a variety of functions including Rho-induced formation of actin stress fibers and focal adhesions (Leung et al., *Mol. Cell Biol.* 1996, 16, 5313-5327; Amano et al., *Science* 1997, 275, 1308-1311; Ishizaki et al., *FEBS Lett.* 1997, 404, 118-124) and in downregulation of myosin phosphatase (Kimura et al., *Science* 1996, 273, 245-248), platelet activation (Klages et al., *J. Cell. Biol.* 1999, 144, 745-754), aortic smooth muscle contraction by various stimuli (Fu et al., *FEBS Lett.* 1998, 440, 183-187), thrombin-induced responses of aortic smooth muscle cells (Seasholtz et al., *Cir. Res.* 1999, 84, 1186-1193), hypertrophy of cardiomyocytes (Kuwahara et al., *FEBS Lett.*, 1999, 452, 314-318), bronchial smooth muscle contraction (Yoshii et al., *Am. J. Respir. Cell Mol. Biol.* 1999, 20, 1190-1200), smooth muscle contraction and cytoskeletal reorganization of non-muscle cells (Fukata et al., *Trends in Pharm. Sci.* 2001, 22, 32-39), activation of volume-regulated anion channels (Nilius et al., *J. Physiol.* 1999, 516, 67-74), neurite retraction (Hirose et al., *J. Cell. Biol.* 1998, 141, 1625-1636), neutrophil chemotaxis (Niggli, *FEBS Lett.* 1999, 445, 69-72), wound healing (Nobes and Hall, *J. Cell. Biol.* 1999, 144, 1235-1244), tumor invasion (Itoh et al., *Nat. Med.* 1999, 5, 221-225) and cell transformation (Sahai et al., *Curr. Biol.* 1999, 9, 136-145). Accordingly, the development of inhibitors of ROCK kinase would be useful as therapeutic agents for the treatment of disorders mediated by the ROCK kinase pathway.

ZAP-70 is essential for T-cell receptor signalling. Expression of this tyrosine kinase is restricted to T-cells and natural killer cells. The importance of ZAP-70 in T-cell function has been demonstrated in human patients, human T-cell lines and mice. Human patients suffering from a rare form of severe combined deficiency syndrome (SCID) possess homozygous mutations in ZAP-70 (reviewed in Elder *J. of Pedriatric Hematology/Oncology* 1997, 19(6), 546-550). These patients have profound immunodeficiency, lack CD8+ T-cells and have CD4+ T-cells that are unresponsive to T-cell receptor (TCR)-mediated stimulation. Following TCR activation these CD4+ cells show severe defects in Ca2+ mobilization, tyrosine phosphorylation of down-stream substrates, proliferation and IL-2 production 70 (reviewed in *Elder Pedriatric Research* 39, 743-748). Human Jurkat cells lacking ZAP-70 also provide important insights into the critical role of ZAP-70 in T-cell receptor signalling. A Jurkat clone (p116) with no detectable ZAP-70 protein was shown to have defects in T-cell receptor signalling which could be corrected by re-introduction of wild type ZAP-70 (Williams et al., *Molecular and Cellular Biology* 1998, 18 (3), 1388-1399). Studies of mice lacking ZAP-70 also demonstrate a requirement of ZAP-70 in T-cell receptor signalling. ZAP-70-deficient mice have profound defects in T-cell development and T-cell receptor signalling in thymocytes is impaired (Negishi et al., *Nature* 1995 376, 435-438).

The importance of the kinase domain in ZAP-70 function is demonstrated by studies of human patients and mice expressing identical mutations in the DLAARN motif within the kinase domain of ZAP-70. Inactivation of kinase activity by this mutation results in defective T-cell receptor signalling (Elder et al., *J. Immunology* 2001, 656-661). Catalytically inactive ZAP-70 (Lys369Arg) was also defective in restoring T-cell receptor signalling in a ZAP-70 deficient Jurkat cell clone (p116) (Williams et al., *Molecular and Cellular Biology* 1998, 18 (3), 1388-1399).

The Janus kinases (JAK) are a family of tyrosine kinases consisting of JAK1, JAK2, JAK3 and TYK2. The JAKs play a critical role in cytokine signaling. The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas. The pharmaceutical intervention in the JAK/STAT pathway has been reviewed [Frank Mol. Med. 5: 432-456 (1999) & Seidel, et al, Oncogene 19: 2645-2656 (2000)].

JAK1, JAK2, and TYK2 are ubiquitously expressed, while JAK3 is predominantly expressed in hematopoietic cells. JAK3 binds exclusively to the common cytokine receptor gamma chain ($\gamma_c$) and is activated by IL-2, IL-4, IL-7, IL-9, and IL-15. The proliferation and survival of murine mast cells induced by IL-4 and IL-9 have, in fact, been shown to be dependent on JAK3- and $\gamma_c$-signaling [Suzuki et al, Blood 96: 2172-2180 (2000)].

Cross-linking of the high-affinity immunoglobulin (Ig) E receptors of sensitized mast cells leads to a release of proinflammatory mediators, including a number of vasoactive cytokines resulting in acute allergic, or immediate (type I) hypersensitivity reactions [Gordon et al, Nature 346: 274-276 (1990) & Galli, N. Engl. J. Med., 328: 257-265 (1993)]. A crucial role for JAK3 in IgE receptor-mediated mast cell responses in vitro and in vivo has been established [Malaviya, et al, Biochem. Biophys. Res. Commun. 257: 807-813 (1999)]. In addition, the prevention of type I hypersensitivity reactions, including anaphylaxis, mediated by mast cell-activation through inhibition of JAK3 has also been reported [Malaviya et al, J. Biol. Chem. 274:27028-27038 (1999)]. Targeting mast cells with JAK3 inhibitors modulated mast cell degranulation in vitro and prevented IgE receptor/antigen-mediated anaphylactic reactions in vivo.

A recent study described the successful targeting of JAK3 for immune suppression and allograft acceptance. The study demonstrated a dose-dependent survival of Buffalo heart allograft in Wistar Furth recipients upon administration of inhibitors of JAK3 indicating the possibility of regulating unwanted immune responses in graft versus host disease [Kirken, transpl. proc. 33: 3268-3270 (2001)].

IL-4-mediated STAT-phosphorylation has been implicated as the mechanism involved in early and late stages of rheumatoid arthritis (RA). Up-regulation of proinflammatory cytokines in RA synovium and synovial fluid is a characteristic of the disease. It has been demostrated that IL-4-mediated activation of IL-4/STAT pathway is mediated through the Janus Kinases (JAK 1 & 3) and that IL-4-associated JAK kinases are expressed in the RA synovium [Muller-Ladner, et al, J. Immunol. 164: 3894-3901 (2000)].

Familial amyotrophic lateral sclerosis (FALS) is a fatal neurodegenerative disorder affecting about 10% of ALS patients. The survival rates of FALS mice were increased upon treatment with a JAK3 specific inhibitor. This confirmed that JAK3 plays a role in FALS [Trieu, et al, Biochem. Biophys. Res. Commun. 267: 22-25 (2000)].

Signal transducer and activator of transcription (STAT) proteins are activated by, among others, the JAK family kinases. Results form a recent study suggested the possibility of intervention in the JAK/STAT signaling pathway by targeting JAK family kinases with specific inhibitors for the treatment of leukemia [Sudbeck, et al, Clin. Cancer Res. 5: 1569-1582 (1999)]. JAK3 specific compounds were shown to inhibit the clonogenic growth of JAK3-expressing cell lines DAUDI, RAMOS, LC1; 19, NALM-6, MOLT-3 and HL-60.

In animal models, TEL/JAK2 fusion proteins have induced myeloproliferative disorders and in hematopoietic cell lines, introduction of TEL/JAK2 resulted in activation of STAT1, STAT3, STAT5, and cytokine-independent growth [Schwaller, et al, EMBO J. 17: 5321-5333 (1998)].

Inhibition of JAK 3 and TYK 2 abrogated tyrosine phosphorylation of STAT3, and inhibited cell growth of mycosis fungoides, a form of cutaneous T cell lymphoma. These results implicated JAK family kinases in the constitutively activated JAK/STAT pathway that is present in mycosis fungoides [Nielsen, et al, Proc. Nat. Acad. Sci. U.S.A. 94: 6764-6769 (1997)]. Similarly, STAT3, STAT5, JAK1 and JAK2 were demonstrated to be constitutively activated in mouse T cell lymphoma characterized initially by LCK over-expression, thus further implicating the JAK/STAT pathway in abnormal cell growth [Yu, et al, J. Immunol. 159: 5206-5210 (1997)]. In addition, IL-6-mediated STAT3 activation was blocked by an inhibitor of JAK, leading to sensitization of myeloma cells to apoptosis [Catlett-Falcone, et al, Immunity 10:105-115 (1999)].

As a result of the biological importance of protein kinases, there is current interest in therapeutically effective protein kinase inhibitors. Accordingly, there is still a great need to develop inhibitors of protein kinases that are useful in treating various diseases or conditions associated with protein kinase activation.

SUMMARY OF THE INVENTION

It has now been found that compounds of this invention, and compositions thereof, are effective as protein kinase inhibitors. In certain embodiments, the present compounds are inhibitors of ERK2, AKT3, GSK3, p70s6k, PDK1, Aurora-2, ROCK, SRC, SYK, ZAP70, JNK3, JAK3, TEC, LCK, FLT3, and/or CDK2. These compounds have the general formulae I and V:

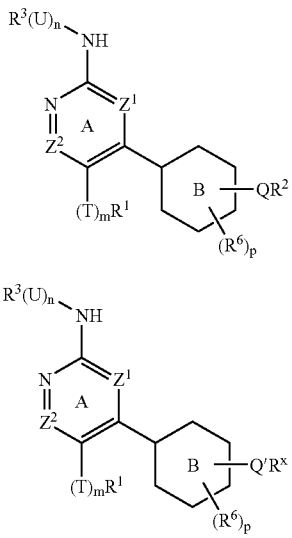

or a pharmaceutically acceptable salt thereof, wherein Ring B, $Z^1$, $Z^2$, U, T, m, n, p, Q, Q', $R^1$, $R^2$, $R^x$, $R^3$, and $R^6$ are as defined below.

These compounds, and pharmaceutically acceptable compositions thereof, are useful for treating or lessening the severity of a variety of disorders, including stroke, Alzheimer's disease, immunodeficiency disorders, inflammatory diseases, allergic diseases, autoimmune diseases, destructive bone disorders such as osteoporosis, inflammatory disorders, proliferative disorders such as cancer, and conditions associated with organ transplantation.

DESCRIPTION OF THE INVENTION

The present invention provides a compound of formula I:

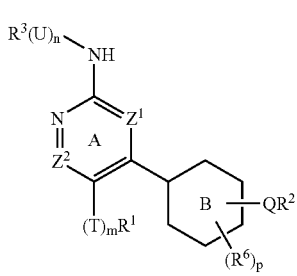

or a pharmaceutically acceptable salt thereof, wherein:

Ring B is a 6-membered aryl ring having 0-3 nitrogens;

$Z^1$ and $Z^2$ are each independently selected from N or CH;

T and Q are each independently selected from a saturated or unsaturated $C_{1-6}$ alkylidene chain wherein:
  up to two methylene units of the chain are optionally and independently replaced by —C(O)—, —C(O)C(O)—, —C(O)NR—, —C(O)NRNR—, —CO$_2$—, —OC(O)—, —NRCO$_2$—, —O—, —NRC(O)NR—, —OC(O)NR—, —NRNR—, —NRC(O)—, —S—, —SO—, —SO$_2$—, —NR—, —SO$_2$NR—, or —NRSO$_2$—;

each R is independently selected from hydrogen or an optionally substituted $C_{1-6}$ aliphatic group, or:
  two R on the same nitrogen are taken together with the nitrogen to form a 5-8 membered heterocyclyl or heteroaryl ring having 1-3 heteroatoms independently selected from nitrogen, oxygen, or sulfur;

U is selected from —NR—, —NRC(O)—, —NRC(O)NR—, —NRCO$_2$—, —O—, —C(O)NR—, —C(O)—, —CO$_2$—, —OC(O)—, —NRSO$_2$—, —SO$_2$NR—, —NRSO$_2$NR—, or —SO$_2$—;

m and n are each independently selected from zero or one;

p is selected from 0, 1, 2, 3, or 4;

$R^1$ is selected from R or Ar;

each Ar is an optionally substituted ring selected from a 6-10 membered aryl ring, a 5-10 membered heteroaryl ring having 1-4 heteroatoms independently selected from nitrogen, oxygen, or sulfur, or a 3-10 membered heterocyclyl ring having 1-4 heteroatoms independently selected from nitrogen, oxygen, or sulfur;

$R^2$ is selected from —(CH$_2$)$_y$CH($R^5$)$_2$ or —(CH$_2$)$_y$CH($R^4$)CH($R^5$)$_2$;

y is 0-6;

$R^3$ is selected from R, Ar, —(CH$_2$)$_y$CH($R^5$)$_2$, or CN;

$R^4$ is selected from R, (CH$_2$)$_w$OR, (CH$_2$)$_w$N(R)$_2$, or (CH$_2$)$_w$SR;

w is 0-4;

each $R^5$ is independently selected from optionally substituted $C_{1-6}$ aliphatic, Ar, OR, CO$_2$R, (CH$_2$)$_y$N(R)$_2$, N(Ar)(R), SR, NRC(O)R, NRC(O)N(R)$_2$, C(O)N(R)$_2$, SO$_2$R, NRSO$_2$R, C(O)R, CN, or SO$_2$N(R)$_2$; and each $R^6$ is independently selected from R, F, Cl, $N(R)_2$, OR, SR, NRC(O)R, $NRC(O)N(R)_2$, $C(O)N(R)_2$, $SO_2R$, $NRSO_2R$, C(O)R, CN, $SO_2N(R)_2$, N(R)O, ON(R), or N(R)N(R).

The present invention also relates to a compound of formula V:

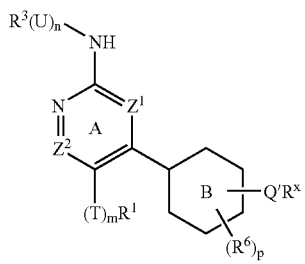

or a pharmaceutically acceptable salt thereof, wherein:
Ring B is a 6-membered aryl ring having 0-3 nitrogens;
$Z^1$ and $Z^2$ are each independently selected from N or CH;
T is a saturated or unsaturated $C_{1-6}$ alkylidene chain wherein:
  up to two methylene units of the chain are optionally and independently replaced by —C(O)—, —C(O)C(O)—, —C(O)NR—, —C(O)NRNR—, —$CO_2$—, —OC(O)—, —$NRCO_2$—, —O—, —NRC(O)NR—, —OC(O)NR—, —NRNR—, —NRC(O)—, —S—, —SO—, —$SO_2$—, —NR—, —$SO_2$NR—, or —$NRSO_2$—;
each R is independently selected from hydrogen or an optionally substituted $C_{1-6}$ aliphatic group, or:
  two R on the same nitrogen are taken together with the nitrogen to form a 5-8 membered heterocyclyl or heteroaryl ring having 1-3 heteroatoms independently selected from nitrogen, oxygen, or sulfur;
Q' is a saturated or unsaturated $C_{1-6}$ alkylidene chain wherein:
  one or two methylene units of the chain are optionally and independently replaced by —C(O)NR'—, —NR'$CO_2$—, —OC(O)NR'—, —NR'C(O)—, —NR'—, —$SO_2$NR'—, or —NR'$SO_2$—;
each R' is independently selected from a $C_{1-6}$ aliphatic group, wherein said aliphatic group is substituted with one Ar group and optionally substituted with 1-2 additional groups independently selected from halogen, —OR, —SR, —$NO_2$, —CN, —$N(R)_2$, —NRC(O)R, —$NRC(O)N(R)_2$, —$NRCO_2R$, —NRNRC(O)R, —$NRNRC(O)N(R)_2$, —$NRNRCO_2R$, —C(O)C(O)R, —C(O)$CH_2$C(O)R, —$CO_2R$, or —C(O)R;
U is selected from —NR—, —NRC(O)—, —NRC(O)NR—, —$NRCO_2$—, —O—, —C(O)NR—, —C(O)—, —$CO_2$—, —OC(O)—, —$NRSO_2$—, —$SO_2$NR—, —$NRSO_2$NR—, or —$SO_2$—;
m and n are each independently selected from zero or one;
p is selected from 0, 1, 2, 3, or 4;
$R^1$ is selected from R or Ar;
each Ar is an optionally substituted ring selected from a 6-10 membered aryl ring, a 5-10 membered heteroaryl ring having 1-4 heteroatoms independently selected from nitrogen, oxygen, or sulfur, or a 3-10 membered heterocyclyl ring having 1-4 heteroatoms independently selected from nitrogen, oxygen, or sulfur;
y is 0-6;
$R^x$ is —$(CH_2)_yR^5$ $R^3$ is selected from R, Ar, —$(CH_2)_yCH(R^5)_2$, or CN;
w is 0-4;
each $R^5$ is independently selected from optionally substituted $C_{1-6}$ aliphatic, Ar, OR, $CO_2R$, $(CH_2)_yN(R)_2$, N(Ar)(R), SR, NRC(O)R, $NRC(O)N(R)_2$, $C(O)N(R)_2$, $SO_2R$, $NRSO_2R$, C(O)R, CN, or $SO_2N(R)_2$; and
each $R^6$ is independently selected from R, F, Cl, $N(R)_2$, OR, SR, NRC(O)R, $NRC(O)N(R)_2$, $C(O)N(R)_2$, $SO_2R$, $NRSO_2R$, C(O)R, CN, $SO_2N(R)_2$, N(R)O, ON(R), or N(R)N(R).

As used herein, the following definitions shall apply unless otherwise indicated. The phrase "optionally substituted" is used interchangeably with the phrase "substituted or unsubstituted." Unless otherwise indicated, an optionally substituted group may have a substituent at each substitutable position of the group, and each substitution is independent of the other.

The term "aliphatic" or "aliphatic group" as used herein means a straight-chain or branched $C_1$-$C_{12}$ hydrocarbon chain that is completely saturated or that contains one or more units of unsaturation, or a monocyclic $C_3$-$C_8$ hydrocarbon or bicyclic $C_8$-$C_{12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3-7 members. For example, suitable aliphatic groups include, but are not limited to, linear or branched or alkyl, alkenyl, alkynyl groups and hybrids thereof such as (cycloalkyl)alkyl, (cycloalkenyl)alkyl or (cycloalkyl)alkenyl.

The terms "alkyl", "alkoxy", "hydroxyalkyl", "alkoxyalkyl", and "alkoxycarbonyl", used alone or as part of a larger moiety includes both straight and branched chains containing one to twelve carbon atoms. The terms "alkenyl" and "alkynyl" used alone or as part of a larger moiety shall include both straight and branched chains containing two to twelve carbon atoms.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or $NR^+$ (as in N-substituted pyrrolidinyl).

The term "aryl" used alone or as part of a larger moiety as in "aralkyl", "aralkoxy", or "aryloxyalkyl", refers to monocyclic, bicyclic and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heterocycle", "heterocyclyl", or "heterocyclic" as used herein means non-aromatic, monocyclic, bicyclic or tricyclic ring systems having five to fourteen ring members in which one or more ring members is a heteroatom, wherein each ring in the system contains 3 to 7 ring members.

The term "heteroaryl", used alone or as part of a larger moiety as in "heteroaralkyl" or "heteroarylalkoxy", refers to monocyclic, bicyclic and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl, heteroaryl, aralkyl, or heteroaralkyl group are selected from halogen, —R°, —OR°, —SR°, 1,2-methylene-dioxy, 1,2-ethylenedioxy, protected OH (such as acyloxy), phenyl (Ph), Ph substituted with R°, —O(Ph), O-(Ph) substituted with R°, —CH$_2$(Ph), —CH$_2$(Ph) substituted with R°, —CH$_2$CH$_2$(Ph), —CH$_2$CH$_2$(Ph) substituted with R°, —NO$_2$, —CN, —N(R°)$_2$, —NR°C(O)R°, —NR°C(O)N(R°)$_2$, —NR°CO$_2$R°, —NR°NR°C(O)R, —NR°NR°C(O)N(R°)$_2$, —NR°NR°CO$_2$R°, —C(O)C(O)R°, —C(O)CH$_2$C(O)R, —CO$_2$R, —C(O)R°, —C(O)N(R°)$_2$, —OC(O)N(R°)$_2$, —S(O)$_2$R°, —SO$_2$N(R°)$_2$, —S(O)R°, —NR°SO$_2$N(R°)$_2$, —NR°SO$_2$R°, —C(=S)N(R°)$_2$, —C(=NH)—N(R°)$_2$, or —(CH$_2$)$_y$NHC(O)R°, wherein each R° is independently selected from hydrogen, optionally substituted C$_{1-6}$ aliphatic, an unsubstituted 5-6 membered heteroaryl or heterocyclic ring, phenyl (Ph), —O(Ph), or —CH$_2$(Ph)—CH$_2$(Ph). Substituents on the aliphatic group of R° are selected from NH$_2$, NH(C$_{1-4}$ aliphatic), N(C$_{1-4}$ aliphatic)$_2$, halogen, C$_{1-4}$ aliphatic, OH, O—(C$_{1-4}$ aliphatic), NO$_2$, CN, CO$_2$H, CO$_2$(C$_{1-4}$ aliphatic), —O(halo C$_{1-4}$ aliphatic), or halo C$_{1-4}$ aliphatic.

An aliphatic group or a non-aromatic heterocyclic ring may contain one or more substituents. Suitable substituents on the saturated carbon of an aliphatic group or of a non-aromatic heterocyclic ring are selected from those listed above for the unsaturated carbon of an aryl or heteroaryl group and the following: =O, =S, =NNHR*, =NN(R*)$_2$, =N—, =NNHC(O)R*, =NNHCO$_2$(alkyl), =NNHSO$_2$(alkyl), or =NR*, where each R* is independently selected from hydrogen or an optionally substituted C$_{1-6}$ aliphatic. Substituents on the aliphatic group of R* are selected from NH$_2$, NH(C$_{1-4}$ aliphatic), N(C$_{1-4}$ aliphatic)$_2$, halogen, C$_{1-4}$ aliphatic, OH, O—(C$_{1-4}$ aliphatic), NO$_2$, CN, CO$_2$H, CO$_2$(C$_{1-4}$ aliphatic), —O(halo C$_{1-4}$ aliphatic), or halo C$_{1-4}$ aliphatic.

Substituents on the nitrogen of a non-aromatic heterocyclic ring are selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein R$^+$ is hydrogen, an optionally substituted C$_{1-6}$ aliphatic, optionally substituted phenyl (Ph), optionally substituted —O(Ph), optionally substituted —CH$_2$(Ph), optionally substituted —CH$_2$CH$_2$(Ph), or an unsubstituted 5-6 membered heteroaryl or heterocyclic ring. Substituents on the aliphatic group or the phenyl ring of R$^+$ are selected from NH$_2$, NH(C$_{1-4}$ aliphatic), N(C$_{1-4}$ aliphatic)$_2$, halogen, C$_{1-4}$ aliphatic, OH, O—(C$_{1-4}$ aliphatic), NO$_2$, CN, CO$_2$H, CO$_2$(C$_{1-4}$ aliphatic), —O(halo C$_{1-4}$ aliphatic), or halo C$_{1-4}$ aliphatic.

The term "alkylidene chain" refers to a straight or branched carbon chain that may be fully saturated or have one or more units of unsaturation and has two points of connection to the rest of the molecule.

The compounds of this invention are limited to those that are chemically feasible and stable. Therefore, a combination of substituents or variables in the compounds described above is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention.

Compounds of this invention may exist in alternative tautomeric forms. Unless otherwise indicated, the representation of either tautomer is meant to include the other.

Preferred (T)$_m$R$^1$ groups of formula I are selected from hydrogen, N(R)$_2$, halogen, OH, 3-6 membered carbocyclyl, or an optionally substituted group selected from C$_{1-6}$ aliphatic, a 6 membered aryl ring, or a 5-6 membered heteroaryl ring having 1-3 heteroatoms independently selected from nitrogen, oxygen, or sulfur. When R$^1$ is an optionally substituted phenyl or aliphatic group, preferred substituents on the phenyl or aliphatic group are R°, halo, nitro, alkoxy, and amino. Examples of such preferred (T)$_m$R$^1$ groups include chloro, fluoro, methyl, ethyl, propyl, cyclopropyl, cyclohexyl, CH$_2$OCH$_3$, CH$_2$OH, NH$_2$, NHCH$_3$, NHAc, NHC(O)NHCH$_3$, and CH$_2$NHCH$_3$. More preferred (T)$_m$R$^1$ groups of formula I are those listed in Table 1 below.

Preferred R$^3$ groups of formula I are hydrogen, OR, optionally substituted 3-7 membered carbocyclyl or an optionally substituted group selected from C$_{1-4}$ aliphatic, a 3-6 membered heterocyclic ring having 1-3 heteroatoms independently selected from nitrogen, oxygen, or sulfur, or a 5-6 membered aryl or heteroaryl ring having 1-3 heteroatoms independently selected from nitrogen, oxygen, or sulfur. Examples of such groups include methyl, ethyl, propyl, isopropyl, isobutyl, cyclopropyl, cyclohexyl, 4-hydroxycyclohexyl, phenyl, benzyl, isoxazolyl, tetrahydrofuranyl, OEt, OMe, O-isopropyl, OCH$_2$cyclopropyl, isoxazol-3-yl, pyridyl, and isopropyl. When R$^3$ is optionally substituted phenyl, preferred substituents on the phenyl ring are halogen, R°, OR°, N(R°)$_2$, CO$_2$R°, and SO$_2$N(R°)$_2$. Examples of such substituents include fluoro, NH$_2$, Cl, Br, OCH$_2$phenyl, morpholin-4-yl, CO$_2$Me, OMe, haloalkyl (e.g. CF$_3$), Obenzyl, Ophenyl, OCF$_3$, OH, SO$_2$NH$_2$, and methylene dioxy. When R$^3$ is —(CH$_2$)$_y$CH(R$^5$)$_2$, examples of such groups include —CH(CH$_3$)CH$_2$OH, —CH$_2$pyridyl, —CH(CH$_2$OH)phenyl, —CH(CH$_2$OH)ethyl, —CH(CH$_2$OH)$_2$, —CH(CH$_2$OH)isopropyl, and —CH(CH$_2$OH)CH$_2$cyclopropyl.

Preferred U groups of formula I, when present, are —CH$_2$—, —O—, —NR—, —NHC(O)—, and —NHCO$_2$—. More preferred (U)$_n$R$^3$ groups of formula I are those listed in Table 1 below.

Preferred Q groups of formula I are selected from a C$_{1-4}$ alkylidene chain wherein one or two methylene units of Q are independently replaced by C(O), OC(O), C(O)NH, OC(O)NH, SO$_2$, SO$_2$NH, NHC(O), NHC(O)O, or NHSO$_2$. More preferred Q groups of formula I are C(O), SO$_2$, C(O)NH, or SO$_2$NH. Most preferred Q groups of formula I are C(O) and C(O)NH.

According to another embodiment, Q of formula I is NRC(O) or NRSO$_2$. More preferably, Q is NHC(O).

When R of formula I is (CH$_2$)$_y$CH(R$^5$)$_2$ preferred R$^5$ groups are independently selected from optionally substituted C$_{1-4}$ aliphatic, C$_{5-6}$ cycloalkyl, phenyl, a 5-9 membered heteroaryl ring having 1-2 heteroatoms independently selected from nitrogen, oxygen, or sulfur, or a 5-6 membered heterocyclic ring having 1-2 heteroatoms independently selected from nitrogen, oxygen, or sulfur. More preferred R$^5$ groups are independently selected from pyridin-3-yl, pyridin-4-yl, morphlin-4-yl, thiomorpholin-4-yl, imidazolyl, furan-2-yl, 1,2,3,4-tetrahydroisoquinoline, tetrahydrofuran-2-yl, cyclohexyl, phenyl, benzyl, —CH$_2$OH, —(CH$_2$)$_2$OH, and isopropyl, wherein each group is optionally substituted. Preferred substituents on R$^5$ are halogen, R°, NO$_2$, OR°, or SR°. Examples of such substituents are chloro, fluoro, methyl, ethyl, isopropyl, OCH$_3$, —OH, SCH$_3$, pyridyl, piperidinyl, and optionally substituted phenyl.

According to another embodiment, when R$^2$ of formula I is (CH$_2$)$_y$CH(R$^5$)$_2$ preferred R$^5$ groups are selected from OR, CO$_2$R, (CH$_2$)$_y$N(R)$_2$, or N(Ar)(R) wherein each R is independently selected from hydrogen or an optionally substituted C$_{1-4}$ aliphatic group and Ar is C$_{5-6}$ cycloalkyl, phenyl, a 5-9 membered heteroaryl ring having 1-2 heteroatoms independently selected from nitrogen, oxygen, or sulfur, or a 5-6 membered heterocyclic ring having 1-2 heteroatoms independently selected from nitrogen, oxygen, or sulfur. Preferred substituents on R are selected from OR°, —SR°, phenyl, —O(Ph), —CH$_2$(Ph), —N(R°)$_2$, —NR°C(O)R°, —NR°C(O)N(R°)$_2$, —NR°CO$_2$R°, —CO$_2$R°, —C(O)R°, or —C(O)N(R°)$_2$, wherein each R° is independently selected from hydrogen, a C$_{1-4}$ aliphatic group, or an unsubstituted 5-6 membered heteroaryl or heterocyclic ring having 1-3 heteroatoms independently selected from nitrogen, oxygen, or sulfur, phenyl (Ph), —O(Ph), or —CH$_2$(Ph)CH$_2$(Ph). Substituents on the aliphatic group of R° are selected from NH$_2$, NH(C$_{1-4}$ aliphatic), N(C$_{1-4}$ aliphatic)$_2$, halogen, C$_{1-4}$ aliphatic, OH, O—(C$_{1-4}$ aliphatic), NO$_2$, CN, CO$_2$H, CO$_2$(C$_{1-4}$ aliphatic), —O(halo C$_{1-4}$ aliphatic), or halo C$_{1-4}$ aliphatic.

When R$^2$ of formula I is —(CH$_2$)$_y$CH(R$^4$)CH(R$^5$)$_2$, preferred R$^4$ groups are R and OR, such as OH and CH$_2$OH, and preferred R$^5$ are as described above. Preferred —(CH$_2$)$_y$CH(R$^4$)CH(R$^5$)$_2$ groups of formula I are —CH(OH)CH(OH)phenyl and —CH(Me)CH(OH)phenyl. Other preferred —QR$^2$ groups are those listed in Table 1 below.

According to one embodiment, the present invention relates to a compound of formula I wherein Ring B is phenyl.

According to another embodiment, the present invention relates to a compound of formula I wherein Ring B is pyridyl.

According to another embodiment, the present invention relates to a compound of formula I wherein Ring B is pyrimidinyl.

According to another embodiment, the present invention relates to a compound of formula I wherein Ring B is pyrazinyl.

According to another embodiment, the present invention relates to a compound of formula I wherein Ring B is triazinyl.

Preferred (T)$_m$R$^1$ groups of formula V are those described above for compounds of formula I.

Preferred R$^3$ groups of formula V are those described above for compounds of formula I.

Preferred U groups of formula V, when present, are those described above for compound of formula I.

Preferred Q' groups of formula V are selected from —C(O)NR'—, —NR'CO$_2$—, —OC(O)NR'—, —NR°C(O)—, —SO$_2$NR'—, or —NR'SO$_2$—, wherein each R' is independently selected from a C$_{1-4}$ aliphatic group, wherein said aliphatic group is substituted with one Ar group and optionally substituted with one additional group selected from halogen, —OR, —SR, —NO$_2$, —CN, —N(R)$_2$, —NRC(O)R, —NRC(O)N(R)$_2$, —NRCO$_2$R, —NRNRC(O)R, —NRNRC(O)N(R)$_2$, —NRNRCO$_2$R, —C(O)C(O)R, —C(O)CH$_2$C(O)R, —CO$_2$R, or —C(O)R. Preferred Ar substituents of the R' groups of Q' are selected from an optionally substituted phenyl or 5-6 membered heteroaryl ring having 1-4 heteroatoms independently selected from nitrogen, oxygen, or sulfur. More preferably Q' of formula V is —C(O)NR'— or —NR'C(O)— wherein each R' is a C$_{1-2}$ aliphatic group, wherein said aliphatic group is substituted with Ar and Ar is an optionally substituted phenyl, 5-6 membered heteroaryl ring having 1-4 heteroatoms independently selected from nitrogen, oxygen, or sulfur, or a 3-6 membered heterocyclyl ring having 1-2 heteroatoms independently selected from nitrogen, oxygen, or sulfur. More preferably the Ar substituent on R' is selected from phenyl, pyridyl, thienyl, or pyrimidyl.

Preferred R$^x$ groups of formula V are —(CH$_2$)$_y$R$^5$, wherein y is one or two and R$^5$ is Ar, wherein Ar is a 3-6 membered heterocyclic ring having 1-2 heteroatoms independently selected from nitrogen, oxygen, or sulfur, or an optionally substituted phenyl or 5-6 membered heteroaryl ring having 1-4 heteroatoms independently selected from nitrogen, oxygen, or sulfur. More preferably R$^x$ is —(CH$_2$)$_y$R$^5$, wherein y is one or two and R$^5$ is selected from morpholin-4-yl, thiomorpholin-4-yl, piperidinyl, piperazinyl, or pyrrolidinyl.

According to one embodiment, the present invention relates to a compound of formula V wherein Ring B is phenyl.

According to another embodiment, the present invention relates to a compound of formula V wherein Ring B is pyridyl.

According to another embodiment, the present invention relates to a compound of formula V wherein Ring B is pyrimidinyl.

According to another embodiment, the present invention relates to a compound of formula V wherein Ring B is pyrazinyl.

According to another embodiment, the present invention relates to a compound of formula V wherein Ring B is triazinyl.

Accordingly, the present invention relates to compounds of formula I wherein Ring A is a pyridine (I-A), pyrimidine (I-B), or triazine (I-C) ring as shown below:

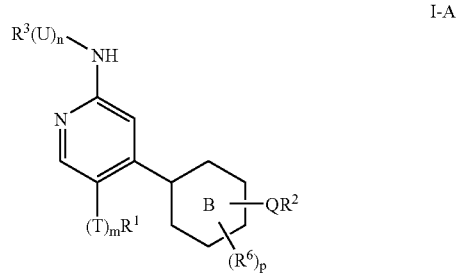

I-A

-continued

I-B

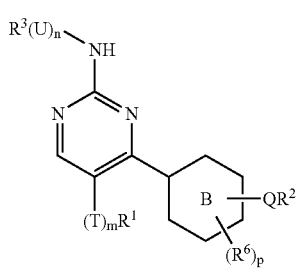

I-C

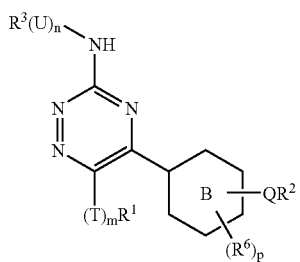

or a pharmaceutically acceptable salt thereof, wherein Ring B, $Z^1$, $Z^2$, U, T, m, n, p, Q, $R^1$, $R^2$, $R^3$, and $R^6$ are as defined above.

Preferred $(T)_m R^1$ groups of any of formulae I-A, I-B, and I-C are those described above for compounds of formula I.

Preferred U groups of any of formulae I-A, I-B, and I-C are those described above for compounds of formula I.

Preferred $R^3$ groups of any of formulae I-A, I-B, and I-C are those described above for compounds of formula I.

Preferred Q groups of any of formulae I-A, I-B, and I-C are those described above for compounds of formula I.

Preferred $R^2$ groups of any of formulae I-A, I-B, and I-C are those described above for compounds of formula I.

The present invention also relates to compounds of formula V wherein Ring A is a pyridine (V-A), pyrimidine (V-B), or triazine (V-C) ring as shown below:

V-A

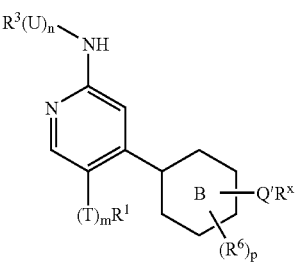

V-B

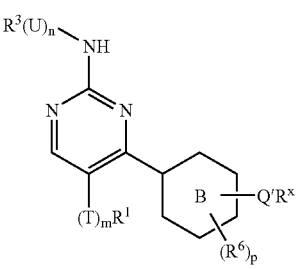

V-C

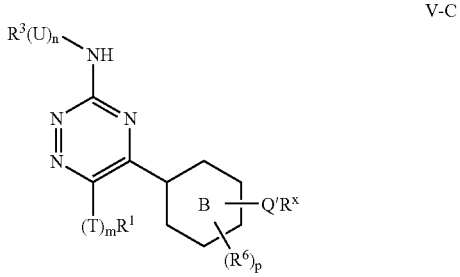

or a pharmaceutically acceptable salt thereof, wherein Ring B, $Z^1$, $Z^2$, U, T, m, n, p, Q', $R^1$, $R^x$, $R^3$, and $R^6$ are as defined above.

Preferred $(T)_m R^1$ groups of any of formulae V-A, V-B, and V-C are those described above for compounds of formula I.

Preferred U groups of any of formulae V-A, V-B, and V-C are those described above for compounds of formula I.

Preferred $R^3$ groups of any of formulae V-A, V-B, and V-C are those described above for compounds of formula I.

Preferred Q' groups of any of formulae V-A, V-B, and V-C are those described above for compounds of formula V.

Preferred $R^x$ groups of any of formulae V-A, V-B, and V-C are those described above for compounds of formula V.

Suitable Ring B moieties of the present invention include:

i

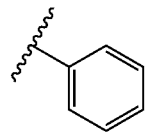

ii

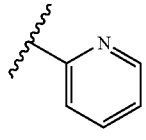

iii

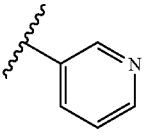

iv

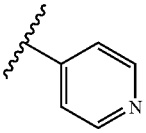

v

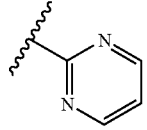

vi

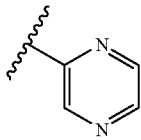

vii
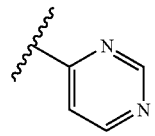
viii
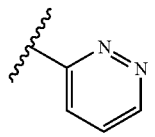
ix
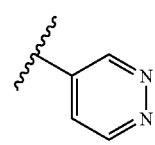
x
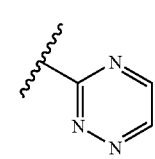
xi
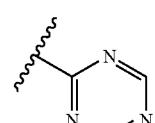
xii
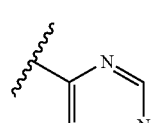
Accordingly, the present invention relates to the following compounds of formula I:
I-Ai
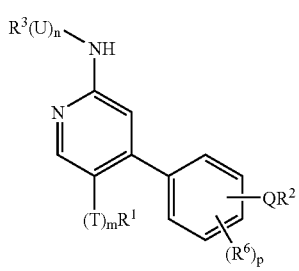
I-Aii
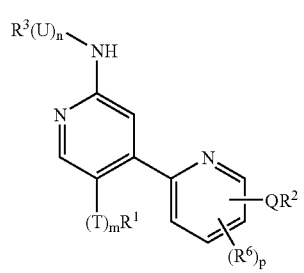
I-Aiii
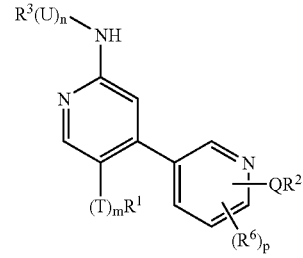
I-Aiv
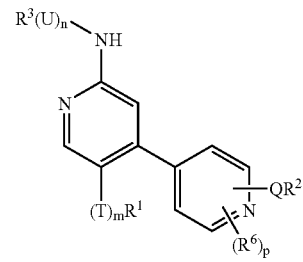
I-Av
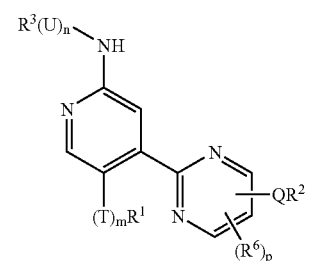
I-Avi
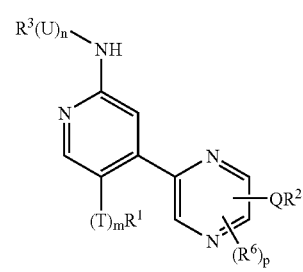
I-Avii
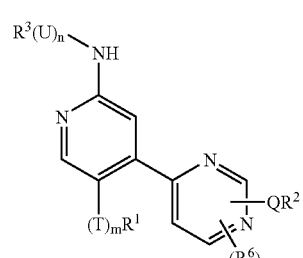
I-Aviii
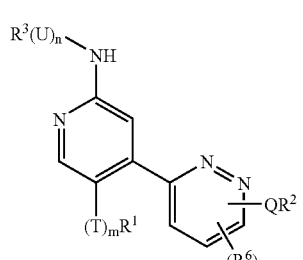

-continued

I-Aix

I-Ax

I-Axi

I-Axii

I-Bi

I-Bii

-continued

I-Biii

I-Biv

I-Bv

I-Bvi

I-Bvii

I-Bviii

-continued
I-Bix
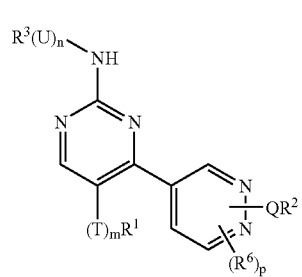
I-Bx
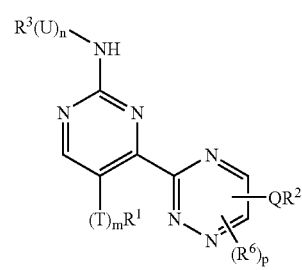
I-Bxi
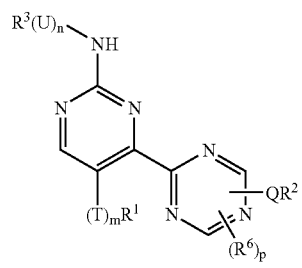
I-Bxii
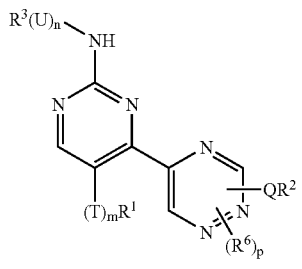
I-Ci
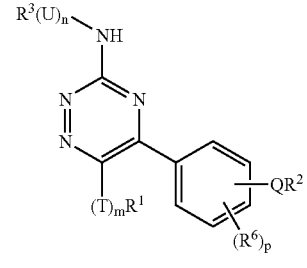
I-Cii
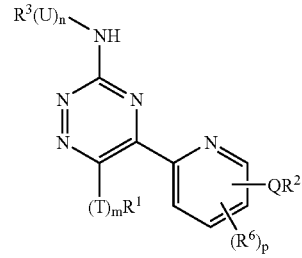
-continued
I-Ciii
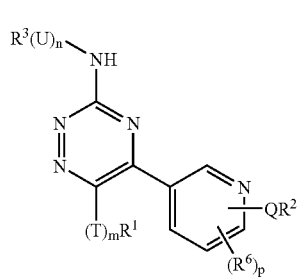
I-Civ
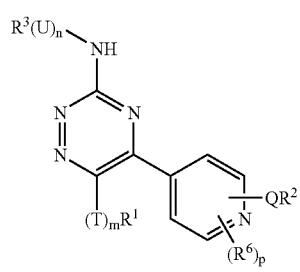
I-Cv
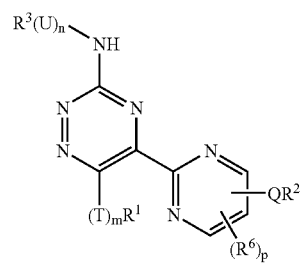
I-Cvi
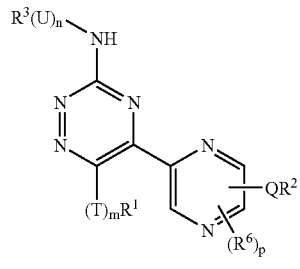
I-Cvii
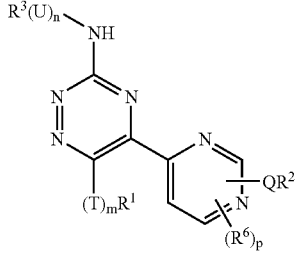
I-Cviii
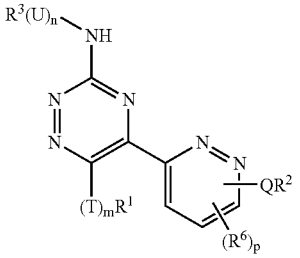

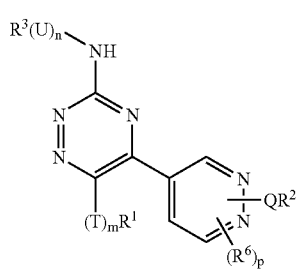

I-Cix

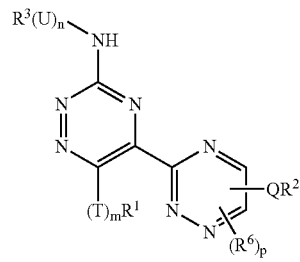

I-Cx

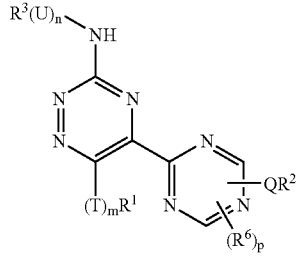

I-Cxi

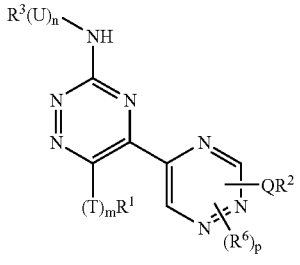

I-Cxii

Preferred $(T)_mR^1$ groups of any of formulae I-Ai, I-Aii, I-Aiii, I-Aiv, I-Av, I-Avi, I-Avii, I-Aviii, I-Aix, I-Ax, I-Axi, I-Axii, I-Bi, I-Bii, I-Biii, I-Biv, I-Bv, I-Bvi, I-Bvii, I-Aviii, I-Bix, I-Bx, I-Bxi, I-Bxii, I-Ci, I-Cii, I-Ciii, I-Civ, I-Cv, I-Cvi, I-Cvii, I-Cviii, I-Cix, I-Cx, I-Cxi, and I-Cxii are those described above for compounds of formula I.

Preferred U groups of any of formulae I-Ai, I-Aii, I-Aiii, I-Aiv, I-Av, I-Avi, I-Avii, I-Aviii, I-Aix, I-Ax, I-Axi, I-Axii, I-Bi, I-Bii, I-Biii, I-Biv, I-Bv, I-Bvi, I-Bvii, I-Aviii, I-Bix, I-Bx, I-Bxi, I-Bxii, I-Ci, I-Cii, I-Ciii, I-Civ, I-Cv, I-Cvi, I-Cvii, I-Cviii, I-Cix, I-Cx, I-Cxi, and I-Cxii are those described above for compounds of formula I.

Preferred $R^3$ groups of any of formulae I-Ai, I-Aii, I-Aiii, I-Aiv, I-Av, I-Avi, I-Avii, I-Aviii, I-Aix, I-Ax, I-Axi, I-Axii, I-Bi, I-Bii, I-Biii, I-Biv, I-Bv, I-Bvi, I-Bvii, I-Aviii, I-Bix, I-Bx, I-Bxi, I-Bxii, I-Ci, I-Cii, I-Ciii, I-Civ, I-Cv, I-Cvi, I-Cvii, I-Cviii, I-Cix, I-Cx, I-Cxi, and I-Cxii are those described above for compounds of formula I.

Preferred Q groups of any of formulae I-Ai, I-Aii, I-Aiii, I-Aiv, I-Av, I-Avi, I-Avii, I-Aviii, I-Aix, I-Ax, I-Axi, I-Axii, I-Bi, I-Bii, I-Biii, I-Biv, I-Bv, I-Bvi, I-Bvii, I-Aviii, I-Bix, I-Bx, I-Bxi, I-Bxii, I-Ci, I-Cii, I-Ciii, I-Civ, I-Cv, I-Cvi, I-Cvii, I-Cviii, I-Cix, I-Cx, I-Cxi, and I-Cxii are those described above for compounds of formula I.

Preferred $R^2$ groups of any of formulae I-Ai, I-Aii, I-Aiii, I-Aiv, I-Av, I-Avi, I-Avii, I-Aviii, I-Aix, I-Ax, I-Axi, I-Axii, I-Bi, I-Bii, I-Biii, I-Biv, I-Bv, I-Bvi, I-Bvii, I-Aviii, I-Bix, I-Bx, I-Bxi, I-Bxii, I-Ci, I-Ci, I-Ciii, I-Civ, I-Cv, I-Cvi, I-Cvii, I-Cviii, I-Cix, I-Cx, I-Cxi, and I-Cxii are those described above for compounds of formula I.

The present invention also relates to the following compounds of formula V:

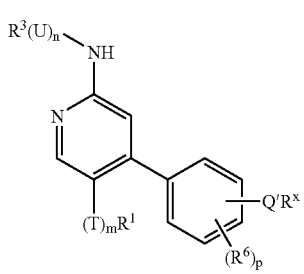

V-Ai

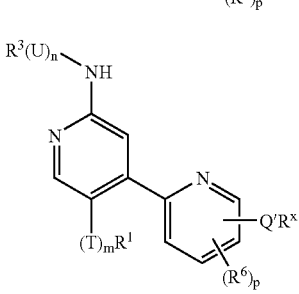

V-Aii

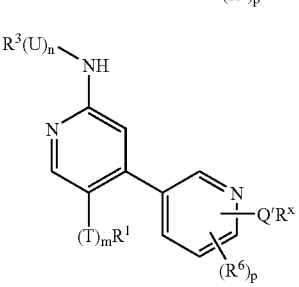

V-Aiii

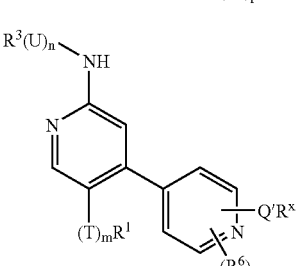

V-Aiv

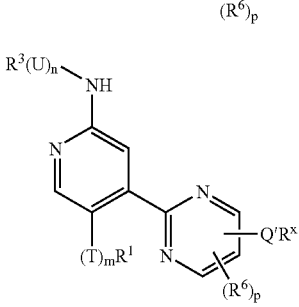

V-Av

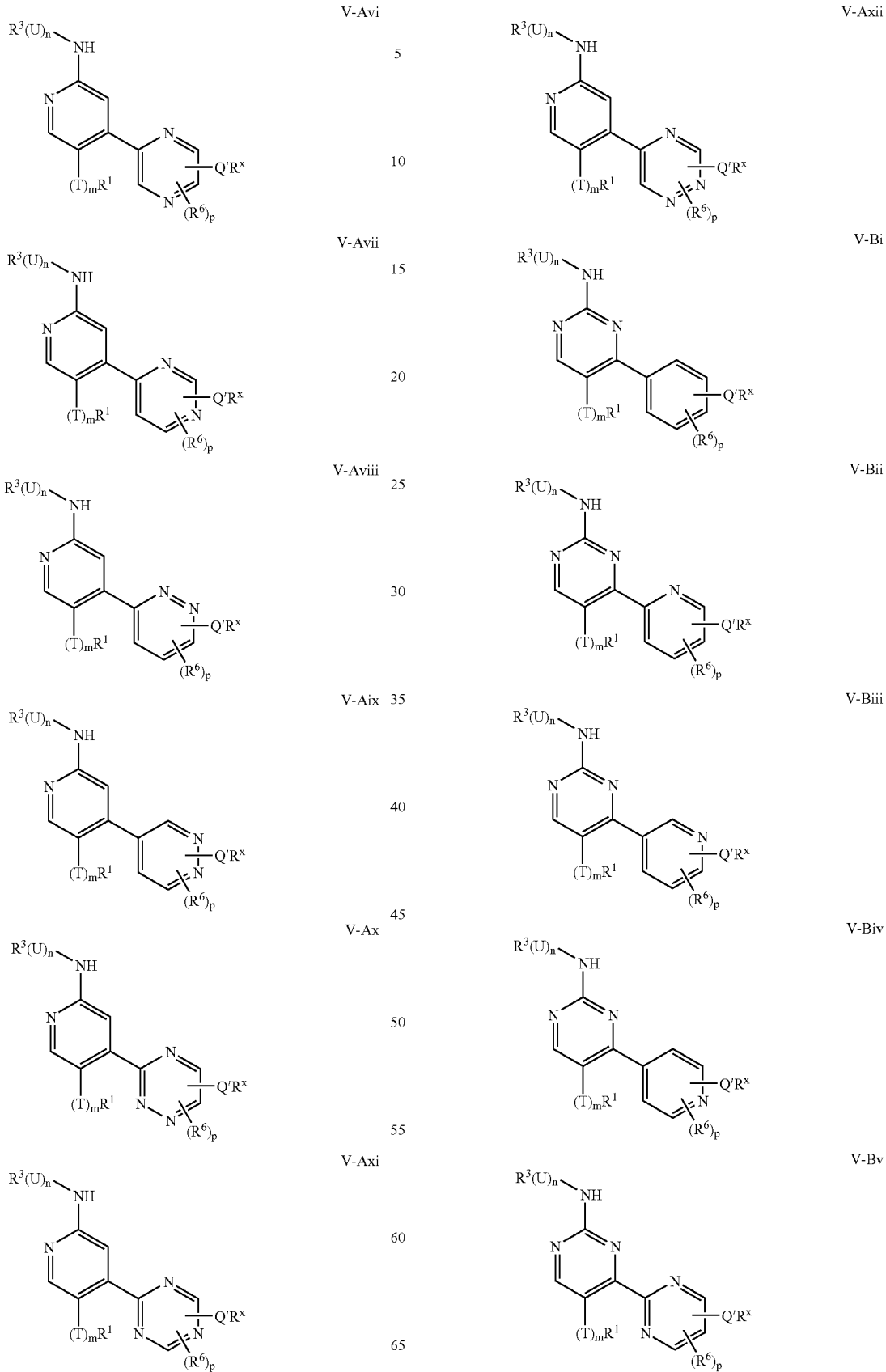

-continued
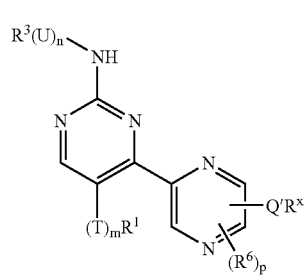
V-Bvi
V-Bvii
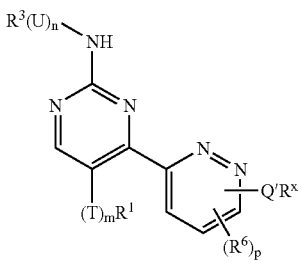
V-Bviii
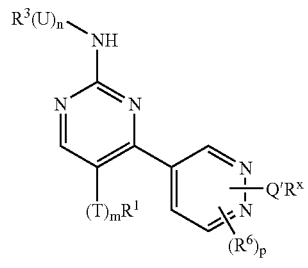
V-Bix
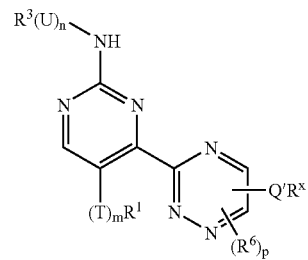
V-Bx
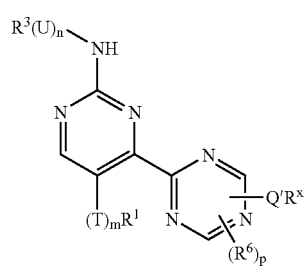
V-Bxi
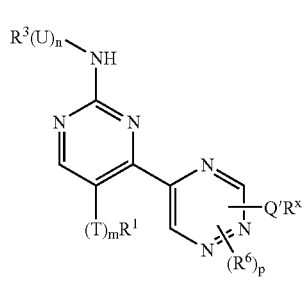
V-Bxii
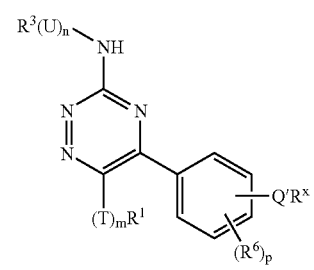
V-Ci
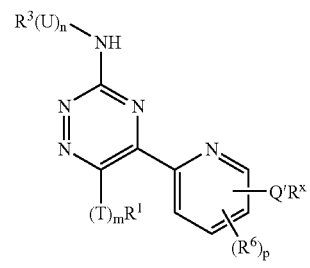
V-Cii
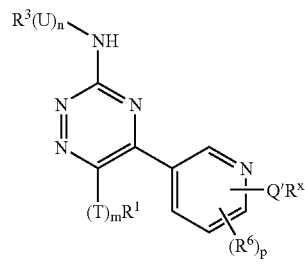
V-Ciii
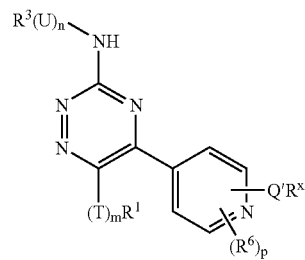
V-Civ
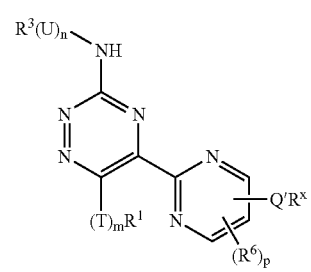
V-Cv

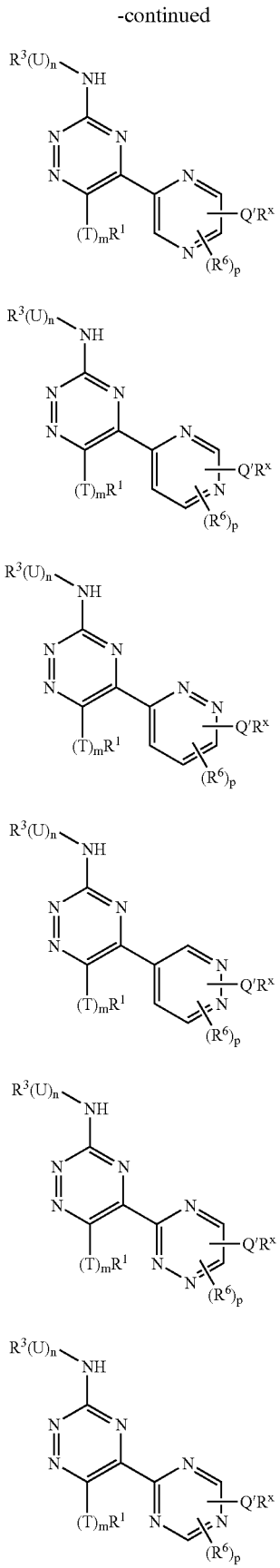

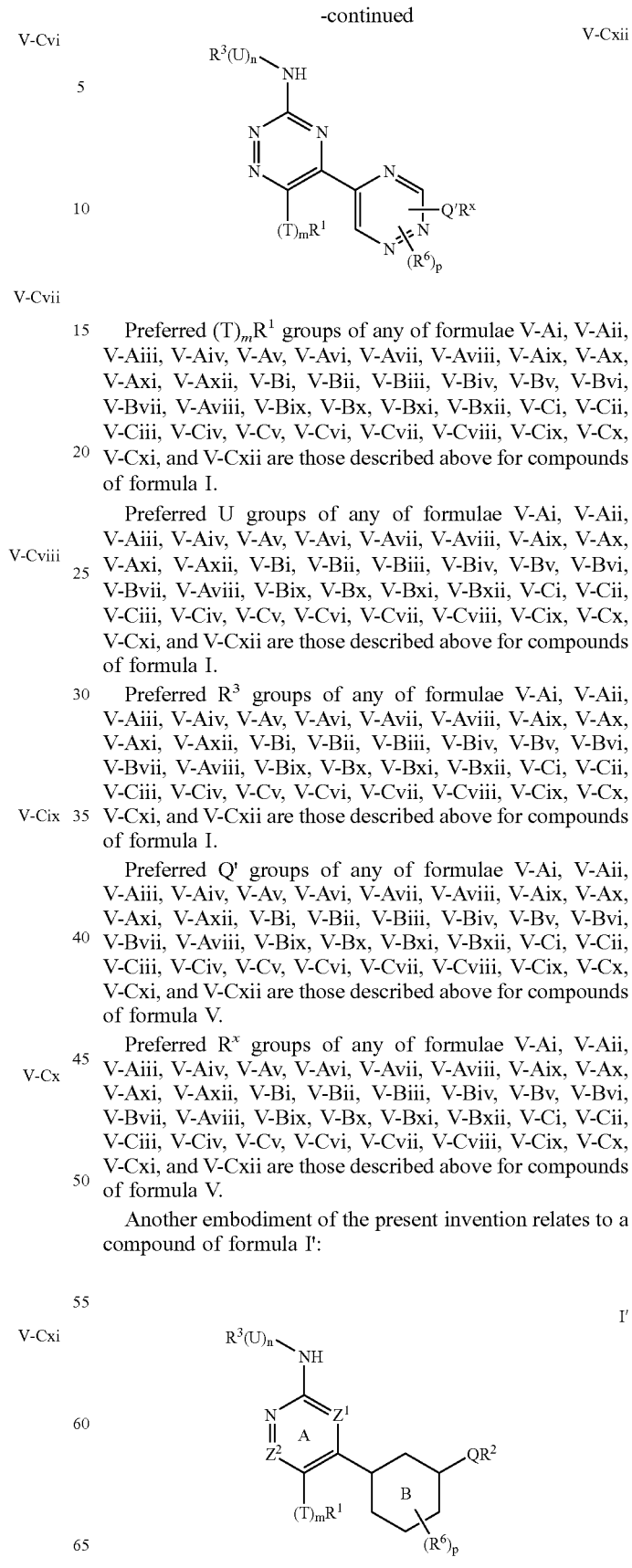

Preferred $(T)_mR^1$ groups of any of formulae V-Ai, V-Aii, V-Aiii, V-Aiv, V-Av, V-Avi, V-Avii, V-Aviii, V-Aix, V-Ax, V-Axi, V-Axii, V-Bi, V-Bii, V-Biii, V-Biv, V-Bv, V-Bvi, V-Bvii, V-Aviii, V-Bix, V-Bx, V-Bxi, V-Bxii, V-Ci, V-Cii, V-Ciii, V-Civ, V-Cv, V-Cvi, V-Cvii, V-Cviii, V-Cix, V-Cx, V-Cxi, and V-Cxii are those described above for compounds of formula I.

Preferred U groups of any of formulae V-Ai, V-Aii, V-Aiii, V-Aiv, V-Av, V-Avi, V-Avii, V-Aviii, V-Aix, V-Ax, V-Axi, V-Axii, V-Bi, V-Bii, V-Biii, V-Biv, V-Bv, V-Bvi, V-Bvii, V-Aviii, V-Bix, V-Bx, V-Bxi, V-Bxii, V-Ci, V-Cii, V-Ciii, V-Civ, V-Cv, V-Cvi, V-Cvii, V-Cviii, V-Cix, V-Cx, V-Cxi, and V-Cxii are those described above for compounds of formula I.

Preferred $R^3$ groups of any of formulae V-Ai, V-Aii, V-Aiii, V-Aiv, V-Av, V-Avi, V-Avii, V-Aviii, V-Aix, V-Ax, V-Axi, V-Axii, V-Bi, V-Bii, V-Biii, V-Biv, V-Bv, V-Bvi, V-Bvii, V-Aviii, V-Bix, V-Bx, V-Bxi, V-Bxii, V-Ci, V-Cii, V-Ciii, V-Civ, V-Cv, V-Cvi, V-Cvii, V-Cviii, V-Cix, V-Cx, V-Cxi, and V-Cxii are those described above for compounds of formula I.

Preferred Q' groups of any of formulae V-Ai, V-Aii, V-Aiii, V-Aiv, V-Av, V-Avi, V-Avii, V-Aviii, V-Aix, V-Ax, V-Axi, V-Axii, V-Bi, V-Bii, V-Biii, V-Biv, V-Bv, V-Bvi, V-Bvii, V-Aviii, V-Bix, V-Bx, V-Bxi, V-Bxii, V-Ci, V-Cii, V-Ciii, V-Civ, V-Cv, V-Cvi, V-Cvii, V-Cviii, V-Cix, V-Cx, V-Cxi, and V-Cxii are those described above for compounds of formula V.

Preferred $R^x$ groups of any of formulae V-Ai, V-Aii, V-Aiii, V-Aiv, V-Av, V-Avi, V-Avii, V-Aviii, V-Aix, V-Ax, V-Axi, V-Axii, V-Bi, V-Bii, V-Biii, V-Biv, V-Bv, V-Bvi, V-Bvii, V-Aviii, V-Bix, V-Bx, V-Bxi, V-Bxii, V-Ci, V-Cii, V-Ciii, V-Civ, V-Cv, V-Cvi, V-Cvii, V-Cviii, V-Cix, V-Cx, V-Cxi, and V-Cxii are those described above for compounds of formula V.

Another embodiment of the present invention relates to a compound of formula I':

or a pharmaceutically acceptable salt thereof, wherein Ring B, $Z^1$, $Z^2$, U, T, m, n, p, Q, $R^1$, $R^2$, $R^3$, and $R^6$ are as defined above.

Accordingly, the present invention relates to compounds of formula I' wherein Ring A is a pyridine (I'-A), pyrimidine (I'-B), or triazine (I'-C) ring as shown below:

I'-A

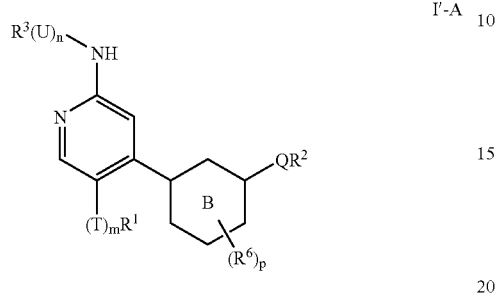

I'-B

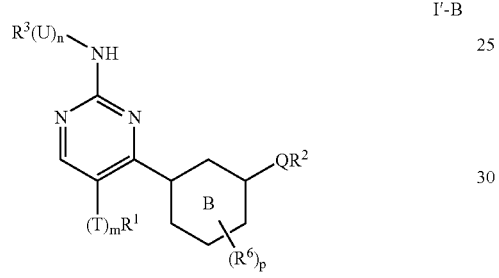

I'-C

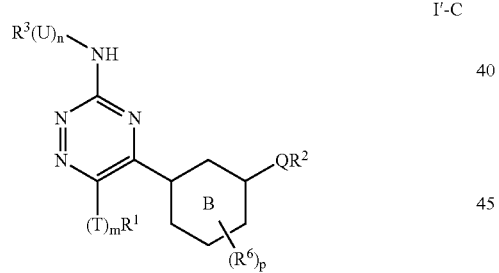

or a pharmaceutically acceptable salt thereof, wherein Ring B, $Z^1$, $Z^2$, U, T, m, n, p, Q, $R^1$, $R^2$, $R^3$, and $R^6$ are as defined above.

Preferred $(T)_mR^1$ groups of any of formulae I'-A, I'-B, and I'-C are those described above for compounds of formula I.

Preferred U groups of any of formulae I'-A, I'-B, and I'-C are those described above for compounds of formula I.

Preferred $R^3$ groups of any of formulae I'-A, I'-B, and I'-C are those described above for compounds of formula I.

Preferred Q groups of any of formulae I'-A, I'-B, and I'-C are those described above for compounds of formula I.

Preferred $R^2$ groups of any of formulae I'-A, I'-B, and I'-C are those described above for compounds of formula I.

According to another embodiment, the present invention relates to the following compounds of formula I':

I'-Ai

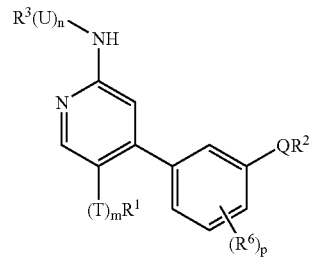

I'-Aii

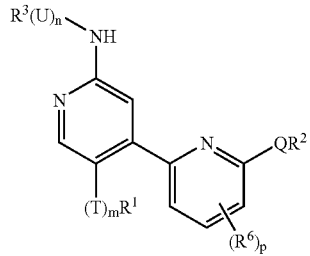

I'-Aiii

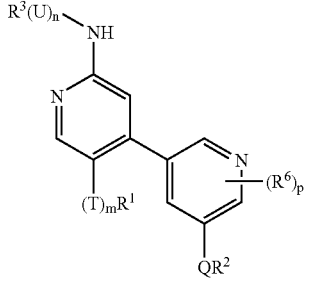

I'-Aiv

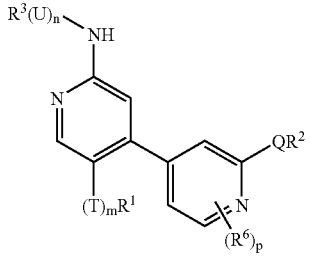

I'-Av

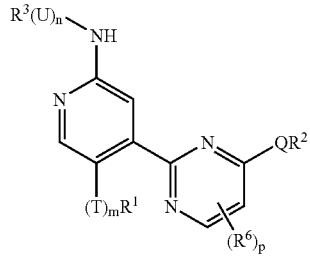

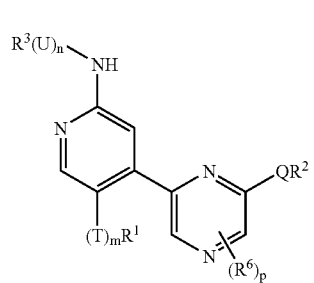
I'-Avi
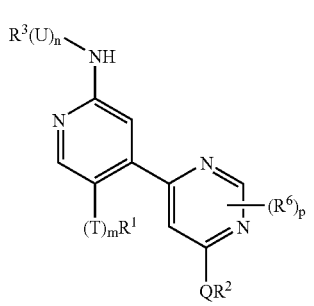
I'-Avii
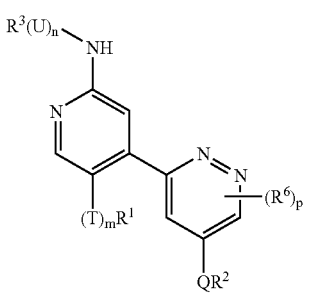
I'-Aviii
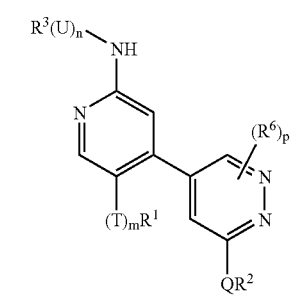
I'-Aix
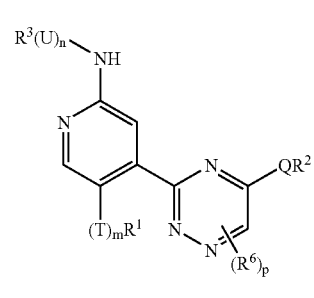
I'-Ax
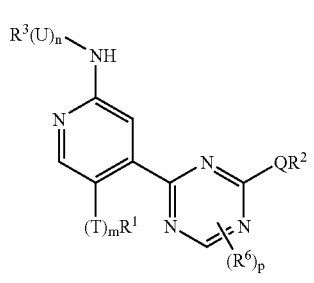
I'-Axi
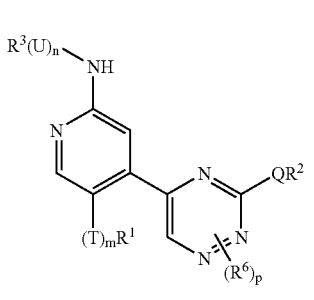
I'-Axii
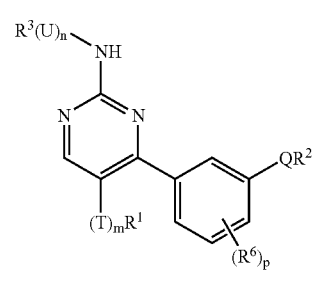
I'-Bi
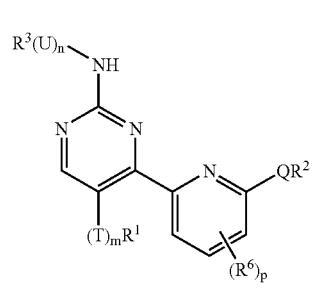
I'-Bii
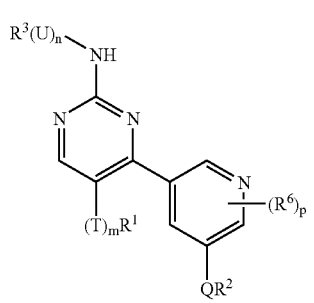
I'-Biii I'-Biv
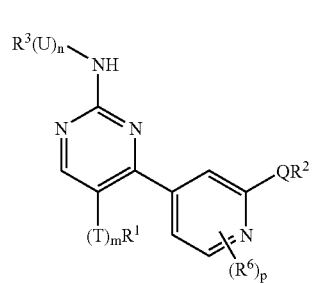
I'-Bv
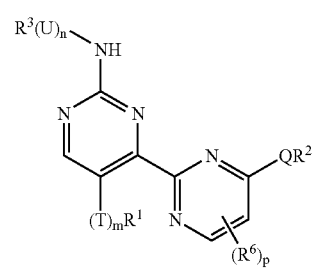
I'-Bvi
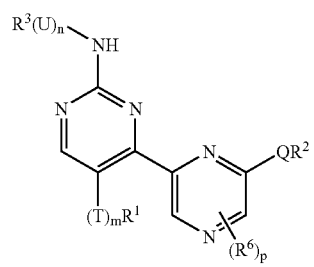
I'-Bvii
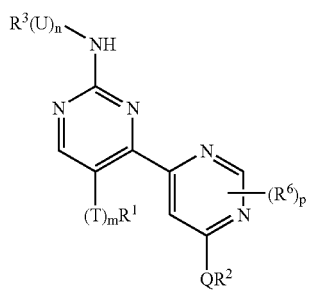
I'-Bviii
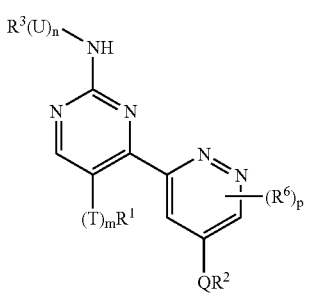
I'-Bix
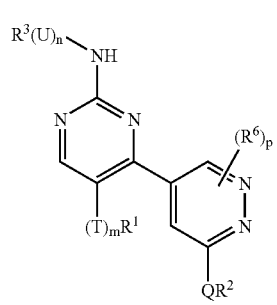
I'-Bx
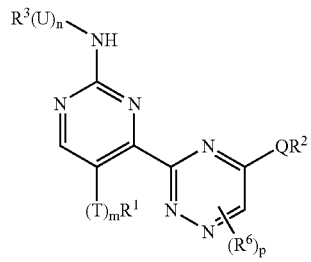
I'-Bxi
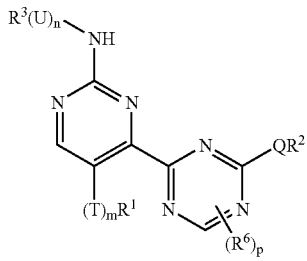
I'-Bxii
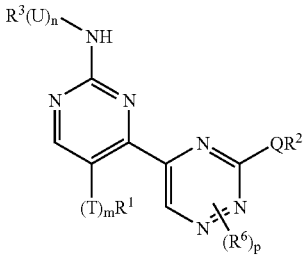
I'-Ci
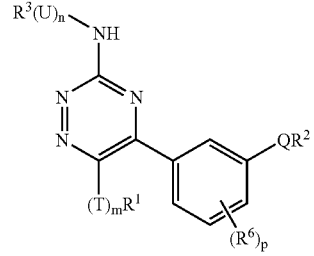
I'-Cii
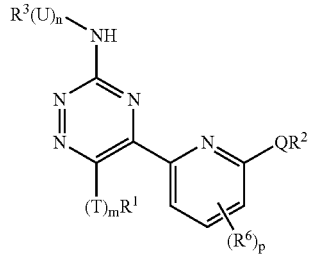

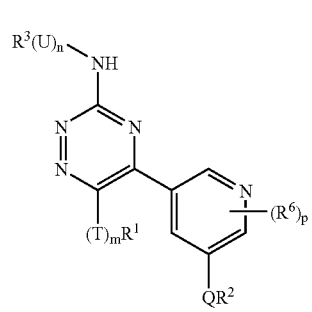 I'-Ciii
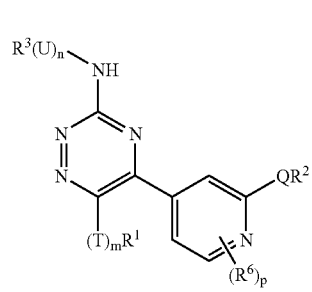 I'-Civ
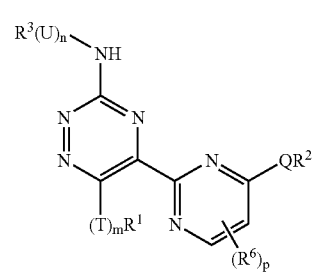 I'-Cv
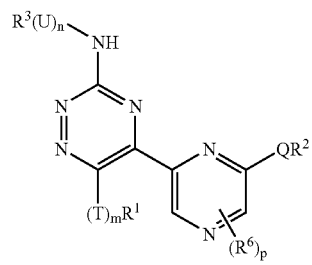 I'-Cvi
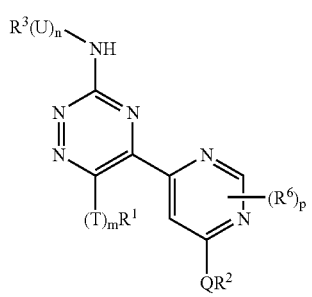 I'-Cvii
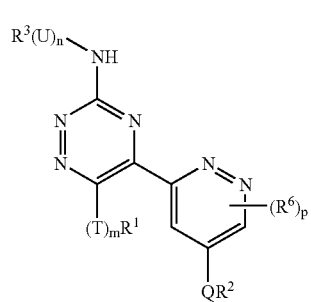 I'-Cviii
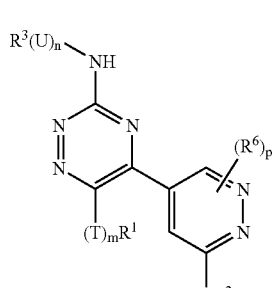 I'-Cix
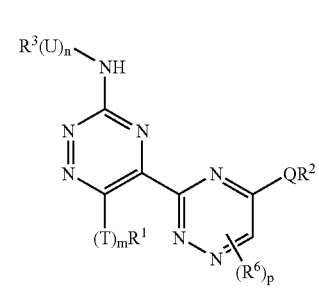 I'-Cx
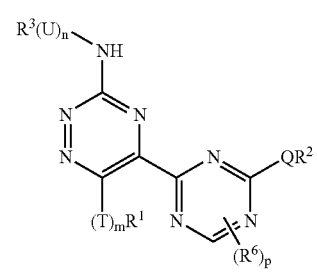 I'-Cxi
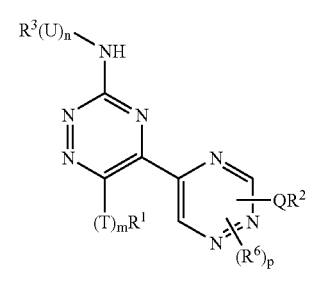 I'-Cxii Preferred $(T)_mR^1$ groups of any of formulae I'-Ai, I'-Aii, I'-Aiii, I'-Aiv, I'-Av, I'-Avi, I'-Avii, I'-Aviii, I'-Aix, I'-Ax, I'-Axi, I'-Axii, I'-Bi, I'-Bii, I'-Biii, I'-Biv, I'-Bv, I'-Bvi, I'-Bvii, I'-Aviii, I'-Bix, I'-Bx, I'-Bxi, I'-Bxii, I'-Ci, I'-Cii, I'-Ciii, I'-Civ, I'-Cv, I'-Cvi, I'-Cvii, I'-Cviii, I'-Cix, I'-Cx, I'-Cxi, and I'-Cxii are those described above for compounds of formula I.

Preferred U groups of any of formulae I'-Ai, I'-Aii, I'-Aiii, I'-Aiv, I'-Av, I'-Avi, I'-Avii, I'-Aviii, I'-Aix, I'-Ax, I'-Axi, I'-Axii, I'-Bi, I'-Bii, I'-Biii, I'-Biv, I'-Bv, I'-Bvi, I'-Bvii, I'-Aviii, I'-Bix, I'-Bx, I'-Bxi, I'-Bxii, I'-Ci, I'-Cii, I'-Ciii, I'-Civ, I'-Cv, I'-Cvi, I'-Cvii, I'-Cviii, I'-Cix, I'-Cx, I'-Cxi, and I'-Cxii are those described above for compounds of formula I.

Preferred $R^3$ groups of any of formulae I'-Ai, I'-Aii, I'-Aiii, I'-Aiv, I'-Av, I'-Avi, I'-Avii, I'-Aviii, I'-Aix, I'-Ax, I'-Axi, I'-Axii, I'-Bi, I'-Bii, I'-Biii, I'-Biv, I'-Bv, I'-Bvi, I'-Bvii, I'-Aviii, I'-Bix, I'-Bx, I'-Bxi, I'-Bxii, I'-Ci, I'-Cii, I'-Ciii, I'-Civ, I'-Cv, I'-Cvi, I'-Cvii, I'-Cviii, I'-Cix, I'-Cx, I'-Cxi, and I'-Cxii are those described above for compounds of formula I.

Preferred Q groups of any of formulae I'-Ai, I'-Aii, I'-Aiii, I'-Aiv, I'-Av, I'-Avi, I'-Avii, I'-Aviii, I'-Aix, I'-Ax, I'-Axi, I'-Axii, I'-Bi, I'-Bii, I'-Biii, I'-Biv, I'-Bv, I'-Bvi, I'-Bvii, I'-Aviii, I'-Bix, I'-Bx, I'-Bxi, I'-Bxii, I'-Ci, I'-Cii, I'-Ciii, I'-Civ, I'-Cv, I'-Cvi, I'-Cvii, I'-Cviii, I'-Cix, I'-Cr, I'-Cxi, and I'-Cxii are those described above for compounds of formula I.

Preferred $R^2$ groups of any of formulae I'-Ai, I'-Aii, I'-Aiii, I'-Aiv, I'-Av, I'-Avi, I'-Avii, I'-Aviii, I'-Aix, I'-Ax, I'-Axi, I'-Axii, I'-Bi, I'-Bii, I'-Biii, I'-Biv, I'-Bv, I'-Bvi, I'-Bvii, I'-Aviii, I'-Bix, I'-Bx, I'-Bxi, I'-Bxii, I'-Ci, I'-Cii, I'-Ciii, I'-Civ, I'-Cv, I'-Cvi, I'-Cvii, I'-Cviii, I'-Cix, I'-Cx, I'-Cxi, and I'-Cxii are those described above for compounds of formula I.

Another embodiment of the present invention relates to a compound of formula I'':

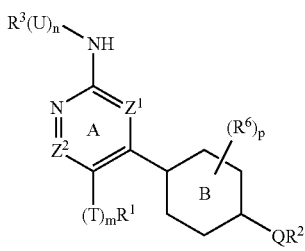

I'' or a pharmaceutically acceptable salt thereof, wherein Ring B, $Z^1$, $Z^2$, U, T, m, n, p, Q, $R^1$, $R^2$, $R^3$, and $R^6$ are as defined above.

Accordingly, the present invention relates to compounds of formula I'' wherein Ring A is a pyridine (I''-A), pyrimidine (I''-B), or triazine (I''-C) ring as shown below:

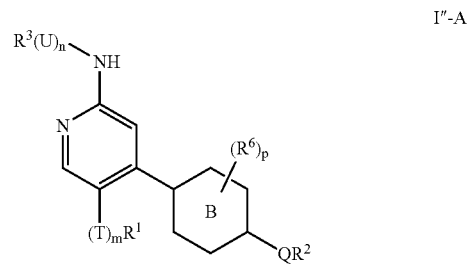

I''-A

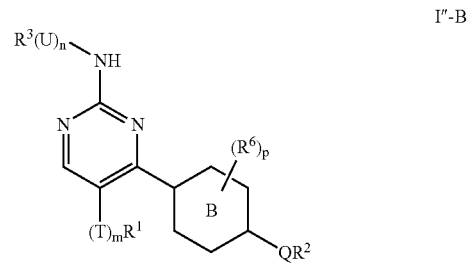

I''-B

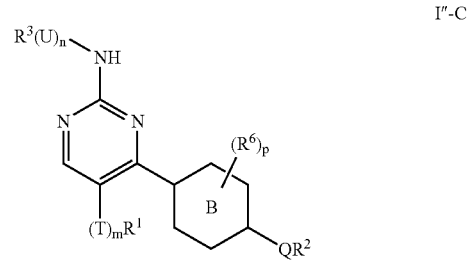

I''-C or a pharmaceutically acceptable salt thereof, wherein $Z^1$, $Z^2$, U, T, m, n, p, Q, $R^1$, $R^2$, $R^3$, and $R^6$ are as defined above.

Preferred $(T)_mR^1$ groups of any of formulae I''-A, I''-B, and I''-C are those described above for compounds of formula I.

Preferred U groups of any of formulae I''-A, I''-B, and I''-C are those described above for compounds of formula I.

Preferred $R^3$ groups of any of formulae I''-A, I''-B, and I''-C are those described above for compounds of formula I.

Preferred Q groups of any of formulae I''-A, I''-B, and I''-C are those described above for compounds of formula I.

Preferred $R^2$ groups of any of formulae I''-A, I''-B, and I''-C are those described above for compounds of formula I.

According to another embodiment, the present invention relates to the following compounds of formula I'':

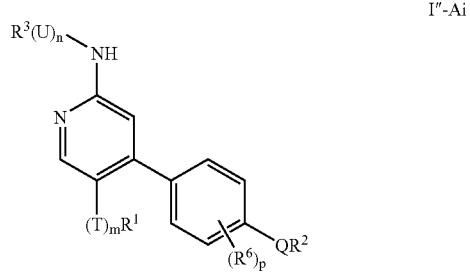

I''-Ai

-continued

-continued

I''-Bx

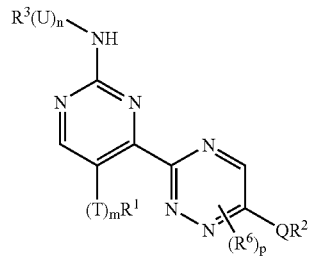

I''-Ci

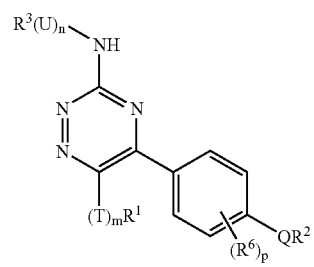

I''-Cii

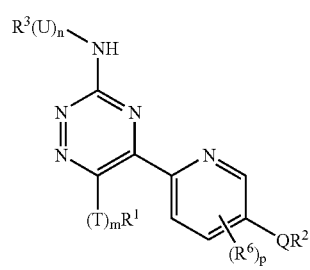

I''-Ciii

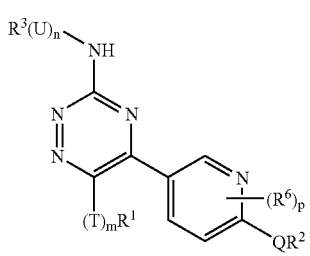

I''-Cv

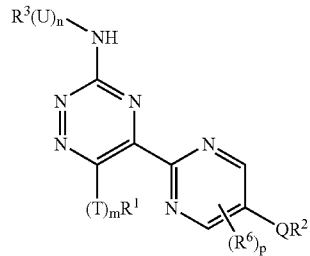

I''-Cvi

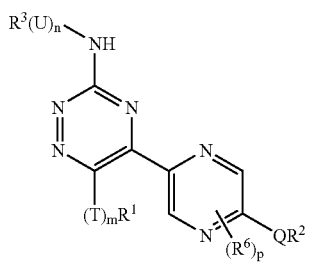

-continued

I''-Cviii

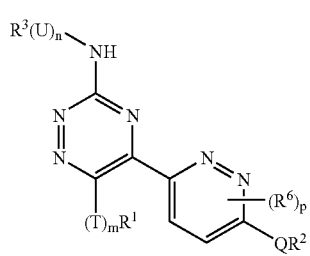

I''-Cx

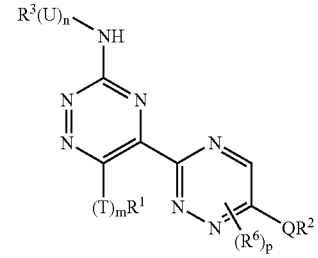

Preferred (T)$_m$R$^1$ groups of any of formulae I''-Ai, I''-Aii, I''-Aiii, I''-Av, I''-Avi, I''-Aviii, I''-Ax, I''-Bi, I''-Bii, I''-Biii, I''-Bv, I''-Bvi, I''-Bviii, I''-Bx, I''-Ci, I''-Cii, I''-Ciii, I''-Cv, I''-Cvi, I''-Cviii, and I''-CAx are those described above for compounds of formula I.

Preferred U groups of any of formulae I''-Ai, I''-Aii, I''-Aiii, I''-Av, I''-Avi, I''-Aviii, I''-Ax, I''-Bi, I''-Bii, I''-Biii, I''-Bv, I''-Bvi, I''-Bviii, I''-Bx, I''-Ci, I''-Cii, I''-Ciii, I''-Cv, I''-Cvi, I''-Cviii, and I''-CAx are those described above for compounds of formula I.

Preferred R$^3$ groups of any of formulae I''-Ai, I''-Aii, I''-Aiii, I''-Av, I''-Avi, I''-Aviii, I''-Ax, I''-Bi, I''-Bii, I''-Biii, I''-Bv, I''-Bvi, I''-Bviii, I''-Bx, I''-Ci, I''-Cii, I''-Ciii, I''-Cv, I''-Cvi, I''-Cviii, and I''-CAx are those described above for compounds of formula I.

Preferred Q groups of any of formulae I''-Ai, I''-Aii, I''-Aiii, I''-Av, I''-Avi, I''-Aviii, I''A, I''-Bi, I''-Bii, I''-Biii, I''-Bv, I''-Bvi, I''-Bviii, I''-Bx, I''-Ci, I''-Cii, I''-Ciii, I''-Cv, I''-Cvi, I''-Cviii, and I''-CAx are those described above for compounds of formula I.

Preferred R$^2$ groups of any of formulae I''-Ai, I''-Aii, I''-Aiii, I''-Av, I''-Avi, I''-Aviii, I''-Ax, I''-Bi, I''-Bii, I''-Biii, I''-Bv, I''-Bvi, I''-Bviii, I''-Bx, I''-Ci, I''-Cii, I''-Ciii, I''-Cv, I''-Cvi, I''-Cviii, and I''-CAx are those described above for compounds of formula I.

Another preferred embodiment of this invention relates to a compound of formula II:

II

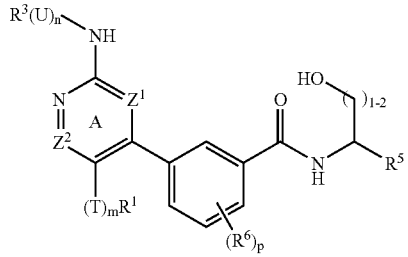

or a pharmaceutically acceptable salt thereof, wherein:

$Z^1$ and $Z^2$ are each independently selected from N or CH;

T is a saturated or unsaturated $C_{1-6}$ alkylidene chain wherein:
  up to two methylene units of the chain are optionally and independently replaced by —C(O)—, —C(O)C(O)—, —C(O)NR—, —C(O)NRNR—, —CO$_2$—, —OC(O)—, —NRCO$_2$—, —O—, —NRC(O)NR—, —OC(O)NR—, —NRNR—, —NRC(O)—, —S—, —SO—, —SO$_2$—, —NR—, —SO$_2$NR—, or —NRSO$_2$—;

U is selected from —NR—, —NRC(O)—, —NRC(O)NR—, —NRCO$_2$—, —O—, —C(O)NR—, —C(O)—, —CO$_2$—, —OC(O)—, —NRSO$_2$—, —SO$_2$NR—, —NRSO$_2$NR—, or —SO$_2$—;

m and n are each independently selected from zero or one;

p is selected from 0, 1, 2, 3, or 4;

$R^1$ is selected from R or Ar;

each R is independently selected from hydrogen or an optionally substituted $C_{1-6}$ aliphatic group, or:
  two R on the same nitrogen are taken together with the nitrogen to form a 5-8 membered heterocyclyl or heteroaryl ring having 1-3 heteroatoms independently selected from nitrogen, oxygen, or sulfur;

each Ar is an optionally substituted ring selected from a 6-10 membered aryl ring, a 5-10 membered heteroaryl ring having 1-4 heteroatoms independently selected from nitrogen, oxygen, or sulfur, or a 3-10 membered heterocyclyl ring having 1-4 heteroatoms independently selected from nitrogen, oxygen, or sulfur;

y is 0-6;

$R^3$ is selected from R, Ar, —(CH$_2$)$_y$CH(R$^5$)$_2$, or CN;

each $R^5$ is independently selected from optionally subtituted $C_{1-6}$ aliphatic, Ar, OR, CO$_2$R, (CH$_2$)$_y$N(R)$_2$, N(R)$_2$, SR, NRC(O)R, NRC(O)N(R)$_2$, C(O)N(R)$_2$, SO$_2$R, NRSO$_2$R, C(O)R, CN, or SO$_2$N(R)$_2$; and each $R^6$ is independently selected from R, F, Cl, N(R)$_2$, OR, SR, NRC(O)R, NRC(O)N(R)$_2$, C(O)N(R)$_2$, SO$_2$R, NRSO$_2$R, C(O)R, CN, SO$_2$N(R)$_2$, N(R)O, ON(R), or N(R)N(R).

Accordingly, the present invention relates to compounds of formula II wherein Ring A is a pyridine (II-A), pyrimidine (II-B), or triazine (II-C) ring as shown below:

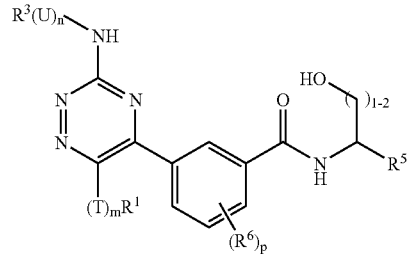

II-A

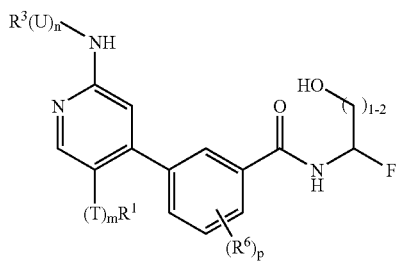

II-B

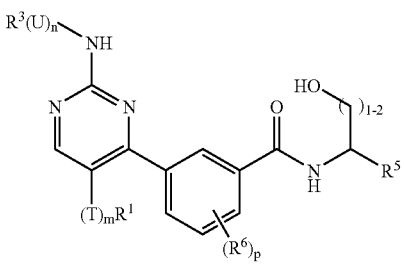

II-C

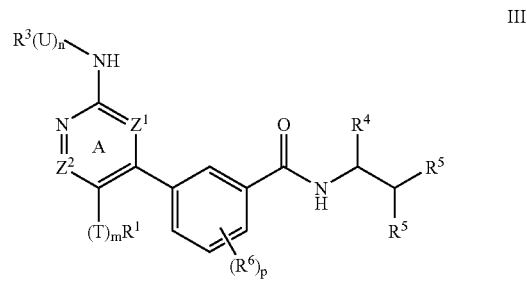

or a pharmaceutically acceptable salt thereof, wherein T, U, m, n, p, $R^1$, $R^3$, $R^5$, and $R^6$ are as defined above.

Preferred $T_mR^1$ groups of any of formulae II-A, II-B, and II-C are those described above for compounds of formula I.

Preferred $R^3$ groups of any of formulae II-A, II-B, and II-C are those described above for compounds of formula I.

Preferred $R^5$ groups of any of formulae II-A, II-B, and II-C are those described above for compounds of formula I.

Another preferred embodiment of this invention relates to a compound of formula III:

III or a pharmaceutically acceptable salt thereof, wherein:

$Z^1$ and $Z^2$ are each independently selected from N or CH;

T and Q are each independently selected from a saturated or unsaturated $C_{1-6}$ alkylidene chain wherein:
  up to two methylene units of the chain are optionally and independently replaced by —C(O)—, —C(O)C(O)—, —C(O)NR—, —C(O)NRNR—, —CO$_2$—, —OC(O)—, —NRCO$_2$—, —O—, —NRC(O)NR—, —OC(O)NR—, —NRNR—, —NRC(O)—, —S—, —SO—, —SO$_2$—, —NR—, —SO$_2$NR—, or —NRSO$_2$—;

U is selected from —NR—, —NRC(O)—, —NRC(O)NR—, —NRCO$_2$—, —O—, —C(O)NR—, —C(O)—, —CO$_2$—, —OC(O)—, —NRSO$_2$—, —SO$_2$NR—, —NRSO$_2$NR—, or —SO$_2$—;

m and n are each independently selected from zero or one;

p is selected from 0, 1, 2, 3, or 4;

$R^1$ is selected from R or Ar;

each R is independently selected from hydrogen or an optionally substituted $C_{1-6}$ aliphatic group, or:
  two R on the same nitrogen are taken together with the nitrogen to form a 5-8 membered heterocyclyl or heteroaryl ring having 1-3 heteroatoms independently selected from nitrogen, oxygen, or sulfur;

each Ar is an optionally substituted ring selected from a 6-10 membered aryl ring, a 5-10 membered heteroaryl ring having 1-4 heteroatoms independently selected from nitrogen, oxygen, or sulfur, or a 3-10 membered heterocyclyl ring having 1-4 heteroatoms independently selected from nitrogen, oxygen, or sulfur;

$R^4$ is selected from R, $(CH_2)_wOR$, $(CH_2)_wN(R)_2$, or $(CH_2)_wSR$, wherein w is 0-4;

y is 0-6;

$R^3$ is selected from R, Ar, —$(CH_2)_yCH(R^5)_2$, or CN;

each $R^5$ is independently selected from optionally substituted $C_{1-6}$ aliphatic, Ar, OR, $CO_2R$, $(CH_2)_yN(R)_2$, $N(R)_2$, SR, NRC(O)R, NRC(O)N(R)$_2$, C(O)N(R)$_2$, SO$_2$R, NRSO$_2$R, C(O)R, CN, or SO$_2$N(R)$_2$; and each $R^6$ is independently selected from R, F, Cl, N(R)$_2$, OR, SR, NRC(O)R, NRC(O)N(R)$_2$, C(O)N(R)$_2$, SO$_2$R, NRSO$_2$R, C(O)R, CN, SO$_2$N(R)$_2$, N(R)O, ON(R), or N(R)N(R).

Accordingly, the present invention relates to compounds of formula III wherein Ring A is a pyridine (III-A), pyrimidine (III-B), or triazine (III-C) ring as shown below:

III-A

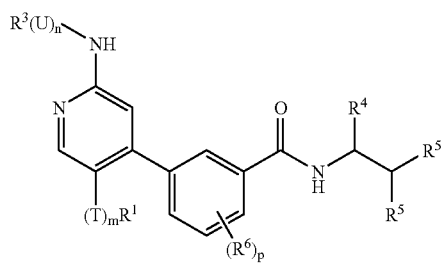

III-B

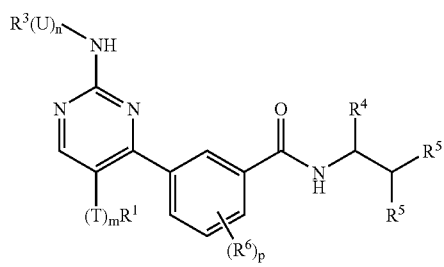

III-C

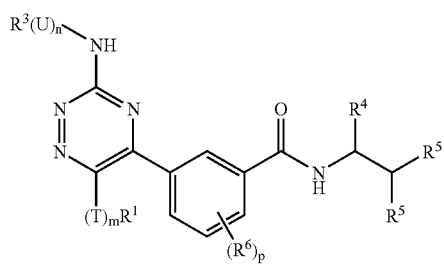

or a pharmaceutically acceptable salt thereof, wherein T, U, m, n, p, $R^1$, $R^3$, $R^4$, $R^5$, and $R^6$ are as defined above.

Preferred $(T)_mR^1$ groups of any of formulae III-A, III-B, and III-C are those described above for compounds of formula I.

Preferred U groups of any of formulae III-A, III-B, and III-C are those described above for compounds of formula I.

Preferred $R^3$ groups of any of formulae III-A, III-B, and III-C are those described above for compounds of formula I.

Preferred $R^5$ groups of any of formulae III-A, III-B, and III-C are those described above for compounds of formula I.

Preferred $R^4$ groups of any of formulae III-A, III-B, and III-C are those described above for compounds of formula I.

Another preferred embodiment of this invention relates to a compound of formula IV:

IV

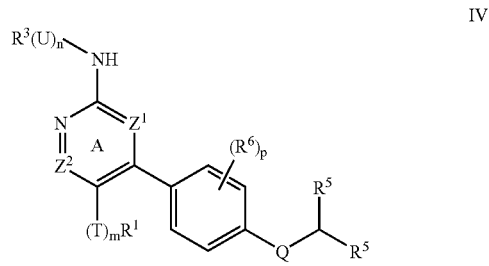

or a pharmaceutically acceptable salt thereof, wherein:

$Z^1$ and $Z^2$ are each independently selected from N or CH;

Q is selected from NRC(O), C(O)NR, NRSO$_2$, or SO$_2$NR;

T is a saturated or unsaturated $C_{1-6}$ alkylidene chain wherein:
  up to two methylene units of the chain are optionally and independently replaced by —C(O)—, —C(O)C(O)—, —C(O)NR—, —C(O)NRNR—, —CO$_2$—, —OC(O)—, —NRCO$_2$—, —O—, —NRC(O)NR—, —OC(O)NR—, —NRNR—, —NRC(O)—, —S—, —SO—, —SO$_2$—, —NR—, —SO$_2$NR—, or —NRSO$_2$—;

U is selected from —NR—, —NRC(O)—, —NRC(O)NR—, —NRCO$_2$—, —O—, —C(O)NR—, —C(O)—, —CO$_2$—, —OC(O)—, —NRSO$_2$—, —SO$_2$NR—, —NRSO$_2$NR—, or —SO$_2$—;

m and n are each independently selected from zero or one;

p is selected from 0, 1, 2, 3, or 4;

$R^1$ is selected from R or Ar;

each R is independently selected from hydrogen or an optionally substituted $C_{1-6}$ aliphatic group, or:
  two R on the same nitrogen are taken together with the nitrogen to form a 5-8 membered heterocyclyl or heteroaryl ring having 1-3 heteroatoms independently selected from nitrogen, oxygen, or sulfur;

each Ar is an optionally substituted ring selected from a 6-10 membered aryl ring, a 5-10 membered heteroaryl ring having 1-4 heteroatoms independently selected from nitrogen, oxygen, or sulfur, or a 3-10 membered heterocyclyl ring having 1-4 heteroatoms independently selected from nitrogen, oxygen, or sulfur;

y is 0-6;

$R^3$ is selected from R, Ar, —$(CH_2)_yCH(R^5)_2$, or CN;

each $R^5$ is independently selected from optionally substituted $C_{1-6}$ aliphatic, Ar, OR, $CO_2R$, $(CH_2)_yN(R)_2$, $N(R)_2$, SR, NRC(O)R, NRC(O)N(R)$_2$, C(O)N(R)$_2$, SO$_2$R, NRSO$_2$R, C(O)R, CN, or SO$_2$N(R)$_2$; and each R is independently selected from R, F, Cl, N(R)$_2$, OR, SR, NRC(O)R, NRC(O)N(R)$_2$, C(O)N(R)$_2$, SO$_2$R, NRSO$_2$R, C(O)R, CN, SO$_2$N(R)$_2$, N(R)O, ON(R), or N(R)N(R).

Accordingly, the present invention relates to compounds of formula IV wherein Ring A is a pyridine (IV-A), pyrimidine (IV-B), or triazine (IV-C) ring as shown below:

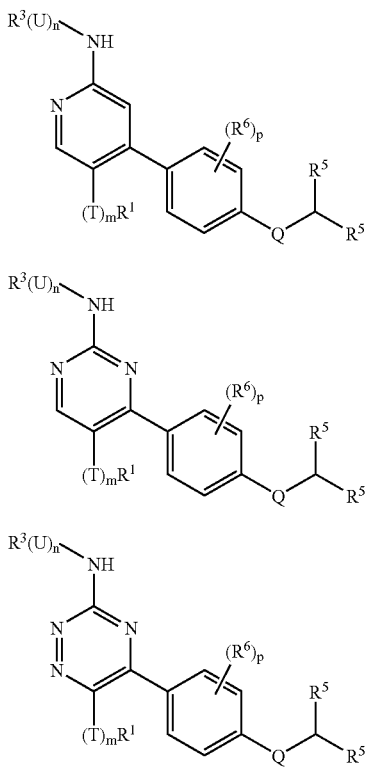

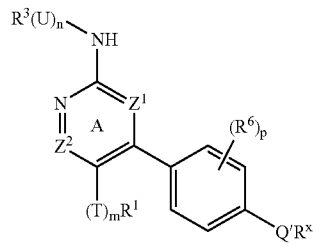

or a pharmaceutically acceptable salt thereof, wherein Q, T, U, m, n, p, $R^1$, $R^3$, $R^5$, and $R^6$ are as defined above.

Preferred Q groups of any of formulae IV-A, IV-B, and IV-C are selected from NRC(O) or C(O)NR. More preferably, Q is NHC(O) or C(O)NH.

Preferred $T_mR$ groups of any of formulae IV-A, IV-B, and IV-C are those described above for compounds of formula I.

Preferred $R^3$ groups of any of formulae IV-A, IV-B, and IV-C are those described above for compounds of formula I.

Preferred $R^5$ groups of any of formulae IV-A, IV-B, and IV-C are those described above for compounds of formula I.

More preferred $R^5$ groups of any of formulae IV-A, IV-B, and IV-C are selected from $C_{5-6}$ cycloalkyl, phenyl, a 5-9 membered heteroaryl ring having 1-2 heteroatoms independently selected from nitrogen, oxygen, or sulfur, or a 5-6 membered heterocyclic ring having 1-2 heteroatoms independently selected from nitrogen, oxygen, or sulfur. Examples of such more preferred $R^5$ groups are pyridin-3-yl, pyridin-4-yl, morphlin-4-yl, thiomorpholin-4-yl, imidazolyl, furan-2-yl, 1,2,3,4-tetrahydroisoquinoline, tetrahydrofuran-2-yl, cyclohexyl, or phenyl, wherein each group is optionally substituted.

According to another preferred embodiment, one of the $R^5$ groups of any of formulae IV-A, IV-B, and IV-C is selected from phenyl or a 5-9 membered heteroaryl ring having 1-2 heteroatoms independently selected from nitrogen, oxygen, or sulfur, and the other of the $R^5$ groups of any of formulae IV-A, IV-B, and IV-C is selected from a 5-6 membered heterocyclic ring having 1-2 heteroatoms independently selected from nitrogen, oxygen, or sulfur. More preferably one of the $R^5$ groups of any of formulae IV-A, IV-B, and IV-C is selected from optionally substituted phenyl, pyridyl, thiazolyl, imidazolyl, or furanyl and the other of the $R^5$ groups of any of formulae IV-A, IV-B, and IV-C is selected from optionally substituted morpholinyl, thiomorpholinyl, piperidinyl, piperazinyl, or pyrrolidinyl.

Another embodiment of this invention relates to a compound of formula V':

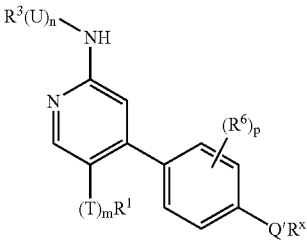

or a pharmaceutically acceptable salt thereof, wherein $Z^1$, $Z^2$, U, T, m, n, p, Q', $R^1$, $R^x$, $R^3$, and $R^6$ are as defined above.

Accordingly, the present invention relates to compounds of formula V' wherein Ring A is a pyridine (V'-A), pyrimidine (V'-B), or triazine (V'-C) ring as shown below:

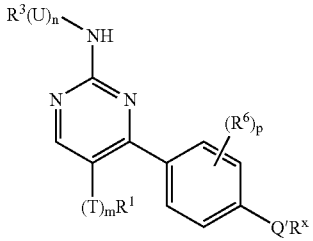

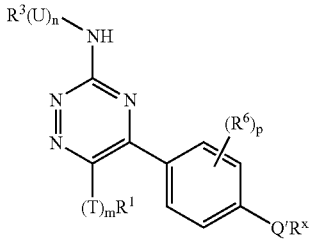

or a pharmaceutically acceptable salt thereof, wherein Q', T, U, m, n, p, $R^1$, $R^3$, $R^x$, and $R^6$ are as defined above.

Preferred $(T)_mR^1$ groups of any of formulae V'-A, V'-B, and V'-C are those described above for compounds of formula I.

Preferred U groups of any of formulae V'-A, V'-B, and V'-C are those described above for compounds of formula I.

Preferred $R^3$ groups of any of formulae V'-A, V'-B, and V'-C are those described above for compounds of formula I.

Preferred Q' groups of any of formulae V'-A, V'-B, and V'-C are those described above for compounds of formula V.

Preferred R$^x$ groups of any of formulae V'-A, V'-B, and V'-C are those described above for compounds of formula V.

Another embodiment of this invention relates to a compound of formula VI:

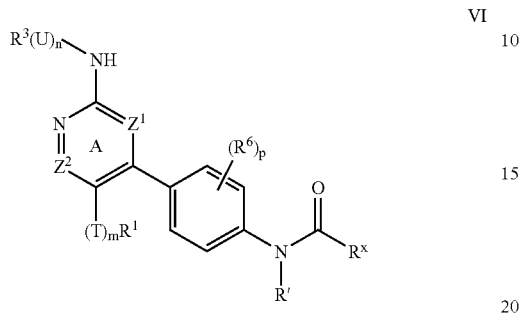

VI or a pharmaceutically acceptable salt thereof, wherein:

T is a saturated or unsaturated C$_{1-6}$ alkylidene chain wherein:
  up to two methylene units of the chain are optionally and independently replaced by —C(O)—, —C(O)C(O)—, —C(O)NR—, —C(O)NRNR—, —CO$_2$—, —OC(O)—, —NRCO$_2$—, —O—, —NRC(O)NR—, —OC(O)NR—, —NRNR—, —NRC(O)—, —S—, —SO—, —SO$_2$—, —NR—, —SO$_2$NR—, or —NRSO$_2$—;

each R is independently selected from hydrogen or an optionally substituted C$_{1-6}$ aliphatic group, or:
  two R on the same nitrogen are taken together with the nitrogen to form a 5-8 membered heterocyclyl or heteroaryl ring having 1-3 heteroatoms independently selected from nitrogen, oxygen, or sulfur;

each R' is independently selected from a C$_{1-6}$ aliphatic group, wherein said aliphatic group is substituted with one Ar group and optionally substituted with 1-2 additional groups independently selected from halogen, —OR, —SR, —NO$_2$, —CN, —N(R)$_2$, —NRC(O)R, —NRC(O)N(R)$_2$, —NRCO$_2$R, —NRNRC(O)R, —NRNRC(O)N(R)$_2$, —NRNRCO$_2$R, —C(O)C(O)R, —C(O)CH$_2$C(O)R, —CO$_2$R, or —C(O)R;

U is selected from —NR—, —NRC(O)—, —NRC(O)NR—, —NRCO$_2$—, —O—, —C(O)NR—, —C(O)—, —CO$_2$—, —OC(O)—, —NRSO$_2$—, —SO$_2$NR—, —NRSO$_2$NR—, or —SO$_2$—;

m and n are each independently selected from zero or one;

p is selected from 0, 1, 2, 3, or 4;

R$^1$ is selected from R or Ar;

each Ar is an optionally substituted ring selected from a 6-10 membered aryl ring, a 5-10 membered heteroaryl ring having 1-4 heteroatoms independently selected from nitrogen, oxygen, or sulfur, or a 3-10 membered heterocyclyl ring having 1-4 heteroatoms independently selected from nitrogen, oxygen, or sulfur;

y is 0-6;

R$^x$ is —(CH$_2$)$_y$R$^5$

R$^3$ is selected from R, Ar, —(CH$_2$)$_w$CH(R$^5$)$_2$, or CN;

w is 0-4;

each R$^5$ is independently selected from optionally substituted C$_{1-6}$ aliphatic, Ar, OR, CO$_2$R, (CH$_2$)$_y$N(R)$_2$, N(R)$_2$, SR, NRC(O)R, NRC(O)N(R)$_2$, C(O)N(R)$_2$, SO$_2$R, NRSO$_2$R, C(O)R, CN, or SO$_2$N(R)$_2$; and each R$^6$ is independently selected from R, F, Cl, N(R)$_2$, OR, SR, NRC(O)R, NRC(O)N(R)$_2$, C(O)N(R)$_2$, SO$_2$R, NRSO$_2$R, C(O)R, CN, SO$_2$N(R)$_2$, N(R)O, ON(R), or N(R)N(R).

Accordingly, the present invention relates to compounds of formula VI wherein Ring A is a pyridine (VI-A), pyrimidine (VI-B), or triazine (VI-C) ring as shown below:

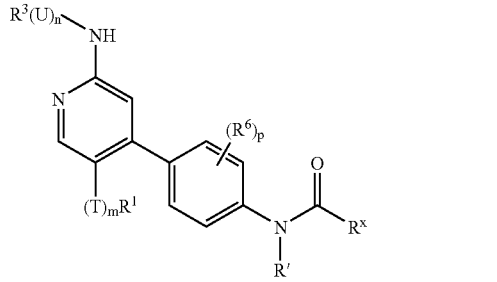

VI-A

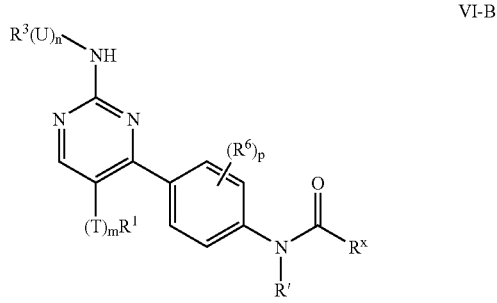

VI-B

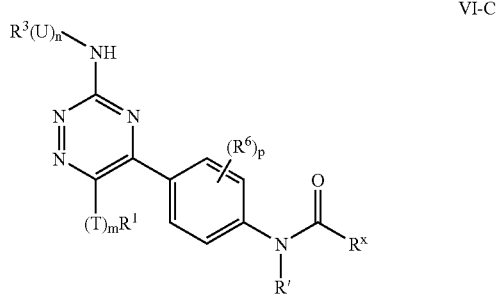

VI-C or a pharmaceutically acceptable salt thereof, wherein U, T, m, n, p, R', R$^1$, R$^x$, R$^3$, and R$^6$ are as defined above.

Preferred (T)$_m$R$^1$ groups of any of formulae VI-A, VI-B, and VI-C are those described above for compounds of formula I.

Preferred U groups of any of formulae VI-A, VI-B, and VI-C are those described above for compounds of formula I.

Preferred R$^3$ groups of any of formulae VI-A, VI-B, and VI-C are those described above for compounds of formula I.

Preferred R' groups of any of formulae VI-A, VI-B, and VI-C are those described above for compounds of formula V.

Preferred R$^x$ groups of any of formulae VI-A, VI-B, and VI-C are those described above for compounds of formula V.

Exemplary structures of compounds of formula I' are set forth in Table 1 below.

TABLE 1
Compounds of Formula I'
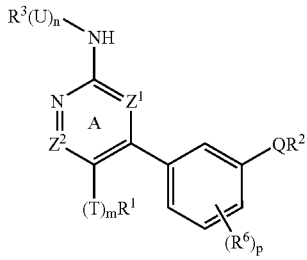
I'
| No. I'- | R³Uₙ | TₘR¹ | Q-R² |
|---|---|---|---|
| 1 | phenyl | H | 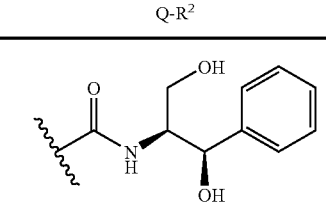 |
| 2 | phenyl | H | 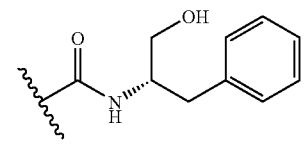 |
| 3 | phenyl | H | 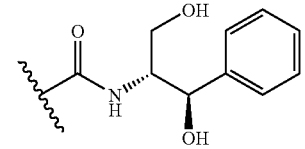 |
| 4 | phenyl | H | 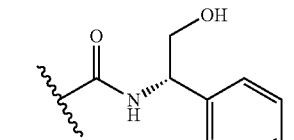 |
| 5 | phenyl | H | 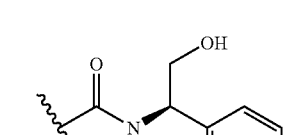 |
| 6 | phenyl | H | 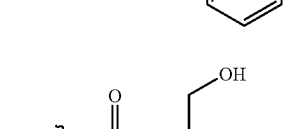 |
| 7 | phenyl | H | |

TABLE 1-continued
Compounds of Formula I'
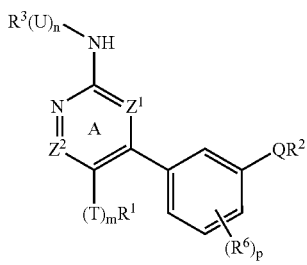
I'
| No. I'- | R³Uₙ | TₘR¹ | Q-R² |
|---|---|---|---|
| 8 | phenyl | H | 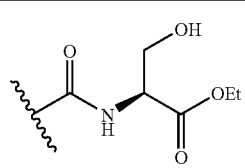 |
| 9 | phenyl | H | 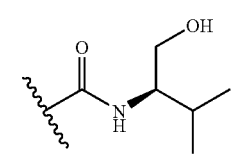 |
| 10 | phenyl | H | 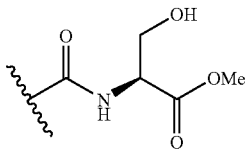 |
| 11 | phenyl | H | 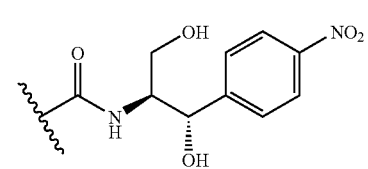 |
| 12 | phenyl | H | 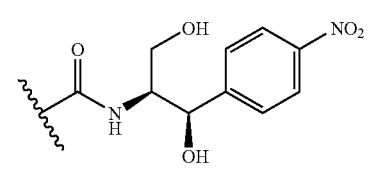 |
| 13 | phenyl | H | 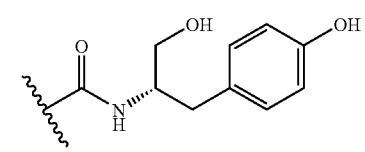 |
| 14 | phenyl | H | 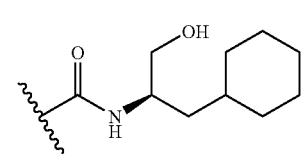 |

TABLE 1-continued

Compounds of Formula I'

| No. I'- | R³Uₙ | TₘR¹ | Q-R² |
|---|---|---|---|
| 15 | phenyl | H | (2-hydroxy-1-(hydroxymethyl)-2-(4-methylthiophenyl)ethyl)amide |
| 16 | phenyl | H | (1-(hydroxymethyl)-2-methylpropyl)amide |
| 17 | phenyl | H | (1-(hydroxymethyl)-2-methylbutyl)amide |
| 18 | H | methyl | (2-hydroxy-1-phenylethyl)amide |
| 19 | H | methyl | (2-hydroxy-1-phenylethyl)amide |
| 20 | H | methyl | (2-hydroxy-1-phenylethyl)amide |
| 21 | phenyl | methyl | (2-hydroxy-1-phenylethyl)amide |

TABLE 1-continued
Compounds of Formula I'
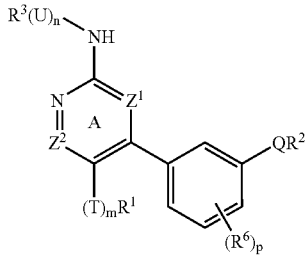
| No. I'- | R³Uₙ | TₘR¹ | Q-R² |
|---|---|---|---|
| 22 | ethyl | methyl | 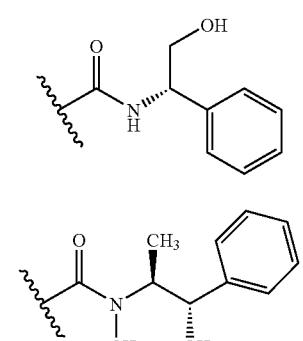 |
| 23 | H | H | 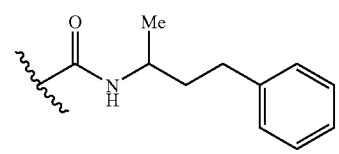 |
| 24 | phenyl | methyl | 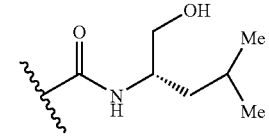 |
| 25 | methyl | methyl | 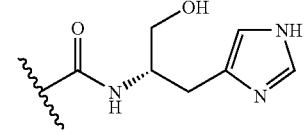 |
| 26 | phenyl | methyl | 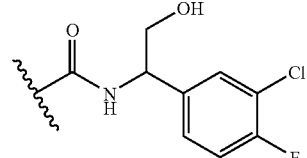 |
| 27 | methyl | methyl | 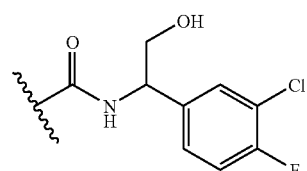 |
| 28 | phenyl | methyl | |

TABLE 1-continued

Compounds of Formula I'

| No. I'- | R³Uₙ | TₘR¹ | Q-R² |
|---|---|---|---|
| 29 | 3-F-phenyl | methyl | (S)-NHCH(CH₂OH)(phenyl) amide |
| 30 | 3-OMe-phenyl | methyl | (S)-NHCH(CH₂OH)(phenyl) amide |
| 31 | 3-OH-phenyl | methyl | (S)-NHCH(CH₂OH)(phenyl) amide |
| 32 | benzo[1,3]dioxol-5-yl | methyl | (S)-NHCH(CH₂OH)(phenyl) amide |
| 34 | 4-SO₂NH₂-phenyl | methyl | (S)-NHCH(CH₂OH)(phenyl) amide |
| 35 | trans-4-OH-cyclohexyl | methyl | (S)-NHCH(CH₂OH)(phenyl) amide |

TABLE 1-continued

Compounds of Formula I'

| No. I'- | R³Uₙ | TₘR¹ | Q-R² |
|---|---|---|---|
| 36 | phenyl | methyl | -C(O)NH-CH(CH₂OH)-(3-F,4-Me-phenyl) |
| 37 | 3-F-phenyl | methyl | -C(O)NH-CH(CH₂OH)-(3-F,4-Me-phenyl) |
| 38 | 3-CF₃-phenyl | methyl | -C(O)NH-CH(CH₂OH)-phenyl |
| 39 | CH₂phenyl | methyl | -C(O)NH-CH(CH₂OH)-phenyl |
| 40 | 3,4-Me₂-phenyl | methyl | -C(O)NH-CH(CH₂OH)-phenyl |
| 41 | CH(CH₃)₂ | methyl | -C(O)NH-CH(CH₂OH)-phenyl |

TABLE 1-continued

Compounds of Formula I'

| No. I'- | R³Uₙ | TₘR¹ | Q-R² |
|---|---|---|---|
| 42 | (S)-2-phenyl-2-(hydroxymethyl)ethyl (CH(CH₂OH)Ph) | methyl | -C(O)NH-CH(CH₂OH)(Ph) |
| 43 | 2-OMe-phenyl | methyl | -C(O)NH-CH(CH₂OH)(Ph) |
| 44 | 4-OCF₃-phenyl | methyl | -C(O)NH-CH(CH₂OH)(Ph) |
| 45 | CH₂CH(CH₃)₂ | methyl | -C(O)NH-CH(CH₂OH)(Ph) |
| 46 | CH₂cyclopropyl | methyl | -C(O)NH-CH(CH₂OH)(Ph) |
| 47 | phenyl | CH₂OCH₃ | -C(O)NH-CH(CH₂OH)(Ph) |
| 48 | H | CH₂OCH₃ | -C(O)NH-CH(CH₂OH)(Ph) |

TABLE 1-continued

Compounds of Formula I'

| No. I'- | R³Uₙ | TₘR¹ | Q-R² |
|---------|------|------|------|
| 49 | cyclopropyl | methyl | –C(O)NH–CH(Ph)–CH₂OH |
| 50 | (CH₂)₂CH₃ | methyl | –C(O)NH–CH(Ph)–CH₂OH |
| 51 | phenyl | CH₂OCH₃ | –C(O)NH–CH(Ph)–CH₂OH |
| 52 | phenyl | CH₂OH | –C(O)NH–CH(Ph)–CH₂OH |
| 53 | PhCH(CH₂OH)– | methyl | –C(O)NH–CH(Ph)–CH₂OH |
| 54 | ethyl | methyl | –C(O)NH–CH(CH₃)–CH(OH)Ph |

TABLE 1-continued

Compounds of Formula I'

| No. I'- | R³U_n | T_mR¹ | Q-R² |
|---|---|---|---|
| 55 | ethyl | methyl | *C(=O)NH-CH(CH₃)-CH(OH)-phenyl* |
| 56 | ethyl | methyl | *C(=O)NH-CH₂-CH(OH)-phenyl* |
| 57 | ethyl | methyl | *C(=O)NH-CH(CH₂OH)-CH(OH)-phenyl* |
| 58 | ethyl | methyl | *C(=O)NH-CH(CH₂OH)-CH(OH)-phenyl* (other stereoisomer) |
| 59 | ethyl | methyl | *C(=O)NH-CH(phenyl)-CH₂-CH₂OH* |
| 60 | ethyl | methyl | *C(=O)NH-CH(phenyl)-CH₂-CH₂OH* (other stereoisomer) |

TABLE 1-continued

Compounds of Formula I'

| No. I'- | R³Uₙ | TₘR¹ | Q-R² |
|---|---|---|---|
| 61 | (hydroxymethyl)cyclopropyl group | methyl | —C(O)NH—CH(CH₂OH)(phenyl) |
| 62 | CH₂CH₂OH | methyl | —C(O)NH—CH(CH₂OH)(phenyl) |
| 63 | HOCH₂—CH(CH₃)— | methyl | —C(O)NH—CH(CH₂OH)(phenyl) |
| 64 | H | H | —C(O)NH—CH(CH₃)—CH(OH)(phenyl) |
| 65 | H | H | —C(O)NH—CH(CH₃)—CH(OH)(phenyl) |
| 66 | H | H | —C(O)N(CH₃)—CH₂—CH(OH)(phenyl) |
| 67 | H | H | —C(O)N(Me)—CH(CH₃)—CH(OH)(phenyl) |

TABLE 1-continued

Compounds of Formula I'

| No. I'- | $R^3U_n$ | $T_mR^1$ | $Q-R^2$ |
|---|---|---|---|
| 68 | H | H | *N-methyl-N-((1S,2R)-2-hydroxy-1-methyl-2-phenylethyl)amide* |
| 69 | ethyl | CH$_2$OCH$_3$ | *N-((S)-2-hydroxy-1-phenylethyl)amide* |
| 70 | ethyl | methyl | *N-(2-hydroxy-1-(pyridin-3-yl)ethyl)amide* |
| 71 | ethyl | CH$_2$OH | *N-((S)-2-hydroxy-1-phenylethyl)amide* |
| 72 | ethyl | methyl | *N-(1-(3-fluorophenyl)-2-hydroxyethyl)amide* |
| 73 | ethyl | methyl | *N-(1-(2-fluorophenyl)-2-hydroxyethyl)amide* |

TABLE 1-continued

Compounds of Formula I'

I'

| No. I'- | R³Uₙ | TₘR¹ | Q-R² |
|---|---|---|---|
| 74 | 2,3-Me₂-phenyl | methyl | phenyl-C(O)NH-CH(CH₂OH)- (S) |
| 75 | OCH₂CH₃ | methyl | phenyl-C(O)NH-CH(CH₂OH)- (S) |
| 76 | HOCH₂CH(iPr)- | methyl | phenyl-C(O)NH-CH(CH₂OH)- (S) |
| 77 | cyclopropyl | methyl | 2-OMe-phenyl-C(O)NH-CH(CH₂OH)- |
| 78 | cyclopropyl | methyl | 3-Cl-phenyl-C(O)NH-CH(CH₂OH)- |

TABLE 1-continued

Compounds of Formula I'

I'

| No. I'- | R³Uₙ | TₘR¹ | Q-R² |
|---|---|---|---|
| 79 | cyclopropyl | methyl | 3-methylphenyl-CH(CH₂OH)-NH-C(O)- |
| 80 | O-Me | methyl | phenyl-CH(CH₂OH)-NH-C(O)- |
| 81 | O-isopropyl | methyl | phenyl-CH(CH₂OH)-NH-C(O)- |
| 83 | 2-OH-phenyl | methyl | 3-methylphenyl-CH(CH₂OH)-NH-C(O)- |
| 84 | 2,3-Me₂-phenyl | methyl | 3-methylphenyl-CH(CH₂OH)-NH-C(O)- |

TABLE 1-continued

Compounds of Formula I'

| No. I'- | R³Uₙ | TₘR¹ | Q-R² |
|---|---|---|---|
| 85 | 2-Me-phenyl | methyl | (S)-phenylglycinol amide |
| 86 | pyridin-3-yl | methyl | (S)-phenylglycinol amide |
| 87 | (tetrahydrofuran-2-yl)methyl | methyl | (S)-phenylglycinol amide |
| 88 | ((R)-tetrahydrofuran-2-yl)methyl | methyl | (S)-phenylglycinol amide |
| 89 | CH₂pyridin-3-yl | methyl | (S)-phenylglycinol amide |
| 90 | cyclopropylmethoxy | methyl | (S)-phenylglycinol amide |

TABLE 1-continued
Compounds of Formula I'
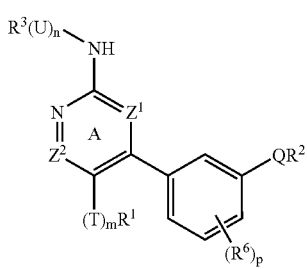
I'
| No. I'- | R³Uₙ | TₘR¹ | Q-R² |
|---|---|---|---|
| 91 | isoxazol-3-yl | methyl | 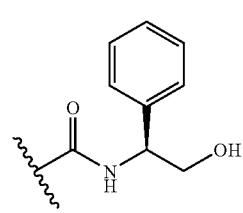 |
| 92 | 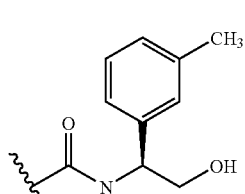 | methyl | 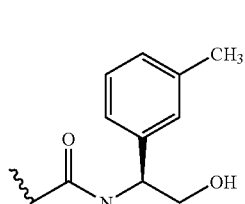 |
| 93 | 2-Me-phenyl | methyl | 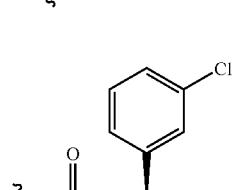 |
| 94 | 2-Me-phenyl | methyl | 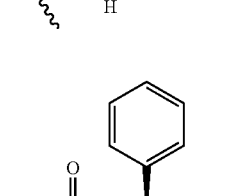 |
| 95 | O(CH₂)₂OH | methyl |  |

TABLE 1-continued

Compounds of Formula I'

I'

| No. I'- | R³Uₙ | TₘR¹ | Q-R² |
|---|---|---|---|
| 96 | N(Me)₂ | methyl | -C(O)NH-CH(Ph)-CH₂OH |
| 97 | 2-CF₃-phenyl | methyl | -C(O)NH-CH(Ph)-CH₂OH |
| 98 | morpholin-4-yl | methyl | -C(O)NH-CH(Ph)-CH₂OH |
| 99 | 5-methylisoxazol-3-yl | methyl | -C(O)NH-CH(Ph)-CH₂OH |
| 100 | 3-chloro-4-fluorophenyl-CH(CH₂OH)- | methyl | -C(O)NH-CH(Ph)-CH₂OH |

TABLE 1-continued

Compounds of Formula I'

| No. I'- | R³Uₙ | TₘR¹ | Q-R² |
|---|---|---|---|
| 111 | phenyl | methyl | (S)-NH-CH(CH₂OH)-(3-F-phenyl), attached via C(=O) |
| 122 | 2-(hydroxymethyl)butyl (CH₃CH₂CH(CH₂OH)-) | methyl | (S)-NH-CH(CH₂OH)-(3-Cl-phenyl), attached via C(=O) |
| 123 | 2-(hydroxymethyl)butyl | methyl | (S)-NH-CH(CH₂OH)-(3-CH₃-phenyl), attached via C(=O) |
| 124 | (S)-2-(hydroxymethyl)butyl | H | (S)-NH-CH(CH₂OH)-(3-Cl-phenyl), attached via C(=O) |
| 125 | 3,5-Me₂-phenyl | H/and R⁶ is OMe | NH-CH(phenyl)(CH₂-phenyl), attached via C(=O) |
| 126 | 3,5-Me₂-phenyl | H/and R⁶ is OMe | (S)-NH-CH(CH₂OH)(CH₂-phenyl), attached via C(=O) |

Exemplary structures of compounds of formula I" are set forth in Table 2 below.
TABLE 2
Compounds of Formula I"
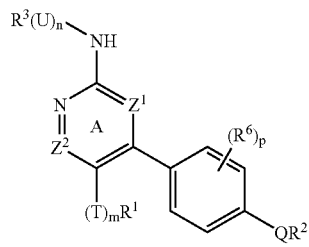
I"
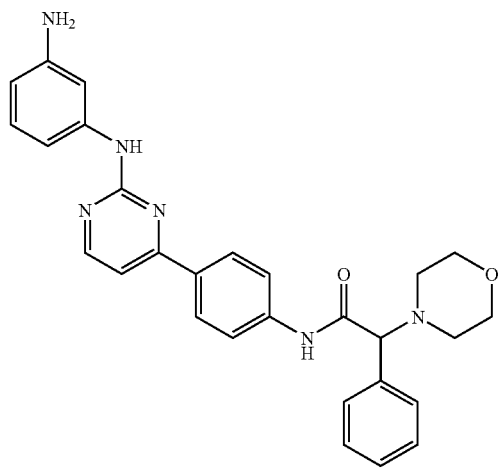
I"-1
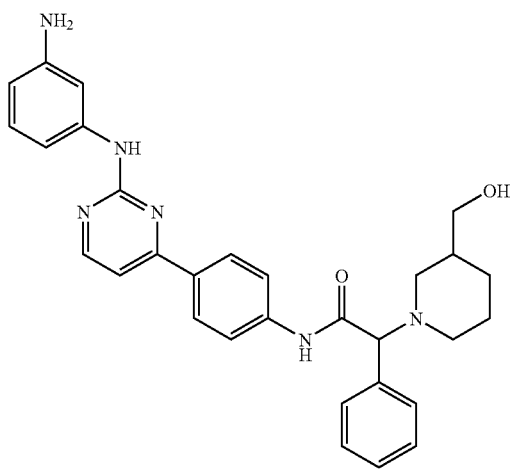
I"-2

TABLE 2-continued
Compounds of Formula I″
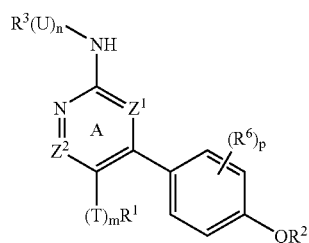
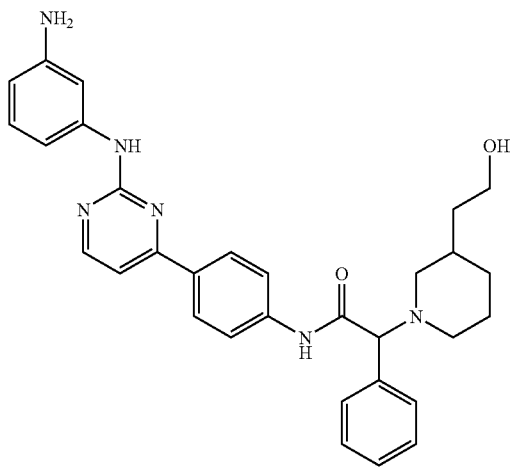
I″-3
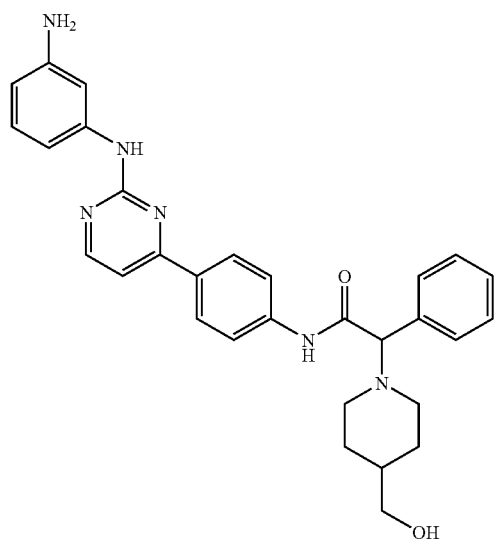
I″-4

TABLE 2-continued
Compounds of Formula I″
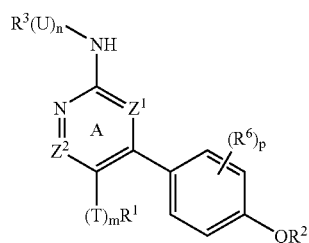
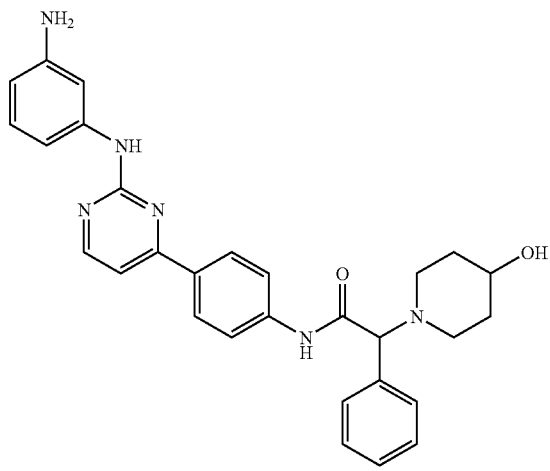
I″-5
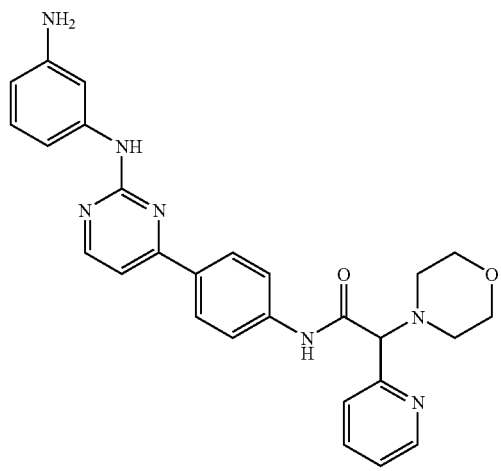
I″-6

TABLE 2-continued
Compounds of Formula I''
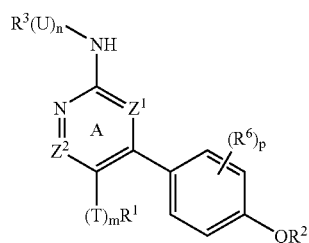
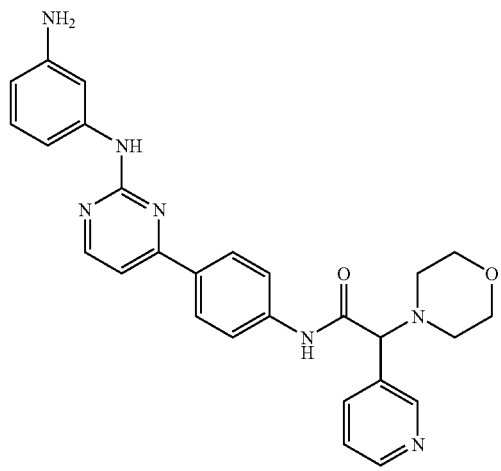
I''-7
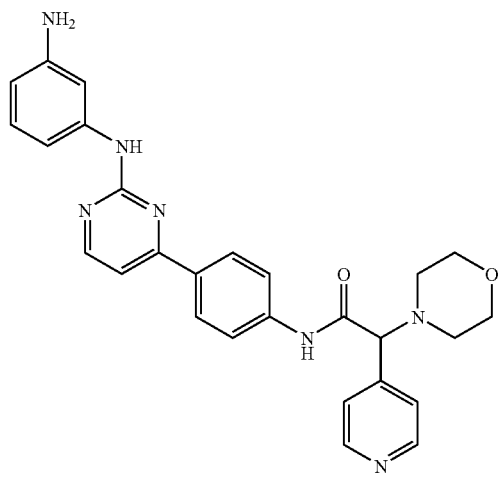
I''-8

TABLE 2-continued
Compounds of Formula I''
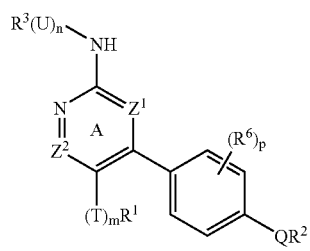
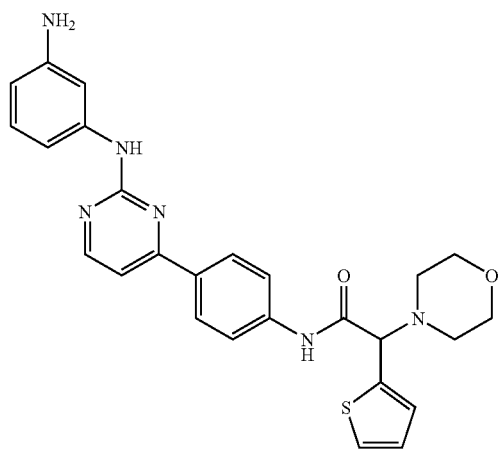
I''-9
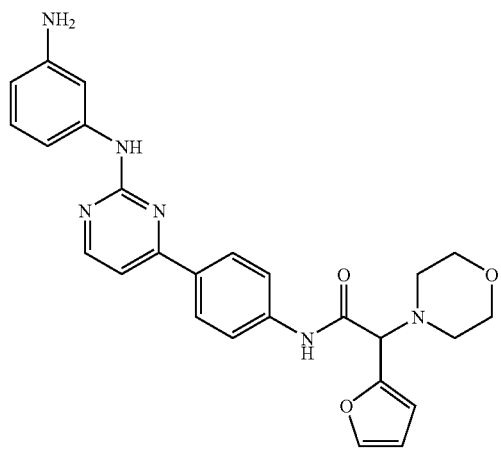
I''-10

TABLE 2-continued
Compounds of Formula I″
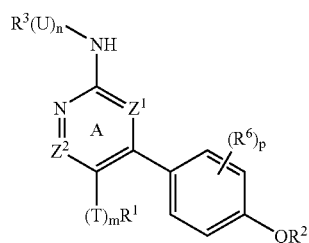
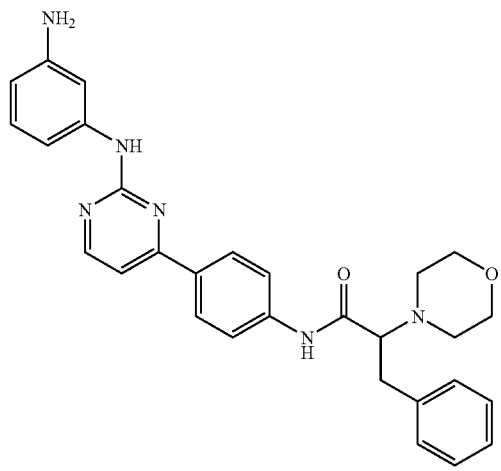
I″-11
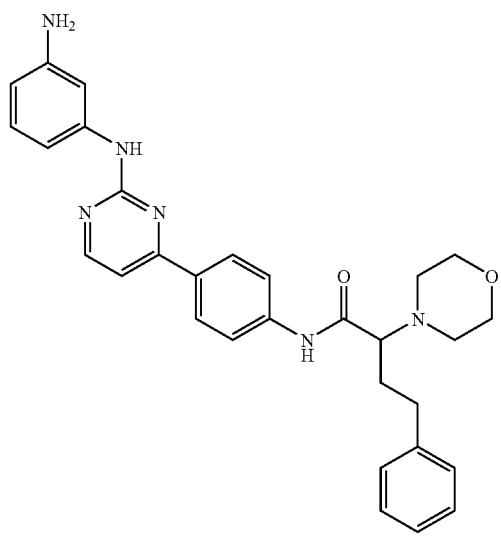
I″-12

TABLE 2-continued
Compounds of Formula I″
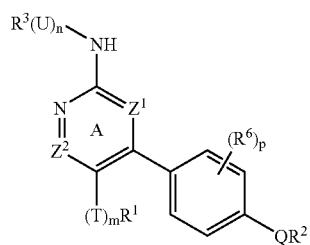
I″
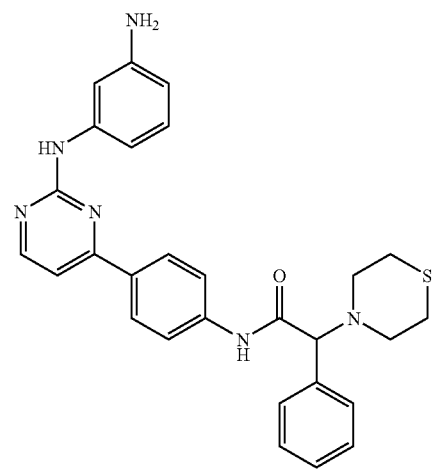
I″-13
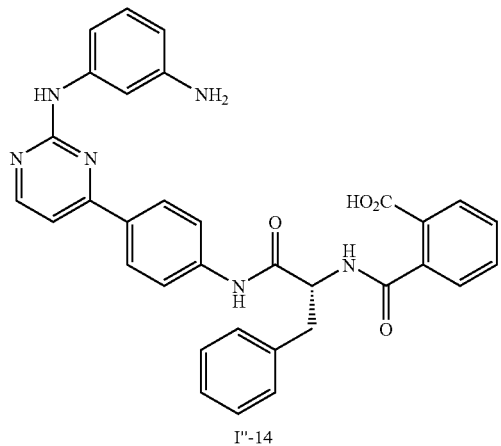
I″-14

TABLE 2-continued
Compounds of Formula I″
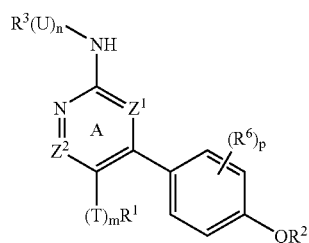
I″
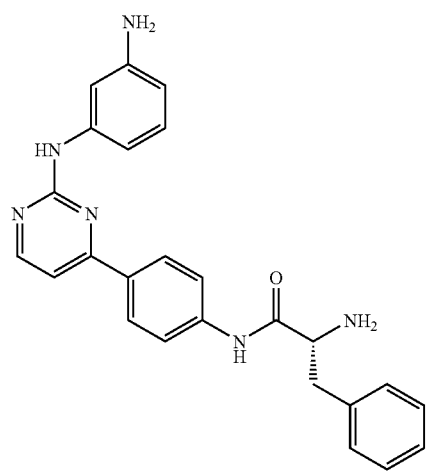
I″-15
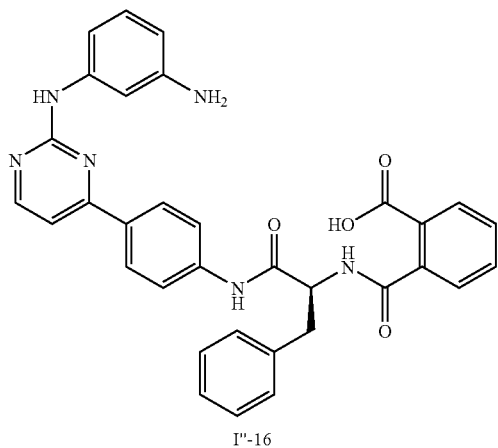
I″-16

TABLE 2-continued
Compounds of Formula I''
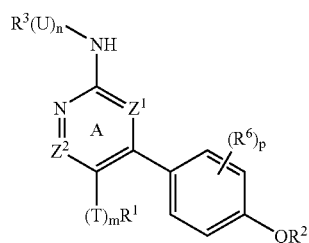
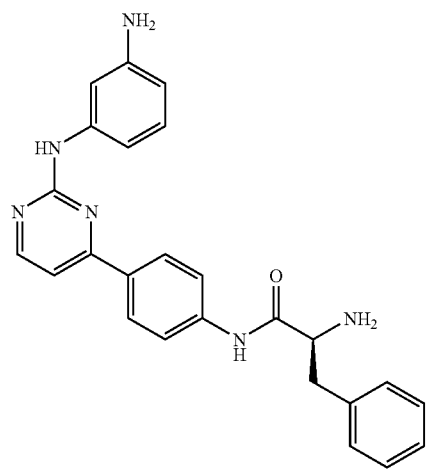
I''-17
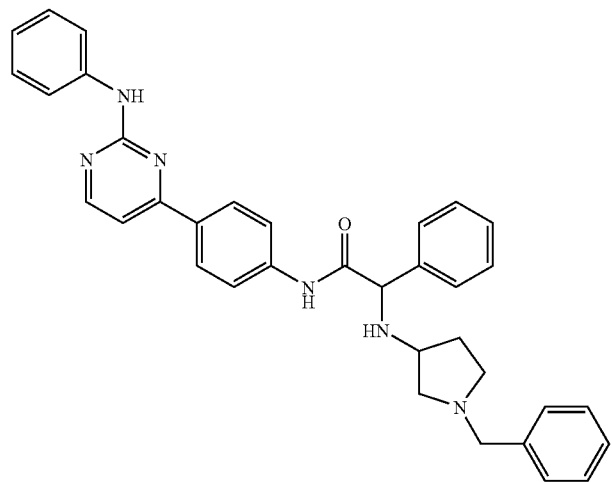
I''-18

TABLE 2-continued
Compounds of Formula I″
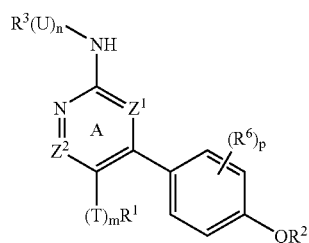
I″
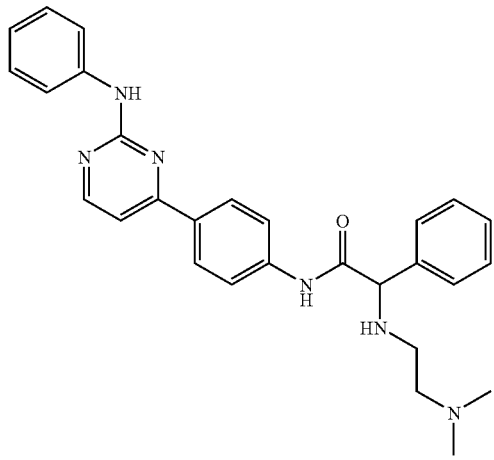
I″-19
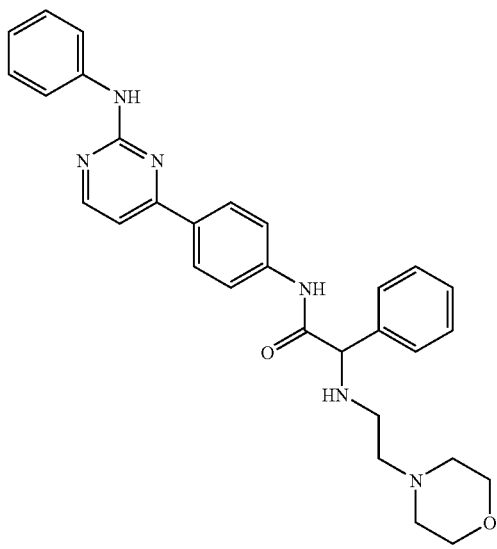
I″20

TABLE 2-continued
Compounds of Formula I''
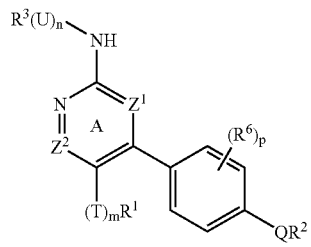
I''
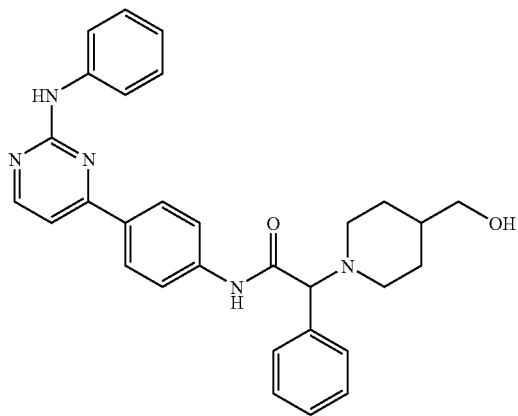
I''-21
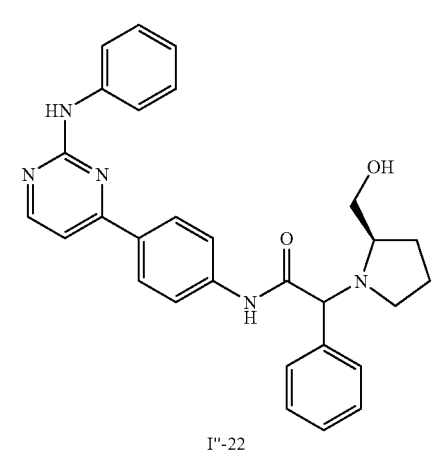
I''-22
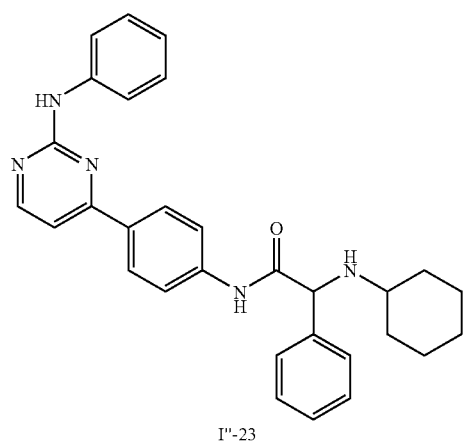
I''-23

TABLE 2-continued
Compounds of Formula I″
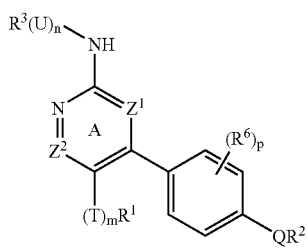
I″
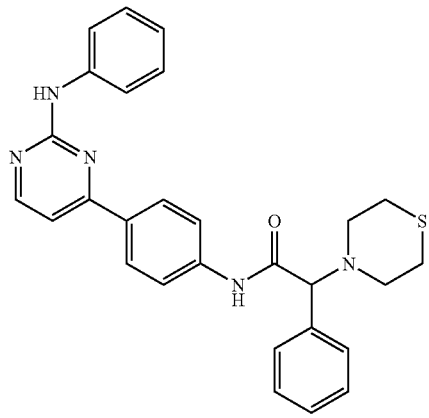
I″-24
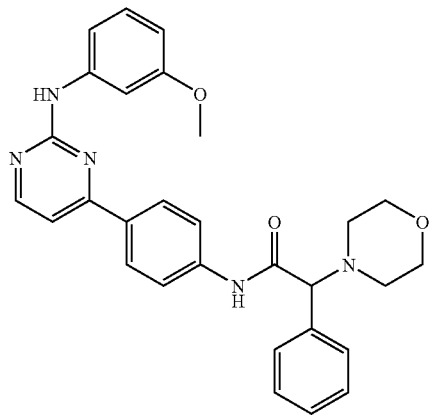
I″-25

TABLE 2-continued
Compounds of Formula I''
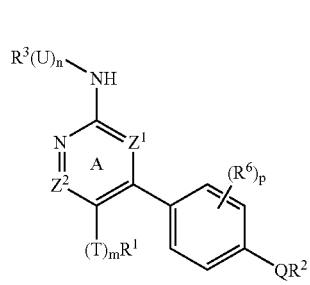
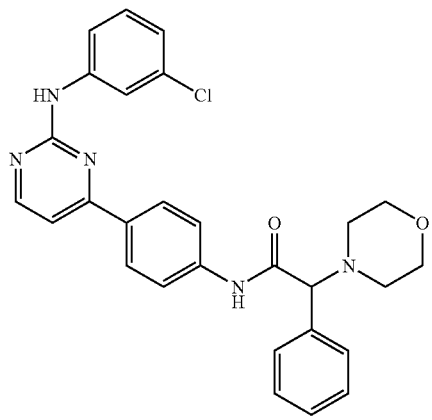
I''-26
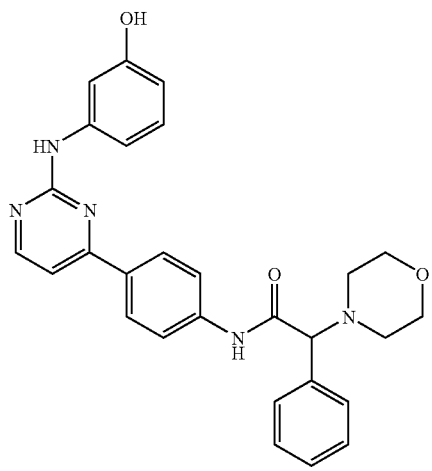
I''-27

TABLE 2-continued
Compounds of Formula I″
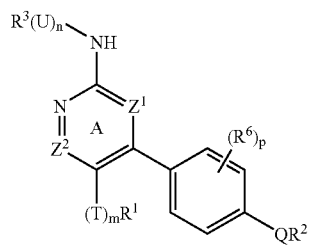
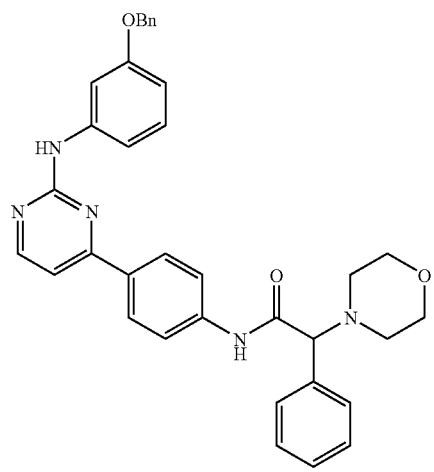
I″-28
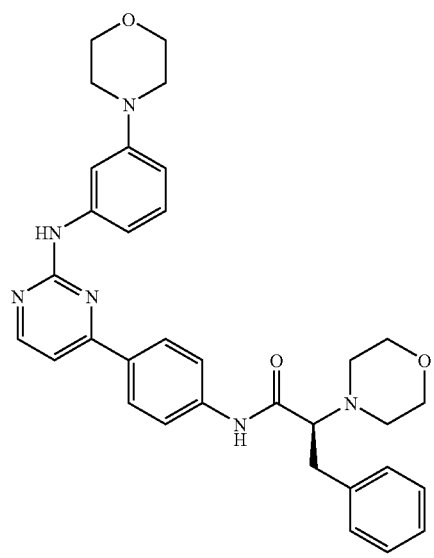
I″-29

TABLE 2-continued
Compounds of Formula I″
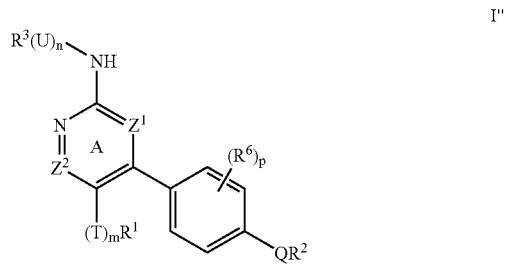
I″
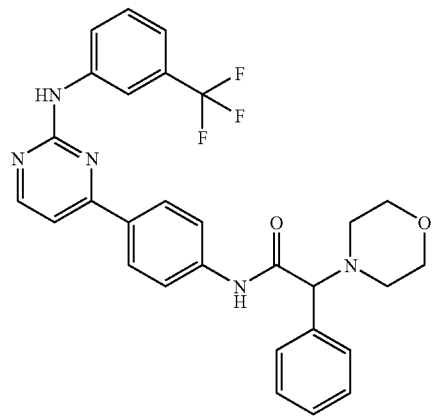
I″-30
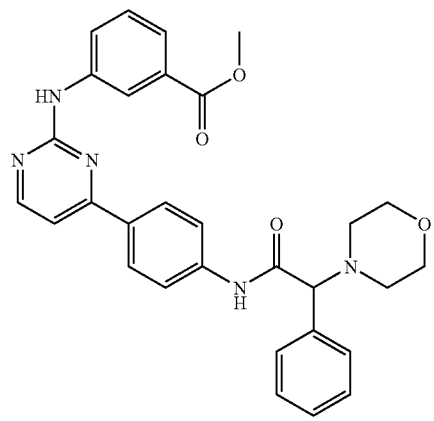
I″-31
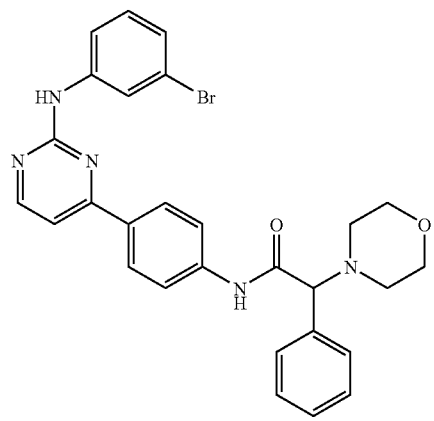
I″-32

TABLE 2-continued
Compounds of Formula I"
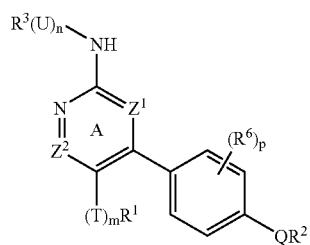
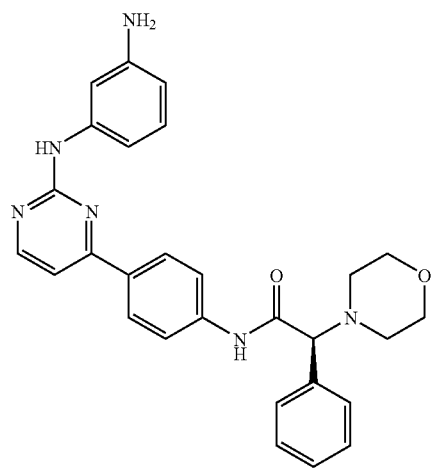
I"-33
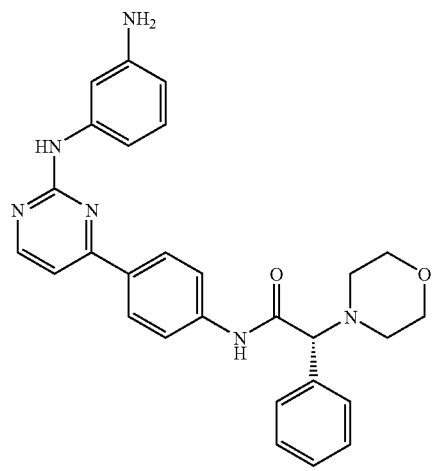
I"-34

TABLE 2-continued
Compounds of Formula I"
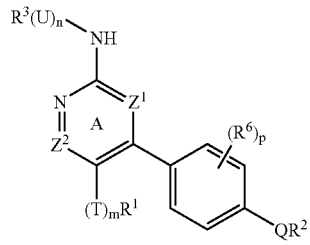
I"
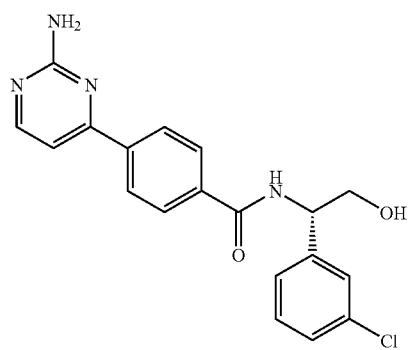
I"-35
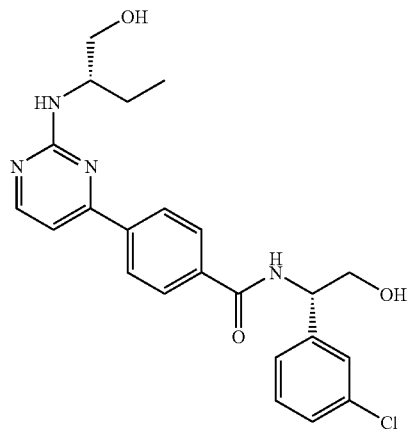
I"-36
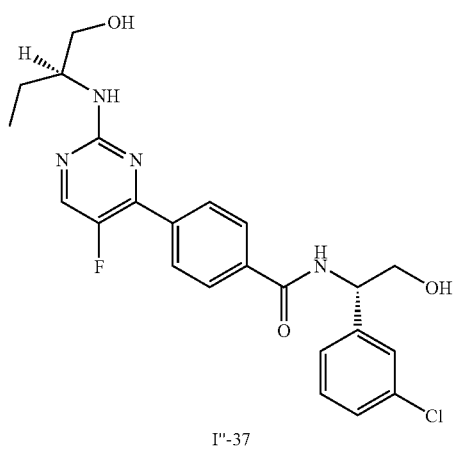
I"-37

TABLE 2-continued
Compounds of Formula I"
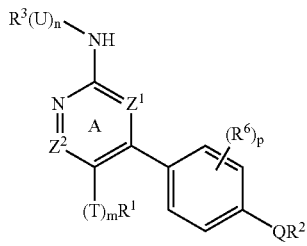
I"
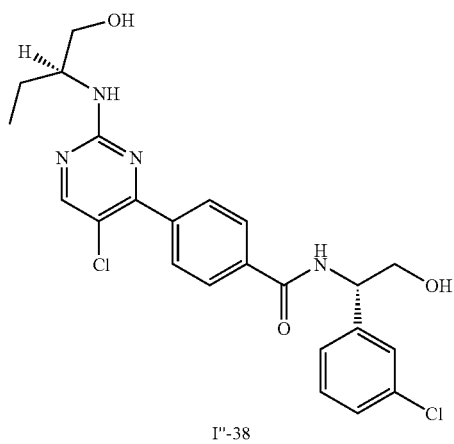
I"-38
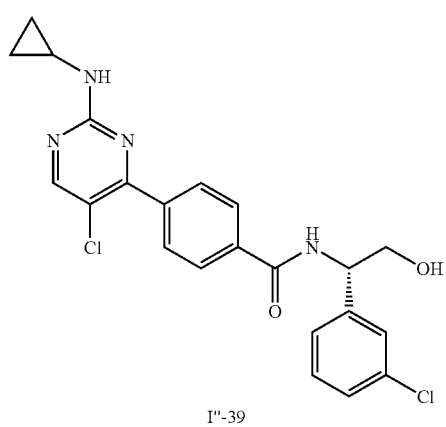
I"-39
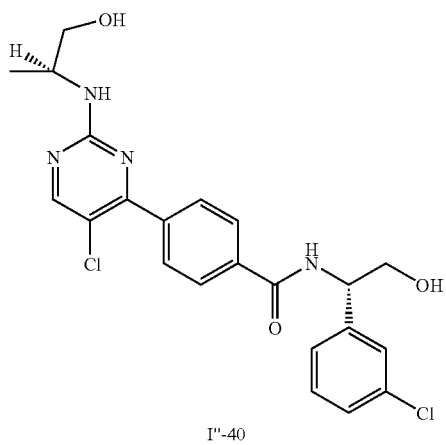
I"-40

TABLE 2-continued
Compounds of Formula I″
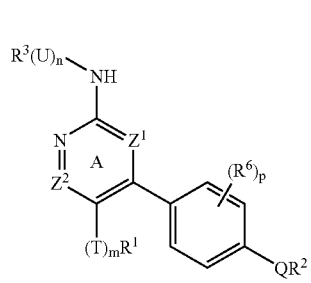
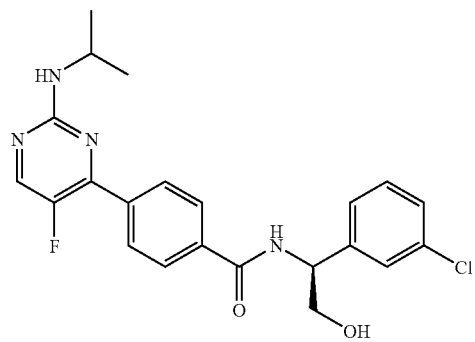
I″-41
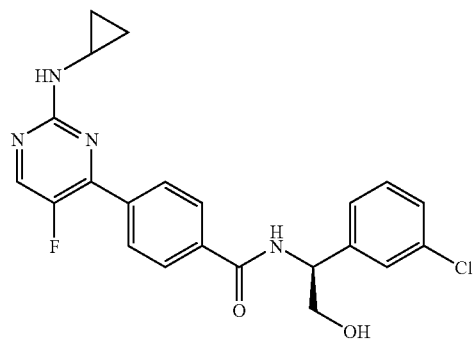
I″-42
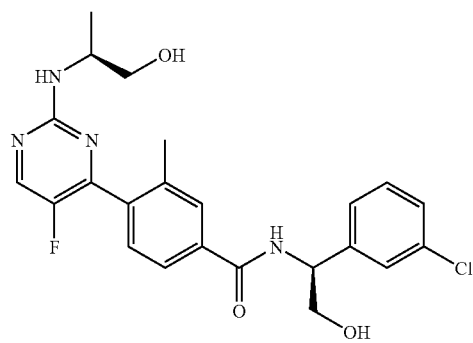
I″-43

TABLE 2-continued
Compounds of Formula I″
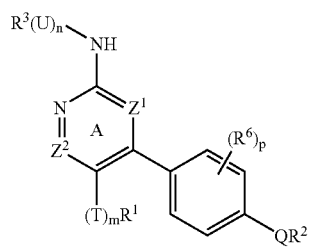
I″
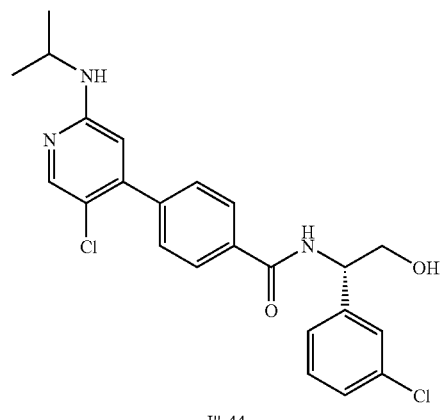
I″-44
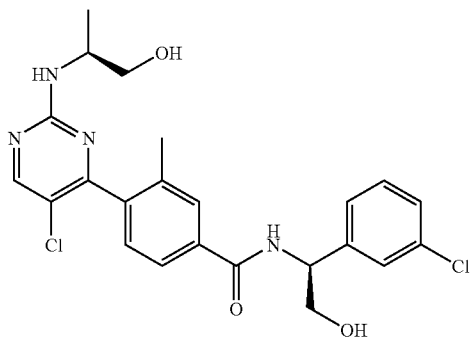
I″-45
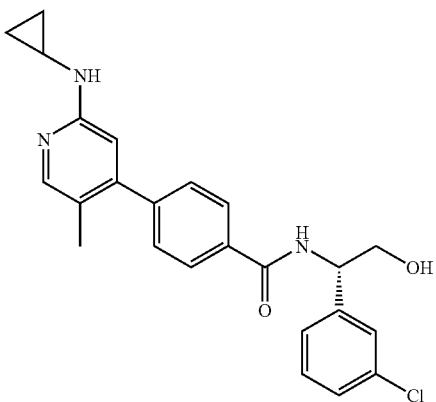
I″-46

TABLE 2-continued
Compounds of Formula I''
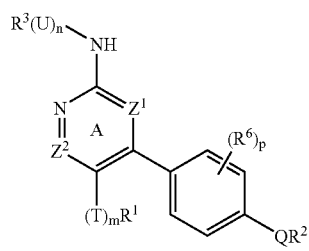
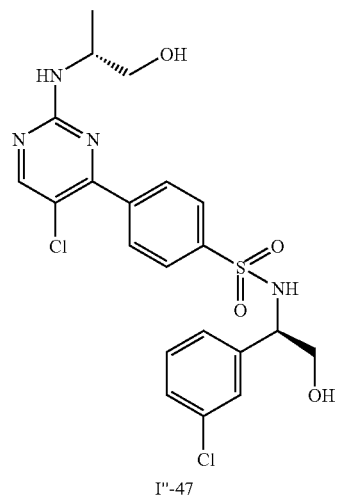
I''-47
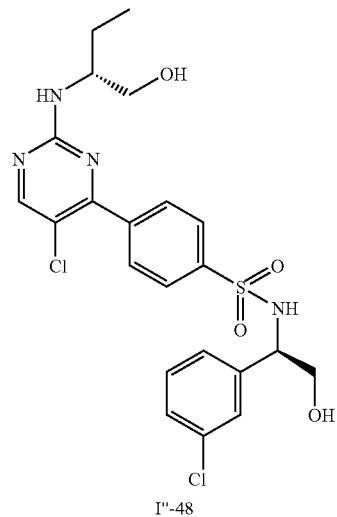
I''-48

TABLE 2-continued
Compounds of Formula I″
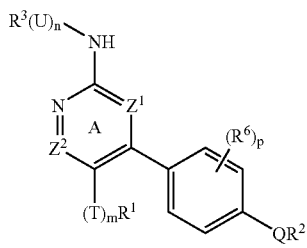
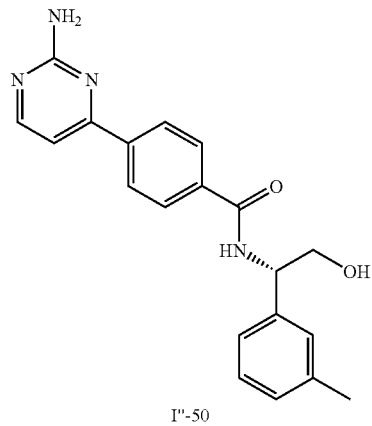
I″-49
I″-50
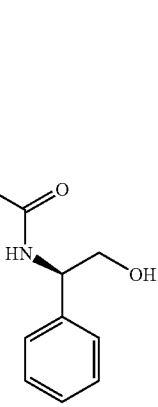
I″-51

TABLE 2-continued
Compounds of Formula I"
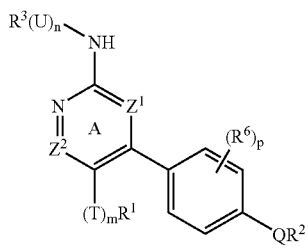
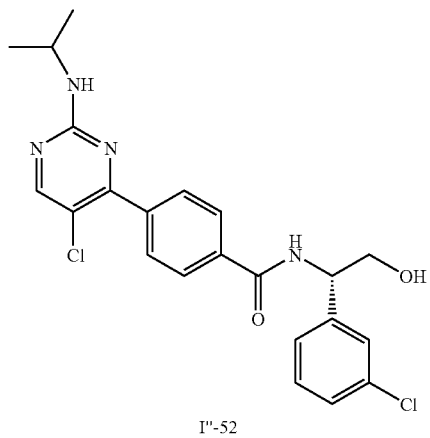
I"-52
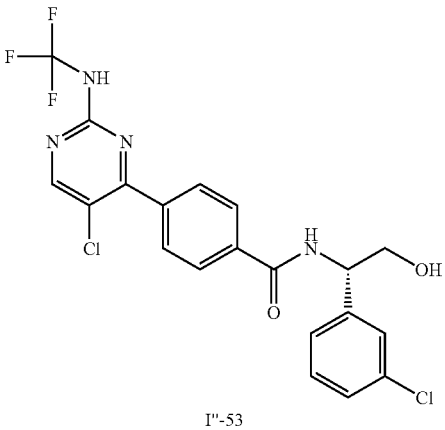
I"-53
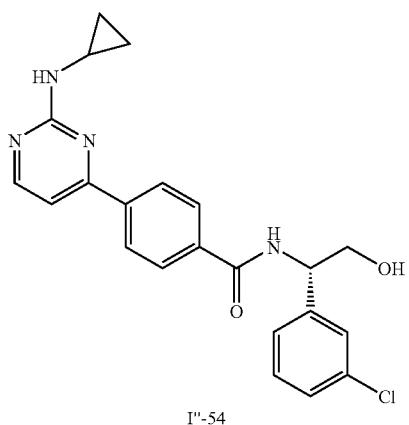
I"-54

TABLE 2-continued
Compounds of Formula I″
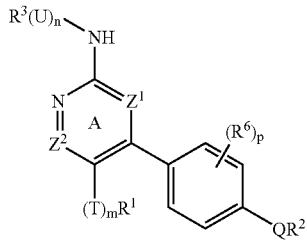
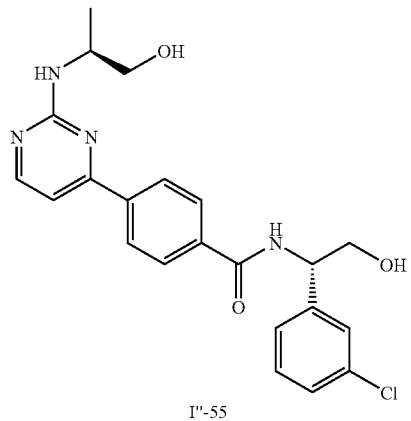
I″-55
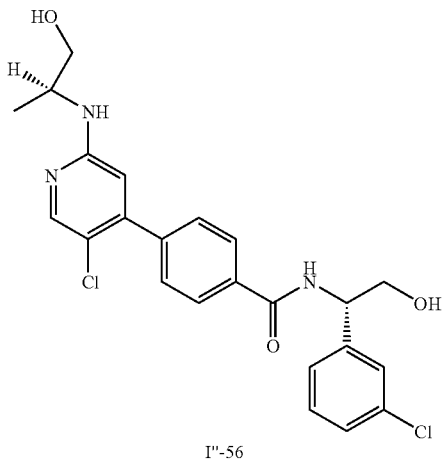
I″-56
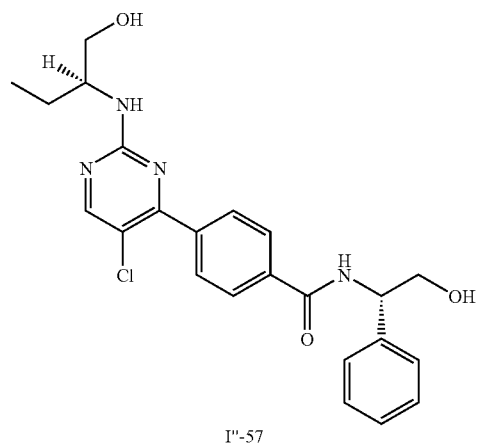
I″-57

TABLE 2-continued
Compounds of Formula I''
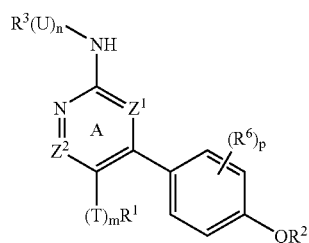
I''
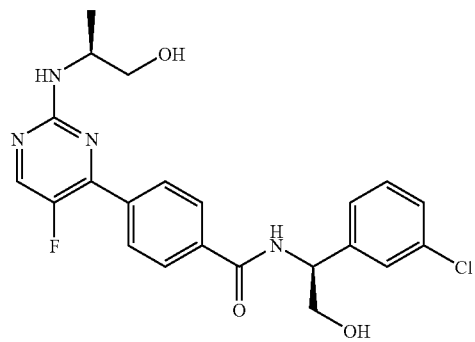
I''-58
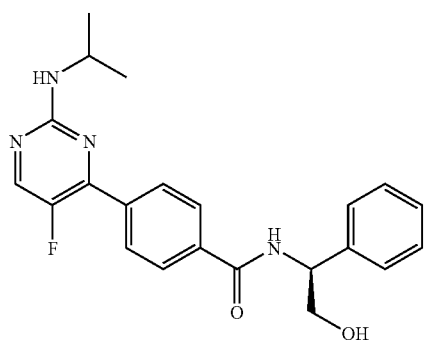
I''-59
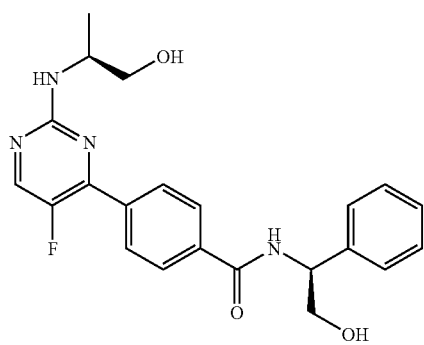
I''-60

TABLE 2-continued
Compounds of Formula I''
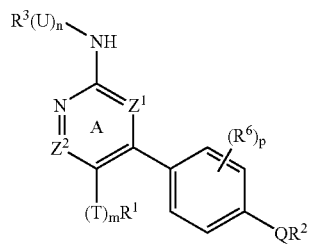
I''
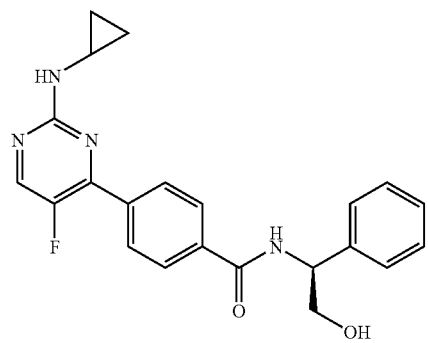
I''-61
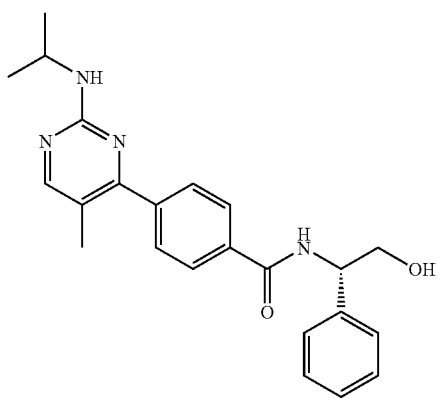
I''-62
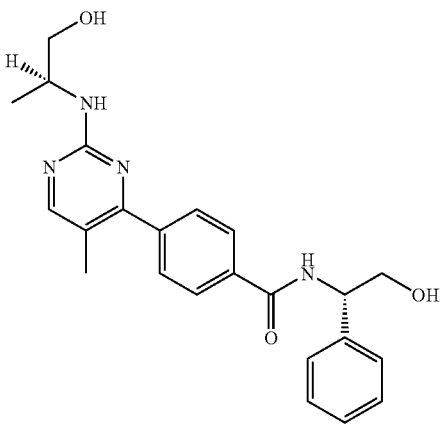
I''-63

TABLE 2-continued
Compounds of Formula I″
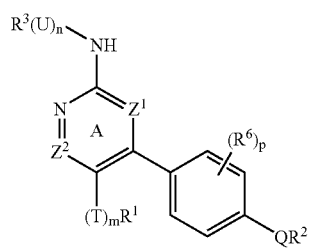
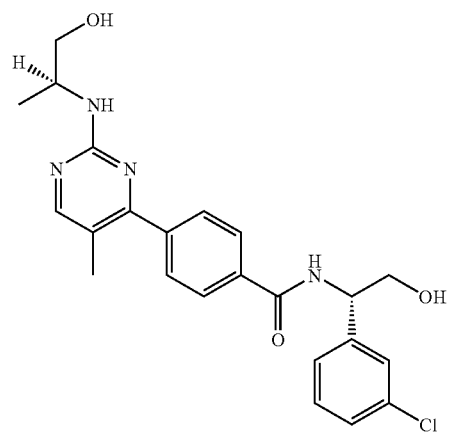
I″-64
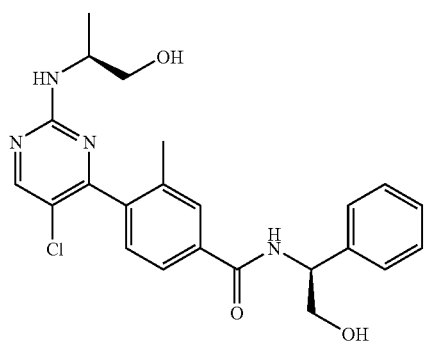
I″-65
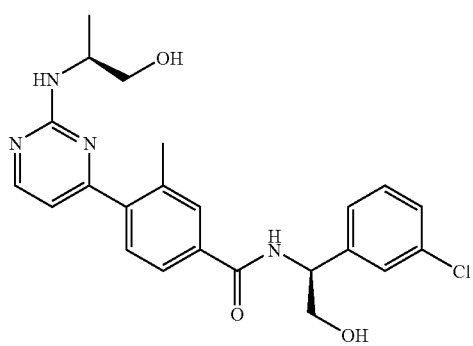
I″-66

TABLE 2-continued
Compounds of Formula I″
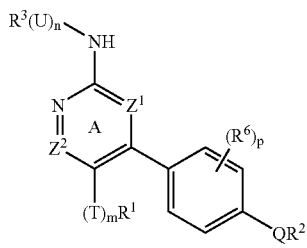
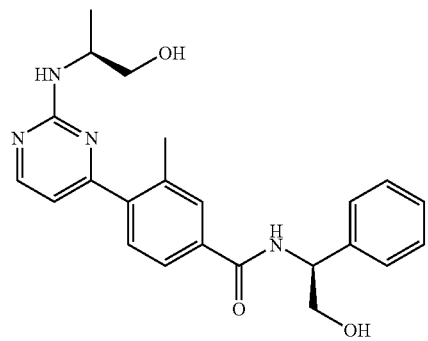
I″-67
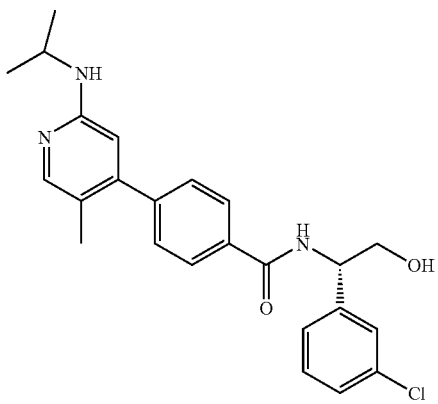
I″-68
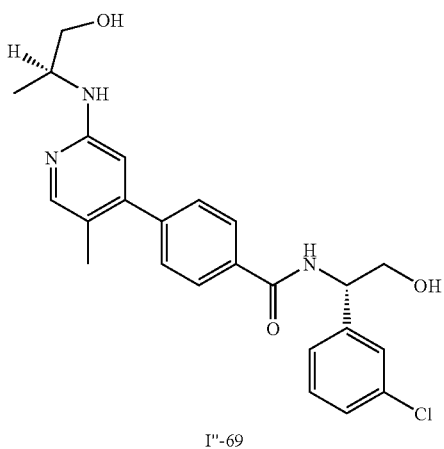
I″-69

TABLE 2-continued
Compounds of Formula I″
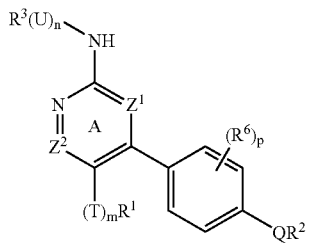
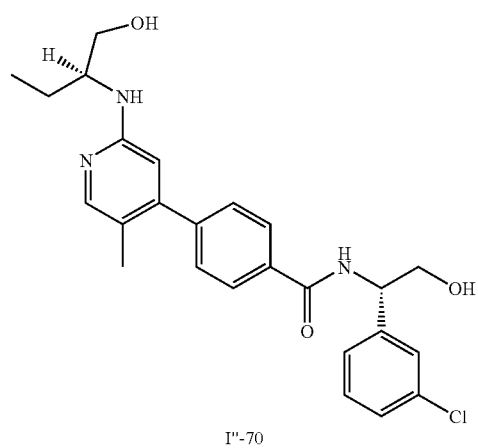
I″-70
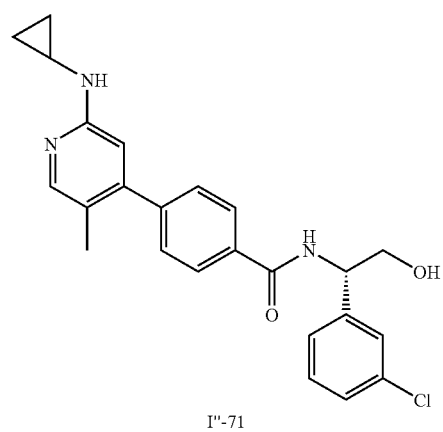
I″-71
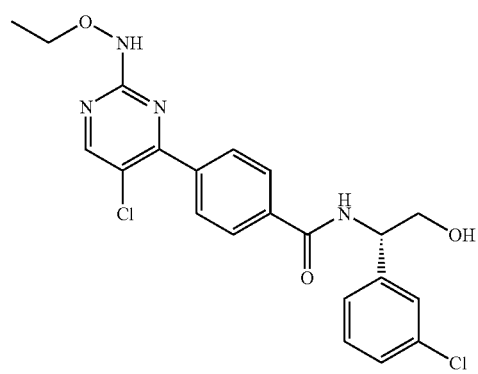
I″-72

Exemplary structures of compounds of formula V' are set forth in Table 3 below.
TABLE 3
Compounds of Formula V'
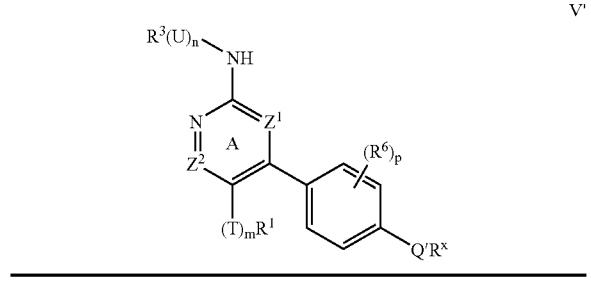
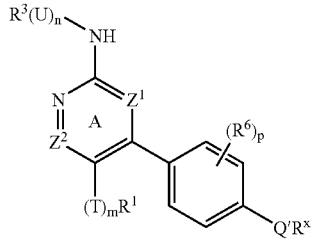
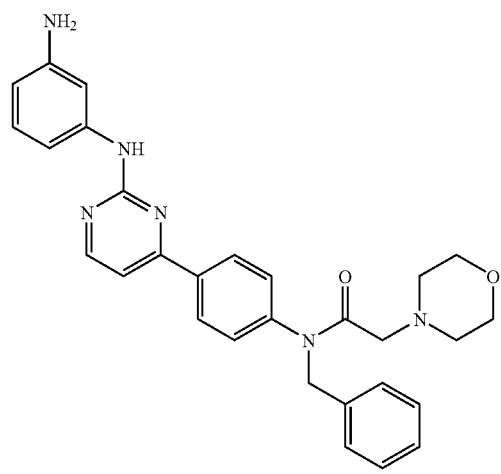
V'-1
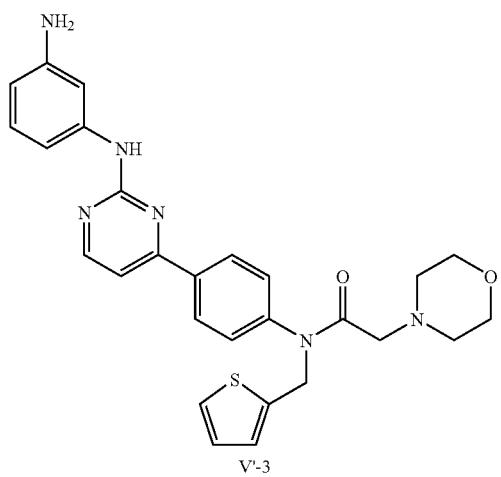
V'-3
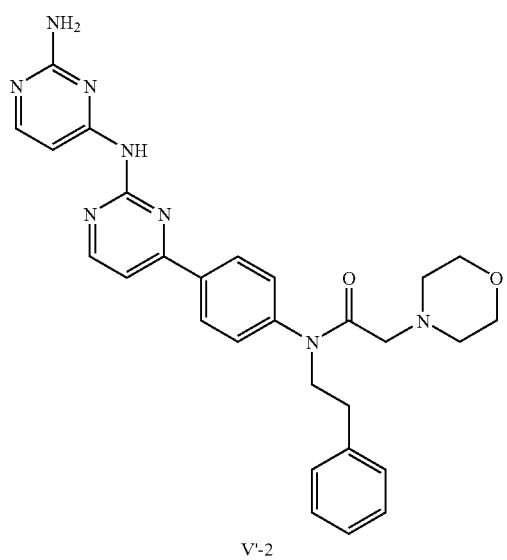
V'-2
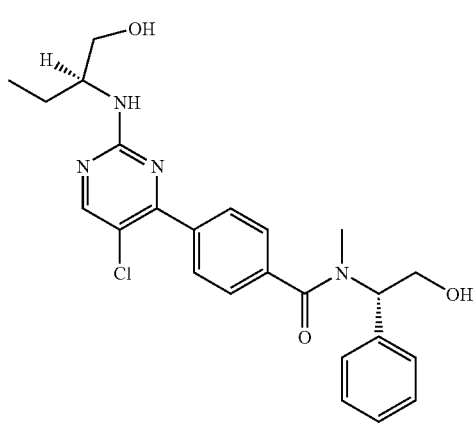
V'-4

TABLE 3-continued

Compounds of Formula V'

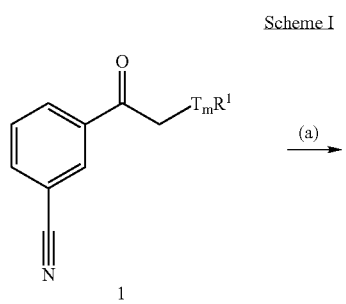

The present compounds may be prepared in general by methods known to those skilled in the art for analogous compounds, as illustrated by the general Schemes I, II, III, IV, V, VI, VII, and VIII and the synthetic examples set forth below.

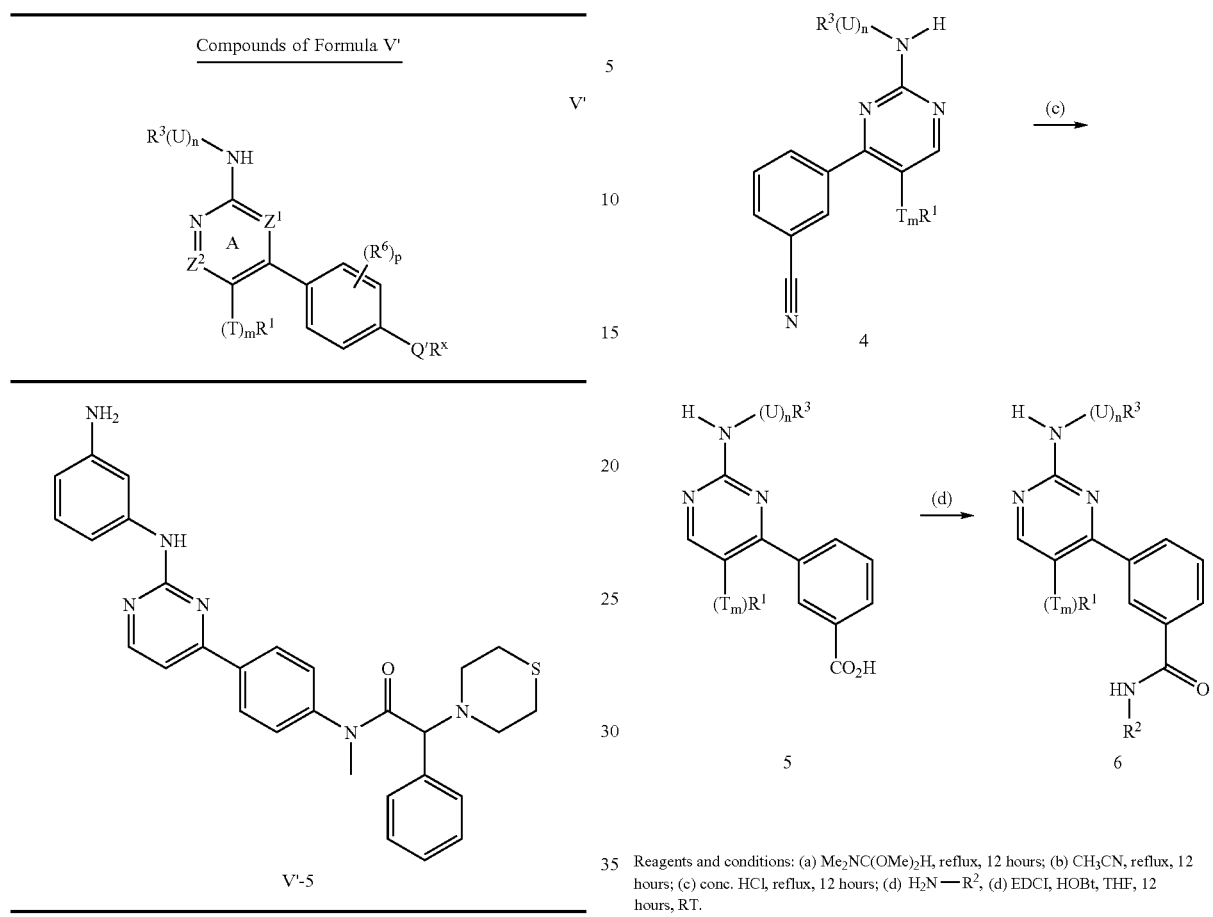

Reagents and conditions: (a) Me$_2$NC(OMe)$_2$H, reflux, 12 hours; (b) CH$_3$CN, reflux, 12 hours; (c) conc. HCl, reflux, 12 hours; (d) H$_2$N—R$^2$, (d) EDCI, HOBt, THF, 12 hours, RT.

Scheme I above shows a general synthetic route that is used for preparing of formula I of this invention when Q is C(O)NH. In step (a), the enamine intermediate 2 is prepared by treating 1 with Me$_2$NC(OMe)$_2$H at reflux.

The formation of the pyrimidine compound 4 at step (b) is achieved by the treatment of enamine 2 with guanidine 3 at elevated temperature. The cyano group of intermediate 4 is hydrolized according to step (c) to form the carboxylic acid 5 which is then treated with a variety of amines of formula R$^2$—NH$_2$ to form the amide compounds of formula 6. It would be apparent to one of skill in the art that a wide variety of amines of formula R$^2$—NH$_2$ are amenable to couple to the carboxylic acid 5 by methods known in the art.

Scheme II

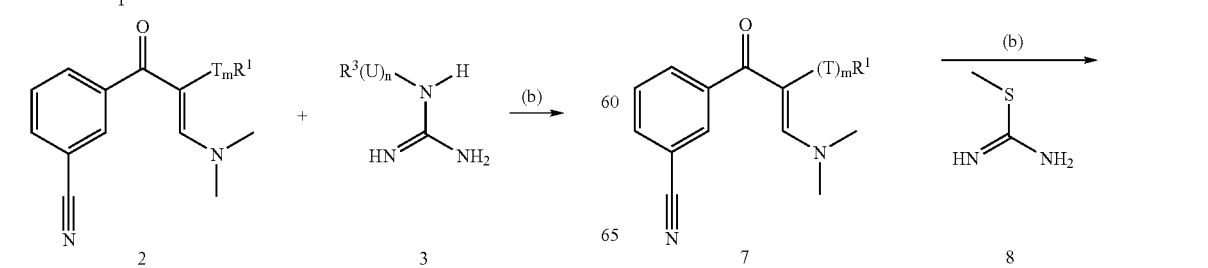

Scheme III

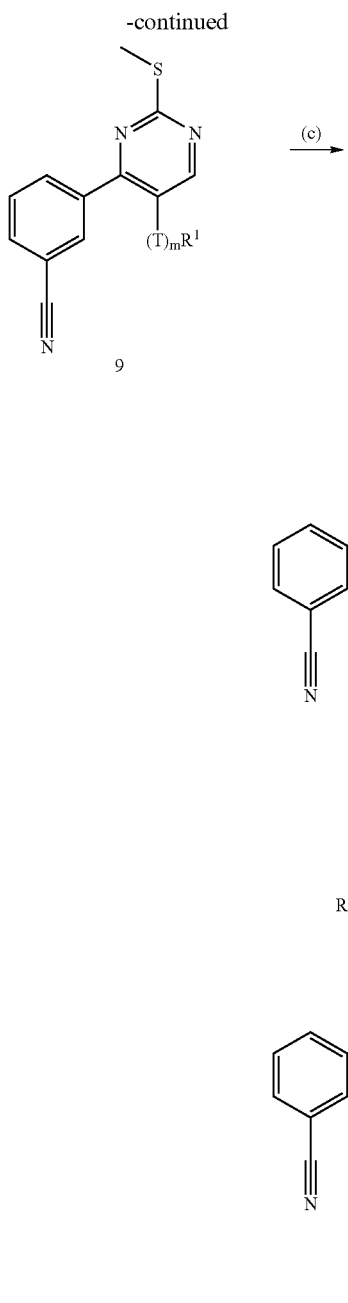

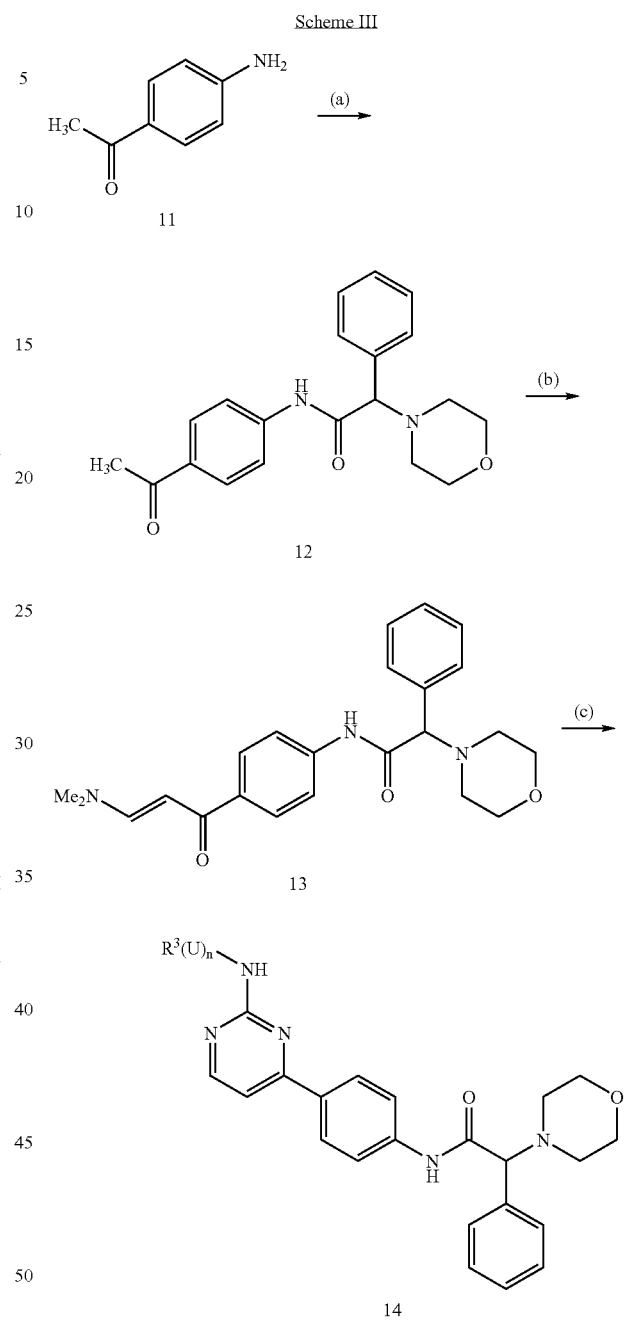

Reagents and conditions: (a) MeOH, K$_2$CO$_3$, reflux; (b) m-chloroperbenzoic acid, CH$_2$Cl$_2$; (c) H$_2$N—R$^2$, THF, reflux, 12 hours.

Scheme II above shows an alternative method for preparing the pyrimidine compounds 4, which are useful for preparing compounds of the present invention using the methods described at Scheme I above and by methods known to one of skill in the art.

At step (a) the enamine 2, as described at Scheme I above, is cyclized with S-methyl thiourea to form the 2-thiomethylpyrimidine 9 which may in turn be oxidized with m-CPBA to the sulfone 10. The sulfonyl group may be subsequently displaced by an amine of formula R$^3$(U)$_n$—NH$_2$ to generate the substituted aminopyrimidine 4.

Reagents and conditions: a) i. α-bromo-2-phenylacetic acid, oxalyl chloride, ii. morpholine, diisopropylethylamine; b) DMF-DMA, 115° C.; c) R$^3$(U)$_n$-guanidine, K$_2$CO$_3$, DMF, 115° C.

Scheme III above sets forth a general method for preparing compounds of formula IV. At step (a), 1-(4-aminophenyl)-ethanone is treated with α-bromo-2-phenylacetic acid, oxalyl chloride and then morpholine in the presence of diisopropylethylamine to form compound 12. Although Scheme III depicts the use of α-bromo-2-phenylacetic acid and morpholine at step (a), one of ordinary skill in the art would recognize that other arylacetic acids and heterocyclic groups would be amenable to the reaction of step (a) to prepare a variety of compound of formula IV. Compound 12 is then treated with DMF-DMA, at 115° C., in a manner substantially similar to that of Scheme I at step (a) to form the enamine 13. Enamine 13 is treated with a guanidine to form the amino-pyrimidine compound 14. One of ordinary skill in the art would recognize that a variety of guanidines, including substituted and unsubstituted guanidines are amenable to the reaction at step (c) to prepare a variety of compounds of formula IV using methods known in the art.

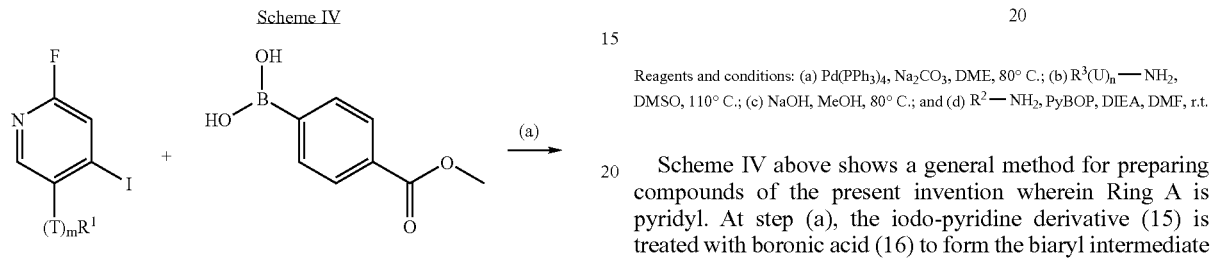

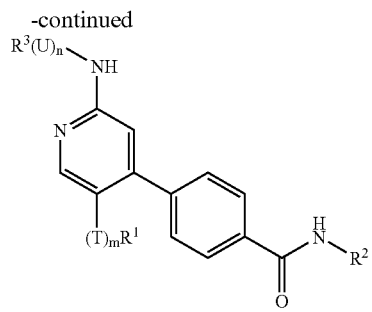

Reagents and conditions: (a) Pd(PPh$_3$)$_4$, Na$_2$CO$_3$, DME, 80° C.; (b) R$^3$(U)$_n$—NH$_2$, DMSO, 110° C.; (c) NaOH, MeOH, 80° C.; and (d) R$^2$—NH$_2$, PyBOP, DIEA, DMF, r.t.

Scheme IV above shows a general method for preparing compounds of the present invention wherein Ring A is pyridyl. At step (a), the iodo-pyridine derivative (15) is treated with boronic acid (16) to form the biaryl intermediate (17). The fluoro group of compound 17 is displaced with a R$^3$(U)$_n$—NH$_2$ to form the ester compound (18). The ester functionality is then hydrolyzed and coupled with the desired amine to form compound (20). One of skill in the art would recognize that a variety of amines are amenable to coupling with the carboxylate compound 19 to form a variety of compounds of the present invention.

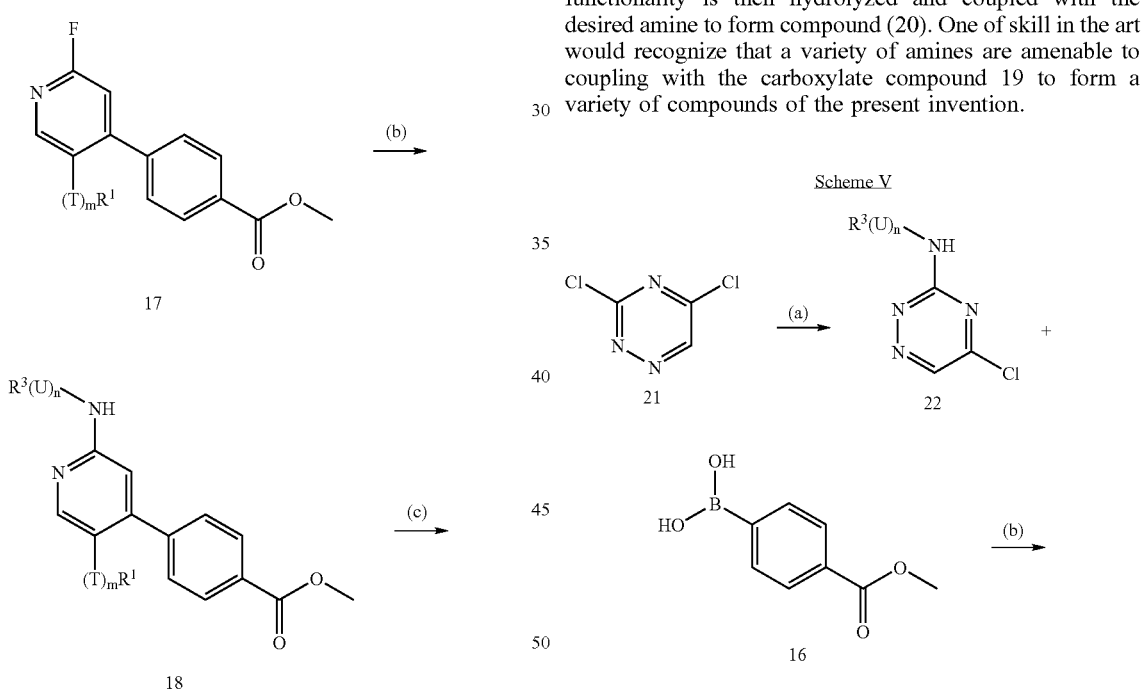

Reagents and conditions: (a) R$^3$(U)$_n$—NH$_2$, TEA, DCM, 0° C.; and (b) Pd(PPh$_3$)$_4$, Na$_2$CO$_3$, DME, 80° C.

Scheme V above shows a general method for preparing compounds of the present invention wherein Ring A is triazinyl. At step (a), the dichlorotriazine compounds (21) is treated with an amine of formula $R^3(U)_n$—$NH_2$ to form the mono-chloro compound (22). The chloro intermediate (22) is then treated with a boronic acid (16) to form the biaryl intermediate (17). Compound (17) is used to prepare compounds of the present invention by the general methods described above.

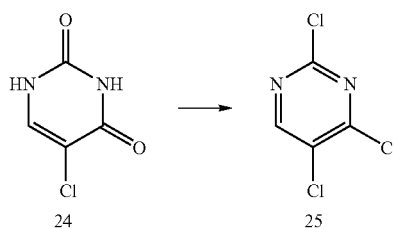

Scheme VI

24 → 25

Scheme VII above shows a general method for preparing 2,4,5-trichloropyrimidine, useful as an intermediate for preparing the compounds of the present invention. 5-Chlorouracil is treated with phosphorous oxytrichloride and N,N-dimethylaniline to form 2,4,5-trichloropyrimidine.

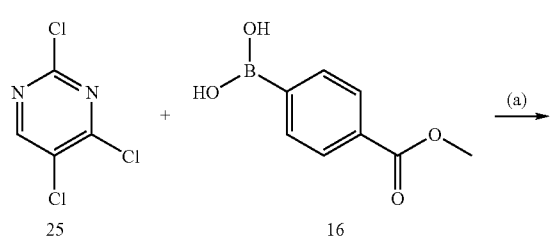

Scheme VII

25 + 16

26

27

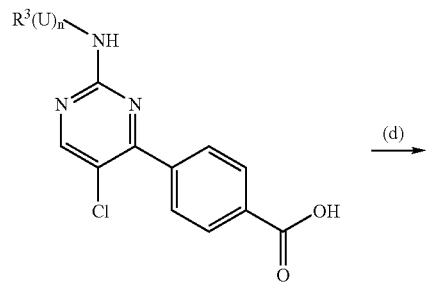

-continued

28

29

Reagents and conditions: (a) Pd(PPh₃)₄, Na₂CO₃, DME, 80° C.; (b) $R^3(U)_n$—$NH_2$, DMSO, 110° C.; (c) NaOH, MeOH, 80° C.; and (d) $R^2$—$NH_2$, PyBOP, DIEA, DMF, r.t.

Scheme VII above shows an alternative method for preparing pyrimidine compounds of the present invention wherein $T_{(m)}R^1$ is chloro. 2,4,5-Trichloropyrimidine is treated with a boronic acid (16) to form the biaryl intermediate (26). Steps (b), (c), and (d) are performed in a manner substantially similar to that described in the general schemes above and by the synthetic examples set forth herein.

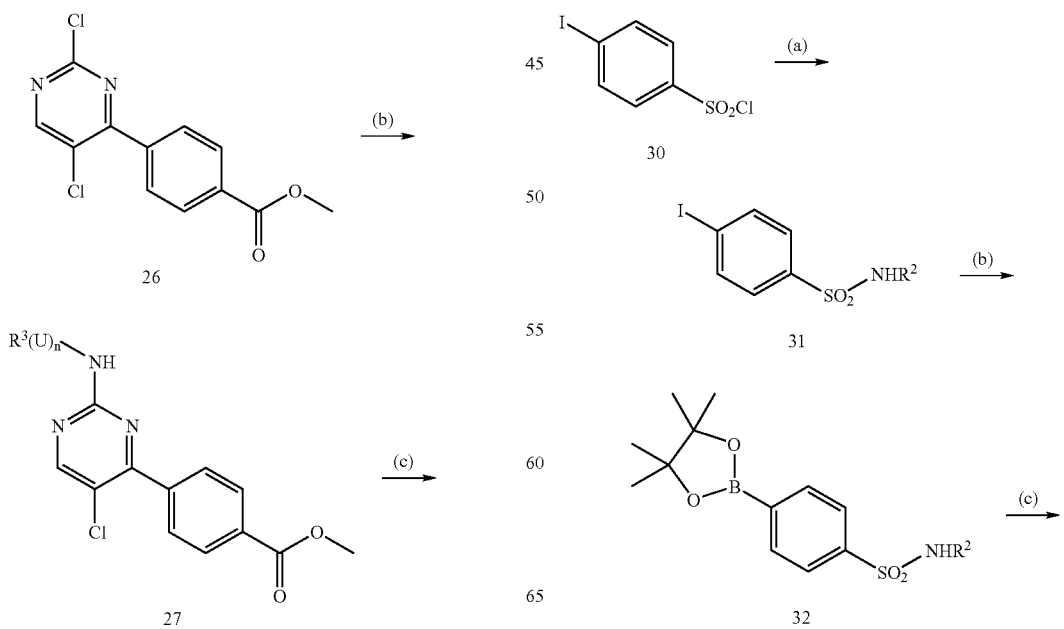

Scheme VIII

30

31

32

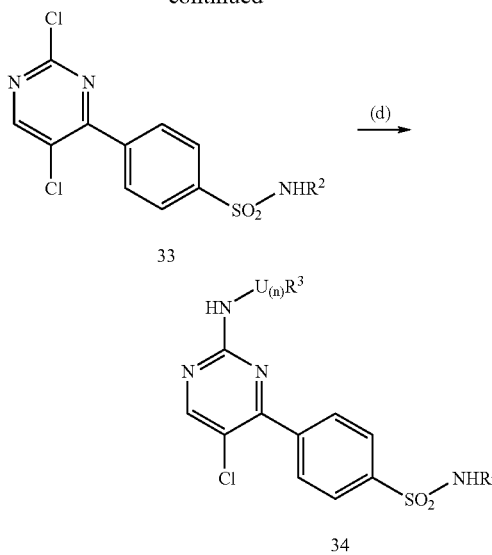

Reagents and conditions: (a) R²NH₂, TEA, DCM, r.t.; (b) bis(pinacolato)diboron, Pd(pddf)₂, DMF, 70° C.; (c) 2,4,6-trichloropyrimidine, Pd(PPh₃)₄, THF, 80° C.; (d) U₍ₙ₎R³NH₂, DMSO, 75° C.

Scheme VIII above shows a general method for preparing the compounds of the present invention wherein Q is —SO₂NH—. At step (a), iodobenzenesulfonylchloride ("pipsyl chloride") is treated with R²NH₂ to form the sulfonamide compound (31). Steps (b), (c), and (d) are performed in a manner substantially similar to that described in the general schemes above and by the synthetic examples set forth herein.

The compounds and compositions described herein are generally useful for the inhibition of protein kinase activity of one or more enzymes. Further information relating to kinase structure, function and their role in disease or disease symptoms is available at the Protein Kinase Resource website (http://kinases.sdsc.edu/html/index.shtml).

Examples of kinases that are inhibited by the compounds and compositions described herein and against which the methods described herein are useful include, but are not limited to, ERK1, ERK2, AKT3, GSK3, ROCK, SRC, SYK, ZAP70, JNK3, JAK1, JAK2, JAK3, CDK1, CDK2, CDK5, LCK, LYN, FLT3, MK2, MKK4, MKK6, MEK1, Mapkap1, PDK1, p70s6k, Aurora-1, Aurora-2, Aurora-3, cMET, IRAK1, IRAK2, TEC, FGF1R (=FGR-1), FGF2R (=FGR-2), IKK-1 (=IKK-alpha=CHUK), IKK-2 (=IKK-beta), KIT, PKA, PKB (including all PKB subtypes), PKC (including all PKC subtypes), REDK, CHK, SAPK, PIM, and BARK, and all subtypes of these kinases. The compounds and compositions of the invention are therefore also particularly suited for the treatment of diseases and disease symptoms that involve one or more of the aforementioned kinases.

In one particular embodiment, the compounds and compositions of the invention are inhibitors of one or more of ERK2, AKT3, GSK3, p70s6k, PDK1, Aurora-2, ROCK, SRC, SYK, ZAP70, JNK3, JAK3, TEC, LCK, FLT3, and CDK2, and thus the compounds and compositions are particularly useful for treating or lessening the severity of disease or disease symptoms associated with ERK2, AKT3, GSK3, p70s6k, PDK1, Aurora-2, ROCK, SRC, SYK, ZAP70, JNK3, JAK3, TEC, LCK, FLT3, and/or CDK2.

The activity of a compound utilized in this invention as an inhibitor of ERK2, AKT3, GSK3, p70s6k, PDK1, Aurora-2, ROCK, SRC, SYK, ZAP70, JNK3, JAK3, TEC, LCK, FLT3, and/or CDK2, may be assayed in vitro, in vivo or in a cell line. In vitro assays include assays that determine inhibition of either the phosphorylation activity or ATPase activity of activated ERK2, AKT3, GSK3, p70s6k, PDK1, Aurora-2, ROCK, SRC, SYK, ZAP70, JNK3, JAK3, TEC, LCK, FLT3, and/or CDK2. Alternate in vitro assays quantitate the ability of the inhibitor to bind to ERK2, AKT3, GSK3, p70s6k, PDK1, Aurora-2, ROCK, SRC, SYK, ZAP70, JNK3, JAK3, TEC, LCK, FLT3, and/or CDK2. Inhibitor binding may be measured by radiolabelling the inhibitor prior to binding, isolating the inhibitor/ERK2, inhibitor/AKT3, inhibitor/GSK3, inhibitor/p70s6k, inhibitor/PDK1, inhibitor/Aurora-2, inhibitor/ROCK, inhibitor/SRC, inhibitor/SYK, inhibitor/ZAP70, inhibitor/JNK3, inhibitor/JAK3, inhibitor/TEC, inhibitor/LCK, inhibitor/FLTS, or inhibitor/CDK2, complex and determining the amount of radiolabel bound. Alternatively, inhibitor binding may be determined by running a competition experiment where new inhibitors are incubated with ERK2, AKT3, GSK3, p70s6k, PDK1, Aurora-2, ROCK, SRC, SYK, ZAP70, JNK3, JAK3, TEC, LCK, FLT3, and/or CDK2 bound to known radioligands. Detailed conditions for assaying a compound utilized in this invention as an inhibitor of ERK2, AKT3, GSK3, p70s6k, PDK1, Aurora-2, ROCK, SRC, SYK, ZAP70, JNK3, JAK3, TEC, LCK, FLT3, and CDK2 kinase are set forth in the Examples below.

According to another embodiment, the invention provides a composition comprising a compound of this invention or a pharmaceutically acceptable derivative thereof and a pharmaceutically acceptable carrier, adjuvant, or vehicle. The amount of compound in the compositions of this invention is such that is effective to detectably inhibit a protein kinase, particularly ERK2, AKT3, GSK3, p70s6k, PDK1, Aurora-2, ROCK, SRC, SYK, ZAP70, JNK3, JAK3, TEC, LCK, FLT3, and/or CDK2 kinase, in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "detectably inhibit", as used herein means a measurable change in ERK2, AKT3, GSK3, p70s6k, PDK1, Aurora-2, ROCK, SRC, SYK, ZAP70, JNK3, JAK3, TEC, LCK, FLT3, and/or CDK2 activity between a sample comprising said composition and a ERK2, AKT3, GSK3, p70s6k, PDK1, Aurora-2, ROCK, SRC, SYK, ZAP70, JNK3, JAK3, TEC, LCK, FLT3, and/or CDK2 kinase and an equivalent sample comprising ERK2, AKT3, GSK3, p70s6k, PDK1, Aurora-2, ROCK, SRC, SYK, ZAP70, JNK3, JAK3, TEC, LCK, FLT3, and/or CDK2 kinase in the absence of said composition.

As used herein, the term "JNK" is used interchangeably with the terms "JNK kinase" and "a JNK family kinase". Preferably JNK refers to JNK3 kinase.

As used herein, the term "JAK" is used interchangeably with the terms "JAK kinase" and "a JAK family kinase". Preferably JAK refers to JAK3 kinase.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of ERK2, AKT3, GSK3, p70s6k, PDK1, Aurora-2, ROCK, SRC, SYK, ZAP70, JNK3, JAK3, TEC, LCK, FLT3, and/or CDK2 kinase.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N+(C1-4 alkyl)4 salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting ERK2, AKT3, GSK3, p70s6k, PDK1, Aurora-2, ROCK, SRC, SYK, ZAP70, JNK3, JAK3, TEC, LCK, FLT3, and/or CDK2 kinase activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of protein kinase, or a protein kinase selected from ERK2, AKT3, GSK3, p70s6k, PDK1, Aurora-2, ROCK, SRC, SYK, ZAP70, JNK3, JAK3, TEC, LCK, FLT3, and/or CDK2 kinase, activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting ERK2, AKT3, GSK3, p70s6k, PDK1, Aurora-2, ROCK, SRC, SYK, ZAP70, JNK3, JAK3, TEC, LCK, FLT3, and/or CDK2 kinase activity in a patient comprising the step of administering to said patient a compound of the present invention, or a composition comprising said compound.

According to another embodiment, the invention provides a method for treating or lessening the severity of an ERK2-mediated disease or condition in a patient comprising the step of administering to said patient a composition according to the present invention.

The term "ERK-mediated disease" or "condition", as used herein means any disease or other deleterious condition in which ERK is known to play a role. Accordingly, another embodiment of the present invention relates to treating or lessening the severity of one or more diseases in which ERK is known to play a role. Specifically, the present invention relates to a method of treating or lessening the severity of a disease or condition selected from cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases, wherein said method comprises administering to a patient in need thereof a composition according to the present invention.

According to another embodiment, the present invention relates to a method of treating a cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia.

Another embodiment relates to a method of treating melanoma, breast cancer, colon cancer, or pancreatic cancer in a patient in need thereof.

The term "AKT-mediated disease" or "condition", as used herein means any disease or other deleterious condition in which AKT is known to play a role. Accordingly, another embodiment of the present invention relates to treating or lessening the severity of one or more diseases in which AKT is known to play a role. Specifically, the present invention relates to a method of treating or lessening the severity of a disease or condition selected from proliferative disorders, cancer, and neurodegenerative disorders, wherein said method comprises administering to a patient in need there of a composition according to the present invention.

The term "GSK3-mediated disease" or "condition", as used herein means any disease or other deleterious condition in which GSK3 is known to play a role. Accordingly, another embodiment of the present invention relates to treating or lessening the severity of one or more diseases in which GSK3 is known to play a role. Specifically, the present invention relates to a method of treating or lessening the severity of a disease or condition selected from autoimmune disease, an inflammatory disease, a metabolic disorder, a psychiatric disorder, diabetes, an angiogenic disorder, tauopothy, a neurological or neurodegenerative disorder, a spinal cord injury, glaucoma, baldness, or a cardiovascular disease wherein said method comprises administering to a patient in need thereof a composition according to the present invention.

According to another embodiment, the present invention relates to a method for treating or lessening the severity of a disease or condition selected from allergy, asthma, diabetes, Alzheimer's disease, Huntington's disease, Parkinson's disease, AIDS-associated dementia, amyotrophic lateral sclerosis (ALS, Lou Gehrig's disease), multiple sclerosis (MS), an injury due to head trauma, schizophrenia, anxiety, bipolar disorder, tauopothy, a spinal cord or peripheral nerve injury, myocardial infarction, cardiomyocyte hypertrophy, glaucoma, attention deficit disorder (ADD), depression, a sleep disorder, reperfusion/ischemia, stroke, an angiogenic disorder, or baldness, wherein said method comprises administering to a patient in need thereof a compound of the present invention or composition thereof.

According to a preferred embodiment, the method of the present invention relates to treating or lessening the severity of stroke.

According to another preferred embodiment, the method of the present invention relates to treating or lessening the severity of a neurodegenerative or neurological disorder.

Another aspect of the present invention relates to a method of decreasing sperm motility in a male patient comprising administering to said patient a compound of the present invention or composition thereof.

The term "p70S6K-mediated condition" or "disease", as used herein, means any disease or other deleterious condition in which p70S6K is known to play a role. The term "p70S6K-mediated condition" or "disease" also means those diseases or conditions that are alleviated by treatment with a p70S6K inhibitor. Accordingly, another embodiment of the present invention relates to treating or lessening the severity of one or more diseases in which p70S6K is known to play a role. Specifically, the present invention relates to a method of treating or lessening the severity of a disease or condition selected from proliferative disorders, such as cancer and tuberous sclerosis, wherein said method comprises administering a patient in need thereof a composition according to the present invention.

The term "PDK1-mediated condition" or "disease", as used herein, means any disease or other deleterious condition in which PDK1 is known to play a role. The term "PDK1-mediated condition" or "disease" also means those diseases or conditions that are alleviated by treatment with a PDK1 inhibitor. Accordingly, another embodiment of the present invention relates to treating or lessening the severity of one or more diseases in which PDK1 is known to play a role. Specifically, the present invention relates to a method of treating or lessening the severity of a disease or condition selected from proliferative disorders, and pancreatic, prostate, or ovarian cancer, wherein said method comprises administering a patient in need thereof a composition according to the present invention.

The term "Tec family tyrosine kinases-mediated condition", as used herein means any disease or other deleterious condition in which Tec family kinases are known to play a role. Accordingly, another embodiment of the present invention relates to treating or lessening the severity of one or more diseases in which Tec family kinases is known to play a role. Specifically, the present invention relates to a method of treating or lessening the severity of a disease or condition selected from autoimmune, inflammatory, proliferative, and hyperproliferative diseases and immunologically-mediated diseases including rejection of transplanted organs or tissues and Acquired Immunodeficiency Syndrome (AIDS), wherein said method comprises administering to a patient in need thereof a composition of the present invention.

For example, diseases and conditions associated with Tec family tyrosine kinases include diseases of the respiratory tract including, without limitation, reversible obstructive airways diseases including asthma, such as bronchial, allergic, intrinsic, extrinsic and dust asthma, particularly chronic or inveterate asthma (e.g. late asthma airways hyper-responsiveness) and bronchitis. Additional diseases and conditions associated with Tec family tyrosine kinases include those conditions characterised by inflammation of the nasal mucus membrane, including acute rhinitis, allergic, atrophic thinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis, seasonal rhinitis including rhinitis nervosa (hay fever) and vasomotor rhinitis, sarcoidosis, farmer's lung and related diseases, fibroid lung and idiopathic interstitial pneumonia.

Further diseases and conditions associated with Tec family tyrosine kinases include diseases of the bone and joints including, without limitation, (pannus formation in) rheumatoid arthritis, seronegative spondyloarthropathis (including ankylosing spondylitis, psoriatic arthritis and Reiter's disease), Behcet's disease, Sjogren's syndrome, and systemic sclerosis.

Further diseases and conditions associated with Tec family tyrosine kinases include diseases and disorders of the skin, including, without limitation, psoriasis, systemic sclerosis, atopical dermatitis, contact dermatitis and other eczematous derrnatitis, seborrhoetic dermatitis, Lichen planus, Pemphigus, bullous Pemphigus, epidermolysis bullosa, urticaria, angiodermas, vasculitides, erythemas, cutaneous eosinophilias, uveitis, Alopecia, areata and vernal conjunctivitis.

Additional diseases and conditions associated with Tec family tyrosine kinases include diseases and disorders of the gastrointestinal tract, including, without limitation, Coeliac disease, proctitis, eosinophilic gastro-enteritis, mastocytosis, pancreatitis, Crohn's disease, ulcerative colitis, food-related allergies which have effects remote from the gut, e.g. migraine, rhinitis and eczema.

Further diseases and conditions associated with Tec family tyrosine kinases include those diseases and disorders of other tissues and systemic disease, including, without limitation, multiple sclerosis, artherosclerosis, acquired immunodeficiency syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia purpura, restenosis following angioplasty, tumours (for example leukemia, lymphomas), artherosclerosis, and systemic lupus erythematosus.

Further diseases and conditions associated with Tec family tyrosine kinases include allograft rejection including, without limitation, acute and chronic allograft rejection following for example transplantation of kidney, heart, liver, lung, bone marrow, skin and cornea; and chronic graft versus host disease.

According to another embodiment, the present invention relates to a method of treating or lessening the severity of one or more of the diseases or conditions associated with Tec family tyrosine kinases, as recited above, wherein said method comprises administering to a patient in need thereof a composition according to the present invention.

The term "Aurora-mediated disease", as used herein, means any disease or other deleterious condition or disease in which an Aurora family protein kinase is known to play a role. Accordingly, another embodiment of the present invention relates to treating or lessening the severity of one or more diseases in which Aurora is known to play a role. Specifically, the present invention relates to a method of treating or lessening the severity of a disease or condition selected from melanoma, leukemia, or a cancer selected from colon, breast, gastric, ovarian, cervical, lung, CNS, renal, prostate, lymphoma, neuroblastoma, pancreatic, leukemia and bladder.

Another aspect of the present invention relates to the disruption of mitosis of cancer cells in a patient, comprising the step of administering to said patient a compound of the present invention or composition thereof.

According to another embodiment, the present invention relates to a method of treating or lessening the severity of a cancer in a patient comprising the step of disrupting mitosis of the cancer cells by inhibiting Aurora-1, Aurora-2, and/or Aurora-3 with a compound of the present invention or composition thereof.

The term "ROCK-mediated condition" or "disease", as used herein, means any disease or other deleterious condition in which ROCK is known to play a role. The term "ROCK-mediated condition" or "disease" also means those diseases or conditions that are alleviated by treatment with a ROCK inhibitor. Accordingly, another embodiment of the present invention relates to treating or lessening the severity of one or more diseases in which ROCK is known to play a role. Specifically, the present invention relates to a method of treating or lessening the severity of a disease or condition selected from hypertension, angina pectoris, cerebrovascular contraction, asthma, peripheral circulation disorder, premature birth, cancer, arteriosclerosis, spasm, retinopathy, inflammatory disorders, autoimmune disorders, AIDS, and osteoporosis, wherein said method comprises administering to a patient in need thereof a composition according to the present invention.

The terms "SRC-mediated disease" or "SRC-mediated condition", as used herein mean any disease or other deleterious condition in which SRC is known to play a role. The terms "SRC-mediated disease" or "SRC-mediated condition" also mean those diseases or conditions that are alleviated by treatment with a SRC inhibitor. Accordingly, another embodiment of the present invention relates to treating or lessening the severity of one or more diseases in which SRC is known to play a role. Specifically, the present invention relates to a method of treating or lessening the severity of a disease or condition selected from hypercalcemia, osteoporosis, osteoarthritis, cancer, symptomatic treatment of bone metastasis, and Paget's disease, wherein said method comprises administering to a patient in need thereof a composition according to the present invention.

The term "SYK-mediated disease" or "SYK-mediated condition", as used herein, means any disease or other deleterious condition in which SYK protein kinase is known to play a role. Accordingly, another embodiment of the present invention relates to treating or lessening the severity of one or more diseases in which SYK is known to play a role. Specifically, the present invention relates to a method of treating or lessening the severity of a disease or condition selected from an allergic disorders, wherein said method comprises administering to a patient in need thereof a composition according to the present invention.

According to another embodiment, the present invention relates to a method of treating or lessening the severity of asthma in a patient in need thereof, wherein said method comprises administering to a patient in need thereof a composition according to the present invention. As used herein, the term "asthma" includes bronchial, allergic, intrinsic, extrinsic and dust asthma, particularly chronic or inveterate asthma (e.g. late asthma airways hyper-responsiveness) and bronchitis.

The term "ZAP70-mediated condition", as used herein means any disease or other deleterious condition in which ZAP70 is known to play a role. Accordingly, another embodiment of the present invention relates to treating or lessening the severity of one or more diseases in which ZAP70 is known to play a role. Specifically, the present invention relates to a method of treating or lessening the severity of a disease or condition selected from autoimmune, inflammatory, proliferative and hyperproliferative diseases, and immunologically-mediated diseases, wherein said method comprises administering to a patient in need thereof a composition according to the present invention.

According to another embodiment, the present invention relates to a method of treating or lessening the severity of a disease or condition selected from rejection of transplanted organs or tissues, Acquired Immunodeficiency Syndrome (AIDS), allograft rejection including, without limitation, acute and chronic allograft rejection following for example transplantation of kidney, heart, liver, lung, bone marrow, skin and cornea; and chronic graft versus host disease.

According to another embodiment, the present invention relates to a method of treating or lessening the severity of a disease or conditions characterised by inflammation of the nasal mucus membrane, including acute rhinitis, allergic, atrophic thinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis, seasonal rhinitis including rhinitis nervosa (hay fever) and vasomotor rhinitis, sarcoidosis, farmer's lung and related diseases, fibroid lung and idiopathic interstitial pneumonia.

According to another embodiment, the present invention relates to a method of treating or lessening the severity of a disease or condition of the bone and joints including (pannus formation in) rheumatoid arthritis, seronegative spondyloarthropathis (including ankylosing spondylitis, psoriatic arthritis and Reiter's disease), Behcet's disease, Sjogren's syndrome, and systemic sclerosis.

According to another embodiment, the present invention relates to a method of treating or lessening the severity of a disease or condition of the skin, including, without limitation, psoriasis, systemic sclerosis, atopical dermatitis, contact dermatitis and other eczematous dermatitis, seborrhoetic dermatitis, Lichen planus, Pemphigus, bullous Pemphigus, epidermolysis bullosa, urticaria, angiodermas, vasculitides, erythemas, cutaneous eosinophilias, uveitis, Alopecia, areata and vernal conjunctivitis.

According to another embodiment, the present invention relates to a method of treating or lessening the severity of a disease or condition of the gastrointestinal tract, including, without limitation, Coeliac disease, proctitis, eosinophilic gastro-enteritis, mastocytosis, pancreatitis, Crohn's disease, ulcerative colitis, food-related allergies which have effects remote from the gut, e.g. migraine, rhinitis and eczema.

Another embodiment, the present invention relates to a method of treating or lessening the severity of a disease or condition selected from multiple sclerosis, artherosclerosis, acquired immunodeficiency syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia purpura, restenosis following angioplasty, tumours (for example leukemia, lymphomas), artherosclerosis, and systemic lupus erythematosus.

The term "FLT3-mediated disease", as used herein means any disease or other deleterious condition in which a FLT3 family kinase is known to play a role. Accordingly, another embodiment of the present invention relates to treating or lessening the severity of one or more diseases in which FLT3 is known to play a role. Specifically, the present invention relates to a method of treating or lessening the severity of a disease or condition selected from, hematopoietic disorders, in particular, acute-myelogenous leukemia (AML), acute-promyelocytic leukemia (APL), and acute lymphocytic leukemia (ALL), wherein said method comprises administering to a patient in need thereof a composition according to the present invention.

The terms "LCK-mediated disease" or "LCK-mediated condition", as used herein, mean any disease state or other deleterious condition in which LCK is known to play a role. The terms "LCK-mediated disease" or "LCK-mediated condition" also mean those diseases or conditions that are alleviated by treatment with an LCK inhibitor. Accordingly, another embodiment of the present invention relates to treating or lessening the severity of one or more diseases in which LCK is known to play a role. Specifically, the present invention relates to a method of treating or lessening the severity of a disease or condition selected from an autoimmune disease, such as transplant rejection, allergies, rheumatoid arthritis, and leukemia, comprising the step of administering to a patient in need thereof a composition according to the present invention.

According to another embodiment, the invention provides a method for treating or lessening the severity of a JNK-mediated disease or condition in a patient comprising the step of administering to said patient a composition according to the present invention.

The term "JNK-mediated disease" or "condition", as used herein means any disease or other deleterious condition in which JNK is known to play a role. Accordingly, another embodiment of the present invention relates to treating or lessening the severity of one or more diseases in which JNK is known to play a role. Specifically, the present invention relates to a method of treating or lessening the severity of a disease or condition selected from inflammatory diseases, autoimmune diseases, destructive bone disorders, proliferative disorders, cancer, infectious diseases, neurodegenerative diseases, allergies, reperfusion/ischemia in stroke, heart attacks, angiogenic disorders, organ hypoxia, vascular hyperplasia, cardiac hypertrophy, thrombin-induced platelet aggregation, and conditions associated with prostaglandin endoperoxidase synthase-2, wherein said method comprises administering to a patient in need thereof a composition according to the present invention.

Inflammatory diseases which may be treated by the compounds of this invention include, but are not limited to, acute pancreatitis, chronic pancreatitis, asthma, allergies, and adult respiratory distress syndrome.

Autoimmune diseases which may be treated by the compounds of this invention include, but are not limited to, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, or graft vs. host disease.

Destructive bone disorders which may be treated by the compounds of this invention include, but are not limited to, osteoporosis, osteoarthritis and multiple myeloma-related bone disorder.

Proliferative diseases which may be treated by the compounds of this invention include, but are not limited to, acute myelogenous leukemia, chronic myelogenous leukemia, metastatic melanoma, Kaposi's sarcoma, multiple myeloma and HTLV-1 mediated tumorigenesis.

Angiogenic disorders which may be treated by the compounds of this invention include solid tumors, ocular neovasculization, infantile haemangiomas.

Infectious diseases which may be treated by the compounds of this invention include, but are not limited to, sepsis, septic shock, and Shigellosis.

Viral diseases which may be treated by the compounds of this invention include, but are not limited to, acute hepatitis infection (including hepatitis A, hepatitis B and hepatitis C), HIV infection and CMV retinitis.

Neurodegenerative diseases which may be treated by the compounds of this invention include, but are not limited to, Alzheimer's disease, Parkinson's disease, amyotrophic lateral sclerosis (ALS), epilepsy, seizures, Huntington's disease, traumatic brain injury, ischemic and hemorrhaging stroke, cerebral ischemias or neurodegenerative disease, including apoptosis-driven neurodegenerative disease, caused by traumatic injury, acute hypoxia, ischemia or glutamate neurotoxicity.

The term "JNK-mediated disease" or "condition" also includes ischemia/reperfusion in stroke, heart attacks, myocardial ischemia, organ hypoxia, vascular hyperplasia, cardiac hypertrophy, hepatic ischemia, liver disease, congestive heart failure, pathologic immune responses such as that caused by T cell activation and thrombin-induced platelet aggregation.

In addition, compounds of the present invention may be capable of inhibiting the expression of inducible pro-inflammatory proteins. Therefore, other "JNK-mediated diseases" or "conditions" which may be treated by the compounds of this invention include edema, analgesia, fever and pain, such as neuromuscular pain, headache, cancer pain, dental pain and arthritis pain.

According to another embodiment, the invention provides a method for treating or lessening the severity of a JAK-mediated disease or condition in a patient comprising the step of administering to said patient a composition according to the present invention.

The term "JAK-mediated disease", as used herein means any disease or other deleterious condition in which a JAK family kinase is known to play a role. Accordingly, another embodiment of the present invention relates to treating or lessening the severity of one or more diseases in which LCK is known to play a role. Specifically, the present invention relates to a method of treating or lessening the severity of a disease or condition selected from immune responses such as allergic or type I hypersensitivity reactions, asthma, autoimmune diseases such as transplant rejection, graft versus host disease, rheumatoid arthritis, amyotrophic lateral sclerosis, and multiple sclerosis, neurodegenerative disorders such as Familial amyotrophic lateral sclerosis (FALS), as well as in solid and hematologic malignancies such as leukemias and lymphomas, wherein said method comprises administering to a patient in need thereof a composition according to the present invention.

The compounds of this invention are also useful as inhibitors of CDK2 kinase. Accordingly, these compounds are useful for treating or lessening the severity of CDK2-mediated diseases or conditions.

The term "CDK2-mediated disease", as used herein means any disease or other deleterious condition in which CDK2 is known to play a role. Accordingly, these compounds are useful for treating diseases or conditions that are known to be affected by the activity of CDK2 kinase. Such diseases or conditions include viral infections, neurodegenerative disorders, and disorders associated with thymocyte apoptosis. Such diseases or conditions also include proliferative disorders resulting from the deregulation of the cell cycle, especially of the progression from $G_1$ to S phase.

According to another embodiment, the present invention relates to a method of treating or lessening the severity of a cancer comprising the step of blocking the transition of cancer cells into their proliferative phase by inhibiting CDK2 with a compound of the present invention, or pharmaceutically acceptable composition thereof.

Depending upon the particular condition, or disease, to be treated, additional therapeutic agents, which are normally administered to treat that condition, may also be present in the compositions of this invention. As used herein, additional therapeutic agents that are normally administered to treat a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as betablockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Those additional agents may be administered separately from the compound-containing composition, as part of a multiple dosage regimen. Alternatively, those agents may be part of a single dosage form, mixed together with the compound of this invention in a single composition. If administered as part of a multiple dosage regime, the two active agents may be submitted simultaneously, sequentially or within a period of time from one another normally within five hours from one another.

The amount of both, the compound and the additional therapeutic agent (in those compositions which comprise an additional therapeutic agent as described above)) that may be combined with the carrier materials to produce a single dosage form will vary depending upon the host treated and the particular mode of administration. Preferably, the compositions of this invention should be formulated so that a dosage of between 0.01-100 mg/kg body weight/day of a compound of formula I can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-100 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition. Implantable devices coated with a compound of this invention are another embodiment of the present invention.

Each of the aforementioned methods directed to the inhibition of one or more protein kinases, or the treatment of a disease alleviated thereby, is preferably carried out with a preferred compound of formula I, I', I", II, III, IV, or V, as described above. More preferably, each of the aforementioned methods is carried out with a preferred compound of formula I', I", II, III, IV, or V', and most preferably with a compound of formula I" or V'.

In order that the invention described herein may be more fully understood, the following examples are set forth. It should be understood that these examples are for illustrative purposes only and are not to be construed as limiting this invention in any manner.

SYNTHETIC EXAMPLES

Example 1

3-(3-Dimethylamino-acryloyl)-benzonitrile

A mixture of 3-Acetyl-benzonitrile (36.2 g, 249 mmol) in dimethylformamide dimethylacetal (200 mL, excess) was heated to reflux overnight. The solvent was evaporated in vacuo to afford an orange solid. The solid was dissolved in dichloromethane and filtered over a plug of silica gel eluting with 20% ethyl acetate/dichloromethane. The filtrate was concentrated in vacuo to afford 42.0 g (84%) of the title compound as an orange solid.

Example 2

3-(2-Phenylamino-pyrimidin-4-yl)-benzonitrile

To a solution of 3-(3-dimethylamino-acryloyl)-benzonitrile (30.4 g, 152 mmol) in acetonitrile (250 mL) was added a solution of phenylguanidine (21.0 g, 155 mmol) in acetonitrile (250 mL) and the mixture was heated at reflux for two hours. The solution was cooled and the resulting solid was filtered and washed with acetonitrile to afford the title compound.

Example 3

3-(2-Phenylamino-pyrimidin-4-yl)-benzoic acid

To a suspension of 3-(2-phenylamino-pyrimidin-4-yl)-benzonitrile (10 g, 36.7 mmol) in acetic acid (20 mL) was added concentrated hydrochloric acid (30 mL) and the suspension was heated at 100° C. overnight. The starting material completely dissolved and then a solid precipitated. The reaction mixture was filtered and precipitate was washed with ether and methanol to afford 9 g (84%) of the title compound.

Example 4

A series of compounds of the present invention was prepared from 3-(2-phenylamino-pyrimidin-4-yl)-benzoic acid in the following manner: To a solution of 3-(2-phenylamino-pyrimidin-4-yl)-benzoic acid (100 mg, 343 µmol) in DMF was added EDC (105 mg, 548 µmol), HOBT (90 mg, 666 µmol) and ethyldiisopropylamine (177 µl, 1.02 mmol). The reaction mixture was stirred at room temperature for 1 hour. The amine (3 eq) was added and the reaction was stirred at room temperature overnight. The reaction mixture was diluted with ethyl acetate and washed sequentially with water, brine, and dried (MgSO$_4$). The organic layer was concentrated to afford the crude product as a yellow oil. The crude product was purified by preparative HPLC (Column: Kiomasil, 150×21 mm, C8, 10 mm Gradient: 20% CH$_3$CN-->90% CH$_3$CN over 15 minutes) to afford the desire amide product.

Example 5

N-(4-Acetyl-phenyl)-2-morpholin-4-yl-2-phenyl-acetamide

To a solution of α-bromo-2-phenyl acetic acid (1 g) in CH$_2$Cl$_2$ (15 mL) was added oxalyl chloride (5 mL of 2M in CH$_2$Cl$_2$). To the resulting solution was added 1 DMF (10 µL). After 2 hours, the solution was concentrated and azeotroped from toluene (2×10 mL) then re-dissolved in CH$_2$Cl$_2$ (15 mL). The stirred solution was treated with of 4-aminoacetophenone (1.0 g). After 30 minutes, the resulting suspension was treated sequentially with diisopropylethylamine (3 mL), and morpholine (2 mL). The resulting dark solution was allowed to stir for 8 hours at room temperature and then concentrated via rotary evaporation. The crude product was purified by silica gel chromatography (1:1 CH$_2$Cl$_2$:EtOAc) to yield 200 mg of the title compound as a yellow oil. $^1$H NMR (500 MHz, CDCl$_3$) δ 9.32 (1 H, s), 7.95 (2 H, d), 7.70 (2 H, d), 7.40 (5 H, m), 4.0 (1 H, s), 3.8 (4 H, m), 2.60 (3 H, s), 2.55 (4 H, m) ppm. FIA MS: 339.2 (M+H).

Example 6

N-{4-[2-(3-Amino-phenylamino)-pyrimidin-4-yl]-phenyl}-2-morpholin-4-yl-2-phenyl-acetamide (I"-1)

Compound I"-1 was prepared from N-(4-acetyl-phenyl)-2-morpholin-4-yl-2-phenyl-acetamide by methods substantially similar to those set forth above at Examples 1-4. $^1$H NMR (CDCl$_3$, 500 MHz) δ 9.2 (1 H, s), 8.35 (1 H, d), 8.0 (2 H, d), 8.65 (2 H, d), 7.3 (5H, m), 7.15 (1 H, m), 7.0 (1 H, m), 6.9 (1 H, d), 6.32 (1 H, m), 3.95 (1 H, s), 3.70 (4 H, m), 2.50 (4 H, m) ppm. M+1481.3.

Example 7

4-[5-Chloro-2-(1-(S)-hydroxymethylethylamino)-pyrimidin-4-yl]-N-[1-(3-(S)-chlorophenyl)-2-hydroxyethyl]-benzamide (I"-40)

5-Chlorouracil (25 g, 0.17 mol) was place in a dry flask (250 mL) and phosphorous oxytrichloride (100 mL) was added at ambient temperature. To this solution was added N,N-dimethylaniline (1 mL). The resulting solution was heated at 110° C. for 3 days or until reaction mixture becomes homogenous. The solvent was evaporated under reduce pressure and the residue was solubilised in ethyl acetate then wash twice with water, brine. The organic layer was dried over sodium sulfate and the crude product was then purified by chromatography on silica (ethyl acetate 3% in hexanes) to afford 25 g of 2,4,5-trichloropyrimidine as a yellowish liquid. The structure was confirmed by $^1$H NMR.

In a flask was added 2,4,5-trichloro-pyrimidine (1.3 equivalents, 2.66 g, 14.6 mmol), the commercially available 4-carboxyphenyl boronic acid methyl ester (1.0 equivalent, 2.02 g, 11.2 mmol), tetrakis triphenylphosphine palladium (0.1 equivalent, 1.3 g, 1.12 mmol), lithium chloride (3.0 equivalents, 1.4 g, 33.6 mmol), sodium carbonate (2N, 5 mL) and 1,2-dimethoxyethane (20 mL). The resulting mixture was heat at 80° C. for 24 hours then dissolved in ethyl acetate, washed with hydrochloric acid (1N), brine and dried over sodium sulfate. The crude product was purified by chromatography on silica (ethyl acetate, 10% in hexane) to afford 1.21 g of 4-(2,5-dichloro-pyrimidin-4-yl)-benzoic acid methyl ester as a white solid. The structure was confirmed by $^1$H NMR.

In a flask containing 1.0 eq. of 4-(2,5-dichloro-pyrimidin-4-yl)-benzoic acid methyl ester (1.0 equivalent, 1.415 g, 5 mmol) in dry ethanol (8 mL) was added (S)-(+)-alaminol (3.0 equivalents, 1.12 g, 15 mmol). The solution was heated for 12 hours, the solvent was evaporated and the crude product purified by chromatography on silica (ethyl acetate 25-40% in hexanes) to afford 780 mg of 4-[5-chloro-2-(1-(S)-hydroxymethyl-ethylamino)-pyrimidin-4-yl]-benzoic acid methyl ester as a colorless oil. The structure was confirmed by $^1$H NMR and LCMS: ES+=322.0.

To a solution of f 4-[5-chloro-2-(1-(S)-hydroxymethyl-ethylamino)-pyrimidin-4-yl]-benzoic acid methyl ester (780 mg, 2.43 mmol) in MeOH (7 mL) was added sodium hydroxide (3 mL, 1N) was added. The solution was heat at 80° C. for 24 hours. The reaction mixture pH was adjusted to ~3 by addition of hydrochloric acid (12N) at ambient temperature. The solvent was then evaporated under reduce pressure and the crude product, 4-[5-chloro-2-(1-(S)-hydroxymethylethylamino)-pyrimidin-4-yl]-benzoic acid, was dried under high vacuum and used at as is in the next step. The structure was confirmed by LCMS: ES+=308.0, ES-=306.1.

To a solution of 4-[5-chloro-2-(1-(S)-hydroxymethylethylamino)-pyrimidin-4-yl]-benzoic acid (760 mg, 2.47 mmol) and HOBt (1.2 equivalents, 400 mg, 2.96 mmol) in DMF (6 mL) was added EDC (1.3 equivalents, 617 mg, 3.21 mmol) and DIEA (2.2 equivalents, 950 uL, 5.43 mmol). After 45 minutes of stirring, (S)-(+)-3-chlorophenyl glycinol hydrochloride (1.1 equivalents, 565 mg, 2.72 mmol) was added. The reaction was monitored by HPLC. After approximately 24 hours, the solution was diluted with ethyl acetate and washed with water, brine and dried over sodium sulfate. The crude product was purified by chromatography on silica (MeOH 0-2% in ethyl acetate) to afford 230 mg of the title product. $^1$H NMR 500 MHz (MeOH-d4): 8.23 (s, 1H), 7.82 (m, 2H), 7.79 (m, 2H), 7.30 (s, 1H), 7.20 (m, 3H), 5.10 (m, 1H), 4.02 (m, 1H), 3.78 (m, 2H), 3.50 (m, 2H), 1.12 (d, 3H). LCMS: ES+=461, ES-=459.2.

Example 8

N-[1-(3-(S)-chlorophenyl)-2-hydroxyethyl]-4-[2-(1-(S)-hydroxymethyl-propylamino)-pyrimidin-4-yl]-benzamide (I"-36)

To a solution of 4-(2-amino-pyrimidin-4-yl)-benzoic acid (1.0 equivalent, 661 mg, 3.1 mmol) and HOBt (1.1 equivalents, 467 mg, 3.4 mmol) in DMF (6 mL) was added DIEA (2.2 equivalents, 1.18 mL, 6.8 mmol) and EDC (1.2 equivalents, 708 mg, 3.7 mmol). The solution was stirred for 10 minutes, then (S)-(+)-3-chlorophenyl glycinol hydrochloride (1.1 equivalents, 703 mg, 3.4 mmol) was added. After 24 hours of stirring, the solution was diluted in ethyl acetate and the organic layer washed with sodium bicarbonate, brine and dried over MgSO4. The crude material was purified by chromatography on silica (MeOH 5% in $CH_2Cl_2$) to afford 9.4 mg of 4-(2-aminopyrimidin-4-yl)-N-[1-(3-(S)-chlorophenyl)-2-hydroxyethyl]-benzamide. $^1$H NMR 500 MHz (DMSO-$d_6$): 8.4 (d, 1H), 8.0-8.2 (dd, 4H), 7.5(s, 1H), 7.2-7.4 (m, 4H), 5.15 (m, 1H), 3.7 (m, 2H). LCMS: ES+=369, ES-=367.2.

To a solution of 4-(2-aminopyrimidin-4-yl)-N-[1-(3-(S)-chlorophenyl)-2-hydroxyethyl]-benzamide (1.0 equivalent, 264 mg, 0.71 mmol) in THF (5 mL) was added 800 uL of hydrofluoric acid pyridine complex at 0° C. After 5 minutes, 200 uL of t-butylnitrite was added. The solution was stir overnight an allowed to warm to ambient temperature. The reaction was quenched over ice/water and the aqueous solution n extracted twice with ethyl acetate, washed with sodium bicarbonate, brine and dried over sodium sulfate. The solvent was evaporated and the crude product, N-[1-(3-chloro-(S)-phenyl)-2-hydroxy-ethyl]-4-(2-fluoro-pyrimidin-4-yl)-benzamide, was used directly in the next step. LCMS: ES+=372.0, ES-=370.5.

To a solution of N-[1-(3-(S)-chlorophenyl)-2-hydroxyethyl]-4-(2-fluoro-pyrimidin-4-yl)-benzamide (59 mg, pure at ~80%) in EtOH (1 mL) was added (S)-(+)-2-amino-1-butanol (10.0 equivalents, 140 uL). The solution was heated at 80° C. for 3 hours and the crude solution purified by reverse phase preparative HPCL (silica, MeOH 10% in $CH_2Cl_2$) to afford 7.0 mg of N-[1-(3-(S)-chlorophenyl)-2-hydroxyethyl]-4-[2-(1-(S)-hydroxymethyl-propylamino)-pyrimidin-4-yl]-benzamide. $^1$H NMR 500 MHz (MeOH-d4): 7.9-8.3 (3×s, 5H), 7.1-7.4 (m, 5H), 5.2 (m, 1H), 3.85 (d, 2H), 3.6 (m, 2H), 1.5-1.75 (2×m, 2H), 1.05 (t, 3H). LCMS: ES+=441.2, ES-=439.1.

Example 9

N-[1-(3-Chlorophenyl)-2-(S)-hydroxyethyl]-4-(2-cyclopropylamino-5-methylpyridin-4-yl)-benzamide (I"-46)

2-Fluoro-4-iodo-5-methyl-pyridine (0.90 g, 3.8 mmol), 4-carboxymethyl-phenyl boronic acid (0.72 g, 4.0 mmol), potassium phosphate (2.5 g, 11.8 mmol), and dichloro[1,1'-bis(diphenylphoshino)ferrocene]palladium (II) dichloromethane adduct (0.30 g, 0.37 mmol) were combined in a screw cap tube and 1.4-dioxane (20 mL) was added. Argon was bubbled through the reaction mixture, which was then sealed and heated to 95° C. overnight. The reaction mixture was diluted with water and extracted with ethyl acetate. The organic layer was dried over sodium sulfate and concentrated to a red solid, which was purified by chromatography on silica (EtOAc 0 to 40% in hexanes) to afford 4-(2-fluoro-5-methyl-pyridin-4-yl)-benzoic acid methyl ester, 0.62 g, 2.5 mmol, 66% yield. $^1$H NMR 500 MHz (CDCl$_3$): 8.05 (m, 3H), 7.33 (d, 2H), 6.74 (s, 1H), 3.90 (s, 3H), 2.15 (s, 3H).

4-(2-Fluoro-5-methyl-pyridin-4-yl)-benzoic acid methyl ester (0.31 g, 1.3 mmol) was dissolved in 10 mL THF. To this solution 100 mg (2.5 mmol) lithium hydroxide monohydrate dissolved in 2 mL water was added and the reaction mixture stirred overnight. 6N HCl (0.4 mL) was added and the reaction mixture concentrated to a white solid. To this solid was added 3-(S)-chlorophenylglycinol hydrochloride (0.30 g, 1.4 mmol), EDC (0.38 g, 2.0 mmol), and HOBt (0.27 g, 2.0 mmol) and dissolved in 5 mL DMF. To this reaction mixture DIEA (0.5 mL) was added and the reaction mixture was stirred at room temperature overnight. The reaction mixture was diluted with ethyl acetate, and washed with 10% citric acid, saturated sodium bicarbonate. The organic layer was dried and concentrated to an oil, which was purified by chromatography on silica (EtOAc 40 to 100%/hexanes) to afford N-[1-(3-(S)-chlorophenyl)-2-hydroxyethyl]-4-(2-fluoro-5-methylpyridin-4-yl)-benzamide, 0.40 g, 1.04 mmol, 80% yield. $^1$H NMR 500 MHz (CDCl$_3$): 8.05 (s, 1H), 7.88 (d, 2H), 7.33 (d, 2H), 6.90 (m, 1H), 7.25 (m, 4H), 6.74 (s, 1H), 5.20 (m, 1H), 3.94 (m, 2H), 2.15 (s, 3H), 2.04 (m, 1H).

In a flask containing 1.0 eq. of N-[1-(3-(S)-Chloro-phenyl)-2-hydroxy-ethyl]-4-(2-fluoro-5-methyl-pyridin-4-yl)-benzamide (23 mg, 60 uM), in 500 uL of DMSO was added 100 uL of cyclopropylamine. The solution was stirred at 110° C. for 3 days. The crude was purified by preparative HPLC to afford 5.1 mg of N-[1-(3-(S)-chlorophenyl)-2-(S)-hydroxyethyl]-4-(2-cyclopropylamino-5-methyl-pyridin-4-yl)-benzamide. $^1$H NMR 500 MHz (MeOH-d4): 8.0 (d, 2H), 7.8 (s, 1H), 7.25-7.6 (m, 6H), 5.2 (t, 1H), 3.85 (d, 2H), 2.7 (m, 1H), 2.15 (s, 3H), 1.0 (m, 2H), 0.7 (m, 2H). LCMS: ES+=422.2, ES−=420.3.

Example 10

N-[1-(3-Chloro-phenyl)-2-hydroxy-ethyl]-4-[5-fluoro-2-(1-hydroxymethyl-propylamino)-pyrimidi-4-yl]-benzamide (I"37)

2,4-Dichloro-5-fluoropyrimidine (0.50 g, 3.0 mmol) and 4-carboxyphenyl boronic acid (0.5 g, 3.0 mmol) were dissolved in dimethoxyethane (20 mL) in a screw cap test tube and 6 mL 2M Na$_2$CO$_3$ was added followed by 80 mg (0.069 mmol) tetrakis(triphenylphosphine)palladium. Argon was bubbled through the reaction mixture for 5 minutes and then the reaction mixture was heated to 85° C. overnight. The reaction mixture was poured into water and extracted with ethyl acetate. The organic layer was washed with brine, dried over sodium sulfate and concentrated to a solid, which was purified by chromatography on silica (MeOH 5%/CH$_2$Cl$_2$) to give 0.22 g (0.87 mmol, 29% yield) of 4-(2-chloro-5-fluoropyrimidin-4-yl)-benzoic acid as a white solid. $^1$H NMR 500 MHz (MeOH-d4): 8.85 (m, 1H), 8.20 (m, 4H).

4-(2-Chloro-5-fluoropyrimidin-4-yl)-benzoic acid (0.11 g, 0.44 mmol), 3-(S)-chloro phenylglycinol hydrochloride (0.104 g, 0.50 mmol), EDC (0.114 g, 0.60 mmol), and HOBt (68 mg, 0.50 mmol) were combined in DMF. To this reaction mixture DIEA (0.4 mL) was added and the reaction mixture was stirred at room temperature for 3 days. The reaction mixture was diluted with ethyl acetate, and washed with 1N HCl, and brine. The organic layer was dried over sodium sulfate and concentrated to an oil, which was purified by chromatography on silica (EtOAc 25-65%/hexanes) to give 40 mg of 4-(2-chloro-5-fluoro-pyrimidin-4-yl)-N-[1-(3-(S)-chlorophenyl)-2-hydroxy ethyl]-benzamide, 0.01 mmol, 23% yield.

4-(2-Chloro-5-fluoropyrimidin-4-yl)-N-[1-(3-(S)-chlorophenyl)-2-hydroxyethyl]-benzamide (40 mg, 0.01 mmol) was dissolved in ethanol (0.5 mL), 90 mg of (S)-2-aminobutan-1-ol was added and the reaction mixture heated to 85° C. for 3 days. The reaction mixture was diluted with ethyl acetate, washed with water, and the organic layer dried over sodium sulfate and concentrated to an oil, which was purified by reverse phase HPLC to afford 15 mg of N-[1-(3-(S)-chloro-phenyl)-2-hydroxy-ethyl]-4-[5-fluoro-2-(1-(S)-hydroxymethyl-propylamino)-pyrimidin-4-yl]-benzamide as a yellow solid, 0.033 mmol, 33% yield. $^1$H NMR 500 MHz (MeOH-d4): 8.9 (d, 1H), 8.28 (d, 1H), 8.20 (m, 2H), 8.00 (d, 2H), 7.48 (s, 1H), 7.30 (m, 3H), 5.20 (m, 1H), 3.98 (m, 1H), 3.87 (m, 2H), 3.69 (m, 2H), 1.80 (m, 1H), 1.60 (m, 1H), 1.00 (t, 3H). LCMS: ES+=459.0.

Example 11

4-[5-Chloro-2-(1-(S)-hydroxymethylpropylamino)-pyrinidin-4-yl]-N-[1-(3-(S)-chlorophenyl)-2-hydroxyethyl]-benzamide (I"-38)

2,4,5-Trichloropyrimidine (0.40 g, 2.2 mmol) and 4-carboxymethylphenyl boronic acid (0.4 g, 2.2 mmol) were dissolved in dimethoxyethane (20 mL) in a screw cap test tube and Na$_2$CO$_3$ (3.3 mL, 2M) was added followed by tetrakis(triphenylphosphine)palladium (40 mg, 0.036 mmol). Argon was bubbled through the reaction mixture for 5 minutes and then the reaction mixture was sealed and heated to 90° C. overnight. The reaction mixture was poured into water and extracted with ethyl acetate. The organic layer was washed with brine, dried over sodium sulfate and concentrated to an oil, which was purified by chromatography on silica (EtOAc 0 to 15%/hexanes) to give 0.31 g (1.1 mmol, 50% yield) of 4-(2,5-dichloropyrimidin-4-yl acid methyl ester as a white solid. $^1$H NMR 500 MHz (CDCl$_3$): 8.78 (s, 1H), 8.27 (d, 2H), 8.04 (d, 2H), 4.02 (s, 3H).

4-(2,5-Dichloropyrimidin-4-yl)-benzoic acid methyl ester (70 mg, 0.25 mmol) was dissolved in ethanol with 0.22 g, 2.5 mmol, of (S)-2-aminobutan-1-ol and the reaction mixture was heated to 80° C. for 6 hours, then allowed to stand at room temperature overnight. The reaction mixture was diluted with ethyl acetate, washed with 0.5 N HCl, brine, dried over sodium sulfate and concentrated to an oil, which was purified by chromatography on silica (EtOAc 20 to 60% in hexanes) to afford 4-[5-chloro-2-(1-hydroxymethylpropylamino)-pyrimidin-4-yl]-benzoic acid methyl ester as a colorless oil, 68 mg, 0.20 mmol, 80%. $^1$H NMR 500 MHz (CDCl$_3$): 8.24 (s, 1H), 8.10 (d, 2H), 7.78 (d, 2H), 5.23 (m, 1H), 3.96 (m, 1H), 3.94 (s, 3H), 3.78 (m, 1H), 3.63 (m, 1H), 2.84 (br s, 1H), 1.56 (m, 2H), 0.96 (t, 3H).

4-[5-Chloro-2-(1-hydroxymethylpropylamino)-pyrimidin-4-yl]-benzoic acid methyl ester (68 mg, 0.20 mmol) was dissolved in 4 mL THF. To this solution 41 mg of lithium hydroxide monohydrate in 2 mL water was added and the reaction mixture stirred for 3 days. The reaction mixture was diluted with 1N HCl and extracted with ethyl acetate. The organic layer was dried over sodium sulfate and concentrated to afford 4-[5chloro-2-(1-hydroxymethylpropylamino)-pyrimidin-4-yl]-benzoic acid as a yellow solid, 64 mg, 0.20 mmol. LCMS ES+=322.1.

4-[5-Chloro-2-(1-(S)-hydroxymethylpropylamino)-pyrimidin-4-yl]-benzoic acid (64 mg, 0.20 mmol,), 3-chloro-(S)-phenylglycinol hydrochloride (62 mg, 0.30 mmol), EDC (0.06 g, 0.30 mmol), and HOBt (40 mg, 0.30 mmol) were combined in DMF. To this reaction mixture DIEA (0.1 mL) was added and the reaction mixture was stirred at room temperature overnight. The reaction mixture was diluted with ethyl acetate, and washed with 1N HCl, and brine. The organic layer was dried over sodium sulfate and concentrated to an oil, which was purified by silica column (MeOH 1 to 10%/CH$_2$Cl$_2$) and then further purified by reverse phase HPLC to give 30 mg (0.063 mmol, 31% yield) of 4-[5-chloro-2-(1-(S)-hydroxymethylpropylamino)-pyrimidin-4-yl]-N-[1-(3-(S)-chlorophenyl)-2-hydroxyethyl]-benzamide. $^1$H NMR 500 MHz (MeOH-d4/CDCl$_3$): 8.31 (s, 1H), 7.98 (d, 2H), 7.87 (m, 2H), 7.48 (s, 1H), 7.25 (m, 3H), 5.24 (t, 1H), 3.97 (m, 3H), 3.80 (dd, 1H), 3.76 (dd, 1H), 1.72 (m, 1H), 1.62 (m, 1H), 1.03 (t, 3H). LCMS: ES+=475.0.

Example 12

4-(5-Chloro-2-cyclopropylamino-pyrimidin-4-yl)-N-[1-(3-(S)-chloro-phenyl)-2-hydroxy-ethyl]-benzamide (I"-39)

4-(2,5-Dichloropyrimidin-4-yl)-benzoic acid methyl ester (85 mg, 0.30 mmol) was dissolved in ethanol with 0.2 mL cyclopropylamine and the reaction mixture heated to 80° C. overnight. The reaction mixture was diluted with water and extracted with ethyl acetate. The organic layer was dried over sodium sulfate and concentrated to afford 4-(5-chloro-2-cyclopropylaminopyrimidin-4-yl)-benzoic acid methyl ester as a solid, 90 mg, 0.30 mmol, 100% yield. LCMS: ES+=304.1.

4-(5-Chloro-2-cyclopropylaminopyrimidin-4-yl)-benzoic acid methyl ester (90 mg, 0.30 mmol) was dissolved in THF and 50 mg (1.2 mmol) of lithium hydroxide monohydrate dissolved in water was added. The reaction mixture was heated to 50° C. for 5 hours, cooled to room temperature, diluted with 1N HCl and extracted with ethyl acetate. The organic layer was dried over sodium sulfate and concentrated to afford 4-(5-chloro-2-cyclopropylaminopyrimidin-4-yl)-benzoic acid as a yellow solid, 78 mg, 0.27 mmol, 90% yield.

4-(5-Chloro-2-cyclopropylaminopyrimidin-4-yl)-benzoic acid, 78 mg (0.27 mmol), 3-(S)-chlorophenylglycinol hydrochloride (80 mg, 0.38 mmol), EDC (0.095 g, 0.50 mmol), and HOBt (62 mg, 0.46 mmol) were combined in DMF. To this reaction mixture DIEA (0.2 mL) was added and the reaction mixture was stirred at room temperature overnight. The reaction mixture was diluted with ethyl acetate, and washed with 1N HCl, saturated sodium bicarbonate, and brine. The organic layer was dried over sodium sulfate and concentrated to an oil which was triturated with diethyl ether to afford 4-(5-chloro-2-cyclopropylamino-pyrimidin-4-yl)-N-[1-(3-(S)-chloro-phenyl)-2-hydroxyethyl]-benzamide as a yellow solid, 75 mg, 0.17 mmol, 62% yield. (CDCl$_3$): 8.33 (s, 1H), 7.87 (s, 4H), 7.28 (s, 1H), 7.24 (m, 3H), 6.95 (d, 1H), 5.40 (s, 1H), 5.18 (m, 1H), 3.93 (m, 2H), 2.74 (m, 1H), 2.23 (t, 1H), 0.80 (m, 2H), 0.50 (m, 2H). LCMS: ES+=442.9.

Example 13

4-(5-Chloro-2-isopropylamino-pyridin-4-yl)-N-[1-(3-chloro-phenyl)-2-hydroxy-ethyl]-benzamide (I"-44)

5-Chloro-2-fluoro-4-iodopyridine, (257 mg, 1 mmol), 4-carboxymethylphenyl boronic acid (0.2 g, 1.1 mmol) were dissolved in dimethoxyethane in a screw cap test tube and 1.5 mL 2M Na$_2$CO$_3$ was added followed by tetrakis(triphenylphosphine)palladium (50 mg, 0.044 mmol). Argon was bubbled through the reaction mixture for 5 min, the tube was sealed, and then the reaction mixture was heated to 85° C. overnight. The reaction mixture was poured into water and extracted with ethyl acetate. The organic layer was washed with brine, dried over sodium sulfate and concentrated to an oil, which was purified by chromatography on silica (EtOAc 0 to 15% in hexanes) to give 90 mg (0.34 mmol, 34% yield) of 4-(5-chloro-2-fluoropyridin-4-yl)-benzoic acid methyl ester. $^1$H NMR 500 MHz (CDCl$_3$): 8.24 (s, 1H), 8.10 (d, 2H), 7.48 (d, 2H), 6.89 (d, 1H), 3.91 (s, 3H). LCMS: ES+=257.9.

4-(5-Chloro-2-fluoropyridin-4-yl)-benzoic acid methyl ester (90 mg, 0.34 mmol) was dissolved in DMSO in a screw cap tube and 0.5 mL isopropylamine was added. The tube was sealed and heated to 90° C. for 2 days. The reaction mixture was diluted with water and extracted with ethyl acetate. The organic layer was washed with brine, dried over sodium sulfate and concentrated to an oil, which was purified by chromatography on silica (EtOAc 0 to 20%/hexanes) to give 70 mg of 4-(5-chloro-2-isopropylamino-pyridin-4-yl)-benzoic acid methyl ester, 0.23 mmol, 67% yield. $^1$H NMR 500 MHz (CDCl$_3$): 8.08 (m, 3H), 7.45 (d, 2H), 6.22 (s, 1H), 4.37 (d, 1H), 3.88 (s, 3H), 3.80 (m, 1H), 1.17 (d, 6H).

4-(5-Chloro-2-isopropylaminopyridin-4-yl)-benzoic acid methyl ester, 70 mg, 0.23 mmol, was dissolved in 3 mL THF. To this solution lithium hydroxide monohydrate (82 mg) in 1 mL water was added and the reaction mixture stirred overnight. 6N HCl (0.5 mL) was added to the reaction mixture and the solution concentrated to give the carboxylic acid as a solid. Half of this material was combined with 3-(S)-chlorophenylglycinol hydrochloride (80 mg, 0.38 mmol), EDC (80 mg, 0.42 mmol), and HOBt (44 mg, 0.33 mmol) and dissolved in 3 mL DMF. To this reaction mixture DIEA (0.5 mL) was added and the reaction mixture was stirred at room temperature for 3 days. The reaction mixture was diluted with ethyl acetate, and washed with 1N HCl, saturated sodium bicarbonate. The organic layer was dried and concentrated to an oil which was purified by reverse phase HPLC to afford 12 mg of 4-(5-chloro-2-isopropylamino-pyridin-4-yl)-N-[1-(3-chloro-phenyl)-2-hydroxyethyl]-benzamide, 0.027 mmol, 24% yield. $^1$H NMR 500 MHz (MeOH-d4); 8.02 (m, 3H) 7.62 (d, 2H), 7.43 (m, 1H), 7.34 (m, 2H), 7.30 (m, 1H), 6.87 (s, 1H), 5.21 (t, 1H), 3.97 (m, 1H), 3.88 (d, 2H), 1.35 (d, 6H). LCMS: ES+=444.0.

Example 14

N-[1-(3-(S)-Chlorophenyl)-2-hydroxy-ethyl]-4-(5-fluoro-2-isopropylamino-pyrimidin-4-yl)-benzamide (I"-41)

To a solution of 2,4-dichloro-5-fluoropyrimidine (0.478 g, 2.86 mmol) and 4-carboxyphenyl boronic acid methyl ester (0.516 g, 2.86 mmol) in 5 mL of ethyleneglycol dimethyl ether was added Pd(PPh$_3$)$_4$ under argon, followed by 2N Na$_2$CO$_3$ and the resulting mixture purged with argon for 2 minutes. The resulting mixture was sealed and heated at 85° C. overnight. After 18 hours, the reaction was diluted with 20 mL of ethyl acetate and washed with H$_2$O. The organic layer was concentrated and purified by chromatography (Silica, 10% ethyl acetate in hexanes) to afford 4-(2-chloro-5-fluoropyrimidin-4-yl)-benzoic acid methyl ester (0.35 g, 46%) as a white solid. LCMS: ES+=267.

To a solution of 4-(2-chloro-5-fluoropyrimidin-4-yl)-benzoic acid methyl ester (0.3 g, 1.13 mmol) in 4 mL of THF was added a solution of LiOH (0.378 g, 9.0 mmol) in 4 mL of H$_2$O and stirred at room temperature for 3 hours. The reaction mixture was extracted with ethyl acetate (10 mL) to remove any byproduct. The aqueous layer was acidified to pH=3 with 6N HCl and the resulting precipitate filtered. To a suspension of these solids in 5 mL of DMF was added EDC (0.26 g, 1.36 mmol), HOBt (0.229 g, 1.70 mmol), and Et$_3$N (0.236 mL, 1.70 mmol) and stirred for 10 minutes. (S)-(+)-3-chlorophenyl glycinol (0.353 g, 1.70 mmol) was added and the reaction stirred overnight. After 18 hours, the reaction was diluted with ethyl acetate and washed with 1N HCl, NaHCO$_3$, saturated NaCl. The organic layer was concentrated and the residue purified by chromatography (Silica, 40% ethyl acetate in hexanes) to afford 4-(2-chloro-5-fluoropyrimidin-4-yl)-N-[1-(3-chlorophenyl)-2-hydroxy-ethyl]-benzamide (0.15 g, 55%) as a white solid. $^1$H NMR (CDCl$_3$, 500 MHz): 8.40 (d, 1H), 8.15 (d, 2H), 7.90-7.95 (m, 2H), 7.32 (s, 1H), 7.22-7.29 (m, 2H), 7.05-7.08 (m, 1H), 5.18-5.22 (m, 1H), 3.95-4.00 (m, 2H), 1.80 (s, 2H). LCMS: ES+=406.

To a solution of 4-(2-chloro-5-fluoropyrimidin-4-yl)-N-[1-(3-chlorophenyl)-2-hydroxy-ethyl]-benzamide (0.030 g, 0.074 mmol) in 0.5 mL of DMSO was added isopropylamine (0.20 mL, 2.3 mmol) and heated at 80° C. for 2 hours. The reaction was diluted with 10 mL of ethyl acetate and washed with 5 mL of H$_2$O. The organic layer was concentrated and purified by chromatography (Silica, 50% ethyl acetate in hexanes) to afford N-[1-(3-(S)-chlorophenyl)-2-hydroxy-ethyl]-4-(5-fluoro-2-isopropylamino-pyrimidin-4-yl)-benzamide (0.02 g, 67%) as a white solid. $^1$H NMR(CDCl$_3$, 500 MHz): 8.20 (d, 1H), 8.20-8.22 (d, 2H), 7.85-7.90 (m, 2H), 7.35 (s, 1H), 7.22-7.29 (m, 2H), 6.93-6.95 (m, 1H), 5.20-5.25 (m, 1H), 4.08-4.12 (m, 1H), 3.92-3.95 (m, 2H), 1.20-1.22 (d, 6H). LCMS: ES+=429.

To a solution of 4-(2-chloro-5-fluoropyrimidin-4-yl)-N-[1-(3-(S)-chlorophenyl)-2-hydroxy-ethyl](0.030 g, 0.074 mmol) in 0.5 mL of DMSO was added cyclopropylamine (0.100 mL, 1.44 mmol) and heated at 110° C. for 2 h. The reaction was diluted with 10 mL of ethyl acetate and washed with 5 mL of H$_2$O. The organic layer was concentrated and purified by chromatography (Silica, 50% ethyl acetate in hexanes) to afford N-[1-(3-(S)-chlorophenyl)-2-hydroxy-ethyl]-4-(2-cyclopropylamino-5-fluoropyrimidin-4-yl)-benzamide (0.01 g, 33%) as a white solid. $^1$H NMR (CDCl$_3$, 500 MHz): 8.22 (d, 1H), 8.10 (d, 2H), 7.85 (d, 2H), 7.30 (s, 1H), 7.22-7.29 (m, 2H), 6.92-6.95 (m, 1H), 5.20-5.24 (m, 1H), 3.92-3.98 (m, 2H), 2.70-2.78 (m, 1H), 1.20 (s, 4H). LCMS: ES+=427.

Example 15

N-[1-(3-(S)-Chlorophenyl)-2-hydroxyethyl]-4-[5-fluoro-2-(2-(S)-hydroxy-1-methyl-ethylamino)-4-yl]-3-methyl-benzamide (I"-58)

To a solution of 4-(2-chloro-5-fluoropyrimidin-4-yl)-N-[1-(3-(S)-chlorophenyl)-2-hydroxy-ethyl]-3-methyl-benzamide (0.015 g, 0.036 mmol) in 0.5 mL of DMSO was added (S)-(+)-2-amino-1-propanol (0.05 m]L, 074 mmol) and the resulting mixture heated at 110° C. for 2 hours. The reaction was diluted with 10 mL of ethyl acetate and washed with 5 mL of H$_2$O. The organic layer was concentrated and purified by chromatography (Silica, 40% ethyl acetate in hexanes) to afford the title compound (0.010 g, 63%) as a white solid. $^1$H NMR (CDCl$_3$, 500 MHz): 8.15 (s, 1H), 7.70 (s, 1H), 7.65 (d, 1H), 730-7.35 (m, 3H), 7.20-7.25 (m, 2H), 5.32 (d, 1H), 5.09-5.12 (m, 1H), 4.00-4.08 (m, 1H), 3.80-3.90 (m, 2H), 3.65-3.71 (m, 1H), 3.52-3.55 (m, 1H), 2.30 (s, 3H), 1.21 (d, 3H). LC/MS: ES+=459.

Example 16

4-[5-Chloro-2-(2-hydroxy-1-methylethylamino)-pyrimidin-4-yl]-N-[1-(3-(S)-chloro phenyl)-2-hydroxy-ethyl]-3-methylbenzamide (I"-45)

$^1$H NMR (CDCl$_3$, 500 MHz): 8.25 (s, 1H), 7.70 (s, 1H), 7.65 (d, 1H), 7.30 (s, 1H), 7.20-7.25 (m, 3H), 6.92 (m, 1H), 5.35-5.40 (m, 1H), 5.10-5.15 (m, 1H), 4.02-4.10 (m, 1H), 3.90-3.92 (m, 2H), 3.65-3.70 (m, 1H), 3.55-3.60 (m, 1H), 2.20 (s, 3H), 1.25 (d, 3H). LCMS: ES+=475.

Example 17

4-[5-Chloro-2-(1-(S)-hydroxymethylpropylamino)-pyrimidin-4-yl]-N-[1-(3-(S)-chlorophenyl)-2-hydroxyethyl]-benzenesulfonamide (I"-47)

To a suspension of 3-(S)-chlorophenylglycinol HCl salt (416 mg, 2 mmol) in DCM (10 mL) was added TEA (0.8 mL, 5.7 mmol) and pipsyl chloride (605 mg, 2 mmol). The resulting reaction was stirred for 2 hours at room temperature. The reaction mixture was diluted with DCM (30 mL) and washed with H$_2$O and brine solution. The organic layer was dried over Na$_2$SO$_4$ and concentrated in vacuo. The crude N-[1-(3-(S)-chlorophenyl)-2-hydroxy-ethyl]-4-iodobenzenesulfonamide was used directly.

To a solution of N-[1-(3-(S)-chlorophenyl)-2-hydroxy-ethyl]-4-iodobenzenesulfonamide (2 mmol) in DMF (5 mL) was added bis(pinacolato)diboron (600 mg, 2.4 mmol), 1,1-bis(diphenylphosphino)ferrocene palladium (80 mg, 0.1 mmol) and potassium acetate (600 mg, 6 mmol) under N$_2$. The resulting mixture was stirred for 18 hours at 70° C. then diluted with EtOAc (30 mL) washed with brine (2×) and dried over Na$_2$SO$_4$. The crude product was purified by chromatography (Silica, 30% EtOAc in hexanes) to afford 400 mg of N-[1-(3-(S)-chlorophenyl)-2-hydroxyethyl]-4-(4,4,5,5-tetramethyl-[1,3,2]dioxaborolan-2-yl)-benzenesulfonamide. LCMS: ES+=437.

To a mixture of N-[1-(3-(S)-chlorophenyl)-2-hydroxyethyl]-4-(4,4,5,5-tetramethyl-[1,3,2]dioxaborolan-2-yl)-benzenesulfonamide (390 mg, 0.9 mmol), 2,4,6-trichloro-pyrimidine (200 mg, 1.1 mmol) and tetrakistriphenylphosphine palladium (100 mg, 0.09 mmol) in THF (8 mL) under N$_2$ was added 2 M of Na$_2$CO$_3$ solution (1.35 mL. 2.7 mmol). The resulting solution was stirred for 18 hours at 80° C. then cooled to room temperature. The reaction mixture was diluted with EtOAc (30 mL), washed with brine (2×), dried over anhydrous Na$_2$SO$_4$ and concentrated in vacuo. The crude was purified by chromatography (Silica, 30% EtOAc in hexanes) to afford N-[1-(3-(S)-chlorophenyl)-2-hydroxyethyl]-4-(2,5-dichloro-pyrimidin-4-yl)-benzenesulfonamide as an off white solid (270 mg). LCMS: ES+=458.

A solution of N-[1-(3-(S)-chlorophenyl)-2-hydroxyethyl]-4-(4,4,5,5-tetramethyl-[1,3,2]dioxaborolan-2-yl)-benzenesulfonamide (30 mg) and (S)-(+)-2-amino-1-butanol (50 uL) in DMSO (0.5 mL) was heated to 75° C. for 4 hours. The crude product was purified by preparative HPLC to afford 15 mg of brown oil that was further purified by preparative TLC to afford 7 mg of 4-[5-chloro-2-(1-(S)-hydroxymethylpropylamino)-pyrimidin-4-yl]-N-[1-(3-(S)-chlorophenyl)-2-hydroxyethyl]-benzenesulfonamide as a white solid. LCMS: ES+=511, ES−=509.

Example 18

N-[1-(3-Chlorophenyl)-2-(S)-hydroxyethyl]-4-(2-propylamino-5-methyl-4-phenyl)-benzamide (I"-62)

To a suspension of iron (1.5 g, 27.6 mmol) and ammonium chloride (2.46 g, 46 mmol) in water (50 mL) was slowly added a solution of 3-bromo-4-methyl-1-nitrobenzene (1.0 g, 4.6 mmol) in methanol (25 mL). The resulting mixture was refluxed for 2 hours. The solids formed were filtered through celite while the reaction mixture was still hot, the solvent of the clear filtrate was then removed. The crude residue was redissolved in water, extracted with ethyl acetate and dried over anhydrous sodium sulfate. The crude oil was adsorbed on silica gel and purified by flash chromatography on silica gel (hexanes/EtOAc from 95:5 to 50:50). The product, 3-bromo-4-methylaniline, was isolated as pale red oil (462 mg). HPLC $R_t$ 3.425 minutes.

2-Iodopropane (1.2 mL, 12.4 mmol) was added to a solution of 3-bromo-4-methylaniline (462 mg, 2.48 mmol) in DMF (2 mL). The reaction mixture was stirred at ambient temperature overnight. The crude mixture was poured into water and extracted with ethyl acetate. After drying over anhydrous sodium sulfate, the solvent was removed and the crude was adsorbed on silica gel. After purifying by flash chromatography on silica gel (hexanes/EtOAc from 99:1 to 80:20), the product, NN-(3-bromo-4-methylphenyl)isopropylamine, was isolated as a pale red oil (177 mg). FIA ES+ 228.0, 230.0.

To a solution of 4-carboxyphenylboronic acid (517 mg, 3.11 mmol), 3-chloro-(S)-phenylglycinol hydrochloride (713 mg, 3.42 mmol) and DIEA (1.2 mL, 6.84 mmol) in DMF (6 mL) was added PyBOP (1.1 g, 3.73 mmol) and the resulting mixture was stirred at ambient temperature for 24 hours. The reaction mixture was dissolved in ethyl acetate and washed with water and brine. After drying over anhydrous sodium sulfate, the solvent was removed and the crude oil was purified by reverse phase HPLC, yielding 4-[N-[1-(3-(S)-chlorophenyl)-2-hydroxyethylamino]carboxyphenyl boronic acid as a white solid (620 mg). FIA ES+ 320.3, ES− 318.0.

N,N-(3-Bromo-4-methylphenyl)isopropylamine (88.5 mg, 0.39 mmol) was dissolved in DME (1.5 mL). 4-[N-[1-(3-(S)-chlorophenyl)-2-hydroxyethylamino]carboxyphenyl boronic acid (125 mg, 0.39 mmol) was then added, followed by LiCl (49.6 mg, 1.17 mmol) and a 2 M solution of $Na_2CO_3$ (0.5 mL). Pd(PPh$_3$)$_4$ (45 mg, 0.039 mmol) was added and the vial was sealed. The reaction mixture was heated at 85° C. overnight. The reaction mixture was poured into water and extracted with ethyl acetate. After drying over anhydrous sodium sulfate, the solvent was removed and the crude oil was purified by reverse phase HPLC, yielding N-[1-(3-chlorophenyl)-2-(S)-hydroxyethyl]-4-(2-propylamino-5-methyl-4-phenyl)-benzamide as a white solid (24.7 mg). LCMS 2.5 minutes; ES+ 423.2, ES− 421.2. $^1$H NMR 500 MHz (MeOH-d4); 7.95 (d, 2H), 7.5 (d, 1H), 7.45 (m, 3H), 7.3 (m, 3H), 7.2 (m, 2H), 5.2 (t, 1H), 3.85 (d, 2H), 3.75 (m, 1H), 2.3 (s, 3H), 1.3 (d, 6H).

Example 19

4-(5-Chloro-2-ethoxyaminopyrimidin-4-yl)-N-[1-(3-(S)-chlorophenyl)-2-hydroxyethyl]-benzamide (I"-72)

To a solution of 4-(2-chloro-5-fluoropyrimidin-4-yl)-N-[1-(3-(S)-chlorophenyl)-2-hydroxy-ethyl]-3-methyl-benzamide (50 mg, 0.12 mmol) in 2 mL of DMSO was added O-ethylhydroxylamine.HCl (2 equivalents, 23 mg, 0.24 mmol) and the resulting mixture heated at 110° C. for 5 hours. The crude product was purified by preparative HPLC and to afford 6.7 mg of the title compound. $^1$H NMR 500 MHz (MeOH-d4): 8.4 (s, 1H), 7.9-8.0 (dd, 4H), 7.25-7.4 (m, 4H), 5.2 (m, 1H), 4.0 (m, 2H), 3.85 (m, 2H), 1.3 (t, 3H). LCMS: ES+=447.0, ES−=445.1.

Example 20

Compounds of the present invention were prepared by methods substantially similar to those described in the above Examples 1-19, those illustrated in Schemes I-VIII, and by methods known to one of ordinary skill in the art. The characterization data for these compounds is summarized in Table 4 below and includes LC/MS, HPLC, and $^1$H NMR data. Unless specified otherwise, the $^1$H NMR data was obtained at 500 MHz in CDCl$_3$ and all reported chemical shifts are ppm.

As used herein, the term "$R_t$" refers to the retention time, in minutes, obtained for the compound using the following HPLC method, unless specified otherwise:

Column: YMC ODS AQ, 3×100 mm, C18, 5 mm

Gradient: 10% CH$_3$CN-->90% CH$_3$CN over 8 minutes

HPLC Method B, if denoted with $R_t$ value, corresponds to the HPLC method above wherein the gradient is 15% CH$_3$CN-->90% CH$_3$CN.

Compound numbers correspond to the compound numbers listed in Tables 1, 2, and 3.

TABLE 4

Characterization Data for Selected Compounds of Formula I

| Compound No | M + 1 | M − 1 | $R_t$ | $^1$H NMR |
|---|---|---|---|---|
| I'-1 | 441.32 | — | 3.60 | — |
| I'-2 | 441.30 | — | 3.40 | — |
| I'-3 | 425.31 | — | 4.00 | — |
| I'-4 | 441.31 | — | 3.60 | — |
| I'-5 | 411.33 | — | 3.90 | — |
| I'-6 | 411.32 | — | 3.88 | — |
| I'-7 | 391.35 | — | 3.88 | — |
| I'-8 | 407.31 | — | 3.55 | — |
| I'-9 | 377.36 | — | 3.65 | — |
| I'-10 | 393.28 | — | 3.19 | — |
| I'-11 | 486.30 | — | 3.71 | — |
| I'-12 | 486.33 | — | 3.70 | — |
| I'-13 | N | — | 3.32 | — |
| I'-14 | 431.40 | — | 4.55 | — |
| I'-15 | 487.34 | — | 3.85 | — |
| I'-16 | 377.36 | — | 3.65 | — |
| I'-17 | 391.36 | — | 3.93 | — |
| I'-124 | 441.2 | 439.1 | 2.5 | (CDCl$_3$) 8.42 (1 H, s); 8.26 (1 H, d); 7.97 (1 H, d); 7.88 (1 H, d); 7.50 (1 H, t); 7.31 (1 H, s); 7.22 (3 H, m); 6.98 (1 H, d); 5.30 (1 H, m); 5.18 (1 H, m); 3.90 (3 H, m); 3.79 (1 H, m); 3.70 (1 H, m); 1.53 (1 H, m); |
| I'-125 | 529.3 | — | 5.2 | — |
| I'-126 | 483.3 | — | 4.1 | — |
| I"-1 | 481.3 | — | — | 9.2 (1 H, s), 8.35 (1 H, d), 8.0 (2 H, d), 8.65 (2 H, d), 7.3 (5 H, m), 7.15 (1 H, m), 7.0 (1 H, m), 6.9 (1 H, d), 6.32 (1 H, m), 3.95 (1 H, s), 3.70 (4 H, m), 2.50 (4 H, m) ppm. |
| I"-13 | 497.2 | — | — | DMSO-d6 10.12 (1 H, s), 8.58 (1 h, d), 8.23 (1 H, d), 8.09 (1 H, s), 7.89 (2 H, d), 7.85 (2 H, d), 7.72 (1 H, d), 7.54-7.41 (5 H, m), 7.03 (1 H, d), 5.88 (1 H, s), 3.82 (1 H, br s), 3.45 (1 H, br s), 3.19 (5 H, m), 2.80 (1 H, br s) ppm. |
| I"-14 | 573 | — | — | CD$_3$OD 8.34 (1 H, d), 8.10 (2 H, d), 8.04 (2 H, d), 7.91 (1 H, d), 7.40 (1 H, m), 7.33 (5 H, m), 7.24 (2 H, m), 7.20 (1 H, m), 7.06 (3 H, m), 6.85 (1 H, m), 6.60 (1 H, m), 6.47 (1 H, t), 6.41 (2 H, m), 4.99 (1 H, dd), 3.58 (1 H, dd), 2.9 |

TABLE 4-continued

Characterization Data for Selected Compounds of Formula I

| Compound No | M + 1 | M − 1 | R$_t$ | $^1$H NMR |
|---|---|---|---|---|
| I″-15 | 425.2 | — | — | CD$_3$OD 8.50 (1 H, d), 8.18 (3 H, m), 7.70, m), 7.48 (1 H, t), 7.41 (1 H, d), 7.34 (5 H, m), 7.03 (1 H, d), 4.25 (1 H, t), 3.33 (1 H, dd), 3.19 (1 H, dd) ppm. |
| I″-16 | 573.2 | — | — | CD$_3$OD 8.50 (1 H, d), 8.18 (3 H, m), 7.70, m), 7.48 (1 H, t), 7.41 (1 H, d), 7.34 (5 H, m), 7.03 (1 H, d), 4.25 (1 H, t), 3.33 (1 H, dd), 3.19 (1 H, dd) ppm. |
| I″-17 | 425.2 | — | — | CD$_3$OD 8.50 (1 H, d), 8.18 (3 H, m), 7.70 (1 H, m), 7.48 1 H, t), 7.41 (1 H, d), 7.34 (5 H, m), 7.03 (1 H, d), 4.25 (1 H, t), 3.33 (1 H, dd), 3.19 (1 H, dd), ppm. |
| I″-18 | 555.2 | — | — | DMSO-d6 10.39 (1 H, s), 9.64 (1 H, s), 8.50 (1 H, d), 8.13 (2 H, d), 7.84 (2 H, d), 7.78 (2 H, d), 7.50 (3 H, m), 7.32 (9 H, m), 6.95 (1 H, t), 4.38 (1 H, m), 3.55 (2 H), 3.17 (1 H, m), 2.70 (1 H, m), 2.65 (1 H, m), 2.30 (2 H, m), 1.65 |
| I″-19 | 467.2 | — | — | DMSO-d6 10.45 (1 H, s), 9.64 (1 H, s), 8.50 (1 H, d), 8.15 (2 H, d), 7.85 (4 H, m), 7.48 (2 H, m), 7.35 (6 H, m), 6.95 (1 H, m), 4.41 (1 H, s), 2.60 (2 H, m), 2.37 (2 H, m), 2.12 (6 H, s) ppm. |
| I″-20 | 509.2 | — | — | DMSO-d6 10.45 (1 H, s), 9.64 (1 H, s), 8.50 (1 H, d), 8.15 (2 H, d), 7.85 (4 H, m), 7.48 (2 H, m), 7.35 (6 H, m), 6.95 (1 H, m), 4.41 (1 H, s), 3.55 (4 H, m), 2.65 (2 H, m), 2.12 (6 H, 2.40 (6 H, m) ppm. |
| I″-21 | 494.2 | — | — | MeOD-d4 8.40 (1 H, d), 8.12 (2 H, d), 7.71 (3 H, m), 7.54 (1 H, d), 7.4-7.30 (3 H, m), 7.29 (2 H, t), 7.24 (1 H, d), 6.99 (1 H, t), 5.48 (1 H, s), 3.72 (2 H, m), 3.42 (3 H, m), 3.22 (2 H, m), 2.75 (1 H, m), 1.79 (2 H, m), 1.65 (2 H, m) |
| I″-22 | 480.3 | — | — | CD$_3$OD 8.40 (1 H, d), 8.15 (2 H, d), 7.78 (4 H, m), 7.47 (1 H, d), 7.4-7.30 (5 H, m), 7.26 (1 H, d), 6.99 (1 H, t), 5.49 (1 H, s), 4.15 (1 H, m), 3.99 (1 H, m), 2.40 (1 H, m), 2.15 (2 H, m), 1.90 (2 H, m), 1.65 (2 H, m), 1.50 (2 H, m) |
| I″-23 | 478.2 | — | — | CD$_3$OD 8.40 (1 H, d), 8.15 (2 H, d), 7.78 (4 H, m), 7.47 (1 H, d), 7.4-7.30 (5 H, m), 7.26 (1 H, d), 6.99 (1 H, t), 4.57 (1 H, s), 3.62 (1 H, m), ), 2.35 (2 H, m), 1.90-1.55 (10 H, m) ppm. |
| I″-24 | 482.1 | — | — | CD$_3$OD 7.7-7.10 (16 H, m), 5.30 (1 H, s), 3.70 (4 H, m), 2.77 (4 H, m) ppm. |
| I″-25 | 496.2 | — | — | CD$_3$OD 8.40 (1 H, d), 8.12 (2 H, m), 7.72 (2 H, d), 7.53 (2 H, m), 7.5-7.30 (4 H, m), 7.23 (2 H, m), 7.20 (2 H, m), 6.63 (1 H, m), 3.95 (1 H, s), 3.80 (3 H, s), 3.72 (4 H, m), 2.50 (4 H, m) ppm. |
| I″-26 | 500.13 | — | — | CD$_3$OD 8.42 (1 H, m), 8.12 (2 H, d), 8.05 (1 H, m), 7.72 (2 H, d), 7.55 (2 H, m), 7.4-7.20 (6 H, m), 6.93 (1 H, m), 3.95 (1 H, s), 3.72 (4 H, m), 2.50 (4 H, m) ppm. |
| I″-27 | 482.2 | — | — | 9.16 (1 H, s), 8.35 (1 H, d), 7.99 (2 H, d), 7.63 (2 H, d), 7.38 (1 H, s), 7.29 (5 H, m), 7.12 (1 H, t), 7.02 (2 H, t), 6.45 (1 H, d), 3.93 (1 H, s), 3.71 (4 H, m), 2.45 (4 H, m) ppm |
| I″-28 | 572.3 | — | — | 9.16 (1 H, s), 8.35 (1 H, d), 8.00 (2 H, d), 7.63 (2 H, d), 7.52 (1 H, m), 7.38 (1 H, s), 7.29 (9 H, m), 7.12 (1 H, t), 7.03 (2 H, t), 6.60 (1 H, d), 5.03 (2 H, s), 3.92 (1 H, s), 3.71 (4 H, m), 2.45 (4 H, m) ppm |
| I″-29 | — | — | — | 9.08 (1 H, s), 8.35 (1 H, d), 7.99 (2 H, d), 7.55 (2 H, d), 7.47 (1 H, m), 7.33 (1 H, m), 7.25-7.10 (8 H, m), 7.04 (2 H, m), 6.55 (1 H, d), 3.80 (4 H, m), 3.71 (2 H, m), 3.67 (2 H, m), 3.46 (1 H, t), 3.32 (1 H, dd), 3.15 (4 H, m) |
| I″-30 | 534.1 | — | — | 8.39 (1 H, d), 8.25 (1 H, s), 8.02 (2 H, d), 7.68 (2 H, d), 7.62 (1 H, d), 7.39-7.25 (6 H, m), 7.21 (1 H, d), 7.11 (1 H, d), 3.76 (5 H, m), 2.50 (4 H, m) ppm. |
| I″-31 | 524.2 | — | — | 9.49 (1 H, s), 8.68 (1 H, d), 8.30 (1 H, s), 8.07 (2 H, d), 7.83 (1 H, d), 7.69 (2 H, d), 7.58 (1 H, d), 7.50-7.38 (6 H, m), 7.18 (1 H, d), 3.94 (4 H, m), 3.75 (4 H, m), 3.61 (2 H, m), 3.26 (4 H, m) ppm. |
| I″-32 | 544.1 | — | — | 9.29 (1 H, s), 8.37 (1 H, d), 8.06 (1 H, s), 7.99 (2 H, d), 7.67 (2 H, d), 7.40-7.22 (6 H, m), 7.11-7.07 (3 H, m), 3.74 (4 H, m), 3.40 (1 H, s), 2.52 (4 H, m) ppm. |
| I″-33 | 481.3 | — | — | DMSO-d6 10.39 (1 H, s), 9.30 (1 H, s), 8.42 (1 H, d), 8.12 (2 H, d), 7.80 (2 H, d), 7.55 (2 H, m), 7.38 (2 H, m), 7.30 (2 H, m), 6.90 (2 H, m), 6.20 (1 H, m), 4.90 (1 H, s), 3.65 (4 H, m), 2.38 (4 H, m) ppm. |
| I″-34 | 481.3 | — | — | DMSO-d6 10.39 (1 H, s), 9.30 (1 H, s), 8.42 (1 H, d), 8.12 (2 H, d), 7.80 (2 H, d), 7.55 (2 H, m), 7.38 (2 H, m), 7.30 (2 H, m), 6.90 (2 H, m), 6.20 (1 H, m), 4.90 (1 H, s), 3.65 (4 H, m), 2.38 (4 H, m) ppm. |
| I″-35 | 369 | 367.2 | 2.2 | (DMSO-d6): 8.4 (d, 1 H), 8.0-8.2 (dd, 4 H), 7.5 (s, 1 H) 7.2-7.4 (m, 4 H), 5.15 (m, 1 H), 3.7 (m, 2 H). |
| I″-42 | 427 | 425.2 | 3.5 | 8.22, 1 H, d; 8.10, 2 H, d; 7.85, 2 H, d; 7.30, 1 H, s; 7.22-7.29, 2 H, m; 6.92-6.95, 1 H, m; 5.20-5.24, 1 H, m; 3.92-3.98, 2 H, m; 2.70-2.78, 1 H, m; 1.20, 4 H, s. |
| I″-43 | 459.1 | — | 3.1 | 8.15, 1 H, s; 7.70, 1 H, s; 7.65, 1 H, d; 7.30-7.35, 3 H, m; 7.20-7.25, 2 H, m; 5.32, 1 H, d; 5.09-5.12, 1 H, m; 4.00-4.08, 1 H, m; 3.80-3.90, 2 H, m; 3.65-3.71, 1 H, m; 3.52-3.55, 1 H, m; 2.30, 3 H, s; 1.21, 3 H, d. |
| I″-48 | 511 | 509 | 3.4 | CD$_3$OD 8.3 (s, 1 H); 7.7-7.8 (m, 4 H); 7.0-7.2 (m, 4 H); 4.42 (t, 1 H); 4.0 (t, 1 H); 3.6-3.7 (m, 4 H); 1.5-1.8 (m, 2 H); 1.0 (t, 3 H) |
| I″-49 | 335.14 | — | 1.6/B | — |
| I″-50 | 349.2 | — | 1.86/B | — |
| I″-52 | 445 | — | — | 8.25, 1 H, s; 7.79, 4 H, s; 7.28, 1 H, s; 7.20, 3 H, m; 7.03, 1 H, d; 5.12, 1 H, m; 5.03, 1 H, m; 4.02, 1 H, m; 3.82, 2 H, m; 2.71, 1 H, m; 1.65, 1 H, br s; 1.20, 6 H, d. |
| I″-53 | 484.9 | 483 | 3.9 | (CDCl$_3$/CD$_3$OD) 8.36, 1 H, s; 7.98, 2 H, m; 7.88, 2 H, m; 7.62, 1 H, m; 7.38, 1 H, s; 7.26, 4 H, m; 5.20, 1 H, m; 4.17, 2 H, m; 3.92, 2 H, m. |

TABLE 4-continued

Characterization Data for Selected Compounds of Formula I

| Compound No | M + 1 | M − 1 | $R_t$ | $^1$H NMR |
|---|---|---|---|---|
| I″-54 | 409 | 407.1 | 2.5 | (MeOH-d4): 8.9 (d, 1 H), 8.4 (2 x d, 3 H), 8.0 (d, 2 H), 7.5 (m, 1 H), 7.4 (s, 1 H), 7.2-7.3 (m, 3 H), 5.2 (m, 1 H), 3.85 (d, 2 H), 2.7 (m, 1 H), 1.0 (m, 2 H), 0.75 (m, 2 H). |
| I″-55 | 427 | 425.2 | 2.4 | (MeOH-d4): 8.3 (m, 3 H), 8.0 (d, 2 H), 7.2-7.4 (m, 5 H), 5.2 (m, 1 H), 3.9 (d, 2 H), 3.6-3.7 (m, 2 H), 1.3 (d, 3 H). |
| I″-56 | 460 | 458.2 | 2.6 | (CDCl$_3$/CD$_3$OD) 7.96, 1 H, s; 7.87, 2 H, d; 7.42, 2 H, d; 7.30, 1 H, s; 7.18, 3 H, m; 6.33, 1 H, s; 5.13, 1 H, m; 3.85, 3 H, m; 3.60, 1 H, m; 3.52, 1 H, m; 1.18, 3 H, d. 1.30, 3 H, d; |
| I″-57 | 441 | 439.1 | 3.1 | 8.18, 1 H, s; 7.77, 2 H, d; 7.70, 2 H, d; 7.25, 5 H, m; 5.48, 1 H, d; 5.16, 1 H, m; 3.88, 2 H, m; 3.82, 1 H, m; 3.59, 1 H, m; 3.43, 1 H, br m3.20, 1 H, br m; 1.52, 2 H, m; 0.90, 3 H, t. |
| I″-59 | 395.2 | 393.3 | 3.5 | 8.18, 1 H, m; 8.10, 2 H, d; 7.85, 2 H, d; 7.30-7.35, 3 H, m; 7.25-7.28, 1 H, m; 6.90, 1 H, d; 5.20-5.25, 1 H, m; 5.10-5.18, 1 H, s; 4.05-4.12, 1 H, m; 3.92-4.00, 2 H, m; 1.18-1.22, 6 H, m |
| I″-60 | 411.2 | 409 | 3.5 | (CD$_3$OD) 8.30, 1 H, s; 8.12-8.19, 2 H, m; 7.98, 2 H, d; 7.42, 1 H, d; 7.32-7.35, 2 H, m; 7.25-7.30, 2 H, d; 5.20-5.25, 1 H, m; 4.12-4.15, 1 H, m; 3.82-3.85, 2 H, m; 3.55-3.65, 2 H, m; 1.28, 3 H, d |
| I″-61 | 393.2 | 391.1 | 3.1 | 8.30, 1 H, s; 8.20, 2 H, d; 7.92, 2 H, d; 7.30-7.40, 4 H, m; 6.90, 2 H, d; 5.28-5.31, 1 H, m; 4.05-4.10, 2 H, m; 2.80-2.85, 1 H, m; 0.85-0.92, 2 H, m, 0.60-0.65, 2 H, m |
| I″-63 | 407.2 | — | 2.2 | (CD$_3$OD) 8.28, 1 H, s; 8.05, 2 H, d; 7.83, 2 H, d; 7.44, 2 H, d; 7.30, 3 H, m; 5.23, 1 H, m; 4.23, 1 H, br s; 3.88, 2 H, d; 3.75, 2 H, m; 2.26, 3 H, s; 1.31, 3 H, d. |
| I″-64 | 441.1 |  | 2.5 | (CD$_3$OD) 8.28, 1 H, s; 8.04, 2 H, d; 7.83, 2 H, d; 7.42, 1 H, s; 7.30, 3 H, m; 5.22, 1 H, m; 4.23, 1 H, br s; 3.87, 2 H, d; 3.68, 2 H, m; 2.26, 3 H, s; 1.28, 3 H, d. |
| I″-65 | 441.1 | 439.2 | 3.3 | 8.25, 1 H, s; 7.70, 1 H, s; 7.60, 1 H, d; 7.30-7.35, 3 H, m; 7.21-7.25, 2 H, m; 6.80, 1 H, m; 5.35-5.38, 1 H, m; 5.20- 5.22, 1 H, m; 4.02-4.10, 1 H, m; 3.90-3.95, 2 H, m; 3.65-3.70, 1 H, m; 3.50-3.58, 1 H, m; 2.20, 3 H, s; 1.25, 3 H, d. |
| I″-66 | 441.1 | 439.5 | 2.6 | 8.26, 1 H, d; 7.66, 1 H, s; 7.61, 1 H, d; 7.37, 1 H, d; 7.24, 1 H, s; 7.20-7.25, 2 H, m; 6.98, 1 H, d; 6.60, 1 H, d; 5.30, 1 H, d; 5.12-5.16, 1 H, m; 4,05-4,12 m 1 H, m; 3.88-3.91, 2 H, m; 3.65-3.70, 1 H, m; 3.55-3.58, 1 H, m, 2.35, 3 H, s; 1.20, 3 |
| I″-67 | 407.2 | 405.6 | 2.2 | (CD$_3$OD) 8.30, 1 H, d; 7.85, 1 H, s; 7.80, 1 H, d; 7.55, 1 H, d; 7.40, 1 H, d; 7.30-7.38, 3 H, m; 7.22-7.28, 1 H, m; 6.90, 1 H, d; 5.20-5.22, 1 H, m; 4.18-4.20, 1 H, m; 3.85, d, 2 H); 3.62, 2 H, m; 2.12, 3 H, s; 1.25, 3 H, d. |
| I″-68 | 424.3 | 422.2 | 2.1 | (CD$_3$OD) 7.97, 2 H, d; 7.82, 1 H, s; 7.43, 3 H, m; 7.33, 2 H, m; 7.28, 1 H, m; 6.40, 1 H, s; 5.20, 1 H, t; 3.98, 1 H, m; 3.88, 2 H, d; 2.04, 3 H, s; 1.21, 6 H, d. |
| I″-69 | 440.2 | 438.2 | — | (CD$_3$OD) 7.97, 2 H, d; 7.82, 1 H, s; 7.43, 3 H, m; 7.33, 2 H, m; 7.28, 1 H, m; 6.41, 1 H, s; 5.21, 1 H, t; 3.98, 1 H, m; 3.88, 2 H, d; 3.53, 2 H, m, 2.04, 3 H, s; 1.22, 3 H, d. |
| I″-70 | 454.3 | 452.2 | 2.1 | (CD$_3$OD) 7.96, 2 H, d; 7.81, 1 H, s; 7.43, 3 H, m; 7.33, 2 H, m; 7.29, 1 H, m; 6.42, 1 H, s; 5.22, 1 H, t; 3.88, 2 H, d; 3.73, 1 H, m; 3.53, 2 H, m 2.04, 3 H, s; 1.72, 1 H, m; 1.57, 1 H, m; 1.22, 3 H, t. |
| I″-71 | 422.15 | 420.3 | 2.13 | (CD$_3$OD): 8.0 (d, 2 H), 7.8 (s, 1 H), 7.25-7.6 (M, 6 H), 5.2 (t, 1 H), 3.85 (d, 2 H), 2.7 (m, 1 H), 2.15 (s, 3 H), 1.0 (m, 2 H), 0.7 (m, 2 H). |
| V'-4 | 455.20 | 3.20 | — | 8.24, 1 H, s; 7.78, 2 H, br s; 7.52, 2 H, br s; 7.31, 4 H, m;, 7.18, 1 H, m; 5.89, 1 H, br s; 5.32, 1 H, m;, 5.15, 1 H, br s; 4.28, 1 H, br s; 4.04, 1 H, br s; 3.89, 1 H, br s; 3.70, 1 H, br s; 3 |
| V'-5 | — | — | — | 8.43 (1 H, d), 7.99 (2 H, d), 7.32 (1 H, s), 7.20 (3 H, m), 7.21-7.02 (6 H, m), 6.95 (1 H, d), 6.34 (1 H, d), 4.06 (1 H, s), 2.67 (4 H, m), 2.55 (4 H, m) ppm. |

Example 21

JNK3 Inhibition Assay

Compounds were assayed for the inhibition of JNK3 by a spectrophotometric coupled-enzyme assay. In this assay, a fixed concentration of activated JNK3 (10 nM) was incubated with various concentrations of a potential inhibitor dissolved in DMSO for 10 minutes at 30° C. in a buffer containing 0.1 M HEPES buffer, pH 7.5, containing 10 mM MgCl$_2$, 2.5 mM phosphoenolpyruvate, 200 μM NADH, 150 μg/mL pyruvate kinase, 50 μg/mL lactate dehydrogenase, and 200 μM EGF receptor peptide. The EGF receptor peptide is a phosphoryl acceptor in the JNK3-catalyzed kinase reaction. The reaction was initiated by the addition of 10 μM ATP and the assay plate is inserted into the spectrophotometer's assay plate compartment that was maintained at 30° C. The decrease of absorbance at 340 nm was monitored as a function of time. The rate data as a function of inhibitor concentration was fitted to competitive inhibition kinetic model to determine the $K_i$.

Compounds of the present invention were found to inhibit JNK3.

Example 22

CDK-2 Inhibition Assay

Compounds were screened in the following manner for their ability to inhibit CDK-2 using a standard coupled enzyme assay (Fox et al (1998) *Protein Sci* 7, 2249).

To an assay stock buffer solution containing 0.1M HEPES 7.5, 10 mM MgCl$_2$, 1 mM DTT, 25 mM NaCl, 2.5 mM phosphoenolpyruvate, 300 mM NADH, 30 mg/ml pyruvate kinase, 10 mg/ml lactate dehydrogenase, 100 mM ATP, and 100 µM peptide (MAHHHRSPRKRAKKK, American Peptide, Sunnyvale, Calif.) was added a DMSO solution of a compound of the present invention to a final concentration of 30 µM. The resulting mixture was incubated at 30° C. for 10 minutes.

The reaction was initiated by the addition of 10 µL of CDK-2/Cyclin A stock solution to give a final concentration of 25 nM in the assay. The rates of reaction were obtained by monitoring absorbance at 340 nm over a 5-minute read time at 30° C. using a BioRad Ultramark plate reader (Hercules, Calif.). The $K_i$ values were determined from the rate data as a function of inhibitor concentration.

Compounds of the present invention were found to inhibit CDK2.

Example 23

JAK Inhibition Assay

Compound inhibition of JAK was assayed by the method described by G. R. Brown, et al, *Bioorg. Med. Chem. Lett.* 2000, vol. 10, pp 575-579 in the following manner. Into Maxisorb plates, previously coated at 4° C. with Poly (Glu, Ala, Tyr) 6:3:1 then washed with phosphate buffered saline 0.05% and Tween (PBST), was added 2 µM ATP, 5 mM $MgCl_2$, and a solution of compound in DMSO. The reaction was started with JAK enzyme and the plates incubated for 60 minutes at 30° C. The plates were then washed with PBST, 100 µL HRP-Conjugated 4G10 antibody was added, and the plate incubated for 90 minutes at 30° C. The plate was again washed with PBST, 100 µL TMB solution is added, and the plates were incubated for another 30 minutes at 30° C. Sulfuric acid (100 mL of 1M) was added to stop the reaction and the plate is read at 450 nm to obtain the optical densities for analysis to determine $IC_{50}$ values. Compounds of the present invention were shown to inhibit JAK3.

Example 24

ERK2 Inhibition Assay

Compounds were assayed for the inhibition of ERK2 by a spectrophotometric coupled-enzyme assay (Fox et al *Protein Sci.* 1998, 7, 2249). In this assay, a fixed concentration of activated ERK2 (10 nM) was incubated with various concentrations of a compound of the present invention in DMSO (2.5%) for 10 min. at 30° C. in 0.1 M HEPES buffer (pH 7.5), containing 10 mM $MgCl_2$, 2.5 mM phosphoenolpyruvate, 200 µM NADH, 150 µg/ml pyruvate kinase, 50 µg/ml lactate dehydrogenase, and 200 µM erktide peptide. The reaction was initiated by the addition of 65 µM ATP. The rate of decrease of absorbance at 340 nM was monitored. The $K_i$ values were determined from the rate data as a function of inhibitor concentration.

Compounds of the present invention were found to inhibit ERK2.

Example 25

ERK2 Inhibition: Cell Proliferation Assay

Compounds may be assayed for the inhibition of ERK2 by a cell proliferation assay. In this assay, a complete media is prepared by adding 10% fetal bovine serum and penicillin/streptomycin solution to RPMI 1640 medium (JRH Biosciences). Colon cancer cells (HT-29 cell line) are added to each of 84 wells of a 96 well plate at a seeding density of 10,000 cells/well/150 µL. The cells are allowed to attach to the plate by incubating at 37° C. for 2 hours. A solution of test compound is prepared in complete media by serial dilution to obtain the following concentrations: 20 µM, 6.7 µM, 2.2 µM, 0.74 µM, 0.25 µM, and 0.08 µM. The test compound solution (50 µL) is added to each of 72 cell-containing wells. To the 12 remaining cell-containing wells, only complete media (200 µL) is added to form a control group in order to measure maximal proliferation. To the remaining 12 empty wells, complete media is added to form a vehicle control group in order to measure background. The plates are incubated at 37° C. for 3 days. A stock solution of $^3$H-thymidine (1 mCi/mL, New England Nuclear, Boston, Mass.) is diluted to 20 µCi/mL in RPMI medium then 20 µL of this solution is added to each well. The plates are further incubated at 37° C. for 8 hours then harvested and analyzed for $^3$H-thymidine uptake using a liquid scintillation counter.

Example 26

ERK1 Inhibition Assay

Compounds are assayed for the inhibition of ERK1 by a spectrophotometric coupled-enzyme assay (Fox et al (1998) *Protein Sci* 7, 2249). In this assay, a fixed concentration of activated ERK1 (20 nM) is incubated with various concentrations of the compound in DMSO (2.0%) for 10 minutes at 30° C. in 0.1 M HEPES buffer, pH 7.6, containing 10 mM $MgCl_2$, 2.5 mM phosphoenolpyruvate, 200 µM NADH, 30 µg/mL pyruvate kinase, 10 µg/mL lactate dehydrogenase, and 150 µM erktide peptide. The reaction is initiated by the addition of 140 µM ATP (20 µL). The rate of decrease of absorbance at 340 nM is monitored. The $K_i$ is evaluated from the rate data as a function of inhibitor concentration.

Example 27

AKT-3 Inhibition Assay

Compounds were screened for their ability to inhibit AKT using a standard coupled enzyme assay (Fox et al., *Protein Sci.* 1998 7, 2249). Assays were carried out in a mixture of 100 mM HEPES 7.5, 10 mM $MgCl_2$, 25 mM NaCl, 1 mM DTT and 3% DMSO. Final substrate concentrations in the assay were 170 µM ATP (Sigma Chemicals) and 200 µM peptide (American Peptide, Sunnyvale, Calif.). Assays were carried out at 30° C. and 45 nM AKT. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above, with the exception of AKT, DTT, and the test compound of interest. 55 µl of the stock solution was placed in a 96 well plate followed by addition of 2 µl of 1 mM DMSO stock solution containing a compound of the present invention (final compound concentration 30 µM). The plate was pre-incubated for about 10 minutes at 30° C. and the reaction initiated by addition of 10 µl of enzyme (final concentration 45 nM) and 1 mM DTT. Rates of reaction were obtained using a Molecular Devices SpectraMax Plus plate reader over a 15 minute read time at 30° C. Compounds showing greater than 50% inhibition versus standard wells containing the assay mixture and DMSO without test compound were titrated to determine $IC_{50}$ values.

Compounds of the present invention were found to inhibit AKT3.

Example 28

Aurora-2 Inhibition Assay

Compounds are screened in the following manner for their ability to inhibit Aurora-2 using a standard coupled enzyme assay (Fox et al., *Protein Sci.* 1998, 7, 2249).

To an assay stock buffer solution containing 0.1M HEPES 7.5, 10 mM $MgCl_2$, 1 mM DTT, 25 mM NaCl, 2.5 mM phosphoenolpyruvate, 300 mM NADH, 30 mg/ml pyruvate kinase, 10 mg/ml lactate dehydrogenase, 40 mM ATP, and 800 μM peptide (American Peptide, Sunnyvale, Calif.) is added a DMSO solution of a compound of the present invention to a final concentration of 30 μM. The resulting mixture is incubated at 30° C. for 10 minutes. The reaction is initiated by the addition of 10 μl of Aurora-2 stock solution to give a final concentration of 70 nM in the assay. The rates of reaction are obtained by monitoring absorbance at 340 nm over a 5 minute read time at 30° C. using a BioRad Ultramark plate reader (Hercules, Calif.). The $K_i$ values are determined from the rate data as a function of inhibitor concentration.

Example 29 c-KIT Inhibition Assay

Compounds are screened for their ability to inhibit c-KIT activity using a radiometric filter-binding assay. This assay monitors the $^{33}P$ incorporation into a substrate poly(Glu, Tyr) 4:1 (pE4Y). Reactions are carried out in a solution containing 100 mM HEPES (pH 7.5), 10 mM $MgCl_2$, 25 mM NaCl, 1 mM DTT, 0.01% BSA and 2.5% DMSO. Final substrate concentrations in the assay are 700 μM ATP and 0.5 mg/mL pE4Y (both from Sigma Chemicals, St Louis, Mo.). The final concentration of compounds is generally between 0.01 and 5 μM. Typically, a 12-point titration is conducted by preparing serial dilutions from 10 mM DMSO stock of test compound. Reactions are carried out at room temperature.

Two assay solutions are prepared. Solution 1 contains 100 mM HEPES ($pH_{7.5}$), 10 mM $MgCl_2$, 25 mM NaCl, 1 mg/ml pE4Y and 1.4 mM ATP(containing 0.5 μCi of [γ-$^{33}P$]ATP for each reaction). Solution 2 contains 100 mM HEPES ($pH_{7.5}$), 10 mM $MgCl_2$, 25 mM NaCl, 2 mM DTT, 0.02% BSA and 25 nM c-KIT. The assay is run on a 96 well plate by mixing 33 μL of Solution1 and 1.65 μL of the test compounds. The reaction is initiated with 33 μL of Solution2. After incubation for 20 minutes at room temperature, the reaction is stopped with 50 μL of 10% TCA containing 0.2 mM of ATP. All of the reaction volume is then transferred to a filter plate and washed with 5% TCA by a Harvester9600 from TOMTEC (Hamden, Conn.). The amount of $^{33}P$ incorporation into pE4y is analyzed by a Packard TopCount Microplate Scintillation Counter (Meriden, Conn.). The data is fitted using Prism software to get an $IC_{50}$ or $K_i$.

Example 30

FLT-3 Inhibition Assay

Compounds were screened for their ability to inhibit FLT-3 activity using a radiometric filter-binding assay. This assay monitors the $^{33}P$ incorporation into a substrate poly (Glu, Tyr) 4:1 (pE4Y). Reactions were carried out in a solution containing 100 mM HEPES (pH 7.5), 10 mM $MgCl_2$, 25 mM NaCl, 1 mM DTT, 0.01% BSA and 2.5% DMSO. Final substrate concentrations in the assay were 90 μM ATP and 0.5 mg/ml pE4Y (both from Sigma Chemicals, St Louis, Mo.). The final concentration of a compound of the present invention is generally between 0.01 and 5 μM. Typically, a 12-point titration was conducted by preparing serial dilutions from 10 mM DMSO stock of test compound. Reactions were carried out at room temperature.

Two assay solutions were prepared. Solution 1 contains 100 mM HEPES (pH 7.5), 10 mM $MgCl_2$, 25 mM NaCl, 1 mg/ml pE4Y and 180 μM ATP(containing 0.3 μCi of [γ-$^{33}P$] ATP for each reaction). Solution 2 contains 100 mM HEPES (pH 7.5), 10 mM $MgCl_2$, 25 mM NaCl, 2 mM DTT, 0.02% BSA and 3 nM FLT-3. The assay was run on a 96 well plate by mixing 50 μl each of Solution 1 and 2.5 ml of the compounds of the present invention. The reaction was initiated with Solution 2. After incubation for 20 minutes at room temperature, the reaction was stopped with 50 μl of 20% TCA containing 0.4 mM of ATP. All of the reaction volume was then transferred to a filter plate and washed with 5% TCA by a Harvester 9600 from TOMTEC (Hamden, Conn.). The amount of $^{33}P$ incorporation into pE4y was analyzed by a Packard Top Count Microplate Scintillation Counter (Meriden, Conn.). The data was fitted using Prism software to get an $IC_{50}$ or $K_i$.

Compounds of the present invention were found to inhibit FLT3.

Example 31

GSK-3 Inhibition Assay

Compounds of the present invention were screened for their ability to inhibit GSK-3β (AA 1-420) activity using a standard coupled enzyme system (Fox et al., *Protein Sci.* 1998, 7, 2249). Reactions were carried out in a solution containing 100 mM HEPES (pH 7.5), 10 mM $MgCl_2$, 25 mM NaCl, 300 μM NADH, 1 mM DTT and 1.5% DMSO. Final substrate concentrations in the assay were 20 μM ATP (Sigma Chemicals, St Louis, Mo.) and 300 μM peptide (American Peptide, Sunnyvale, Calif.). Reactions were carried out at 30° C. and 20 nM GSK-30. Final concentrations of the components of the coupled enzyme system were 2.5 mM phosphoenolpyruvate, 300 μM NADH, 30 μg/ml pyruvate kinase and 10 μg/ml lactate dehydrogenase.

An assay stock buffer solution was prepared containing all of the reagents listed above with the exception of ATP and the test compound of the present invention. The assay stock buffer solution (175 μl) was incubated in a 96 well plate with 5 μl of the test compound of the present invention at final concentrations spanning 0.002 μM to 30 μM at 30° C. for 10 min. Typically, a 12 point titration was conducted by preparing serial dilutions (from 10 mM compound stocks) with DMSO of the test compounds of the present invention in daughter plates. The reaction was initiated by the addition of 20 μL of ATP (final concentration 20 μM). Rates of reaction were obtained using a Molecular Devices Spectramax plate reader (Sunnyvale, Calif.) over 10 min at 30° C. The $K_i$ values were determined from the rate data as a function of inhibitor concentration.

Compounds of the present invention were found to inhibit GSK3.

Example 32

MK2 Inhibition Assay

Compounds are screened for their ability to inhibit MK2 activity using a standard coupled enzyme system (Fox et al., *Protein Sci.* 1998, 7, 2249). Reactions are carried out in a solution containing 100 mM HEPES (pH 7.5), 10 mM MgCl$_2$, 25 mM NaCl, 300 µM NADH, 1 mM DTT and 1.5% DMSO. Final substrate concentrations in the assay are 30 µM ATP (Sigma Chemicals, St Louis, Mo.) and 300 µM peptide (American Peptide, Sunnyvale, Calif.). Reactions are carried out at 30° C. and 30 nM MK2. Final concentrations of the components of the coupled enzyme system are 2.5 mM phosphoenolpyruvate, 300 µM NADH, 30 µg/ml pyruvate kinase and 10 µg/ml lactate dehydrogenase.

An assay stock buffer solution is prepared containing all of the reagents listed above with the exception of ATP and a test compound of the present invention. The assay stock buffer solution (175 µl) is incubated in a 96 well plate with 5 µl of the test compound of the present invention at final concentrations spanning 0.014 µM to 30 µM at 30° C. for 10 minutes. Typically, a 12 point titration is conducted by preparing serial dilutions (from 10 mM compound stocks) with DMSO of the test compounds of the present invention in daughter plates. The reaction is initiated by the addition of 20 µl of ATP (final concentration 30 µM). Rates of reaction are obtained using a Molecular Devices Spectramax plate reader (Sunnyvale, Calif.) over 10 min at 30° C. The $K_i$ values are determined from the rate data as a function of inhibitor concentration.

Example 33

PDK-1 Inhibition Assay

Compounds are screened for their ability to inhibit PDK-1 using a radioactive-phosphate incorporation assay (Pitt and Lee, *J. Biomol. Screen.* 1996, 1, 47). Assays are carried out in a mixture of 100 mM HEPES (pH 7.5), 10 mM MgCl$_2$, 25 mM NaCl, 2 mM DTT. Final substrate concentrations in the assay are 40 µM ATP (Sigma Chemicals) and 65 µM peptide (PDKtide, Upstate, Lake Placid, N.Y.). Assays are carried out at 30° C. and 25 nM PDK-1 in the presence of ~27.5 nCi/µl of [γ-$^{32}$P]ATP (Amersham Pharmacia Biotech, Amersham, UK). An assay stock buffer solution is prepared containing all of the reagents listed above, with the exception of ATP, and the test compound of the present invention. 15 µl of the stock solution is placed in a 96 well plate followed by addition of 1 µl of 0.5 mM DMSO stock containing the test compound of the present invention (final compound concentration 25 µM, final DMSO concentration 5%). The plate is preincubated for about 10 minutes at 30° C. and the reaction initiated by addition of 4 µl ATP (final concentration 40 µM).

The reaction is stopped after 10 minutes by the addition of 100 µl 100 mM phosphoric acid, 0.01% Tween-20. A phosphocellulose 96 well plate (Millipore, Cat No. MAPH-NOB50) is pretreated with 100 µl 100 mM phosphoric acid, 0.01% Tween-20 prior to the addition of the reaction mixture (100 µl). The spots are left to soak for at least 5 minutes, prior to wash steps (4×200 µl 100 mM phosphoric acid, 0.01% Tween-20). After drying, 20 µl Optiphase 'SuperMix' liquid scintillation cocktail (Perkin Elmer) is added to the well prior to scintillation counting (1450 Microbeta Liquid Scintillation Counter, Wallac). Compounds showing greater than 50% inhibition versus standard wells containing the assay mixture and DMSO without test compound are titrated to determine IC$_{50}$ values.

Example 34

PIM-1 Inhibition Assay

Compounds are screened for their ability to inhibit PIM-1 using a standard coupled enzyme assay (Fox et al., Protein Sci. 1998, 7, 2249). Reactions are carried out in 100 mM HEPES (pH 7.5), 10 mM MgCl$_2$, 25 mM NaCl, 1 mM DTT, 20 µg/ml BSA and 1.5% DMSO. Final substrate concentrations in the assay are 120 µM ATP (Sigma chemicals) and 200 µM peptide (American Peptide, Sunnyvale, Calif.). Assays are carried out at 30° C. and 50 nM PIM-1. Final concentrations of the components of the coupled enzyme system are 2.5 mM phosphoenolpyruvate, 350 µM NADH, 30 µg/ml pyruvate kinase, and 10 µg/ml lactate dehydrogenase.

An assay stock buffer solution is prepared containing all of the reagents listed above, with the exception of PIM-1, DTT, BSA and the test compound of the present invention. 56 µl of the test reaction is placed in a 384 well plate followed by addition of 1 µl of 2 mM DMSO stock containing the test compound (final compound concentration 30 µM). The plate is preincubated for 10 minutes at 30° C. and the reaction initiated by addition of 10 µl of enzyme in DTT and BSA (final concentrations: 50 nM PIM-1, 1 mM DTT, and 20 µg/ml BSA). Rates of reaction are obtained using a BioRad Ultramark plate reader (Hercules, Calif.) over a 5 minute read time at 30° C. Test compounds showing >50% inhibition versus standard wells containing DMSO, but no compound, are titrated and IC$_{50}$'s determined using a similar protocol.

Example 35

PKA Inhibition Assay

Compounds were screened for their ability to inhibit PKA using a standard coupled enzyme assay (Fox et al., Protein Sci, 1998, 7, 2249). Assays were carried out in a mixture of 100 mM HEPES (pH 7.5), 10 mM MgCl$_2$, 25 mM NaCl, 1 mM DTT and 3% DMSO. Final substrate concentrations in the assay were 50 µM ATP (Sigma Chemicals) and 80 µM peptide (Kemptide, American Peptide, Sunnyvale, Calif.). Assays were carried out at 30° C. and 18 nM PKA. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above, with the exception of ATP, and the test compound of the present invention. 55 µl of the stock solution was placed in a 96 well plate followed by addition of 2/1 of DMSO stock containing serial dilutions of the test compound of the present invention (typically starting from a final concentration of 51 µM). The plate was preincubated for 10 minutes at 30° C. and the reaction initiated by addition of 5 µl of ATP (final concentration 50 µM). Initial reaction rates were determined with a Molecular Devices SpectraMax Plus plate reader over a 15 minute time course. IC$_{50}$ and K$_i$ data were calculated from non-linear regression analysis using the Prism software package (GraphPad Prism version 3.0a for Macintosh, GraphPad Software, San Diego Calif., USA).

Compounds of the present invention were found to be inhibitors of PKA.

Example 36 p70S6K Inhibition Assay

Compounds were screened for their ability to inhibit p70S6K using a radioactive-phosphate incorporation assay at Upstate Biotechnology (Pitt and Lee, *J. Biomol. Screen.* 1996, 1, 47). Assays were carried out in a mixture of 8 mM MOPS (pH 7.0), 10 mM magnesium acetate, 0.2 mM EDTA. Final substrate concentrations in the assay were 15 µM ATP (Sigma Chemicals) and 100 µM peptide (Upstate Ltd., Dundee, UK). Assays were carried out at 30° C. and in the presence of p70S6K (5-10 mU, Upstate Ltd., Dundee, UK) and [$\gamma$-$^{33}$P] ATP (Specific activity approx. 500 cpm/pmol, Amersham Pharmacia Biotech, Amersham, UK). An assay stock buffer solution was prepared containing all of the reagents listed above, with the exception of ATP, and the test compound of the present invention. 15 µl of the stock solution was placed in a 96 well plate followed by addition of 1 µl of 40 µM or 8 µM DMSO stock containing the test compound of the present invention, in duplicate (final compound concentration 2 µM or 0.4 µM, respectively, final DMSO concentration 5%). The plate was preincubated for about 10 minutes at 30° C. and the reaction initiated by addition of 4 µl ATP (final concentration 15 µM).

The reaction was stopped after 10 minutes by the addition of 5 µl 3% phosphoric acid solution. A phosphocellulose 96 well plate (Millipore, Cat No. MAPHNOB50) was pretreated with 100 µl 100 mM phosphoric acid, 0.01% Tween-20 prior to the addition of the reaction mixture (20 µl). The spots were left to soak for at least 5 minutes, prior to wash steps (4×200 µl 10 mM phosphoric acid, 0.01% Tween-20). After drying, 20 µl Optiphase 'SuperMix' liquid scintillation cocktail (Perkin Elmer) was added to the well prior to scintillation counting (1450 Microbeta Liquid Scintillation Counter, Wallac).

Compounds of the present invention were found to inhibit p70s6k.

Example 37

ROCK Inhibition Assay

Compounds of the present invention were screened for their ability to inhibit ROCK using a standard coupled enzyme assay (Fox et al., *Protein Sci.* 1998, 7, 2249). Reactions were carried out in 100 mM HEPES (pH 7.5), 10 mM MgCl$_2$, 25 mM NaCl, 1 mM DTT and 1.5% DMSO. Final substrate concentrations in the assay were 13 µM ATP (Sigma chemicals) and 200 µM peptide (American Peptide, Sunnyvale, Calif.). Assays were carried out at 30° C. and 200 nM ROCK. Final concentrations of the components of the coupled enzyme system were 2.5 mM phosphoenolpyruvate, 400 µM NADH, 30 µg/ml pyruvate kinase and 10 µg/ml lactate dehydrogenase.

An assay stock buffer solution was prepared containing all of the reagents listed above, with the exception of ROCK, DTT, and the test compound of interest of the present invention. 56 µl of the test reaction was placed in a 384 well plate followed by addition of 1 µl of 2 mM DMSO stock containing the test compound of the present invention (final compound concentration 30 µM). The plate was preincubated for about 10 minutes at 30° C. and the reaction initiated by addition of 10 µl of enzyme (final concentration 100 nM). Rates of reaction were obtained using a BioRad Ultramark plate reader (Hercules, Calif.) over a 5 minute read time at 30° C. Compounds of the present invention showing >50% inhibition versus standard wells containing DMSO, but no compound, were titrated and IC$_{50}$'s determined using a similar protocol.

Compounds of the present invention were found to be inhibitors of ROCK.

Example 38

SRC Inhibition Assay

The compounds of the present invention were evaluated as inhibitors of human Src kinase using either a radioactivity-based assay or spectrophotometric assay.

Src Inhibition Assay A: Radioactivity-based Assay

The compounds of the present invention were assayed as inhibitors of full length recombinant human Src kinase (from Upstate Biotechnology, Cat. No. 14-117) expressed and purified from baculo viral cells. Src kinase activity was monitored by following the incorporation of $^{33}$P from ATP into the tyrosine of a random poly Glu-Tyr polymer substrate of composition, Glu:Tyr=4:1 (Sigma, Cat. No. P-0275). The final concentrations of the assay components were: 0.05 M HEPES (pH 7.6), 10 mM MgCl$_2$, 2 mM DTT, 0.25 mg/ml BSA, 10 µM ATP (1-2 µCi $^{33}$P-ATP per reaction), 5 mg/ml poly Glu-Tyr, and 1-2 units of recombinant human Src kinase. In a typical assay, all the reaction components with the exception of ATP were pre-mixed and aliquoted into assay plate wells. Compounds of the present invention were dissolved in DMSO and added to the wells to give a final DMSO concentration of 2.5%. The assay plate was incubated at 30° C. for 10 min before initiating the reaction with $^{33}$P-ATP. After 20 min of reaction, the reactions were quenched with 150 µl of 10% trichloroacetic acid (TCA) containing 20 mM Na$_3$PO$_4$. The quenched samples were then transferred to a 96-well filter plate (Whatman, UNI-Filter GF/F Glass Fiber Filter, Cat No. 7700-3310) installed on a filter plate vacuum manifold. Filter plates were washed four times with 10% TCA containing 20 mM Na$_3$PO$_4$ and then 4 times with methanol. 200 µl of scintillation fluid was then added to each well. The plates were sealed and the amount of radioactivity associated with the filters was quantified on a TopCount scintillation counter. The radioactivity incorporated was plotted as a function of the compound of the present invention concentration. The data was fitted to a competitive inhibition kinetics model to give the K$_i$ values for the compounds of the present invention.

Src Inhibition Assay B: Spectrophotometric Assay

The ADP produced from ATP by the human recombinant Src kinase-catalyzed phosphorylation of poly Glu-Tyr substrate was quantified using a coupled enzyme assay (Fox et al., *Protein Sci.* 1998, 7, 2249). In this assay one molecule of NADH was oxidised to NAD for every molecule of ADP produced in the kinase reaction. The disappearance of NADH was conveniently followed at 340 nm.

The final concentrations of the assay components were: 0.025 M HEPES (pH 7.6), 10 mM MgCl$_2$, 2 mM DTT, 0.25 mg/ml poly Glu-Tyr, and 25 nM of recombinant human Src kinase. Final concentrations of the components of the coupled enzyme system were 2.5 mM phosphoenolpyruvate, 200 µM NADH, 30 µg/ml pyruvate kinase and 10 µg/ml lactate dehydrogenase.

In a typical assay, all the reaction components with the exception of ATP were pre-mixed and aliquoted into assay plate wells. Compounds of the present invention dissolved in DMSO were added to the wells to give a final DMSO concentration of 2.5%. The assay plate was incubated at 30°

C. for 10 min before initiating the reaction with 100 μM ATP. The absorbance change at 340 nm over time was monitored on a molecular devices plate reader. The data was fitted to a competitive inhibition kinetics model to get the $K_i$ values for the compounds of the present invention.

Compounds of the present invention were found to be inhibitors of SRC.

Example 39

SYK Inhibition Assay

Compounds were screened for their ability to inhibit SYK using a standard coupled enzyme assay (Fox et al., *Protein Sci.* 1998, 7, 2249). Reactions were carried out in 100 mM HEPES (pH 7.5), 10 mM $MgCl_2$, 25 mM NaCl, 1 mM DTT and 1.5% DMSO. Final substrate concentrations in the assay were 200 μM ATP (Sigma chemical Co.) and 4 μM poly Gly-Tyr peptide (Sigma Chemical Co.). Assays were carried out at 30° C. and 200 nM SYK. Final concentrations of the components of the coupled enzyme system were 2.5 mM phosphoenolpyruvate, 300 μM NADH, 30 μg/ml pyruvate kinase and 10 μg/ml lactate dehydrogenase.

An assay stock buffer solution was prepared containing all of the reagents listed above, with the exception of SYK, DTT, and the test compound of interest of the present invention. 56 μl of the test reaction was placed in a 96 well plate followed by the addition of 1 μl of 2 mM DMSO stock containing the test compound of the present invention (final compound concentration 30 μM). The plate was pre-incubated for 10 minutes at 30° C. and the reaction initiated by the addition of 10 μl of enzyme (final concentration 25 nM). Rates of reaction were obtained using a BioRad Ultramark plate reader (Hercules, Calif.) over a 5 minute read time at 30° C., and $K_i$ values for the compounds of the present invention were determined according to standard methods.

Compounds of the present invention were found to be inhibitors of SYK.

Example 40

ZAP-70 Inhibition Assay

Compounds were screened for their ability to inhibit ZAP-70 using a standard coupled enzyme assay (Fox et al., *Protein Sci.* 1998, 7, 2249). Assays were carried out in a mixture of 100 mM HEPES (pH 7.5), 10 mM $MgCl_2$, 25 mM NaCl, 2 mM DTT and 3% DMSO. Final substrate concentrations in the assay were 100 μM ATP (Sigma Chemicals) and 20 μM peptide (poly-4EY, Sigma Chemicals). Assays were carried out at 30° C. and 60 nM ZAP-70. Final concentrations of the components of the coupled enzyme system were 2.5 mM phosphoenolpyruvate, 300 μM NADH, 30 μg/ml pyruvate kinase and 10 μg/ml lactate dehydrogenase.

An assay stock buffer solution was prepared containing all of the reagents listed above, with the exception of ZAP-70 and the test compound of interest of the present invention. 55 μl of the stock solution was placed in a 96 well plate followed by addition of 2 μl of DMSO stock containing serial dilutions of the test compound of the present invention (typically starting from a final concentration of 15 μM). The plate was preincubated for 10 minutes at 30° C. and the reaction initiated by addition of 10 μl of enzyme (final concentration 60 nM). Initial reaction rates were determined with a Molecular Devices SpectraMax Plus plate reader over a 15 minute time course. $K_i$ data was calculated from non-linear regression analysis using the Prism software package (GraphPad Prism version 3.0a for Macintosh, GraphPad Software, San Diego Calif., USA).

Compounds of the present invention were found to be inhibitors of ZAP70.

Example 41

The compounds were evaluated as inhibitors of human Lck kinase using either a radioactivity-based assay or spectrophotometric assay.

Lck Inhibition Assay A: Radioactivity-based Assay

The compounds were assayed as inhibitors of full length bovine thymus Lck kinase (from Upstate Biotechnology, cat. no. 14-106) expressed and purified from baculo viral cells. Lck kinase activity was monitored by following the incorporation of $^{33}P$ from ATP into the tyrosine of a random poly Glu-Tyr polymer substrate of composition, Glu:Tyr=4:1 (Sigma, cat. no. P-0275). The following were the final concentrations of the assay components: 0.025 M HEPES, pH 7.6, 10 mM $MgCl_2$, 2 mM DTT, 0.25 mg/ml BSA, 10 μM ATP (1-2 μCi $^{33}P$-ATP per reaction), 5 mg/ml poly Glu-Tyr, and 1-2 units of recombinant human Src kinase. In a typical assay, all the reaction components with the exception of ATP were pre-mixed and aliquoted into assay plate wells. Inhibitors dissolved in DMSO were added to the wells to give a final DMSO concentration of 2.5%. The assay plate was incubated at 30° C. for 10 minutes before initiating the reaction with $^{33}P$-ATP. After 20 min of reaction, the reactions were quenched with 150 μL of 10% trichloroacetic acid (TCA) containing 20 mM $Na_3PO_4$. The quenched samples were then transferred to a 96-well filter plate (Whatman, UNI-Filter GF/F Glass Fiber Filter, cat no. 7700-3310) installed on a filter plate vacuum manifold. Filter plates were washed four times with 10% TCA containing 20 mM $Na_3PO_4$ and then 4 times with methanol. 200 μl of scintillation fluid was then added to each well. The plates were sealed and the amount of radioactivity associated with the filters was quantified on a TopCount scintillation counter. The radioactivity incorporated was plotted as a function of the inhibitor concentration. The data was fitted to a competitive inhibition kinetics model to get the Ki for the compound.

Lck Inhibition Assay B: Spectrophotometric Assay

The ADP produced from ATP by the human recombinant Lck kinase-catalyzed phosphorylation of poly Glu-Tyr substrate was quanitified using a coupled enzyme assay (Fox et al (1998) *Protein Sci* 7, 2249). In this assay one molecule of NADH is oxidised to NAD for every molecule of ADP produced in the kinase reaction. The disappearance of NADH can be conveniently followed at 340 nm.

The following were the final concentrations of the assay components: 0.025 M HEPES, pH 7.6, 10 mM $MgCl_2$, 2 mM DTT, 5 mg/ml poly Glu-Tyr, and 50 nM of recombinant human Lck kinase. Final concentrations of the components of the coupled enzyme system were 2.5 mM phosphoenolpyruvate, 200 μM NADH, 30 μg/ml pyruvate kinase and 10 μg/ml lactate dehydrogenase.

In a typical assay, all the reaction components with the exception of ATP were pre-mixed and aliquoted into assay plate wells. Inhibitors dissolved in DMSO were added to the wells to give a final DMSO concentration of 2.5%. The assay plate was incubated at 30° C. for 10 minutes before initiating the reaction with 150 μM ATP. The absorbance change at 340 nm with time, the rate of the reaction, was monitored on a molecular devices plate reader. The data of rate as a function of the inhibitor concentration was fitted to competitive inhibition kinetics model to get the $K_i$ for the compound.

Compounds of the present invention were found to be inhibitors of LCK.

While we have presented a number of embodiments of this invention, it is apparent that our basic construction can be altered to provide other embodiments which utilize the compounds and methods of this invention. Therefore, it will be appreciated that the scope of this invention is to be defined by the appended claims rather than by the specific embodiments which have been represented by way of example.

We claim:

1. A compound of formula I':

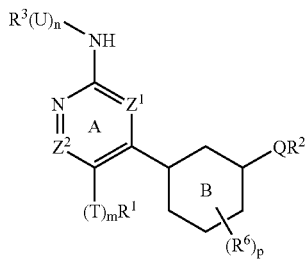

or a pharmaceutically acceptable salt thereof, wherein:
Ring B is a phenyl ring;
$Z^1$ is N and $Z^2$ is CH;
T is selected from a saturated or unsaturated $C_{1-6}$ alkylidene chain wherein: up to two methylene units of the chain are optionally and independently replaced by —C(O)—, —C(O)C(O)—, —C(O)NR—, —C(O)NRNR—, —CO$_2$—, —OC(O)—, —NRCO$_2$—, —O—, —NRC(O)NR—, —OC(O)NR—, —NRNR—, —NRC(O)—, —S—, —SO—, —SO$_2$—, —NR—, —SO$_2$NR—, or —NRSO$_2$—;
each R is independently selected from hydrogen or a $C_{1-6}$ aliphatic group, optionally substituted with halogen, —R°, —OR°, —SR°, 1,2-methylene-dioxy, 1,2-ethylenedioxy, —OC(O)($C_{1-12}$ alkyl), Ph optionally substituted with R°, —O(Ph) optionally substituted with R°, —CH$_2$(Ph) optionally substituted with R°, —CH$_2$CH$_2$(Ph) optionally substituted with R°, —NO$_2$, —CN, —NR°C(O)R°, —NR°C(O)N(R°)$_2$, —NR°CO$_2$R°, —NR°NR°C(O)R°, —NR°NR°C(O)N(R°)$_2$, —NR°NR°CO$_2$R°, —C(O)C(O)R°, —C(O)CH$_2$C(O)R°, —CO$_2$R°, —C(O)R°, —C(O)N(R°)$_2$, —OC(O)N(R°)$_2$, —S(O)$_2$R°, —SO$_2$N(R°)$_2$, —S(O)R°, —NR°SO$_2$N(R°)$_2$, —NR°SO$_2$R°, —C(=S)N(R°)$_2$, —C(=NH)—N(R°)$_2$, —(CH$_2$)$_y$NHC(O)R°, =O, =S, =NNHR*, =NN(R*)$_2$, =NNHC(O)R*, =NNHCO$_2$ ($C_{1-12}$ alkyl), =NNHSO$_2$($C_{1-12}$ alkyl), or =NR*;
each R° is independently selected from hydrogen, optionally substituted $C_{1-6}$ aliphatic, an unsubstituted 5-6 membered heteroaryl or heterocyclic ring, Ph, or —O(Ph) and each R* is independently selected from hydrogen, an optionally substituted $C_{1-6}$ aliphatic, wherein each substituent of said optionally substituted aliphatic of R° and R* is, independently, selected from the group consisting of NH$_2$, NH($C_{1-4}$ aliphatic), N($C_{1-4}$ aliphatic)$_2$, halogen, $C_{1-4}$ aliphatic, OH, O—($C_{1-4}$ aliphatic) NO$_2$, CN, CO$_2$H, CO$_2$($C_{1-4}$ aliphatic), O-(halo $C_{1-4}$ aliphatic), and halo $C_{1-4}$ aliphatic, or: two R on the same nitrogen are taken together with the nitrogen to form a 5-8 membered heterocyclyl or heteroaryl ring having 1-3 heteroatoms independently selected from nitrogen, oxygen, or sulfur;
U is selected from —CH$_2$—, —NR—, —NRC(O)—, —NRC(O)NR—, —NRCO$_2$—, —O—, —C(O)NR—, —C(O)—, —CO$_2$—, —OC(O)—, —NRSO$_2$—, —SO$_2$NR—, —NRSO$_2$NR—, or —SO$_2$—;
m and n are each independently selected from zero or one;
p is selected from 0, 1, 2, 3, or 4;
$R^1$ is selected from R or Ar, or $(T)_mR^1$ is halogen;
each Ar is an optionally substituted ring selected from a 6-10 membered aryl ring, a 5-10 membered heteroaryl ring having 1-4 heteroatoms independently selected from nitrogen, oxygen, or sulfur, or a 3-10 membered heterocyclyl ring having 1-4 heteroatoms independently selected from nitrogen, oxygen, or sulfur, wherein each substituent of said optionally substituted ring is, independently, selected from the group consisting of —R°, —OR°, —SR°, 1,2-methylene-dioxy, 1,2-ethylenedioxy, —OC(O)($C_{1-12}$ alkyl), Ph optionally substituted with R°, —O(Ph) optionally substituted with R°, —CH$_2$(Ph) optionally substituted with R°, —CH$_2$CH$_2$(Ph) optionally substituted with R°, —NO$_2$, —CN, —N(R°)$_2$, —NR°C(O)R°, —NR°C(O)N(R°)$_2$, —NR°CO$_2$R°, —NR°NR°C(O)R°, —NR°NR°C(O)N(R°)$_2$, —NR°NR°CO$_2$R°, —C(O)C(O)R°, —C(O)CH$_2$C(O)R°, —CO$_2$R°, —C(O)R°, —C(O)N(R°)$_2$, —OC(O)N(R°)$_2$, —S(O)$_2$R°, —SO$_2$N(R°)$_2$, —S(O)R°, —NR°SO$_2$N(R°)$_2$, —NR°SO$_2$R°, —C(=S)N(R°)$_2$, —C(=NH)—N(R°)$_2$, and —(CH$_2$)$_y$NHC(O)R°;
QR$^2$ is selected from

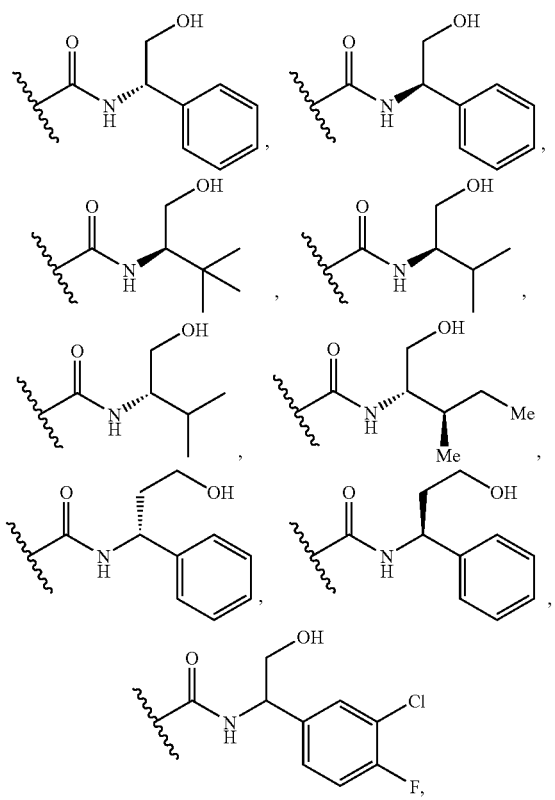

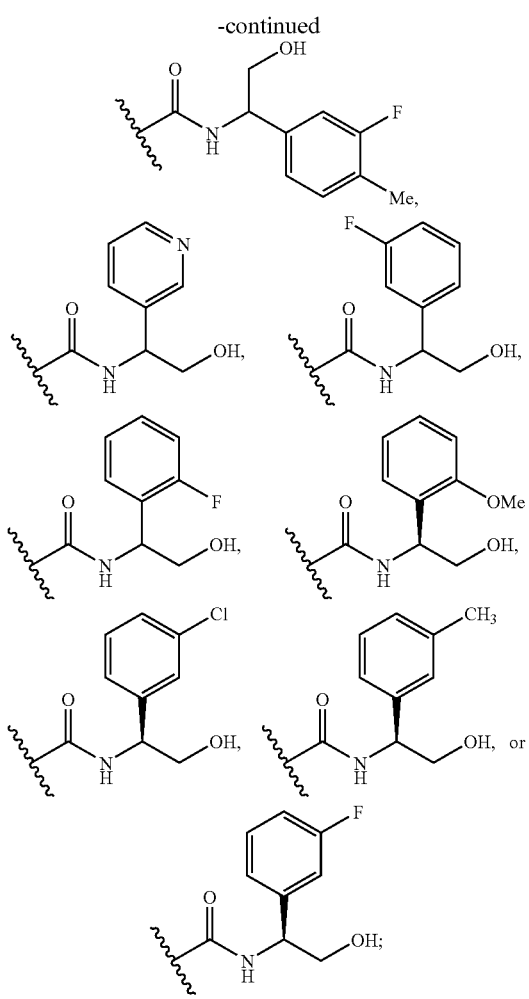

R³ is selected from R, Ar, —(CH₂)ᵧCH(R⁵)₂, optionally substituted 3-7 membered carbocyclyl, or CN, wherein y is 0-6;

each R⁵ is independently selected from optionally substituted pyridin-3-yl, pyridin-4-yl, morpholin-4-yl, thiomorpholin-4-yl, imidazolyl, furan-2-yl, 1,2,3,4-tetrahydroisoquinoline, tetrahydrofuran-2-yl, cyclohexyl, phenyl, —CH₂OH, —(CH₂)₂OH, and isopropyl, wherein each optional substituent is selected from halogen, R°, NO₂, OR°, or SR°; and each R⁶ is independently selected from R, F, Cl, N(R)₂, SR, NRC(O)R, NRC(O)N(R)₂, C(O)N(R)₂, SO₂R, NRSO₂R, C(O)R, CN, or SO₂N(R)₂.

2. The compound according to claim 1, wherein:
T is selected from —NR— or —O—; and
R¹ is hydrogen or an optionally substituted group selected from C₁₋₆ aliphatic or a 5-6 membered aryl or heteroaryl ring having 1-3 heteroatoms independently selected from nitrogen, oxygen, or sulfur; or
(T)ₘR¹ is halogen.

3. The compound according to claim 2, wherein:
R³ is hydrogen, an optionally substituted R, or an optionally substituted Ar, wherein said R is selected from a 3-7 membered carbocyclyl, a C₁₋₄ aliphatic, and a 3-6 membered heterocyclic ring having 1-3 heteroatoms independently selected from nitrogen, oxygen, or sulfur and said Ar is a 5-6 membered aryl or heteroaryl ring having 1-3 heteroatoms independently selected from nitrogen, oxygen, or sulfur; and
U is —CH₂—, —O—, —NR—, —NHC(O)—, or —NHCO₂—.

4. The compound having formula II:

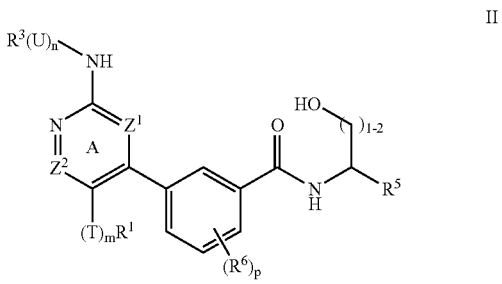

or a pharmaceutically acceptable salt thereof, wherein:
Z¹ and Z² is CH;
T is selected from a saturated or unsaturated C₁₋₆ alkylidene chain wherein: up to two methylene units of the chain are optionally and independently replaced by —C(O)—, —C(O)C(O)—, —C(O)NR—, —C(O)NRNR—, —CO₂—, —OC(O)—, —NRCO₂—, —O—, —NRC(O)NR—, —OC(O)NR—, —NRNR—, —NRC(O)—, —S—, —SO—, —SO₂—, —NR—, —SO₂NR—, or —NRSO₂—;
each R is independently selected from hydrogen or a C₁₋₆ aliphatic group, optionally substituted with halogen, —R°, —OR°, —SR°, 1,2-methylene-dioxy, 1,2-ethylenedioxy, —OC(O)(C₁₋₁₂ alkyl), Ph optionally substituted with R°, —O(Ph) optionally substituted with R°, —CH₂(Ph) optionally substituted with R°, —CH₂CH₂(Ph) optionally substituted with R°, —NO₂, —CN, —NR°C(O)R°, —NR°C(O)N(R°)₂, —NR°CO₂R°, —NR°NR°C(O)R°, —NR°NR°C(O)N(R°)₂, —NR°NR°CO₂R°, —C(O)C(O)R°, —C(O)CH₂C(O)R°, —CO₂R°, —C(O)R°, —C(O)N(R°)₂, —OC(O)N(R°)₂, —S(O)₂R°, —SO₂N(R°)₂, —S(O)R°, —NR°SO₂N(R°)₂, —NR°SO₂R°, —C(=S)N(R°)₂, —C(=NH)—N(R°)₂, —(CH₂)ᵧNHC(O)R°, =O, =S, =NNHR*, =NN(R*)₂, =NNHC(O)R*, =NNHCO₂(C₁₋₁₂ alkyl), =NNHSO₂(C₁₋₁₂ alkyl), or =NR*;
each R° is independently selected from hydrogen, optionally substituted C₁₋₆ aliphatic, an unsubstituted 5-6 membered heteroaryl or heterocyclic ring, Ph, or —O(Ph) and each R* is independently selected from hydrogen, an optionally substituted C₁₋₆ aliphatic, wherein each substituent of said optionally substituted aliphatic of R° and R* is, independently, selected from the group consisting of NH₂, NH(C₁₋₄ aliphatic), N(C₁₋₄ aliphatic)₂, halogen, C₁₋₄ aliphatic, OH, O—(C₁₋₄ aliphatic) NO₂, CN, CO₂H, CO₂(C₁₋₄ aliphatic), O-(halo C₁₋₄ aliphatic), and halo C₁₋₄ aliphatic, or: two R on the same nitrogen are taken together with the nitrogen to form a 5-8 membered heterocyclyl or heteroaryl ring having 1-3 heteroatoms independently selected from nitrogen, oxygen, or sulfur;
U is selected from —CH₂—, —NR—, —NRC(O)—, —NRC(O)NR—, —NRCO₂—, —O—, —C(O)NR—, —C(O)—, —CO₂—, —OC(O)—, —NRSO₂—, —SO₂NR—, —NRSO₂NR—, or —SO₂—;
m and n are each independently selected from zero or one;
p is selected from 0, 1, 2, 3, or 4;
R¹ is selected from R or Ar, or (T)ₘR¹ is halogen;

each Ar is an optionally substituted ring selected from a 6-10 membered aryl ring, a 5-10 membered heteroaryl ring having 1-4 heteroatoms independently selected from nitrogen, oxygen, or sulfur, or a 3-10 membered heterocyclyl ring having 1-4 heteroatoms independently selected from nitrogen, oxygen, or sulfur, wherein each substituent of said optionally substituted ring is, independently, selected from the group consisting of —R°, —OR°, —SR°, 1,2-methylene-dioxy, 1,2-ethylenedioxy, —OC(O)($C_{1-12}$ alkyl), Ph optionally substituted with R°, —O(Ph) optionally substituted with R°, —CH$_2$(Ph) optionally substituted with R°, —CH$_2$CH$_2$(Ph) optionally substituted with R°, —NO$_2$, —CN, —N(R°)$_2$, —NR°C(O)R°, —NR°C(O)N(R°)$_2$, —NR°CO$_2$R°, —NR°NR°C(O)R°, —NR°NR°C(O)N(R°)$_2$, —NR°NR°CO$_2$R°, —C(O)C(O)R°, —C(O)CH$_2$C(O)R°, —CO$_2$R°, —C(O)R°, —C(O)N(R°)$_2$, —OC(O)N(R°)$_2$, —S(O)$_2$R°, —SO$_2$N(R°)$_2$, —S(O)R°, —NR°SO$_2$N(R°)$_2$, —NR°SO$_2$R°, —C(=S)N(R°)$_2$, —C(=NH)—N(R°)$_2$, and —(CH$_2$)$_y$NHC(O)°;

R$^3$ is selected from R, Ar, —(CH$_2$)$_y$CH(R$^5$)$_2$, or CN, wherein y is 0-6;

each R$^5$ is independently selected from optionally substituted pyridin-3-yl, pyridin-4-yl, morpholin-4-yl, thiomorpholin-4-yl, imidazolyl, furan-2-yl, 1,2,3,4-tetrahydroisoquinoline, tetrahydrofuran-2-yl, cyclohexyl, phenyl, —CH$_2$OH, —(CH$_2$)$_2$OH, and isopropyl, wherein each optional substituent is selected from halogen, R°, NO$_2$, OR°, or SR°; and each R$^6$ is independently selected from R, F, Cl, N(R)$_2$, SR, NRC(O)R, NRC(O)N(R)$_2$, C(O)N(R)$_2$, SO$_2$R, NRSO$_2$R, C(O)R, CN, or SO$_2$N(R)$_2$.

5. A compound having formula I'':

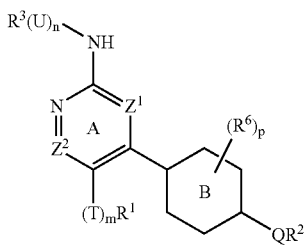

or a pharmaceutically acceptable salt thereof, wherein:
Ring B is a phenyl ring;
Z$^1$ is N and Z$^2$ is CH;
T is selected from a saturated or unsaturated C$_{1-6}$ alkylidene chain wherein: up to two methylene units of the chain are optionally and independently replaced by —C(O)—, —C(O)C(O)—, —C(O)NR—, —C(O)NRNR—, —CO$_2$—, —OC(O)—, —NRCO$_2$—, —O—, —NRC(O)NR—, —OC(O)NR—, —NRNR—, —NRC(O)—, —S—, —SO—, —SO$_2$—, —NR—, —SO$_2$NR—, or —NRSO$_2$—;
each R is independently selected from hydrogen or a C$_{1-6}$ aliphatic group, optionally substituted with halogen, —R°, —OR°, —SR°, 1,2-methylene-dioxy, 1,2-ethylenedioxy, —OC(O)(C$_{1-12}$ alkyl), Ph optionally substituted with R°, —O(Ph) optionally substituted with R°, —CH$_2$(Ph) optionally substituted with R°, —CH$_2$CH$_2$(Ph) optionally substituted with R°, —NO$_2$, —CN, —NR°C(O)R°, —NR°C(O)N(R°)$_2$, —NR°CO$_2$R°, —NR°NR°C(O)R°, —NR°NR°C(O)N(R°)$_2$, —NR°NR°CO$_2$R°, —C(O)C(O)R°, —C(O)CH$_2$C(O)R°, —CO$_2$R°, —C(O)R°, —C(O)N(R°)$_2$, —OC(O)N(R°)$_2$, —S(O)$_2$R°, —SO$_2$N(R°)$_2$, —S(O)R°, —NR°SO$_2$N(R°)$_2$, —NR°SO$_2$R°, —C(=S)N(R°)$_2$, —C(=NH)—N(R°)$_2$, —(CH$_2$)$_y$NHC(O)R°, =O, =S, =NNHR*, =NN(R*)$_2$, =NNHC(O)R*, =NNHCO$_2$(C$_{1-12}$ alkyl), =NNHSO$_2$(C$_{1-12}$ alkyl), or =NR*;

each R° is independently selected from hydrogen, optionally substituted C$_{1-6}$ aliphatic, an unsubstituted 5-6 membered heteroaryl or heterocyclic ring, Ph, or —O(Ph) and each R* is independently selected from hydrogen, an optionally substituted C$_{1-6}$ aliphatic, wherein each substituent of said optionally substituted aliphatic of R° and R* is, independently, selected from the group consisting of NH$_2$, NH(C$_{1-4}$ aliphatic), N(C$_{1-4}$ aliphatic)$_2$, halogen, C$_{1-4}$ aliphatic, OH, O—(C$_{1-4}$ aliphatic) NO$_2$, CN, CO$_2$H, CO$_2$(C$_{1-4}$ aliphatic), O-(halo C$_{1-4}$ aliphatic), and halo C$_{1-4}$ aliphatic, or: two R on the same nitrogen are taken together with the nitrogen to form a 5-8 membered heterocyclyl or heteroaryl ring having 1-3 heteroatoms independently selected from nitrogen, oxygen, or sulfur;

U is selected from —NR—, —NRC(O)—, —NRC(O)NR—, —NRCO$_2$—, —O—, —C(O)NR—, —C(O)—, —CO$_2$—, —OC(O)—, —NRSO$_2$—, —SO$_2$NR—, —NRSO$_2$NR—, or —SO$_2$—;

m and n are each independently selected from zero or one;
p is selected from 0, 1, 2, 3, or 4;
R$^1$ is selected from R or Ar, or (T)$_m$R$^1$ is halogen;
each Ar is an optionally substituted ring selected from a 6-10 membered aryl ring, a 5-10 membered heteroaryl ring having 1-4 heteroatoms independently selected from nitrogen, oxygen, or sulfur, or a 3-10 membered heterocyclyl ring having 1-4 heteroatoms independently selected from nitrogen, oxygen, or sulfur, wherein each substituent of said optionally substituted ring is, independently, selected from the group consisting of —R°, —OR°, —SR°, 1,2-methylene-dioxy, 1,2-ethylenedioxy, —OC(O)(C$_{1-12}$ alkyl), Ph optionally substituted with R°, —O(Ph) optionally substituted with R°, —CH$_2$(Ph) optionally substituted with R°, —CH$_2$CH$_2$(Ph) optionally substituted with R°, —NO$_2$, —CN, —N(R°)$_2$, —NR°C(O)R°, —NR°C(O)N(R°)$_2$, —NR°CO$_2$R°, —NR°NR°C(O)R°, —NR°NR°C(O)N(R°)$_2$, —NR°NR°CO$_2$R°, —C(O)C(O)R°, —C(O)CH$_2$C(O)R°, —CO$_2$R°, —C(O)R°, —C(O)N(R°)$_2$, —OC(O)N(R°)$_2$, —S(O)$_2$R°, —SO$_2$N(R°)$_2$, —S(O)R°, —NR°SO$_2$N(R°)$_2$, —NR°SO$_2$R°, —C(=S)N(R°)$_2$, —C(=NH)—N(R°)$_2$, and —(CH$_2$)$_y$NHC(O)R°;

QR$^2$ is selected from

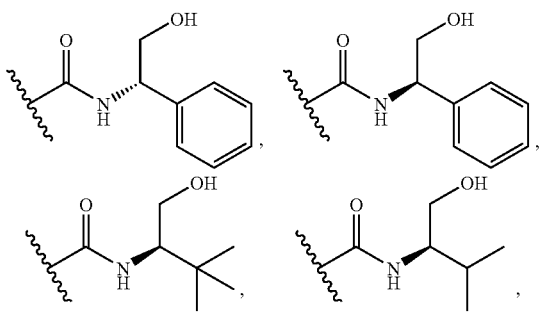

-continued

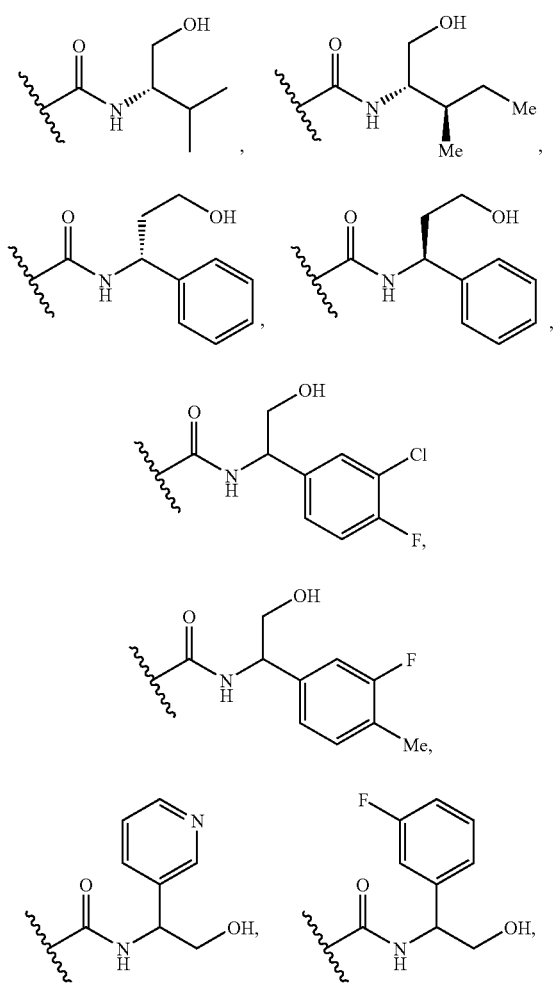

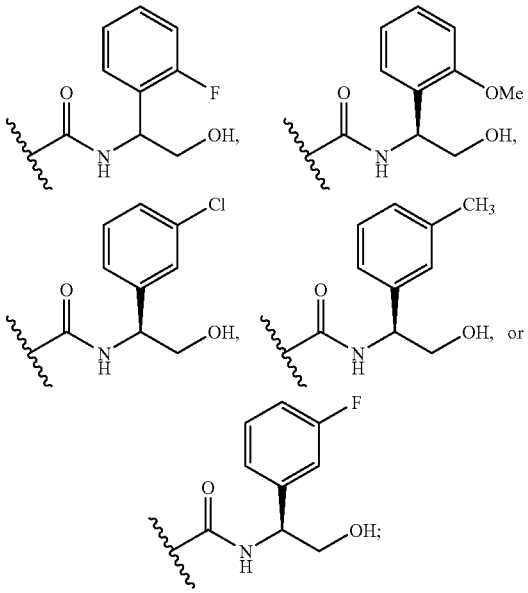

R³ is selected from R, Ar, —(CH₂)_yCH(R⁵)₂, or CN, wherein y is 0-6;

each R⁵ is independently selected from optionally substituted pyridin-3-yl, pyridin-4-yl, morpholin-4-yl, thiomorpholin-4-yl, imidazolyl, furan-2-yl, 1,2,3,4-tetrahydroisoquinoline, tetrahydrofuran-2-yl, cyclohexyl, phenyl, —CH₂OH, —(CH₂)₂OH, and isopropyl, wherein each optional substituent is selected from halogen, R°, NO₂, OR°, or SR°; and each R⁶ is independently selected from R, F, Cl, N(R)₂, SR, NRC(O)R, NRC(O)N(R)₂, C(O)N(R)₂, SO₂R, NRSO₂R, C(O)R, CN, or SO₂N(R)₂.

6. The compound according to claim 1, wherein said compound has formula I', wherein Z¹ is N; Z² is CH; and R³(U)_n, T_mR¹, and Q—R² are as follows:

Compounds of Formula I'

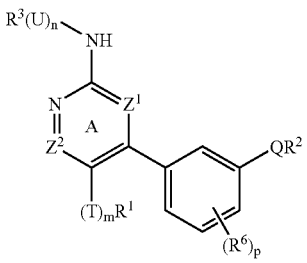

I'

| No. I'- | R³(U)_n | T_mR¹ | Q-R² |
|---|---|---|---|
| 5 | phenyl | H | 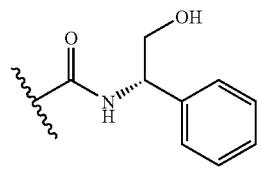 |

-continued
Compounds of Formula I'
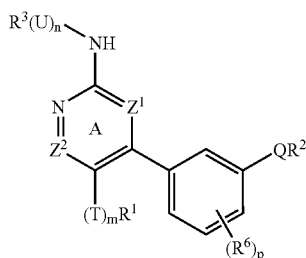
| No. I'- | R³(U)ₙ | TₘR¹ | Q-R² |
|---|---|---|---|
| 6 | phenyl | H | (S)-NHCH(CH₂OH)(phenyl) amide |
| 7 | phenyl | H | (S)-NHCH(CH₂OH)(tBu) amide |
| 9 | phenyl | H | (S)-NHCH(CH₂OH)(iPr) amide |
| 16 | phenyl | H | (R)-NHCH(CH₂OH)(iPr) amide |
| 17 | phenyl | H | (2S,3S)-NHCH(CH₂OH)CH(Me)Et amide |
| 18 | H | methyl | (S)-NHCH(CH₂OH)(phenyl) amide |
| 19 | H | methyl | (S)-NHCH(CH₂CH₂OH)(phenyl) amide |

-continued
Compounds of Formula I'
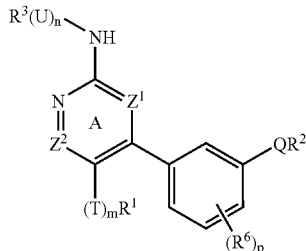
| No. I'- | R³(U)ₙ | TₘR¹ | Q-R² |
|---|---|---|---|
| 20 | H | methyl | *amide-N-CH(CH₂OH)-phenyl* |
| 21 | phenyl | methyl | *amide-N-CH(CH₂OH)-phenyl* |
| 22 | ethyl | methyl | *amide-N-CH(CH₂OH)-phenyl* |
| 27 | methyl | methyl | *amide-N-CH(CH₂OH)-(3-Cl,4-F-phenyl)* |
| 28 | phenyl | methyl | *amide-N-CH(CH₂OH)-(3-Cl,4-F-phenyl)* |
| 29 | 3-F-phenyl | methyl | *amide-N-CH(CH₂OH)-phenyl* |
| 30 | 3-OMe-phenyl | methyl | *amide-N-CH(CH₂OH)-phenyl* |

-continued
Compounds of Formula I'
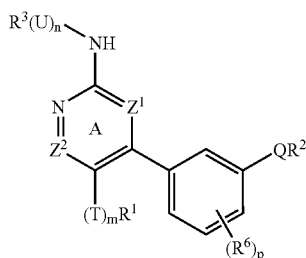
I'
| No. I'- | R³(U)ₙ | TₘR¹ | Q-R² |
|---|---|---|---|
| 31 | 3-OH-phenyl | methyl | 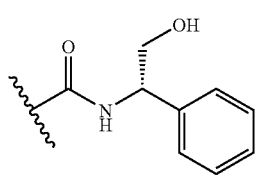 |
| 32 | 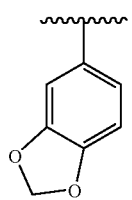 | methyl | 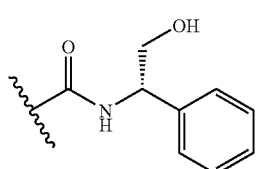 |
| 34 | 4-SO₂NH₂-phenyl | methyl | 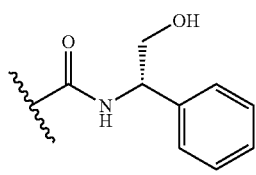 |
| 35 | 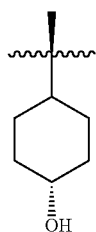 | methyl | 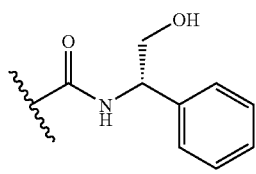 |
| 36 | phenyl | methyl | 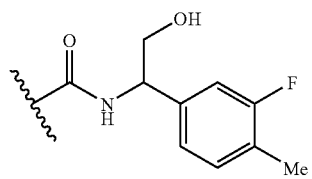 |
| 37 | 3-F-phenyl | methyl | 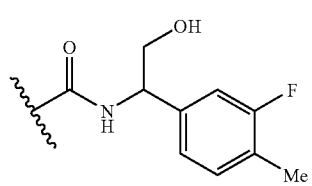 |

-continued
Compounds of Formula I'
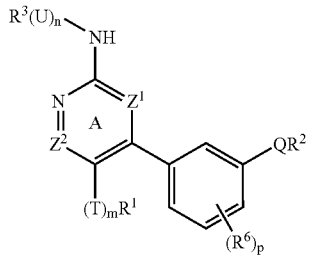
I'
| No. I'- | R³(U)ₙ | TₘR¹ | Q-R² |
|---|---|---|---|
| 38 | 3-CF₃-phenyl | methyl | -C(O)NH-CH(CH₂OH)(phenyl) |
| 39 | CH₂phenyl | methyl | -C(O)NH-CH(CH₂OH)(phenyl) |
| 40 | 3,4-Me₂-phenyl | methyl | -C(O)NH-CH(CH₂OH)(phenyl) |
| 41 | CH(CH₃)₂ | methyl | -C(O)NH-CH(CH₂OH)(phenyl) |
| 42 | CH(CH₂OH)(phenyl) | methyl | -C(O)NH-CH(CH₂OH)(phenyl) |
| 43 | 2-OMe-phenyl | methyl | -C(O)NH-CH(CH₂OH)(phenyl) |
| 44 | 4-OCF₃-phenyl | methyl | -C(O)NH-CH(CH₂OH)(phenyl) |

-continued
Compounds of Formula I'
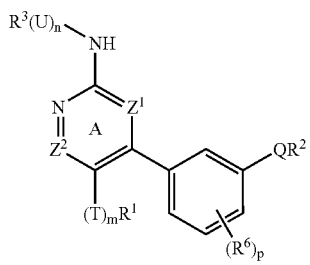
I'
| No. I'- | R³(U)ₙ | TₘR¹ | Q-R² |
|---|---|---|---|
| 45 | CH₂CH(CH₃)₂ | methyl | -C(O)NH-CH(CH₂OH)(phenyl) |
| 46 | CH₂cyclopropyl | methyl | -C(O)NH-CH(CH₂OH)(phenyl) |
| 47 | phenyl | CH₂OCH₃ | -C(O)NH-CH(CH₂OH)(phenyl) |
| 48 | H | CH₂OCH₃ | -C(O)NH-CH(CH₂OH)(phenyl) |
| 49 | cyclopropyl | methyl | -C(O)NH-CH(CH₂OH)(phenyl) |
| 50 | (CH₂)₂CH₃ | methyl | -C(O)NH-CH(CH₂OH)(phenyl) |

-continued
Compounds of Formula I'
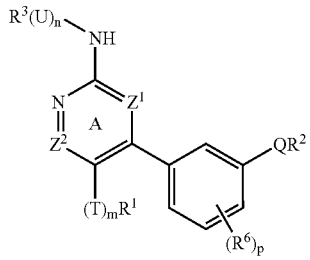
I'
| No. I'- | R³(U)ₙ | TₘR¹ | Q-R² |
|---|---|---|---|
| 51 | phenyl | CH₂OCH₃ | 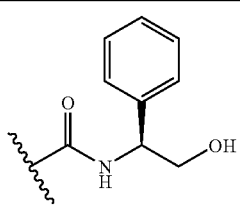 |
| 52 | phenyl | CH₂OH | 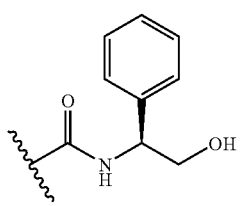 |
| 53 | 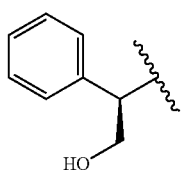 | methyl | 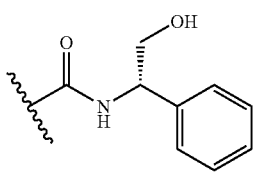 |
| 59 | ethyl | methyl | 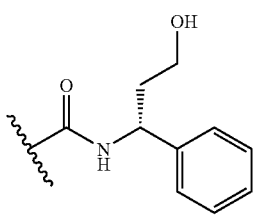 |
| 60 | ethyl | methyl | 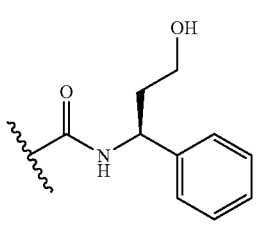 |
| 61 | 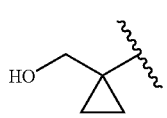 | methyl | 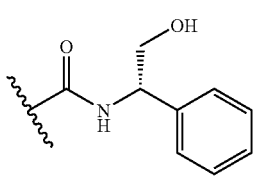 |

-continued
Compounds of Formula I'
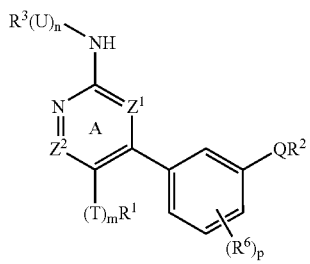
I'
| No. I'- | R³(U)ₙ | TₘR¹ | Q-R² |
|---|---|---|---|
| 62 | CH₂CH₂OH | methyl | 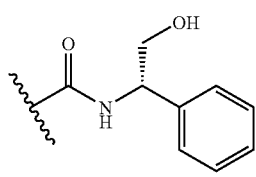 |
| 63 | 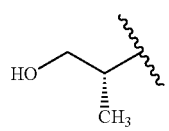 | methyl | 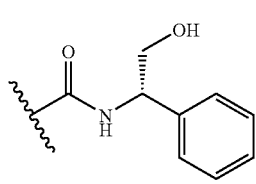 |
| 69 | ethyl | CH₂OCH₃ | 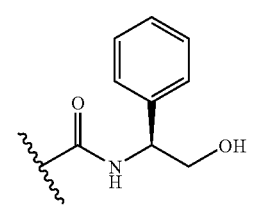 |
| 70 | ethyl | methyl | 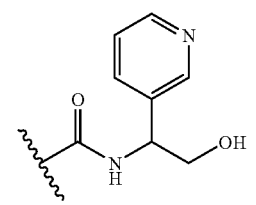 |
| 71 | ethyl | CH₂OH | 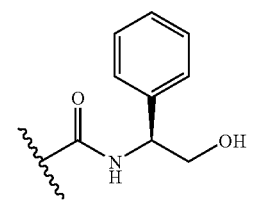 |
| 72 | ethyl | methyl | 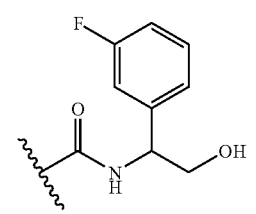 |

-continued
Compounds of Formula I'
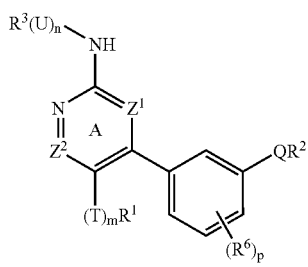
I'
| No. I'- | R³(U)ₙ | TₘR¹ | Q-R² |
|---|---|---|---|
| 73 | ethyl | methyl | 2-F-phenyl-CH(CH₂OH)-NHC(O)- |
| 74 | 2,3-Me₂-phenyl | methyl | phenyl-CH(CH₂OH)-NHC(O)- |
| 75 | OCH₂CH₃ | methyl | phenyl-CH(CH₂OH)-NHC(O)- |
| 76 | HOCH₂-CH(iPr)- | methyl | phenyl-CH(CH₂OH)-NHC(O)- |
| 77 | cyclopropyl | methyl | 2-OMe-phenyl-CH(CH₂OH)-NHC(O)- |

-continued
Compounds of Formula I'
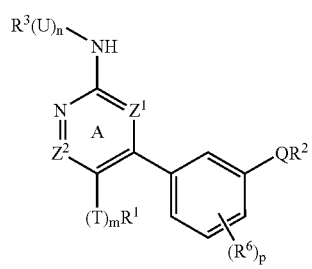
I'
| No. I'- | R³(U)ₙ | TₘR¹ | Q-R² |
|---|---|---|---|
| 78 | cyclopropyl | methyl | *3-Cl-phenyl-CH(CH₂OH)-NH-C(O)-* |
| 79 | cyclopropyl | methyl | *3-CH₃-phenyl-CH(CH₂OH)-NH-C(O)-* |
| 80 | O-Me | methyl | *phenyl-CH(CH₂OH)-NH-C(O)-* |
| 81 | O-isopropyl | methyl | *phenyl-CH(CH₂OH)-NH-C(O)-* |
| 83 | 2-OH-phenyl | methyl | *3-Me-phenyl-CH(CH₂OH)-NH-C(O)-* |

-continued
Compounds of Formula I'
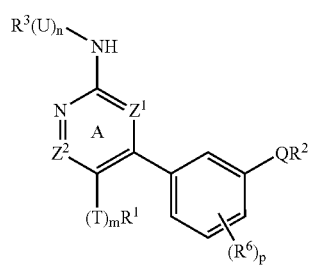
I'
| No. I'- | R³(U)ₙ | TₘR¹ | Q-R² |
|---|---|---|---|
| 84 | 2,3-Me₂-phenyl | methyl | 3-Me-phenyl-CH(CH₂OH)-NH-C(O)- |
| 85 | 2-Me-phenyl | methyl | phenyl-CH(CH₂OH)-NH-C(O)- |
| 86 | pyridin-3-yl | methyl | phenyl-CH(CH₂OH)-NH-C(O)- |
| 87 | (tetrahydrofuran-2-yl)methyl | methyl | phenyl-CH(CH₂OH)-NH-C(O)- |
| 88 | (S)-(tetrahydrofuran-2-yl)methyl | methyl | phenyl-CH(CH₂OH)-NH-C(O)- |

-continued
Compounds of Formula I'
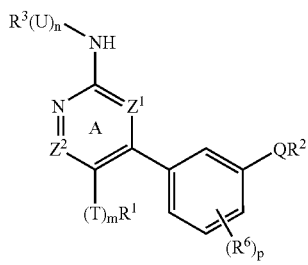
I'
| No. I'- | R³(U)ₙ | TₘR¹ | Q-R² |
|---|---|---|---|
| 89 | CH₂pyridin-3-yl | methyl | phenyl-CH(CH₂OH)-NHC(O)- |
| 90 | cyclopropylmethoxy | methyl | phenyl-CH(CH₂OH)-NHC(O)- |
| 91 | isoxazol-3-yl | methyl | phenyl-CH(CH₂OH)-NHC(O)- |
| 92 | (S)-1-hydroxyprop-2-yl | methyl | 3-Me-phenyl-CH(CH₂OH)-NHC(O)- |
| 93 | 2-Me-phenyl | methyl | 3-Me-phenyl-CH(CH₂OH)-NHC(O)- |

-continued
Compounds of Formula I'
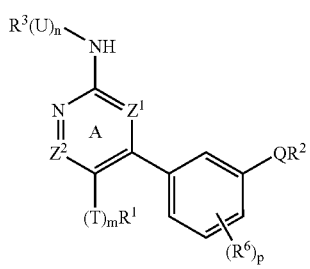
I'
| No. I'- | R³(U)ₙ | TₘR¹ | Q-R² |
|---|---|---|---|
| 94 | 2-Me-phenyl | methyl | -NH-C(O)-) |
| 95 | O(CH₂)₂OH | methyl | -NH-C(O)-) |
| 96 | N(Me)₂ | methyl | -NH-C(O)-) |
| 97 | 2-CF₃-phenyl | methyl | -NH-C(O)-) |
| 98 | morpholin-4-yl | methyl | -NH-C(O)-) |

-continued
Compounds of Formula I'
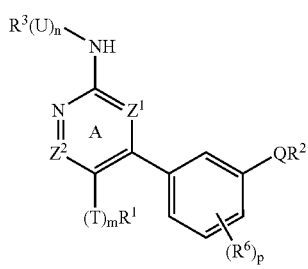
I'
| No. I'- | R³(U)ₙ | TₘR¹ | Q-R² |
|---|---|---|---|
| 99 | 5-methylisoxazol-3-yl | methyl | -C(O)NH-CH(Ph)-CH₂OH |
| 100 | 1-(3-chloro-4-fluorophenyl)-2-hydroxyethyl | methyl | -C(O)NH-CH(Ph)-CH₂OH |
| 111 | phenyl | methyl | -C(O)NH-CH(3-F-Ph)-CH₂OH |
| 122 | 1-(hydroxymethyl)propyl | methyl | -C(O)NH-CH(3-Cl-Ph)-CH₂OH |
| 123 | 1-(hydroxymethyl)propyl | methyl | -C(O)NH-CH(3-CH₃-Ph)-CH₂OH |

-continued
Compounds of Formula I'
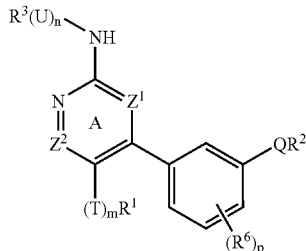
| No. I'- | R³(U)ₙ | TₘR¹ | Q-R² |
|---|---|---|---|
| 124 | (CH₃, H, OH group) | H | (3-Cl phenyl amide with CH₂OH) |
7. The compound according to claim 5, wherein said compound is selected from the following group of compounds:
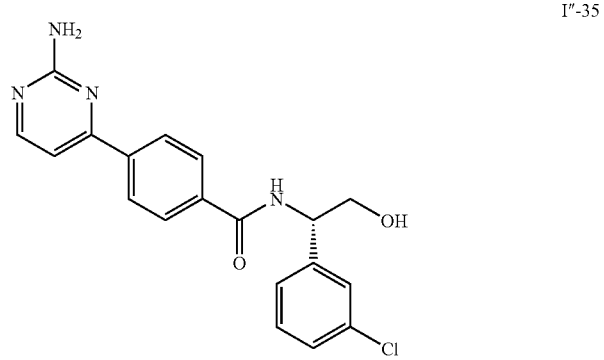
I''-35
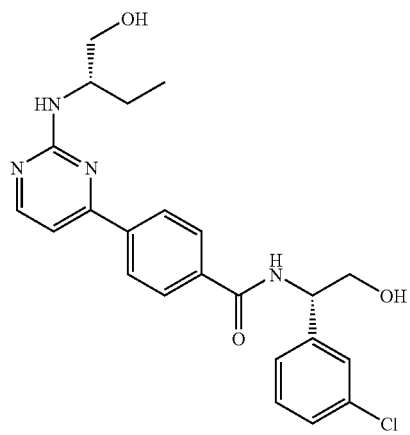
I''-36
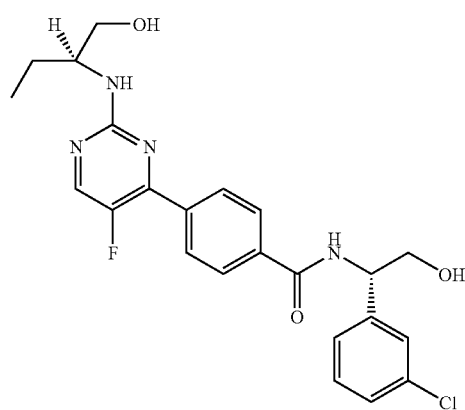
I''-37
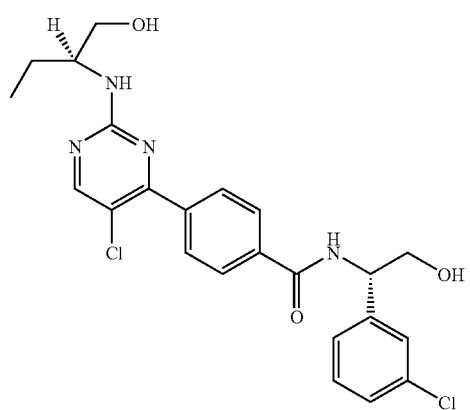
I''-38

-continued
I"-39
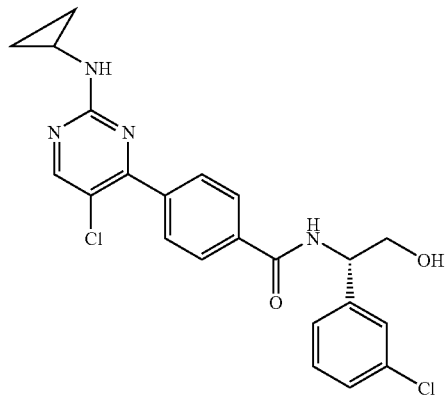
I"-40
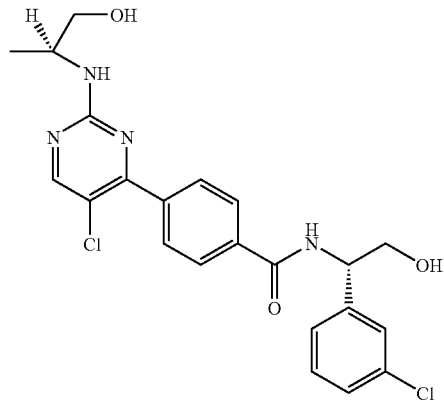
I"-41
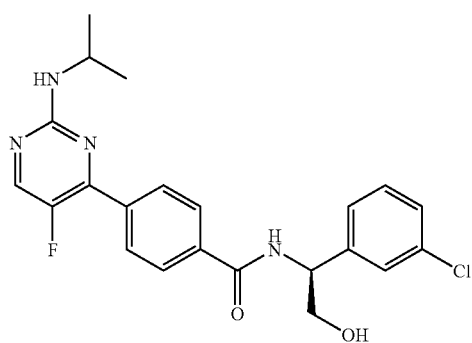
I"-42
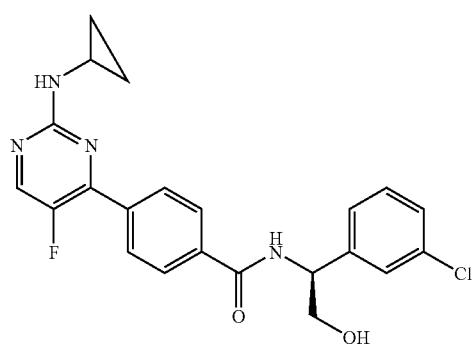
I"-43
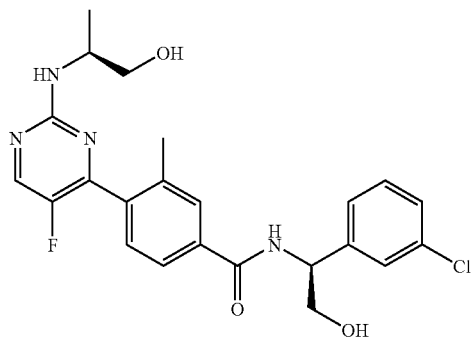
I"-45
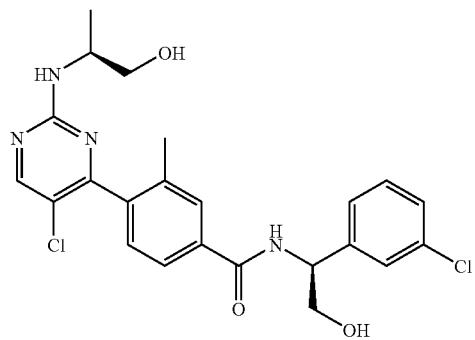
I"-49
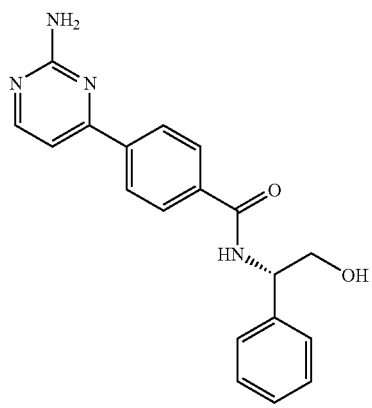
I"-50
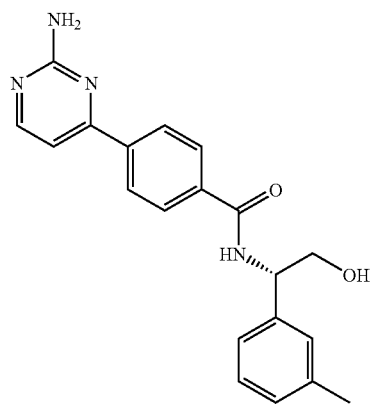

-continued
I''-51
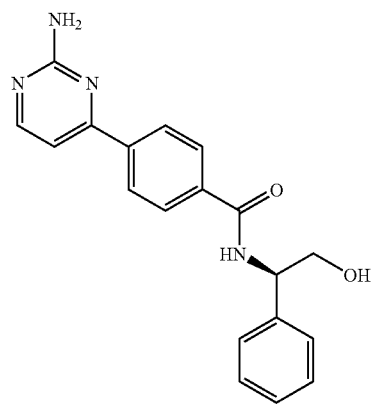
I''-52
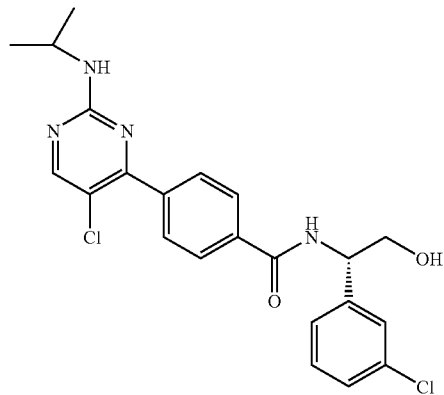
I''-53
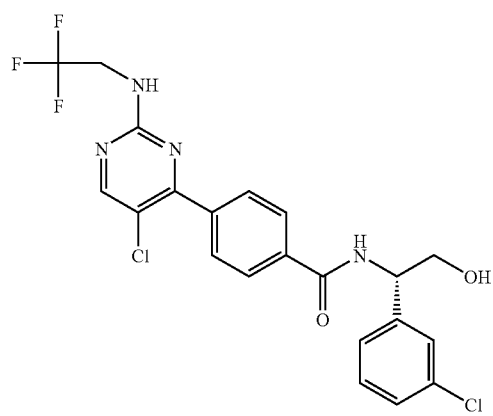
I''-54
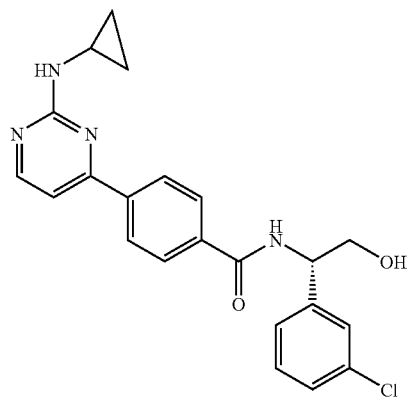
I''-55
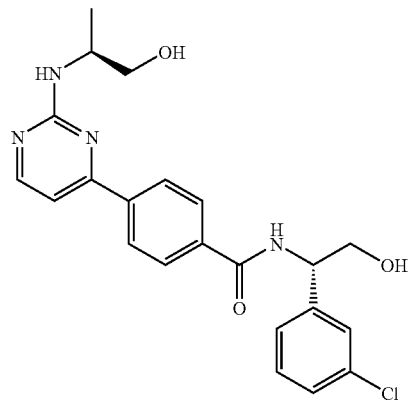
I''-57
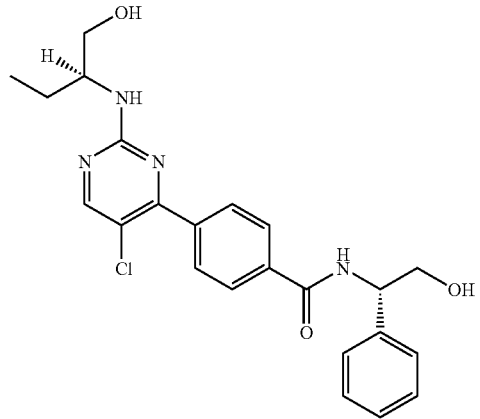
I''-58
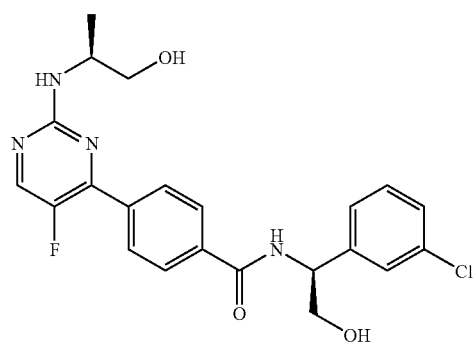
I''-59
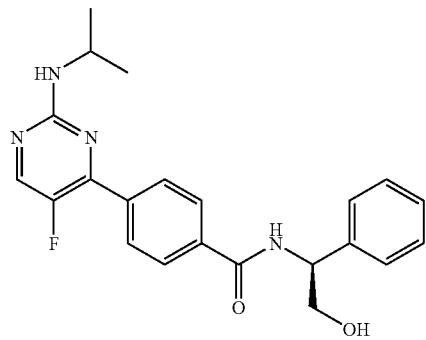

-continued
I''-60
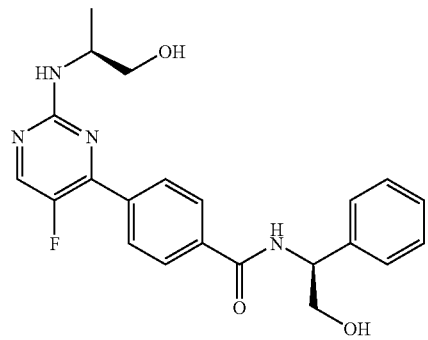
I''-61
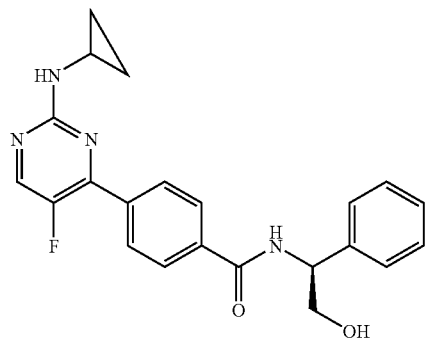
I''-62
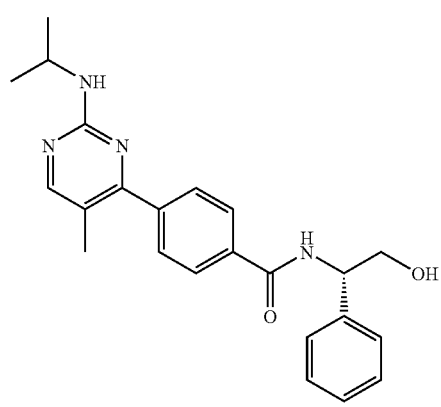
I''-63
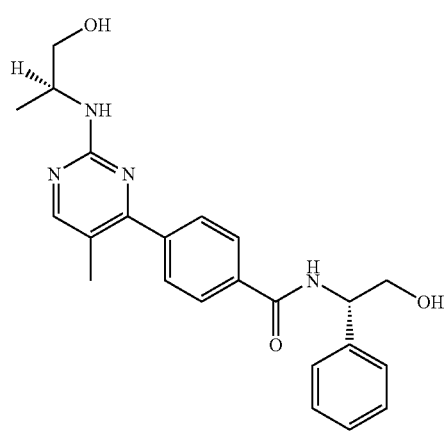
I''-64
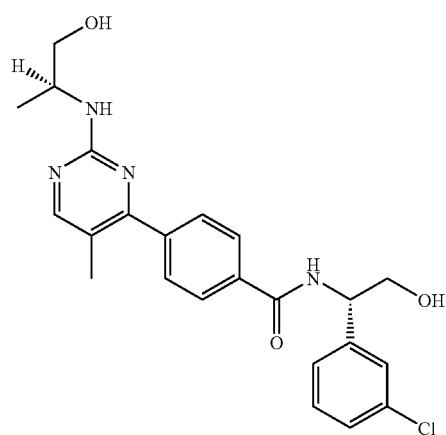
I''-65
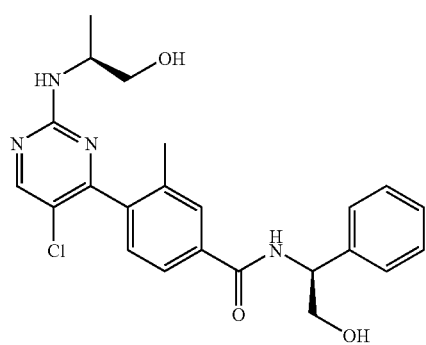
I''-66
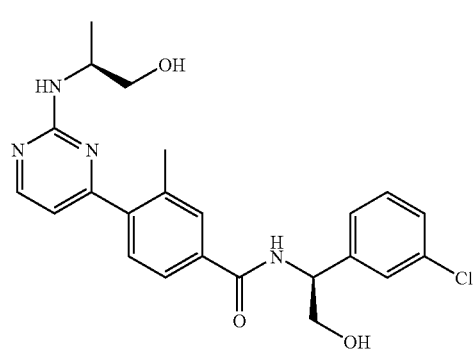
I''-67
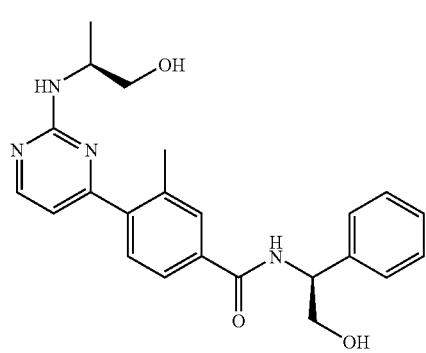

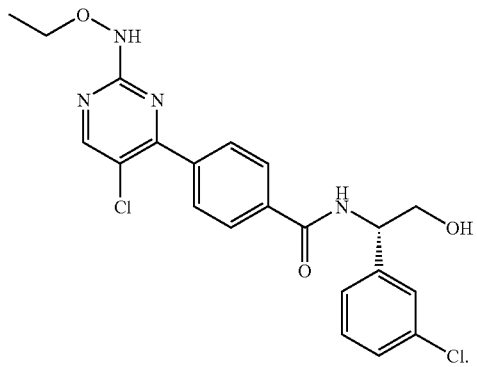

I″-72

8. The following compound:

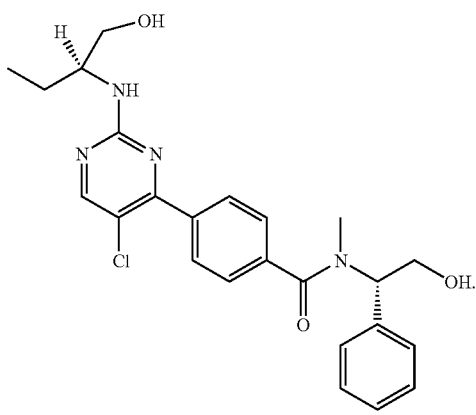

V′-4

9. A composition comprising a compound according to any of claims 1, 4, or 5 and a pharmaceutically acceptable carrier, adjuvant, or vehicle.

10. The composition according to claim 9, additionally comprising a therapeutic agent selected from an anti-proliferative agent, wherein said anti-proliferative agent is imatinib (Gleevec™), adriamycin, dexamethasone, vincristine, cyclophophamide, fluorouracil, topotecan, taxol, an interferon, a platinum derivative; an anti-inflammatory agent, wherein said anti-inflammatory agent is albuterol, a corticosteroids, IL-1 RA, azathiprine, cyclophosphamide, sulfasalazine, or montelukast (Singulair®); an immunomodulatory agent, wherein said immunomodulatory agent is beta interferon, glatiramer (Copaxone®), or mitoxantrone; a neurotrophic factor, wherein said neurotrophic factor is donepezil (Aricept®), rivastigmine (Excelon®), L-DOPA/carbidopa, entacapone, ropinrole, pramipexole, bromocriptine, pergolide, trihexephendyl, zyprexa, risperdal, seroquel, or haloperidol; or an agent for treating cardiovascular disease, wherein said agent is a beta-blocker, an ace inhibitor, a diuretic, a nitrate, a calcium channel blocker, or a statin.

11. A method of treating or lessening the severity of a proliferative disorder, wherein said proliferative disorder is breast cancer, colon cancer, kidney carcinoma, lung cancer, melanoma, ovarian cancer, pancreatic cancer, or prostate cancer; a neurodegenerative disease, wherein said neurodegenerative disease is Alzheimer's disease, Parkinson's disease, Huntington's disease, multiple sclerosis, schizophrenia, or amyotrophic lateral sclerosis; allergy; asthma; a cardiovascular disorder, wherein said cardiovascular disorder is reperfusion/ischemia injury, stroke, heart attack, restenosis, atherosclerosis, or cardiac hypertrophy, comprising the step of administering to a patient in need thereof a composition according to claim 9.

12. The method according to claim 11, wherein said method is used to treat or lessen the severity of asthma or allergies.

13. The method according to claim 11, wherein said method is used to treat or lessen the severity of a proliferative disease selected from breast cancer, colon cancer, kidney carcinoma, lung cancer, melanoma, ovarian cancer, pancreatic cancer, or prostate cancer.

14. The method according to claim 11, wherein said method is used to treat or lessen the severity of a neuro degenerative disease selected from Alzheimer's disease, Parkinson's disease, amyotrophic lateral sclerosis, Huntington's disease, multiple sclerosis, or schizophrenia.

15. The method according to claim 11, wherein said method is used to treat or lessen the severity of ischemia/reperfusion in stroke, myocardial ischemia, renal ischemia, heart attack, organ hypoxia, or thrombin-induced platelet aggregation.

16. The method according to claim 11, wherein said method is used to treat or lessen the severity of restenosis, atherosclerosis, or cardiac hypertrophy.

17. The method according to claim 11, comprising the additional step of administering to said patient an additional therapeutic agent selected from anti-proliferative agent, wherein said anti-proliferative agent is imatinib (Gleevec™), adriamycin, dexamethasone, vincristine, cyclophophamide, fluorouracil, topotecan, taxol, an interferon, or a platinum derivative; an anti-inflammatory agent, wherein said anti-inflammatory agent is albuterol, a corticosteroids, IL-1 RA, azathiprine, cyclophosphamide, sulfasalazine, or montelukast (Singulair®); an immunomodulatory agent, wherein said immunomodulatory agent is beta interferon, glatiramer (Copaxone®), or mitoxantrone; a neurotrophic factor, wherein said neurotrophic factor is donepezil (Aricept®), rivastigmine (Excelon®), L-DOPA/carbidopa, entacapone, ropinrole, pramipexole, bromocriptine, pergolide, trihexephendyl, zyprexa, risperdal, seroquel, or haloperidol; or an agent for treating cardiovascular disease, wherein said agent is a beta-blocker, an ace inhibitor, a diuretic, a nitrate, a calcium channel blocker, or a statin wherein:

said additional therapeutic agent is appropriate for the disease being treated; and said additional therapeutic agent is administered together with said composition as a single dosage form or separately from said composition as part of a multiple dosage form.

18. The method according to claim 15, wherein said disease, disorder, or condition is stroke.

19. The method according to claim 14, wherein said neurodegenerative disease is Alzheimer's disease.

20. A method for treating, or lessening the severity of, diabetes in a patient in need thereof wherein said method comprises administering to said patient a composition according to claim 9.

* * * * *